(12) United States Patent
Greenspan

(10) Patent No.: US 6,551,575 B1
(45) Date of Patent: Apr. 22, 2003

(54) METHODS FOR IDENTIFYING COMPOUNDS FOR MOTION SICKNESS, VERTIGO AND OTHER DISORDERS RELATED TO BALANCE AND THE PERCEPTION OF GRAVITY

(75) Inventor: Ralph J. Greenspan, Coronado, CA (US)

(73) Assignee: Neurosciences Research Foundation, Inc., San Diego, CA (US)

( * ) Notice: Subject to any disclaimer, the term of this patent is extended or adjusted under 35 U.S.C. 154(b) by 9 days.

(21) Appl. No.: 09/669,751

(22) Filed: Sep. 26, 2000

Related U.S. Application Data

(60) Provisional application No. 60/168,579, filed on Dec. 2, 1999.

(51) Int. Cl.$^7$ .............................. C12Q 1/68; A61K 49/00
(52) U.S. Cl. ............................. 424/9.2; 424/9.2; 435/6; 435/69.1; 435/252.3; 435/320.1; 536/23.1; 514/2; 530/350
(58) Field of Search .......................... 424/9.2; 435/69.1, 435/6, 252.3, 320.1; 536/23.1; 514/2; 530/350

(56) References Cited

FOREIGN PATENT DOCUMENTS

WO    WO 97/30722    8/1997

OTHER PUBLICATIONS http:/caat.jhsph.edu/programs/grants/reports/torres.html, (1999).
http://www.cannabis.net/weblife.html (Oct. 2000).
http://www.cavalierdaily.com/ .Archives/1998/Feb./12/he-crack.asp.
http:/www.cling.gu.se/~c15pwall/spiders/spiders.html (Oct. 2000).
http://www.nigms.nih.gov/news/releases/cocaine.html (Jan. 1998).
http://www.stresstips.com/caffeine.html (1998).
Avraham et al., "Characterization of Unconventional MYO6, the Human Homologue of the Gene Responsible for Deafness in Snell's Waltzer Mice," *Hum. Molec. Genet.*, 6(8):1225–1231 (1997).
Baloh et al., "Familial Vestibulopathy: A New Dominantly Inherited Syndrome," *Neurology*, 44:20–25 (1994).
Barinaga, "News of the Week: New Ion Channel May Yield Clues to Hearing," *Science*, 287:2132–2133 (2000).
Bellen, "The Fruit Fly: A Model Organism to Study the Genetics of Alcohol Abuse and Addiction?" *Cell*, 93:909–912 (1998).
Blake et al., "The Products of Ribbon and Raw Are Necessary for Proper Cell Shape and Cellular Localization of Nonmuscle Myosin in Drosophila," *Dev. Biol.*, 203:177–188 (1998).
Boonstra, "Growth Factor–Induced Signal Transduction in Adherent Mammalian Cells is Sensitive to Gravity," *FASEB J.*, 13:S35–S42 (1999).
Brand and Perry, "Drugs Used in Motion Sickness—A Critical Review of the Methods Available for the Study of Drugs of Potential Value in Its Treatment and of the Information Which Has Been Derived by These Methods," *Pharmac. Rev.*, 18(1):895–924, (1966).
Broughton et al., "Endogenously Inhibited Protein Kinase C in Transgenic Drosophila Embryonic Neuroblasts Down Regulates the Outgrowth of Type I and II Processes of Cultured Mature Neurons," *J. Cell. Biochem.*, 60:584–599 (1996).
Broughton et al., "Transport of CaM Kinase Along Processes Elicited by Neuronal Contact Evokes an Inhibition of Arborization and Outgrowth in *D. melanogaster* Cultured Neurons," *J. Cell. Biochem.*, 62:484–494 (1996).
Burg et al., "Genetic and Molecular Identification of a Drosophila Histidine Decarboxylase Gene Required in Photoreceptor Transmitter Synthesis," *EMBO J.*, 12:911–919 (1993).
Byers, "Osteogenesis Imperfecta," in *Connective Tissue and Its Heritable Disorders*, Wiley–Liss, Inc., (1993).
Cashmore et al., "Cryptochromes: Blue Light Receptors for Plants and Animals," *Science*, 284:760–765 (1999).
Ceriani et al., "Light–Dependent Sequestration of TIMELESS by CRYPTOCHROME," *Science*, 285:553–556 (1999).
Cummings et al., "Chaperone Suppression of Aggregation and Altered Subcellular Proteasome Localization Imply Protein Misfolding in SCA1," *Nat. Genet.*, 19:148–154 (1998).
Danik et al., "Localization of Sulfated Glycoprotein–2/Clusterin mRNA in the Rat Brain by In Situ Hybridization," *J. Comp. Neurol.*, 334:209–227 (1993).

(List continued on next page.)

*Primary Examiner*—Christopher S. F. Low
*Assistant Examiner*—Chih-Min Kam
(74) *Attorney, Agent, or Firm*—Campbell & Flores LLP

(57) ABSTRACT

The present invention provides a method of identifying a compound that modulates a mammalian vestibular system. The method consists of administering a test compound to an invertebrate, and measuring a geotactic behavior of the invertebrate, where a compound that modulates the geotactic behavior of the invertebrate is characterized as a compound that modulates a mammalian vestibular system. The invention also provides a method of identifying a gene that modulates a mammalian vestibular system consisting of obtaining a first and a second strain of an invertebrate; subjecting the first and second invertebrate strains to conditions in which the first strain exhibits a geotactic behavior different than a geotactic behavior exhibited by the second strain; measuring gene expression levels in the first and second strains, and identifying one or more genes that are differentially expressed in the first strain relative to the second strain, whereby a mammalian gene having substantially the same nucleic acid sequence as the one or more differentially expressed genes modulates the mammalian vestibular system.

12 Claims, 1 Drawing Sheet

OTHER PUBLICATIONS

Davis et al., "Use of the Teleost Saccule to Identify Genes Involved in Inner Ear Function," *DNA and Cell biol.*, 14(10):833–839 (1995).

Desai et al., "Receptor Tyrosine Phosphatases Are Required for Motor Axon Guidance in the Drosophila Embryo," *Cell*, 84:599–609 (1996).

Doe et al., "The Prospero Gene Specifies Cell Fates in the Drosophila Central Nervous System," *Cell*, 65:451–464 (1991).

Donat and Auger, "Familial Periodic Ataxia," *Arch. Neurol.*, 36:568–569 (1979).

Erlenmeyer–Kimling et al., "Studies in Experimental Behavior Genetics: III. Selection and Hybridization Analyses of Individual Differences in the Sign of Geotaxis," *J. Comp. Physiol. Physchol.*, 55(5): 722–731, (1962).

Fekete, "Cell Fate Specification in the Inner Ear," *Curr. Opin. Neuro.*, 6:533–541 (1996).

Franc et al., "Croquemort, A Novel Drosophila Hemocyte/Macrophage Receptor that Recognizes Apoptotic Cells," *Immunity*, 4:431–443 (1996).

Fransen et al., "High Prevalence of Symptoms of Menière's Disease in Three Families with a Mutation in the COCH Gene," *Hum. Mol. Genet.*, 8(8):1425–1429 (1999).

Gertler et al., "Dosage–Sensitive Modifiers of Drosophila Abl Tyrosine Kinase Function: Prospero, a Regulator of Axonal Outgrowth, and Disabled, a Novel Tyrosine Kinase Substrate," *Genes and Develop.*, 7:441–453 (1993).

Griffith et al., "Inhibition of Calcium/Calmodulin–Dependent Protein Kinase in Drospohila Disrupts Behavioral Plasticity," *Neuron*, 10:501–509 (1993).

Guvakova and Surmacz, "The Activated Insulin–Like Growth Factor I Receptor Induces Depolarization in Breast Epithelial Cells Characterized by Actin Filament Disassembly and Tyrosine Dephosphorylation of FAK, Cas, and Paxillin," *Exp. Cell. Res.*, 251:244–255 (1999).

Helmke et al., "SRC Binding to the Cytoskeleton, Triggered by Growth Cone Attachment to Laminin, is Protein Tyrosine Phosphatase–Dependent," *J. Cell. Sci.*, 111 :2465–2475 (1998).

Hirata et al., "Asymmetric Segregation of the Homeodomain Protein Prospero During Drosophila Development," *Nature*, 377:627–630 (1995).

Hirsch, "Studies in Experimental Behavior Genetics: II. Individual Differences in Geotaxis as a Function of Chromosome Variations in Synthesized Drosophila Populations," *J. Comp. Physiol. Psychol.*, 52(3):304–308 (1959).

Horn, "Gravity" *Comprehensive Insect Physiology Biochemistry and Pharmacology* vol. 6, Pergamon Press (1985).

Hu et al., "Midline Fasciclin: A Drosophila Fasciclin–I–Related Membrane Protein Localized to the CNS Midline Cells and Trachea," *J. Neurobiol.*, 35:77–93 (1998).

Imbert et al., "Cloning of the Gene for Spinocerebellar Ataxia 2 Reveals a Locus with High Sensitivity to Expanded CAG/Glutamine Repeats," *Nature Genet.*, 14:285–291 (1996).

Ingber, "How Cells (Might) Sense Microgravity," *FASEB J.*, 13:S3–S15 (1999).

Jaffrey and Snyder, "PIN: An Associated Protein Inhibitor of Neuronal Nitric Oxide Synthase," *Science*, 274:774–777 (1996).

Kane et al., "Learning without Performance in PKC–Deficient Drosophila," *Neuron*, 18:307–314 (1997).

Kirszbaum et al., "Molecular Cloning and Characterization of the Novel, Human Complement–Associated Protein, SP–40,40: A Link Between the Complement and Reproductive Systems," *EMBO J.*, 8:711–718 (1989).

Krishnan and Nash, "A Genetic Study of the Anesthetic Response: Mutants of *Drosophila melanogaster* Altered in Sensitivity to Halothane," *Proc. Natl. Acad. Sci. USA*, 87:8632–8636 (1990).

Legan et al., "The Mouse Tectorins—Modular Matrix Proteins of the Inner Ear Homologous to Components of the Sperm–Egg Adhesion System," *J. Biol. Chem.*, 272(13):8791–8801 (1997).

Lewis et al., "Spaceflight Alters Microtubules and Increases Apoptosis in Human Lymphocytes (Jurkat)," *FASEB J.*, 12:1007–1018 (1998).

Litt et al., "A Gene for Episodic Ataxia/Myokymia Maps to Chromosome 12p13," *Am. J. Hum. Genet.*, 55:702–709 (1994).

Lundquist et al., "UNC–115, a Conserved Protein with Predicted LIM and Actin–Binding Domains, Mediates Axon Guidance in *C. elegans*," *Neuron*, 21:385–392 (1998).

Luo et al., "Human Amyloid Precursor Protein Ameliorates Behavioral Deficit of Flies Deleted for Appl Gene," *Neuron*, 9:595–605 (1992).

Manolis et al., "A Gene for Non–Syndromic Autosomal Dominant Progressive Postlingual Sensorineural Hearing Loss Maps to Chromosome 14q12–13," *Hum. Mol. Genet.*, 5(7):1047–1050 (1996).

Manski et al., "Endolymphatic Sac Tumors—A Source of Morbid Hearing Loss in Von Hippel–Lindau Disease," *JAMA*, 277(18):1461–1466 (1997).

McClung and Hirsh, "Stereotypic Behavioral Responses to Free–Base Cocaine and the Development of Behavioral Sensitization in Drosophila," *Current Biology*, 8:109–112 (1998).

McMillan and McGuire, "The Homeotic Gene *Spineless–aristapedia* Affects Geotaxis in *Drosophila melanogaster*," *Behav. Genet.*, 22(5):557–573 (1992).

Mitchell et al., "Apoptosis of Neurons in the Vestibular Nuclei of Adult Mice Results from Prolonged Change in the External Environment," *Neurosci. Lett.*, 198:153–156 (1995).

Moore et al., "Ethanol Intoxication in Drosophila: Genetic and Pharmacological Evidence for Regulation by the cAMP Signaling Pathway," *Cell*, 93:997–1007 (1998).

Mustapha et al., "An α–Tectorin Gene Defect Causes a Newly Identified Autosomal Recessive Form of Sensorineural Pre–Lingual Non–Syndromic Deafness, DFNB21," *Hum. Molec. Genet.*, 8(3):409–412 (1999).

Ophoff et al., "Familial Hemiplegic Migraine and Episodic Ataxia Type–2 Are Caused by Mutations in the $Ca^{2+Channel}$ Gene $CACNL1A4$," *Cell*, 87:543–552 (1996).

Osborne et al., "Natural Behavior Polymorphism Due to a cGMP–Dependent Protein Kinase of Drosophila," *Science*, 277:834–836 (1997).

Pan et al., "Histaminergic Ligands Attenuate Barrel Rotation in Rats Following Unilateral Labyrinthectomy," *Methods Find Exp. Clin. Pharmacol.*, 20(9):771–777 (1998).

Park and Hall, "Isolation and Chronobiological Analysis of a Neuropeptide Pigment–Dispersing Factor Gene in *Drosophila melanogaster*," *J. Biol. Rhythms*, 13(3):219–228 (1998).

Pujana et al., "Spinocerebellar Ataxias in Spanish Patients: Genetic Analysis of Familial and Sporadic Cases," *Hum. Genet.*, 104:516–522 (1999).

Pulst et al., "Moderate Expansion of a Normally Biallelic Trinucleotide Repeat in Spinocerebellar Ataxia Type 2," *Nature Genet.*, 14:269–276 (1996).

Reddy and Rodrigues, "Sibling Cell Fate in the Drosophila Adult External Sense Organ Lineage is Specified by Prospero Function, Which is Regulated by Numb and Notch," *Development*, 126:2083–2092 (1999).

Renn et al., "A pdf Neuropeptide Gene Mutation and Ablation of PDF Neurons Each Cause Severe Abnormalities of Behavioral Circadian Rhythms in Drosophila," *Cell*, 99:791–802 (1999).

Ricker and Hirsch, "Genetic Changes Occurring Over 500 Generations in Lines of *Drosophila melanogaster* Selected Divergently for Geotaxis," *Behav. Genet.*, 18(1):13–25, (1988).

Roof et al., "Molecular Characterization of abLIM, a Novel Actin–Binding and Double Zinc Finger Protein," *J. Cell. Biol.*, 138(3):575–588 (1997).

Russo et al., "Fe65 and the Protein Network Centered Around the Cytosolic Domain of the Alzheimer's β–Amyloid Precursor Protein," *FEBS Lett.*, 434:1–7 (1998).

Sanpei et al., "Identification of the Spinocerebellar Ataxia Type 2 Gene Using a Direct Identification of Repeat Expansion and Cloning Technique, Direct," *Nature Genet.*, 14:277–284 (1996).

Schivell et al., "Isoform–Specific, Calcium–Regulated Interaction of the Synaptic Vesicle Proteins SV2 and Synaptotagmin," *J. Biol. Chem.*, 271(44):27770–27775 (1996).

Schwartzkopff, "Mechanoreception" in *The Physiology of Insecta*, Academic Press (1974).

Sedbrook et al., "ARG1 (Altered Response to Gravity) Encodes a DNAJ–Like Protein That Potentially Interacts with the Cytoskeleton," *Proc. Natl. Acad. Sci. USA*, 96:1140–1145 (1999).

Stoltenberg and Hirsch, "A Gene Correlate of Geotaxis Near Adh (2–50.1) in *Drosophila melanogaster*," *J. Comp. Phsychol.*, 110(3):252–259 (1996).

Török et al., "*The Overgrown Hematopoietic Organs–31* Tumor Suppressor Gene of Drosophila Encodes an Importin–Like Protein Accumulating in the Nucleus at the Onset of Mitosis," *J. Cell Biol.*, 129(6):1473–1489 (1995).

Torres and Horowitz, "Cocaethylene Synthesis in Drosophila," *Neuroscience Letters*, 263:201–204 (1999).

Torres and Horowitz, "Drugs of Abuse and Brain Gene Expression," *Psychosomatic Medicine*, 61: 630–650 (1999).

Torres and Horowitz, "Activating Properties of Cocaine and Cocaethylene in a Behavioral Preparation of *Drosophila melanogaster*," *Synapse*, 29:148–161 (1998).

Usami et al., "Non–Syndromic Hearing Loss Associated with Enlarged Vestibular Aqueduct is Caused by PDS Mutations," *Hum. Genet.*, 104:188–192 (1999).

Vaessin et al., "Prospero Is Expressed in Neuronal Precursors and Encodes a Nuclear Protein That Is Involved in the Control of Axonal Outgrowth in Drosophila," *Cell*, 67:941–953 (1991).

Verhoeven et al., "Mutations in the Human α–Tectorin Gene Cause Autosomal Dominant Non–Syndromic Hearing Impairment," *Nature Genet.*, 19:60–62 (1998).

Walker et al., "A Drosophila Mechanosensory Transduction Channel," *Science*, 287:2229–2234 (2000).

Weil et al. "Human Myosin VIIA Responsible for the Usher 1B Syndrome: A Predicted Membrane–Associated Motor Protein Expressed in Developing Sensory Epithelia," *Proc. Natl.Acad.Sci. USA*, 93:3232–3237 (1996).

Willnow et al., "Defective Forebrain Development in Mice Lacking GP330/Megalin," *Proc. Natl. Acad. Sci. USA*, 93:8460–8464 (1996).

Yabe et al., "Medial Vestibular Nucleus in the Guinea–Pig: Histaminergic Receptors, II. An In Vivo Study," *Exp. Brain Res.*, 93: 249–258, (1993).

Young et al., "Morphogenesis in Drosophila Requires Nonmuscle Myosin Heavy Chain Function," *Genes Dev.*, 7:29–41 (1993).

Bermingham et al., "Math1: An Essential Gene for the Generation of Inner Ear Hair Cells," *Science*, 284:1837–1841 (1999).

Robertson et al., "Mutations in a Novel Cochlear Gene Cause DNFA9, a Human Nonsyndromic Deafness with Vestibular Dysfunction," *Nat. Genet.*, 20:299–303 (1998).

Takasu and Harris, "Reduction of Inner Ear Inflammation by Treatment with Anti–ICAM–1 Antibody," *Ann. Otol. Rhinol. Laryngol.*, 106:1070–1075 (1997).

Zheng et al., "Neurotrophin–4/5, Brain–Derived Neurotrophic Factor, and Neurotrophin–3 Promote Survival of Cultured Vestibular Ganglion Neurons and Protect Them Against Neurotoxicity of Ototoxins," *J. Neurobiol.*, 28(3):330–340 (1995).

XP–002173930, *Drosophila melanogaster*, chromosome 3R region 88F–88F, complete sequence, Feb. 19, 2001.

Bainton et al., "Dopamine modulates acute responses to cocaine, nicotine and ethanol in Drosophila," *Current Biology*, 10:187–194 (2000).

METHODS FOR IDENTIFYING COMPOUNDS FOR MOTION SICKNESS, VERTIGO AND OTHER DISORDERS RELATED TO BALANCE AND THE PERCEPTION OF GRAVITY

RELATED APPLICATIONS

This application claims the benefit of U.S. Provisional Application No. 60/168,579, filed Dec. 2, 1999, the entire contents of which is incorporated herein by reference.

BACKGROUND OF THE INVENTION

Motion sickness is a condition produced by road, sea, air, or space travel, or by interacting with virtual environments. It is caused by the effect of any pronounced movement on the organ of balance in the inner ear or by sensory conflict about body motion as perceived by different receptors (visual, vestibular, and body proprioceptors). Symptoms may include headache, excessive sweating and salivation, loss of appetite, malaise, nausea, vomiting, gastrointestinal disturbances and fatigue. Vertigo is the illusion that one's surroundings or self are spinning, either horizontally or vertically, resulting from a disturbance of the semicircular canals in the inner ear or nerve tracts leading from them. It can be induced by motion, zero gravity or disease, and may be accompanied by vomiting, ringing in the ears and unsteadiness.

Travel related motion sickness is experienced by approximately 1% of air travelers and can be as high as 100% of ocean travelers on heavy seas. Children between the ages of 3 and 12 are the most susceptible. 50% of astronauts experience "space motion sickness" during space travel. While a source of discomfort, motion sickness and vertigo can also result in impaired performance by crew members on ships, planes or spacecraft, by drivers suffering from circulatory ailments, or by users of computer-based virtual environments.

Currently available drugs to treat motion sickness and vertigo produce a variety of undesirable side effects, some producing drowsiness, blurred vision, impaired reaction time and pattern recognition, others negatively affecting mood and sleep.

The genes that play important roles in the proper functioning of the vestibular system remain largely uncharacterized. Identification of such genes can provide methods for screening individuals with genetic susceptibility to motion sickness or vertigo and can also provide targets for developing new therapeutic agents that specifically modulate the expression or activity of genes associated with motion sickness or vertigo. Unfortunately, identification of such genes in mammals can be difficult and time consuming.

Therefore, there is a need to identify drugs that alleviate motion sickness and vertigo without undesirable side effects. There also exists a need to identify genes whose expression or activity is associated with conditions such as motion sickness or vertigo. The present invention satisfies these needs and provides related advantages as well.

SUMMARY OF THE INVENTION

The present invention provides a method of identifying a compound that modulates a mammalian vestibular system. The method consists of administering a test compound to an invertebrate, andmeasuring a geotactic behavior of the invertebrate, where a compound that modulates the geotactic behavior of said invertebrate is characterized as a compound that modulates a mammalian vestibular system. The invention also provides a method of identifying a gene that modulates a mammalian vestibular system consisting of obtaining a first and a second strain of an invertebrate; subjecting the first and second invertebrate strains to conditions in which the first strain exhibits a geotactic behavior different than a geotactic behavior exhibited by the second strain; measuring gene expression levels in the first and second strains, and identifying one or more genes that are differentially expressed in the first strain relative to the second strain, whereby a mammalian gene having substantially the same nucleic acid sequence as the one or more differentially expressed genes modulates the mammalian vestibular system.

DETAILED DESCRIPTION OF THE INVENTION

Figure 1:
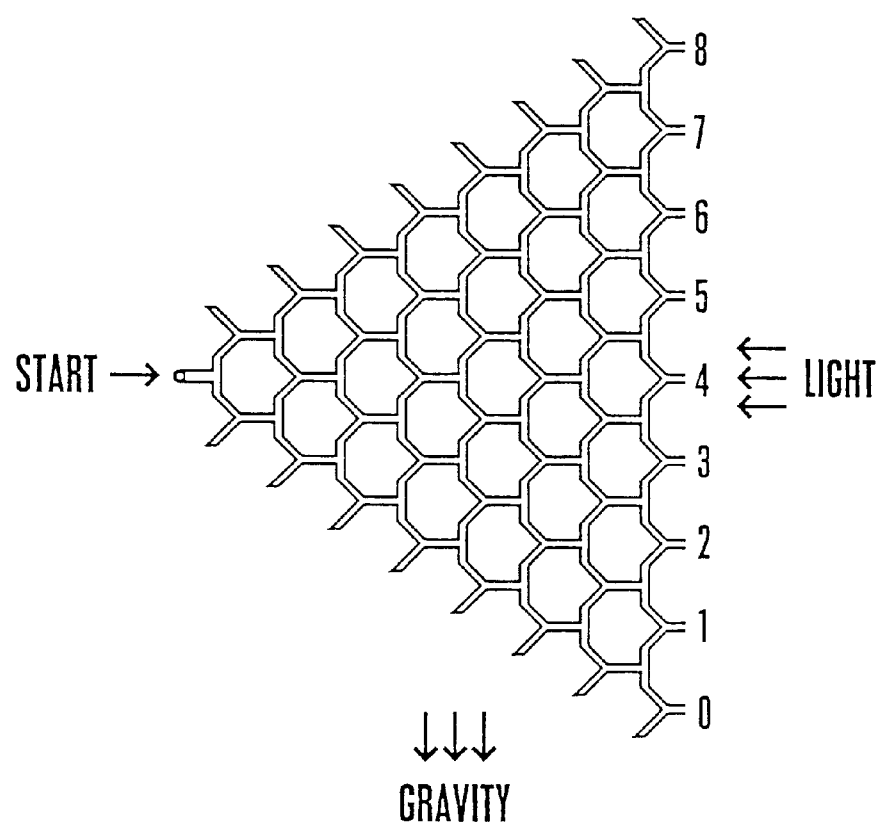
FIG. 1 shows a schematic of the geotaxis maze used in measuring geotactic scores of Drosophila.

The present invention provides methods of rapidly and efficiently identifying compounds that modulate a mammalian vestibular system, including compounds that decrease dizziness or nausea, or increase balance. The compounds identified by the methods of the invention can be used to treat individuals suffering from motion sickness, vertigo, or other graviperceptive disorders. The present invention also provides mammalian genes that modulate a mammalian vestibular system. A compound identified by the method of the invention can act to modulate the activity or expression of a mammalian gene of the invention.

Genetic and molecular studies of perception and response to gravity have not been extensively pursued in multi-cell organisms. As a result, little knowledge exists regarding the molecules that play important roles in perception of gravity and motion. There has been no indication that the manner in which mammals perceive gravity resembles the manner in which invertebrates perceive gravity or that the relative genetic simplicity of invertebrates compared to mammals provides networks of genes controlling graviperceptive behavior in invertebrates that are similar to those operating in mammals. In fact, invertebrates have been shown to have dissimilar pharmaclolgical responses compared to mammals within the same class of receptors. Thus, the use of invertebrates to test compounds affecting mammalian behaviors including, for example, graviperception also has not been pursued.

The methods and compounds disclosed herein are based on the discovery that administration of a compound used for treating motion sickness in humans can be effective in changing geotactic behavior of invertebrates and that the network of genes controlling the mammalian vestibular system is similar to the network of genes controlling geotactic behavior of invertebrates. The invention provides a method of identifying a compound that modulates a mammalian vestibular system. The method consists of administering a test compound to an invertebrate and measuring a geotactic behavior of the invertebrate. A candidate compound that modulates the geotactic behavior of the invertebrate is characterized as a compound that modulates a mammalian vestibular system.

The methods of the invention provide a means to identify a compound that modulates a mammalian vestibular system because the methods are based on screening geotactic behavior of invertebrates which is a natural system that performs a similar function. Thus, the methods provide for screening compounds in a context similar to the context of the mammalian vestibular system. Additionally, compounds that modulate a mammalian system to various degrees can be identified by the methods of the invention because strains of invertebrates that have naturally evolved different geotactic behaviors and degrees of response can be used with the methods of the invention.

According to the methods of the invention, changes in expression of one or more representative genes in a network of genes can be associated with changes in geotactic behavior of an invertebrate to identify compounds that modulate the mammalian vestibular system. Representative genes can include one gene, a set of all genes whose expression changes upon modulation of the mammalian vestibular system, or any subset of genes thereof. The methods of the invention can be used to identify compounds that modulate a mammalian vestibular system by identifying the effects of a compound on a subset of genes involved in the geotactic behavior of invertebrates because the change detected in the subset of genes occurs in the context of a natural network of genes controlling geotactic behavior.

As used herein, the term "modulate" refers to an increase, decrease or alteration. The term can be used to indicate an increase, decrease or alteration of a level, activity or function characteristic of a behavior, organ, protein, or other detectable phenomenon. For example, a mammalian vestibular system can be modulated by a compound that increases or decreases graviperception, increases or decreases neuronal response to a graviperceptive signal, and the like.

As used herein, the term "compound" as used in regard to modulating invertebrate geotaxis, a mammalian vestibular system, or protein expression or activity, refers to an inorganic or organic molecule such as a drug; a peptide, or a variant or modified peptide or a peptide-like molecule such as a peptidomimetic or peptoid; or a protein such as an antibody, a growth factor, or cytokine, or a fragment thereof such as an Fv, Fd or Fab fragment of an antibody, which contains a binding domain; or a nucleic acid or chemically modified nucleic acid such as an antisense nucleic acid; or a carbohydrate or lipid. Methods of determining compounds useful for modulating invertebrate geotaxis, a mammalian vestibular system, or protein expression or activity are provided herein, and include administering a compound to an invertebrate and identifying whether the compound modulates invertebrate geotaxis, administering a compound to an invertebrate or invertebrate cell culture and identifying whether the compound modulates expression of one or more genes associated with invertebrate geotaxis, and administering a compound to a mammal or mammalian cell culture and identifying compounds that modulate the expression or activity of a protein that modulates the mammalian vestibular system. If desired, a candidate compound can be combined with, or dissolved in, an agent that facilitates uptake of the compound by the invertebrate, such as an organic solvent, for example, DMSO or ethanol; or an aqueous solvent, for example, water or a buffered aqueous solution; or food.

A compound identified in the method of the invention modulates a mammalian vestibular system and also modulates geotactic behavior of an invertebrate. A compound that modulates invertebrate geotactic behavior can, for example, increase or decrease a geotactic behavior. Additionally, a compound can increase or decrease a first geotactic behavior while decreasing or increasing, respectively, a second geotactic behavior. For example, a compound can increase geotactic behavior in response to light, while decreasing geotactic behavior in response to heat or humidity.

A compound that modulates the activity or expression of a protein can, for example, increase or decrease the expression level or activity of a protein, or influence both expression and activity. For example, a compound can increase the activity but decreases the expression of a protein, as in the case of increased activity of a transcription factor that auto-regulates by feedback inhibition.

As described in the present invention, a compound that modulates invertebrate geotaxis can also modulate a mammalian vestibular system. Accordingly, a compound that modulates invertebrate geotaxis can increase or decrease the sensitivity of a mammalian vestibular system. For example, a compound that increases negative geotaxis in an invertebrate can decrease the sensitivity of a mammalian vestibular system.

As used herein, the term "mammalian vestibular system" refers to the organ of the inner ear of a mammal containing semicircular ducts and the nerve fibers extending therefrom. The nerve fibers can extend from the inner ear to the central parts of the brain and include, for example, the vestibular nuclei, trochlear nucleus, oculomotor nucleus, abducens nucleus, and vestibulospinal tracts. Typically, a mammalian vestibular system is used to maintain balance, perceive motion and perceive orientation relative to a force vector such as gravity or a physical force such as change in velocity or direction. A mammalian vestibular system can provide signals to the brain that result in graviperceptive disorders.

As used herein, a "graviperceptive disorder" refers to any condition that disturbs normal perception of gravity, motion or orientation. A graviperceptive disorder can have genetic or familial basis or can be induced by sickness or other physical conditions such as high blood pressure, or can be brought about by motion, changes in amplitude or direction of a gravitational or physical force, or changes in orientation. Exemplary graviperceptive disorders include, but are not limited to, labyrinthitis, Meniere's disease, motion sickness, vertigo, acoustic neuroma, multiple sclerosis, syphilis, trauma, infection of the middle ear, exposure to ototoxic agents, epilepsy and the like. A graviperceptive disorder is characterized by one or more symptoms such as dizziness, nausea, headache, excessive sweating and salivation, loss of appetite, malaise, gastrointestinal disturbances and fatigue. A variety of graviperceptive disorders in humans are known in the art and are described in, for example, Brandt, *Vertigo: Its Multisensory Syndromes*, $2^{nd}$ Ed., Springer Verlag (1999).

Mammals are understood to refer to members of the class mammalia, and particularly include placental mammals such as sheep, goats, cows, horses, pigs, dogs, cats, rats, mice, primates, humans and the like.

Modulation of a mammalian vestibular system can decrease or increase the sensitivity of a mammalian vestibular system, influencing the ability of an individual to maintain balance, perceive motion or perceive orientation, and can also result in, for example, a decrease in the symptoms associated with a graviperceptive disorder such as motion sickness, vertigo, labyrinthitis, Meniere's disease, acoustic neuroma, multiple sclerosis, syphilis, trauma, infection of the middle ear, exposure to ototoxic agents, epilepsy and the like. The term "sensitivity" when used in terms of a mammalian vestibular system refers to the responsiveness of semicircular ducts in sensing motion or orientation or the responsiveness in signaling of semicircular ducts or neurons connected thereto. Such sensitivity can influence symptoms of a graviperceptive disorder such as motion sickness, vertigo, labyrinthitis, Meniere's disease, acoustic neuroma, multiple sclerosis, syphilis, trauma, infection of the middle ear, exposure to ototoxic agents and epilepsy. Typically, decreased sensitivity of a mammalian vestibular system will result in a decrease in symptoms associated with a graviperceptive disorder.

A mammalian vestibular system can be modulated by a gene whose expression increases or decreases graviperception, increases or decreases nueronal response to a graviperceptive signal, and the like. In accordance with the present invention, such a gene comprises a nucleic acid sequence substantially the same as an invertebrate gene which modulates invertebrate geotactic behavior.

Examples of such genes are PROX1, comprising substantially the same sequence as SEQ ID NO:15, mammalian tectorin-α, comprising substantially the same sequence as SEQ ID NO:233; mammalian glycoprotein 330, comprising substantially the same sequence as SEQ ID NO:108; mammalian protein inhibitor of nNOS, comprising substantially the same sequence as SEQ ID NO:117; mammalian synaptic vesicle transporter, comprising substantially the same sequence as SEQ ID NO:250; mammalian actin-binding double-zinc-finger protein, comprising substantially the same sequence as SEQ ID NO:21; mammalian spinocerebellar ataxia type 2 protein, comprising substantially the same sequence as SEQ ID NO:1; mammalian APP-binding protein, comprising substantially the same sequence as SEQ ID NO:225; and the like. Further examples are mammalian genes substantially the same as genes containing the nucleic acid sequences of SEQ ID NOS:1–261.

The term "geotactic behavior" or "geotaxis" of an invertebrate refer to the behavioral response of an invertebrate to perception of a force vector such as gravity; a visual stimulus or a combination of the two. Geotactic behavior can be manifested by crawling, walking or flying in a specific direction and/or orientation in response to a force vector such as gravity. For example, an invertebrate having a walking pattern characterized as negative geotactic behavior walks in opposition to the force vector, or "upward." Conversely positive geotactic behavior is displayed by an invertebrate which walks in the same direction as the force vector, or "downward." As another example, the orientation of an invertebrate in flight with respect to a force vector, such as, upright, upside-down and the like, is a geotactic behavior. Wild type geotactic behavior refers to a geotactic behavior in an invertebrate which has not been selected for positive or negative geotactic behavior, abnormal flight behavior or other geotactic variant behavior. Exemplary wild type geotactic behavior can be manifest by an equal likelihood of a specific invertebrate to walk against a force vector "upward" as the likelihood of walking with the force vector "downward." Therefore, wild type geotactic behavior can result an invertebrate exhibiting, on average, neither positive nor negative geotactic behavior. Methods for determining geotactic behavior are disclosed herein and are well known in the art, as exemplified in the publications by Horn, "Gravity" in *Comprehensive Insect Physiology biochemistry and Pharmacology* Vol 6, Pergamon Press (1985) and Schwartzkopff, "Mechanoreception" in *The Physiology of Insecta* Academic Press (1974), which are incorporated herein by reference. These methods include monitoring the crawling direction of an invertebrate with respect to gravity, monitoring the static orientation of an invertebrate with respect to gravity and monitoring the orientation of flight with respect to gravity. An exemplary apparatus for measuring the crawling direction of an insect is provided in Example I.

The modulation of invertebrate geotactic behavior results in increased geotactic behavior, decreased geotactic behavior, or otherwise altering a behavioral response in reaction to a force vector, such as altering flying behavior by, for example, attempting to fly upside-down. As used herein, "increased geotactic behavior" refers to a change from negative to positive geotactic behavior, a lessened extent of negative geotactic behavior, or an increased extent of positive geotactic behavior. Correspondingly, "decreased geotactic behavior" refers to an change from positive to negative geotactic behavior, a lessened extent of positive geotactic behavior, or an increased extent of negative geotactic behavior.

Invertebrates are understood to refer to members of the division invertebrate. As disclosed herein, *Drosophila melanogaster* is an example of an invertebrate that exhibits geotactic behavior that can be measured. Those skilled in the art understand that other Drosophila species are also likely to exhibit similar geotactic behavior and express genes associated with geotactic behavior, including *D. simulans, D. virilis, D. pseudoobscura D. funebris, D. immigrans, D. repleta, D. affinis, D. saltans, D. sulphurigaster albostrigata* and *D. nasuta albomicans*. Likewise, other flies, including, sand flies, mayflies, blowflies, flesh flies, face flies, houseflies, screw worm-flies, stable flies, mosquitos, northern cattle grub, and the like will also exhibit geotactic behavior and express genes associated with geotactic behavior.

Furthermore, insects other than flies can also exhibit geotactic behavior and express genes associated with geotactic behavior. For example, the invention can also be practiced with insects such as cockroaches, honeybees, wasps, termites, grasshoppers, moths, butterflies, fleas, lice, boll weevils, beetles, *Apis mellifera, A. florea, A. cerana, Tenebrio molitor, Bombus terrestris, B. lapidarius,* and members of Hydrocorisae.

Arthropods other than insects also can exhibit geotactic behavior and express genes associated with geotactic behavior. For example, the invention can also be practiced using arthropods such as scorpions, spiders, mites, crustaceans, centipedes and millipedes.

Due to the high degree of genetic similarity across invertebrate species, invertebrates other than arthropods, such as flatworms, nematodes (e.g. *C. elegans*), mollusks (e.g. Aplysia or Hermissenda), echinoderms and annelids will exhibit geotactic behavior and express genes associated with geotactic behavior, and can be used in the methods of the invention.

Those skilled in the art can determine, using the assays described herein, whether a particular invertebrate exhibits geotactic behavior and expresses genes associated with geotactic behavior and, therefore, would be applicable for use in the methods of the invention. The choice of invertebrate will also depend on additional factors, for example, the availability of the invertebrates, the normal activity levels of the invertebrates, the availability of molecular probes for genes associated with geotactic behavior, the number of invertebrates and compounds one intends to use, the ease and cost of maintaining the invertebrates in a laboratory setting, the method of administering and type of compounds being tested, and the particular property being evaluated. Those skilled in the art can evaluate these factors in determining an appropriate invertebrate to use in the screening methods.

For example, if it is desired to evaluate gene expression in the methods of the invention, an invertebrate that is genetically well-characterized, such that homologs of genes associated with geotactic behavior are known or can be readily determined, can be used. Thus, appropriate invertebrates in which to evaluate gene expression can include, for example, Drosophila and *C. elegans*. If it desired to evaluate behavioral properties in the methods of the invention, an invertebrate that exhibits one or more geotactic behaviors, such as fruit flies, cockroaches, honeybees, wasps, moths, mosquitos, scorpions, and the like, can be used.

As used herein, a "strain" refers to a population of organisms of a species having at least one similar phenotype, typically a geotactic phenotype. This population of organisms can have either identical or a somewhat heterogeneous genetic makeup, although heterogeneous populations typically contain individuals that are homozygous for one or more chromosomes. For example, a population of organisms having a similar phenotype can be a population of organisms of a species sharing a similar genetic origin as the result of either being isolated from a particular geographic area, sharing particular chromosomes or alleles, or having been bred for multiple generations for a particular phenotype.

The term "substantially the same" as used herein in reference to the relationship between a mammalian gene and an invertebrate gene refers to a mammalian nucleic acid or corresponding amino acid sequence that has a high degree of homology to an invertebrate nucleic acid or corresponding amino acid sequence and retains at least one function specific to the invertebrate nucleic acid or corresponding amino acid sequence. In the case of a nucleotide sequence, a first nucleic acid that is substantially the same as a second nucleic acid can selectively hybridize to a sequence complementary to the second nucleic acid under moderately stringent conditions or under highly stringent conditions. Therefore, a first nucleic acid molecule having substantially the same sequence compared to a second nucleic acid sequence can include, for example, one or more additions, deletions or substitutions with respect to the second sequence so long as it can selectively hybridize to a complement of that sequence. In the case of an amino acid sequence, a first amino acid sequence that is substantially the same as a second amino acid sequence can contain minor modifications with respect to the second amino acid sequence, so long as the polypeptide containing the first amino acid sequence retains one or more functional activities exhibited by the whole polypeptide containing the second amino acid sequence. Typically, a substantial similarity is represented by at least about 20% identity between mammalian and invertebrate sequences; mammalian and invertebrate sequences that are substantially the same can also share at least about 30% identity, at least about 40% identity, at least about 50% identity, at least about 60% identity, at least about 70% identity, at least about 80% identity, at least about 90% identity, at least about 95% identity, at least about 97% identity, or at least about 99% identity over the length of the two sequences being compared. Those skilled in the art know that two or more polypeptides having low overall sequence similarity can be substantially similar if the polypeptides have similar domains with substantial sequence similarity. For example, polypeptides having 20% overall identity can be substantially similar if the polypeptides contain one or more domains of substantial similarity. A larger number of similar domains between two or more polypeptides correlates with increased similarity. Therefore, substantial similarity can be identified according to sequence identity within similar domains of two or more polypeptides. Examples of methods for determining substantial similarity using sequence identity or a combination of sequence identity and similarity in domain structure are described below.

The appropriate function to be retained will depend on the desired use of the nucleic acid molecule. For example, a mammalian gene substantially the same as an invertebrate gene associated with geotactic behavior can be a polypeptide having substantially the same immunogenicity, antigenicity, enzymatic activity, binding activity, or other biological property, including invertebrate geotactic behavior modulating activity which will correspond to mammalian vestibular system modulating activity, as the polypeptide encoded by the invertebrate nucleic acid molecule.

Methods for determining that two sequences are substantially the same are well known in the art. For example, one method for determining if two sequences are substantially the same is BLAST, Basic Local Alignment Search Tool, which can be used according to default parameters as described by Tatiana et al., *FEMS Microbiol Lett.* 174:247–250 (1999) or on the National Center for Biotechnology Information web page at ncbi.nlm.gov/BLAST/. BLAST is a set of similarity search programs designed to examine all available sequence databases and can function to search for similarities in protein or nucleotide sequences. A BLAST search provides search scores that have a well-defined statistical interpretation. Furthermore, BLAST uses a heuristic algorithm that seeks local alignments and is therefore able to detect relationships among sequences which share only isolated regions of similarity including, for example, protein domains (Altschul et al., *J. Mol. Biol.* 215:403–410 (1990)).

In addition to the originally described BLAST (Altschul et al., supra, 1990), modifications to the algorithm have been made (Altschul et al., *Nucleic Acids Res.* 25:3389–3402 (1997)). One modification is Gapped BLAST, which allows gaps, either insertions or deletions, to be introduced into alignments. Allowing gaps in alignments tends to reflect biologic relationships more closely. For example, gapped BLAST can be used to identify sequence identity within similar domains of two or more proteins. A second modification is PSI-BLAST, which is a sensitive way to search for sequence homologs. PSI-BLAST performs an initial Gapped BLAST search and uses information from any significant alignments to construct a position-specific score matrix, which replaces the query sequence for the next round of database searching. A PSI-BLAST search is often more sensitive to weak but biologically relevant sequence similarities.

A second resource that can be used to determine if two sequences are substantially the same is PROSITE, available on the world wide web at ExPASy. PROSITE is a method of determining the function of uncharacterized proteins translated from genomic or cDNA sequences (Bairoch et al., *Nucleic Acids Res.* 25:217–221 (1997)). PROSITE consists of a database of biologically significant sites and patterns that can be used to identify which known family of proteins, if any, the new sequence belongs. In some cases, the sequence of an unknown protein is too distantly related to any protein of known structure to detect similarity by overall sequence alignment. However, a protein that is substantially the same as another protein can be identified by the occurrence in its sequence of a particular cluster of amino acid residues, which can be called a pattern, motif, signature or fingerprint, that is substantially the same as a particular cluster of amino acid residues in the other protein including, for example, those found in similar domains. PROSITE uses a computer algorithm to search for motifs that identify proteins as family members. PROSITE also maintains a compilation of previously identified motifs, which can be used to determine if a newly identified protein is a member of a known protein family.

The term "moderately stringent conditions," as used here is intended to refer to hybridization conditions equivalent to hybridization of filter-bound nucleic acid in 50% formamide, 5×Denhart's solution, 5×SSPE, 0.2% SDS at 42° C., followed by washing in 0.2×SSPE, 0.2% SDS, at 50°. In contrast, "highly stringent conditions" are conditions equivalent to hybridization of filter-bound nucleic acid in 50% formamide, 5×Denhart's solution, 5×SSPE, 0.2% SDS at 42° C., followed by washing in 0.2×SSPE, 0.2% SDS, at 65°. Other suitable moderately stringent and highly stringent hybridization buffers and conditions are well known to those of skill in the art and are described, for example, in Sambrook et al., *Molecular Cloning: A Laboratory Manual,* Cold Spring Harbor Laboratory, New York (1992) and in Ausubel et al., *Current Protocols in Molecular Biology,* John Wiley and Sons, Baltimore, Md. (1998).

The sequences of corresponding genes associated with geotactic behavior of desired species can be determined by methods well known in the art, which include methods such as PCR or screening genomic, cDNA or expression libraries derived from that species.

A modification of a nucleic acid molecule can also include substitutions that do not change the encoded amino acid sequence due to the degeneracy of the genetic code. Such modifications can correspond to variations that are made deliberately, or which occur as mutations during nucleic acid replication. Additionally, a modification of a nucleic acid molecule can correspond to a splice variant form of the recited sequence.

Additionally, a fragment of a mammalian gene can be substantially the same as an invertebrate gene or a fragment of an invertebrate gene. As used herein, a "fragment" of a gene refers to a portion of a gene that retains at least one biological function of the wild type gene. A mammalian gene can be substantially the same as an invertebrate gene, for example, when one of several domains encoded by a mammalian gene corresponds to a domain encoded by an invertebrate protein. Such a fragment typically is encoded by at least 30 nucleotides, and the mammalian and invertebrate genes encoding that fragment share at least about 50% identity, at least about 60% identity, at least about 70% identity, at least about 80% identity, at least about 90% identity, at least about 95% identity or at least about 98% identity. Methods for determining that a fragment of a mammalian gene is substantially the same as an invertebrate gene or a fragment of an invertebrate gene include those described above for comparing mammalian and invertebrate genes. Such a fragment can be encoded by 30 or more nucleotides, for example, 45 or more nucleotides, 60 or more nucleotides, 90 or more nucleotides, 150 or more nucleotides, 210 or more nucleotides, or 300 or more nucleotides.

Biological functions retained by a fragment can include the ability to modulate a mammalian vestibular system, the ability to modulate invertebrate geotaxis, the ability to bind an antibody that binds to a full-length protein which comprises the fragment, or an enzymatic or binding activity characteristic of the full length protein. For example, a 30 amino acid fragment of prospero interacts with miranda for subcellular localization as described in Hirata et al. *Nature* 377:627–630 (1995) and peptides corresponding to 30 amino acid domains of CaMKII and PKC inhibit the respective full length enzymes as described in Kane et al., *Neuron* 18:307–314 (1997), Broughton et al., *J. Cell. Biochem.* 62:484–494 (1996), Broughton et al., *J. Cell. Biochem.* 60:584–600 (1996) and Griffith et al., *Neuron* 10:501–509 (1993).

The term "administering" a compound refers to any method of delivering a compound to an invertebrate or mammalian subject in such a way that invertebrate geotaxis or a mammalian vestibular system can be modulated. Administration of a compound can be carried out using one of a variety of methods known to those of skill in the art. For example, a compound can be administered intravenously, intramuscularly, by ingestion, inhalation, absorption such as absorption through the skin or tear duct, or any other method of administration known in the art. A compound can be administered, for example, to a fruit fly by ingestion.

An appropriate method of administering a compound to an invertebrate can be determined by those skilled in the art and will depend, for example, on the type and developmental stage of the invertebrate, whether the invertebrate is active or inactive at the time of administering, whether the invertebrate is exhibiting a geotactic behavior at the time of administering, the number of animals being assayed, and the chemical and biological properties of the compound (e.g. solubility, digestibility, bioavailability, stability and toxicity). For example, as shown in Example I below, antihistamine can be administered to *Drosophila melanogaster* by dissolving the drugs in fly food and providing the food to the flies.

A compound that can modulate a mammalian vestibular system, invertebrate geotaxis, or protein expression or activity can be administered to a subject in an effective amount. The term "effective amount" of a compound, as used herein, refers to an amount that causes a change in a mammalian vestibular system, invertebrate geotaxis, or protein expression or activity. Measurement of such a change can be made by one of a variety of assay methods known to one of skill in the art and include monitoring invertebrate geotactic behavior, measurement of gene expression level, or measurement of activity levels of one or more proteins; measurements can also include clinical indices such as assessment of improvement of a graviperceptive disorder such as vertigo or motion sickness in a subject by decreased symptoms related to the graviperceptive disorder, for example, nausea, dizziness, fatigue and the like.

A candidate compound can be administered to an invertebrate in a single dose, or in multiple doses. The modulation of invertebrate geotactic behavior will be dose dependent. An effective amount of a compound used in the methods of the invention can be determined by those skilled in the art, and can depend on the chemical and biological properties of the compound and the method of contacting. Exemplary concentration ranges to test include from about 10 µg/ml to about 500 mg/ml, such as from about 100 µg/ml to 250 mg/ml, including from about 1 mg/ml to 200 mg/ml.

A candidate compound can also be administered to a mammal. Administration to a mammal can be in a single dose, or in multiple doses. The modulation of a mammalian vestibular system will be dose dependent. An effective amount of a compound used in the methods of the invention can be determined by those skilled in the art, and can depend on the chemical and biological properties of the compound and the method of contacting. Exemplary concentration ranges to test include from about 10 µg/ml to about 500 mg/ml, such as from about 100 µg/ml to 250 mg/ml, including from about 1 mg/ml to 200 mg/ml. Exemplary mammals to which a candidate compound can be administered include mice, rats, rabbits, pigs, dogs, cats, non-human primates, an other animals known to be useful for laboratory testing.

A subject with a graviperceptive disorder such as motion sickness, vertigo, labyrinthitis, Meniere's disease, acoustic neuroma, multiple sclerosis, syphilis, trauma, infection of the middle ear, exposure to ototoxic agents or epilepsy sickness can be treated for such a disorder by administering to the subject an effective amount of a compound that modulates a mammalian vestibular system. In treatment of the disorder, administration of an effective amount of the compound can be carried out upon a single occasion or multiple occasions. Administration can be regular, periodic administration such as one administration per day, symptomatic administration such as upon experiencing increasing nausea or dizziness, or prophylactic administration, such as prior to road, sea, air or space travel.

It will be understood that the efficacy and safety of a compound in laboratory mammals can be evaluated before administering the compound to humans or veterinary animals. For example, the compound can be tested for its maximal efficacy and any potential side-effects using several different invertebrates or laboratory mammals, across a range of doses, in a range of formulations, and at various times of day, such as before or after sleeping, before or after eating, and the like. Generally, a compound identified using the methods of the invention will cause few or no deleterious or unwanted side effects.

The term "conditions" when used in the context of invertebrate geotactic behavior refers to environmental and biological factors that can increase, decrease or otherwise modify invertebrate geotactic behavior. Environmental factors encompass the physical environment such as temperature, pressure, light intensity, light position, and the like; components of the gaseous environment such as humidity, % oxygen, presence of a compound such as a drug or hormone, and the like; and the structural makeup of the chamber in which the invertebrate is housed, including volume, particularly as it influences density of invertebrates, shape, composition of the chamber, and the like. Typical environmental conditions are about 20° C., 1 atmosphere, in the presence of a horizontal 15 W fluorescent light source, at ambient air conditions. An exemplary chamber is provided in the Examples below. Biological factors that can influence invertebrate geotaxis can include genetic factors including presence of particular alleles of genes or chromosomes, either naturally occurring or induced in the laboratory, biorhythmic factors such as time of day, relative activity level of an invertebrate, length of time an invertebrate has been active, and the like, also include biochemical factors such as developmental and hormonal state of an invertebrate, fasting state of the invertebrate, presence in the invertebrate of a compound administered by, for example, ingestion, and the like, and further include factors such as gender and age of the invertebrate. Typically, geotactic behavior experiments are carried out on adult invertebrates during the daytime, at least about two hours after sunrise and at least about two hours before sunset, and at least two hours after invertebrates have been at a relatively increased level of activity. An "increased level of activity" as used herein refers to the "alert" state of an invertebrate that often occurs in the daytime in contrast to the "resting" state of an invertebrate that often occurs during the nighttime. Change of some of these conditions can result in a change in geotactic behavior of an invertebrate. For example,addition of a compound such as a drug to the gaseous environment can result in modulated invertebrate geotaxis.

Conditions in which a first invertebrate strain can exhibit a geotactic behavior different than a geotactic behavior in a second invertebrate strain refers to environmental or biorhythmic factors that, when imposed on two different invertebrate strains, results in the two strains exhibiting dissimilar geotactic behavior. For example, conditions can cause a first invertebrate strain to exhibit negative geotaxis while cause a second strain to exhibit positive geotaxis. The first and second strain can be any combination of strains, including a mutant strain and a wild type strain, two different mutant strains, and also can be two different or even identical strains, where the two strains differ in, for example, age, gender, presence of a drug in one strain or different drugs in the two strains, and the like. These conditions also include the structure of the chamber in which the invertebrates are housed. For example, two strains can be placed in a chamber that is so shaped as to have pathways that lead upwards, against the force of gravity, as well as pathways that lead downwards, with the force of gravity. In such a chamber, a first strain can demonstrate strongly negative geotaxictic behavior, thereby rising along the upward pathways, while a second strand can demonstrate normal or "wild-type" geotaxictic behavior, in which no particular preference is manifest for either rising or descending along the various pathways. In a chamber of such a shape, further environmental or biorhythmic factors can be changed, for example, by administering a compound to the invertebrates, which can change the geotactic behavior of one or both invertebrate strains.

Determination of a geotactic behavior of a first invertebrate that is termed "different" than a geotactic behavior of a second invertebrate can be accomplished by analysis of a geotactic behavior of the two invertebrates. For example, in order for a geotactic behavior of a first invertebrate to be different than a geotactic behavior of a second invertebrate, the mean geotatic measurement, typically termed the geotaxis score, of the first invertebrate will differ from the geotaxis score of the second invertebrate strain if a pairwise t-test of two scores is significantly different at the 0.05 level, or if multiple pairwise comparisons between strains are significantly different after applying a correction for experiment wise-error. A significantly different score refers to a score that is different by a statistically meaningful amount. Alternatively, two geotactic scores are considered different if a first mean geotactic score is not within as desired region of the probability distribution of the second geotactic score. For example, a first mean geotactic score can be different if it is not within the 80% probable region of a probability distribution of the second geotactic score, or within the 85%, 90%, 95% or 98% probable region of the distribution of the second geotactic score. Correspondingly, geotactic scores considered to be substantially the same are geotactic scores that do not differ by a more than a desired standard deviation or are within a desired probable region of a probability distribution. Methods for the determination of mean, standard deviation and characteristics of normal distributions are known in the art as demonstrated by texts such as *Biostatistical Analysis, 4th ed.,* Zar, Prentice-Hall Inc. (1999).

Measuring gene expression levels can be carried out by determining the amount of RNA transcribed or protein translated from each of one or more genes. This amount can be relative to another amount, for example, the RNA transcribed from a constitutively expressed gene, relative to total RNA or protein, or can be an absolute measure of the amount of RNA transcribed or protein translated.

A variety of assays well known in the art can be used to evaluate expression of particular genes, including the invertebrate genes comprising SEQ ID NOS: 1–261, and mammalian genes substantially the same as invertebrate genes comprising SEQ ID NOS: 1–261. Assays that detect mRNA expression generally involve hybridization of a detectable agent, such as a complementary primer or probe, to the nucleic acid molecule. Such assays include, for example, RNA or dot blot analysis, primer extension, RNase protection assays, reverse-transcription PCR, competitive PCR, real-time quantitative PCR (TaqMan PCR), nucleic acid array analysis, and the like.

Additionally, constructs containing the promoter of a gene and a reporter gene (e.g. β-galactosidase, green fluorescent protein, luciferase) can be made by known methods, and used to generate transgenic non-human mammals and invertebrates. In transgenic non-human mammals, expression of the reporter gene is a marker for expression of a gene that modulates a mammalian vestibular system. Likewise, expression of a reporter gene in transgenic invertebrates is a marker for expression of a gene that modulate a geotactic behavior.

Assays that detect protein expression can also be used to evaluate expression of particular genes. Such assays generally involve binding of a detectable agent, such as an antibody or selective binding agent, to the polypeptide in a sample of cells or tissue from the animal. Protein assays include, for example, immunohistochemistry, immunofluorescence, ELISA assays, immunoprecipitation, immunoblot or other protein-blot analysis, and the like.

Those skilled in the art will appreciate that the methods of the invention can be practiced in the absence of knowledge of the sequence or function of the genes associated with a geotactic behavior or genes that modulate the mammalian vestibular system whose expression is evaluated. Expression of such genes can thus be evaluated using assays that examine overall patterns of gene expression characteristic of a geotactic behavior. It will be understood that as these genes are identified or sequenced, specific probes, primers, antibodies and other binding agents can be used to evaluate their expression more specifically using any of the above detection methods.

One assay to examine patterns of expression of genes associated with a geotactic behavior or genes that modulate the mammalian vestibular system, that does not require prior knowledge of their sequence, is mRNA differential display, which is described, for example, in Cirelli et al., *Mol. Brain Res.* 56:293 (1998) and Liang and Pardee, *Mol. Biotech.* 10:261–7 (1998). In such a method, RNA from the animal is reverse-transcribed and amplified by PCR using a particular combination of arbitrary primers. A detectable label, such as an enzyme, biotin, fluorescent dye or a radiolabel, is incorporated into the amplification products. The labeled products are then separated by size, such as on acrylamide gels, and detected by any method appropriate for detecting the label, including autoradiography, phosphoimaging or the like.

Such a method allows concurrent examination of expression of thousands of RNA species. Methods for determining which RNA species correspond to a gene associated with a geotactic behavior or a gene that modulates the mammalian vestibular system, are disclosed herein, for example, comparing gene expression levels in invertebrates that exhibit different geotactic behavior. It can be readily determined whether a particular compound alters this pattern of gene expression, such as by increasing or decreasing the intensity of bands corresponding to genes associated with a geotactic behavior or genes that modulate the mammalian vestibular system.

A further assay to examine patterns of expression of genes is array analysis, in which nucleic acids representative of all or a portion of the genome of an invertebrate or mammal, or representative of all or a portion of expressed genes of an invertebrate or mammal, are attached to a solid support, such as a filter, glass slide, chip or culture plate. Detectably labeled probes, such as cDNA probes, are then prepared from mRNA of an animal, and hybridized to the array to generate a characteristic, reproducible pattern of spots associated with, for example, a geotactic behavior. It can be readily determined whether a particular candidate compound alters this pattern of gene expression, such as by increasing or decreasing the intensity of one or more spots.

Following identification of patterns of gene expression, those skilled in the art can clone the genes, if desired, using standard molecular biology approaches. For example, a band identified by differential display can be eluted from a gel and sequenced, or used to probe a library to identify the corresponding cDNA or genomic DNA. Likewise, a gene from an array can be identified based on its known position on the array, or cloned by PCR or by probing a library.

If desired, any of the expression and activity assays described above can be used in combination, either sequentially or simultaneously. Such assays can also be partially or completely automated, using methods known in the art.

Samples of the invertebrate collected for measuring gene expression levels can include any organ known or suspected of influencing geotaxis. Exemplary organs can be found in the head, neck, legs and antennae, and include, for example, a brain. Samples can be collected from an invertebrate at various occasions, including before and/or after feeding, before and/or after administration of a compound, before, during and/or after a period of high activity level, or before and/or after participating in a measurement of the geotactic behavior of the invertebrate. Typically, samples are collected under the same conditions as the conditions that geotactic measurements are carried out, for example at about the same time of day, about the same amount of time after feeding, about the same environmental conditions, and the like. Samples can also be collected immediately following measurement of geotactic behavior. For example, samples from a first and a second invertebrate can be collected immediately after subjecting the first and second invertebrates to conditions in which the first invertebrate exhibits a geotactic behavior different than a geotactic behavior exhibited by the second invertebrate. In the context of sample collection, "immediately after" refers to a short time period following measurement of geotactic behavior in which little or no manipulation of the invertebrate occurs after geotactic measurement but prior to sample collection. Typically, this time period is less than 5 minutes after measuring geotactic behavior, but the time period can also be less than 10 minutes, less than 20 minutes or less than 30 minutes after measuring geotactic behavior.

Assays to evaluate expression of genes can involve sacrificing the animal at a selected time, homogenizing the entire animal, or a portion containing the brain or sensory organs, and extracting either mRNA or proteins therefrom. Alternatively, such assays can be performed in biopsied tissue from the invertebrate.

Gene expression levels can be measured on two or more occasions or in two or more groups of invertebrates, and compared to each other. For example, gene expression can be measured in a strain that exhibits negative geotaxis and gene expression can be measured in a strain showing "normal" (wild type) geotaxis. Gene expression levels of the two strains can then be compared, and genes expressed at significantly different levels identified. Genes that are expressed at significantly different levels can be termed "differentially expressed" genes. Significantly different levels are levels that vary from each other by an amount greater than a reference amount. A reference amount can be, for example, based on the variability of expression levels between invertebrates that ideally would have identical expression levels (i.e., having identical genetic makeup, age, gender, raised under identical conditions, and the like). In such a situation, a significantly different level can be a difference that is greater than the mean difference observed between expression levels, or greater than the largest expression level difference observed between most or all genes in the ideally identical organisms. Alternatively, significantly different levels can be based on the composite variability of gene expression levels between two or more strains. For example, the mean or median difference between gene expression levels can be determined between a large number of different strains. Any difference in expression that is greater than the mean or median difference can be considered differentially expressed. Other reference levels defining a significant difference can be determined by one of skill in the art according to the desired comparison between two or more invertebrates.

Differential expression can also be determined for invertebrates of the same strain that have been subjected to conditions in which a first group of members of a strain exhibit a geotactic behavior different from the geotactic behavior of a second group of members of the strain. This can be carried out, for example, by administration of a compound, presence of light, time of day, and the like. Differential expression is then determined by measuring expression levels in the two groups and identifying genes expressed at significantly different levels.

A gene that is differentially expressed in two invertebrate groups that exhibit different levels of geotactic behavior can be considered a gene associated with invertebrate geotactic behavior. As used in regard to invertebrate geotactic behavior, "associated" refers to the correlation of a gene with a modulation in invertebrate geotactic behavior. For example, a gene associated with geotactic behavior can be a gene identified as more highly expressed in invertebrates that exhibit negative geotactic behavior than in invertebrates that exhibit positive geotactic behavior, or alternatively, wild type geotactic behavior. The sequence and function of such an associated gene can be previously known or unknown. Exemplary genes associated with invertebrate geotactic behavior are protein tyrosine phosphatase, non-muscle myosin heavy-chain, cysteine proteinase-1, serine/threonine protein kinase, macrophage receptor protein, cryptochrome, prospero, pigment-dispersing-factor, cyclin A and pendulin. Additional exemplary genes associated with invertebrate geotactic behavior are genes that contain a nucleic acid sequence selected from SEQ ID NOS:1–261. Such a gene associated with invertebrate geotactic behavior can be substantially the same as at least one mammalian gene that modulates a mammalian vestibular system. Therefore, genes such as protein tyrosine phosphatase, non-muscle myosin heavy-chain, cysteine proteinase-1, serine/threonine protein kinase, macrophage receptor protein, cryptochrome, prospero, Pigment-dispersing factor, cyclin A and pendulin, and genes that contain a nucleic acid sequence selected from SEQ ID NOS:1–261 can be substantially the same as genes that modulate a mammalian vestibular system.

As used herein, the term "expression profile" refers to any read-out that provides a qualitative or quantitative indication of the expression or activity of a single gene, or of multiple genes. An expression profile can, for example, indicate the expression or activity of one, or of least 2, 5, 10, 20, 50, 100, 265, or more genes. An expression profile can, for example, indicate the expression or activity in a mammal of mammalian homologs of one or more genes associated with invertebrate geotactic behavior. An expression profile can also, for example, indicate the expression or activity in an invertebrate of one more genes associated with invertebrate geotactic behavior. An expression profile can indicate expression or activity of one, a few, many, or all of these genes. An expression profile can also indicate expression or activity of other genes not previously associated with geotactic behavior.

The methods of the invention can be used to identify expression levels of any subset of genes desired to characterize a particular graviperceptive disorder. A subset of genes can be chosen based on functional linkage of the genes including, for example, genes expressing proteins that interact in a signal transduction system or a metabolic system; physical linkage of the genes including, for example, proximity on a chromosome or any other criteria.

An expression profile can be, for example, a quantitative or qualitative measure of expression of mRNA expressed by one or more genes. A variety of methods of detecting or quantitating mRNA expression have been described above in connection with invertebrate screening assays and include, but are not limited to, Northern or dot blot analysis, primer extension, RNase protection assays, differential display, reverse-transcription PCR, competitive PCR, real-time quantitative PCR (TaqMan PCR), and nucleic acid array analysis.

An expression profile can also be a quantitative or qualitative measure of expression of polypeptides encoded by one or more genes. Methods of detecting or quantitating protein expression have been described above in connection with invertebrate screening assays, and include, but are not limited to, immunohistochemistry, immunofluorescence, immunoprecipitation, immunoblot analysis, and various types of ELISA analysis, including ELISA analysis using arrays of polypeptide-specific antibodies bound to solid supports. Additional methods include two-dimensional gel electrophoresis, MALDI-TOF mass spectrometry, and ProteinChip™/SELDI mass spectrometry technology.

An expression profile can also be a direct or indirect measure of the biological activity of polypeptides encoded by one or more genes. A direct measure of the biological activity of a polypeptide can be, for example, a measure of its enzymatic activity, using an assay indicative of such enzymatic activity. An indirect measure of the biological activity of a polypeptide can be its state of modification (e.g. phosphorylation, glycosylation, or proteolytic modification) or localization (e.g. nuclear or cytoplasmic), where the particular modification or localization is indicative of biological activity. A further indirect measure of the biological activity of a polypeptide can be the abundance of a substrate or metabolite of the polypeptide, such as a neurotransmitter, where the abundance of the substrate or metabolite is indicative of the biological activity of the polypeptide. Appropriate assays for measuring enzyme activity, polypeptide modifications, and substrates and metabolites or polypeptides, will depend on the biological activity of the particular polypeptide.

The appropriate method to use in determining an expression profile can be determined by those skilled in the art, and will depend, for example, on the number of genes being profiled; whether the method is performed in vivo or in a sample; the type of sample obtained; whether the assay is performed manually or is automated; the biological activity of the encoded polypeptide; the abundance of the transcript, protein, substrate or metabolite being detected; and the desired sensitivity, reproducibility and speed of the method.

An expression profile can be established in vivo, such as by diagnostic imaging procedures using detectably labeled antibodies or other binding molecules, or from a sample obtained from an individual. As changes in gene expression in the brain are likely to be most relevant to modulation of geotactic behavior or of a mammalian vestibular system, appropriate samples can contain neural tissue, cells derived from neural tissues, or extracellular medium surrounding neural tissues, in which polypeptides to be detected or their metabolites are present. Thus, an appropriate sample for establishing a expression profile in humans can be, for example, cerebrospinal fluid, whereas in laboratory animals an appropriate sample can be, for example, a biopsy of the brain.

However, expression of genes can also be modulated in tissues other than neural tissue, and polypeptides or their metabolites can be secreted into bodily fluids. In particular, in the case of genetic disorders, including familial vestibulopathy, periodic vestibulocerebellar ataxia, Meniere's disease, von Hippel-Lindau syndrome, osteogenesis imperfecta, myokymia with periodic ataxia, Friedreichs ataxia, autosomal dominant nonsyndromic sensorineal deafness 9 or enlarged vestibular aqueduct syndrome, any alteration in gene expression or function can be manifest in every cell in the body that expresses the gene. Alternatively, a genetic disorder can be determined using any cell that contains geomic DNA, by detecting a mutation such as an insertion, deletion or modification of a gene associated with invertebrate geotaxis or a gene that modulates a mammalian vestibular system. An expression profile or presence of a genetic mutation can be determined from any convenient cell or fluid sample from the body, including blood, lymph, urine, breast milk, skin, hair follicles, cervix or cheek. Additionally, cells can readily be obtained using slightly more invasive procedures, such as punch biopsies of the breast or muscle, from the bone marrow or, during surgery, from essentially any organ or tissue of the body.

An expression profile can also be determined from cells in culture. These cells can be immortalized cells from a selected individual invertebrate or mammal, or can be cells from any known established invertebrate or mammalian cell line, such as those available from ATCC (Mannassas, Va.). The expression profile of these cells can be measured, for example, in the absence and presence of a compound. A compound that modulates the expression of an invertebrate gene associated with geotactic behavior or of a mammalian gene substantially the same as an invertebrate gene associated with geotactic behavior can be a compound that modulates the mammalian vestibular system.

The number of different compounds to screen in the methods of the invention can be determined by those skilled in the art depending on the application of the method. For example, a smaller number of candidate compounds would generally be used if the type of compound that is likely to modulate geotactic behavior is known or can be predicted, such as when derivatives of a lead compound are being tested. However, when the type of compound that is likely to modulate geotactic behavior is unknown, it is generally understood that the larger the number of candidate compounds screened, the greater the likelihood of identifying a compound that modulates geotactic behavior. Therefore, the methods of the invention can employ screening individual compounds separately or populations of compounds including small populations and large or diverse populations, to identify a compound that modulates geotactic behavior, and thereby also modulates a mammalian vestibular system.

Methods for producing libraries of candidate compounds to use in the methods of the invention, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art. Libraries containing large numbers of natural and synthetic compounds also can be obtained from a variety of commercial sources.

Genetic methods of identifying new genes associated with invertebrate geotactic behavior that are applicable to a variety of invertebrates are known in the art. For example, the invertebrate can be mutagenized using chemicals, radiation or insertions (e.g. transposons, such as P element mutagenesis), appropriate crosses performed, and the progeny screened for phenotypic differences in geotatic behavior compared with normal controls. The gene can then be identified by a variety of methods including, for example, linkage analysis or rescue of the gene targeted by the inserted element. Genetic methods of identifying genes are described for Drosophila, for example, in Greenspan, *Fly Pushing: The Theory and Practice of Drosophila Genetics,* Cold Spring Harbor Laboratory Press (1997).

In accordance with another embodiment of the invention, a method is provided for identifying a gene that modulates a mammalian vestibular system. The invention is carried out by obtaining a first and a second strain of an invertebrate, subjecting the first and second invertebrate strains to conditions in which said first strain exhibits a geotactic behavior different than a geotactic behavior exhibited by the second strain, measuring gene expression levels in the first and second strains, and identifying one or more genes that are differentially expressed in the first strain relative to the second strain, where a mammalian gene containing substantially the same nucleic acid sequence as the one or more differentially expressed genes modulates the mammalian vestibular system.

There are numerous important diagnostic, therapeutic, and screening applications that arise from identification of novel genes that modulate a mammalian vestibular system, together with knowledge that modulation of expression or activity of such genes that modulate a mammalian vestibular system is an effective method of modulating a mammalian vestibular system. For example, an expression or activity profile of one or many genes that modulate a mammalian vestibular system can be established that is a molecular fingerprint of the sensitivity of a mammalian vestibular system or disorder thereof. Thus, in diagnostic applications, it can readily be determined, by comparing the expression profile of an individual to one or more reference profiles, whether that individual suffers from, or is susceptible to, a particular graviperceptive disorder. Likewise, the sensitivity of a mammalian vestibular system and the effect of medications or medical procedures on the sensitivity of a mammalian vestibular system, can be determined at the molecular level. Such determinations allow for more appropriate determination and use of therapeutics for treating graviperceptive disorders.

In screening applications, identification of genes that modulate a mammalian vestibular system and their role in the sensitivity of a mammalian vestibular system allows novel compounds that modulate a mammalian vestibular system to be identified, lead compounds to be validated, and the molecular effects of these compounds and other known compounds that modulate a mammalian vestibular system to be characterized, by determining the effect of these compounds on an expression profile. For example, the ability of a compound to alter an expression profile of an individual to correspond more closely to a desired sensitivity of a mammalian vestibular system can be determined. Likewise, the ability of a compound, administered to an individual with a particular graviperceptive disorder, to alter the expression profile to correspond more closely to the profile of an unaffected or normal individual can be determined. The compounds so identified, validated or characterized from such assays can be administered to unaffected or normal individuals to enhance or reduce sensitivity of a mammalian vestibular system, as desired, or to individuals having a graviperceptive disorder to treat the disorder or induce more normal mammalian vestibular system sensitivity.

The invention thus provides an isolated nucleic acid having mammalian vestibular system-modulating activity, or fragment thereof, comprising substantially the same nucleic acid sequence as a nucleic acid selected from the group consisting of SEQ ID NOS:1–261.

The isolated nucleic acid molecules of the invention having mammalian vestibular system modulating activity contain sequences substantially the same as sequences from genes associated with invertebrate geotactic behavior identified from mRNA differential display analysis performed in *Drosophila melanogaster* (SEQ ID NOS:1–258). SEQ ID NOS: 1–23 correspond to genes that are downregulated in invertebrates that exhibit negative geotactic behavior relative to invertebrates that exhibit positive geotactic behavior. SEQ ID NOS: 24–258 correspond to genes that are upregulated in invertebrates that exhibit negative geotactic behavior relative to invertebrates that exhibit positive geotactic behavior.

In accordance with the present invention, various nucleic acids selected from SEQ ID NOS:1–261 are homologous to known genes. For example, SEQ ID NO:233 is similar to mouse α-tectorin, which is one of the major noncollagenous components of the tectorial membrane of the inner ear (Legan et al., *J. Biol. Chem.* 272:8791–8801 (1997)). Mutations in human α-tectorin cause a variety of hereditary forms of deafness and inner ear disorders (Verhoeven et al., *Nature Genet.* 19:60–62 (1998); Mustapha et al., *Hum. Molec. Genet.* 8:409–412 (1999)).

The nucleic acid of SEQ ID NO:108 is similar to the protein gp330/megalin/SGP2, which encodes an endocytic receptor for apolipoprotein J/clusterin (Kirszbaum et al., *EMBO J.* 8:711–718 (1989)) and is widely expressed in the brain (Danik et al., *J. Comp. Neurol.* 334:209–227 (1993)). Knockout mice die perinatally with altered development of the brain (Wilnow et al., *Proc. Natl. Acad. Sci. USA* 93:8460–8464 (1996)).

SEQ ID NOS:117 and 250 are similar to two human genes involved in regulating synaptic function which are respectively termed PIN, protein inhibitor of neuronal nitric oxide synthase (Jaffrey and Snyder, *Science* 274:774–777 (1996)), and SV2, synaptic vesicle transporter-2 (Schivell et al., *J. Biol. Chem.* 271:7770–7775 (1996)).

SEQ ID NO:225 is similar to a human gene, APP-binding protein, which can be associated with synaptic mechanisms (Russo et al., *FEBS Lett.* 434:1–7 (1998)).

The SCA2/ataxin-2 gene, which is similar to SEQ ID NO:1, is responsible for a hereditary spinocerebellar ataxia in humans and mice (Imbert et al., *Nature Genet.* 14:285–291 (1997)). It is expressed throughout brain especially in the trochlear nuclei which receive projections from the ear (Pulst et al., *Nature Genet.* 14:269–276 (1996)). The protein contains a consensus cleavage site for an obligatory processing step by apopain, a cysteine protease (Sanpei et al., *Nature Genet.* 14:277–284 (1996)). Thus this gene not only plays a role in a hereditary ataxia, but also requires cleavage by a cysteine-protease. SEQ ID NO:113 corresponds to Cp1, the fly's cysteine protease (Blake et al., *Dev. Biol.* 203:177–188 (1998)). In this context, it may be significant that SEQ ID NO:1 and 113 are reciprocally regulated in the two different geotactic strains.

SEQ ID NO:98 corresponds to protein tyrosine phosphorylase Ptp61F. Protein tyrosine phosphatases regulate the cytoskeleton (Helmke et al, *J. Cell. Sci.* 111:2465–2475 (1998); Guvakova and Surmacz, *Exp. Cell. Res.* 251:244–255 (1999); Boonstra, *FASEB J.* 13:S35–S42 (1999)), which is key in the mechanotransduction events associated with gravity perception (Ingber, *FASEB J.* 13:S3–S15 (1999)). Non-muscle myosin heavy chain zip, corresponding to SEQ ID NO:37, is another regulator of the cytoskeleton (Young et al., *Genes Dev.* 7:29–41 (1993)). Non-muscle myosins have also been identified in hereditary ataxias and inner ear disorders such as Usher Syndrome in humans (Weil et al., *Proc Natl. Acad. Sci. USA* 93:3232–3237 (1995)) and Snell's walzer in mice (Avraham et al., *Hum. Molec. Genet.* 6:1225–1231 (1997)). SEQ ID NO:191 is similar to α-tubulin, which also fits into this cytoskeletal group, as does the actin-binding double-zinc-finger protein, similar to SEQ ID NO:21 (Roof et al., *J. Cell. Biol.* 138:575–588 (1997)).

Also relevant as a source of phenotypic differences between the selected strains is axon guidance, which is influenced by proteins such as protein tyrosine phosphatases (Desai et al., *Cell* 84:599–609 (1996)), actin-binding double zinc-finger proteins (Lundquist et al., *Neuron* 21:385–392 (1998)) and serine/threonine kinases, such as the serine/threonine kinase nemo, similar to SEQ ID NO:256 (Broughton et al., *J. Cell. Biochem.* 60:584–600 (1996); Broughton et al., *J. Cell. Biochem.* 62:484–494 (1996)). SEQ ID NO:174 corresponds to the mfas (midline fasciclin) gene, which is also involved in axon guidance (Hu et al., *J. Neurobiol.* 35:77–93 (1998)).

The croquemort gene in Drosophila, corresponding to SEQ ID NO:8, encodes a macrophage receptor for apoptotic cells (Franc et al., *Immunity* 4:431–443 (1996)) and is involved both in apoptosis and in tissue modeling. Of possible relevance to graviperception and response is the onset of apoptosis in vestibular nuclei after prolonged stimulation (Mitchell et al., *Neurosci. Lett.* 198:153–156 (1995)) and in lymphocytes after space-flight (Lewis et al., *FASEB J.* 12:1007–1018 (1998)).

SEQ ID NO:166 is similar to DnaJ, a highly conserved protein that mediates gravity responsiveness in plants (Sedbrook et al., *Proc. Natl. Acad. Sci. USA* 96:1140–1145 (1999)). DNAJ is also associated with spinocerebellar ataxia in humans (Cummings et al., *Nat. Genet.* 19:148–54 (1998)). Cryptochrome (cry), which corresponds to SEQ ID NO:17, is a flavo-protein highly conserved from flies to plants to humans that is involved in responses to environmental stimuli (Cashmore et al., *Science* 284:760–765 (1999)).

Several sequences corresponding to Drosophila genes with roles in neuronal development or signaling also showed differential expression. These include SEQ ID NO:15, corresponding to the prospero gene, a homeobox gene important for sensory neuron specification (Vaessin et al., *Cell* 67:941–953 (1991), Reddy and Rodrigues, *Development* 126:2083–2092 (1999)) SEQ ID NO:3, and homologous to PROX1 (human homolog NP_002754) corresponding to pigment dispersing factor which is involved in mediating circadian rhythms and interacting with circadian clock components, such as cryptochrome (Park and Hall, *J. Biol. Rhythms* 13:219–228 (1998), Ceriani et al., *Science* 285:553–556 (1999)); SEQ ID NO:128, corresponding to the cell cycle gene cyclin A; and SEQ ID NO:258, corresponding to the Pendulin gene homolog of a nuclear import protein (Torok et al., *J. Cell Biol.* 129:1473–1489 (1995)).

The isolated nucleic acid molecules comprising SEQ ID NO: 1–261 hybridize to mammalian genes, and thus can be used in the diagnostic and screening methods described below. Additionally, the isolated nucleic acid molecules containing sequences substantially the same as one of SEQ ID NOS: 1–261 can be administered in gene therapy methods, including antisense and ribozyme methods, to increase or decrease expression of polypeptides that modulate a mammalian vestibular system. The isolated nucleic acid molecules of the invention can also be used as probes or primers to identify larger cDNAs or genomic DNA, or to identify homologs of the nucleic acid molecules in other species. The isolated nucleic acid molecules can further be expressed to produce polypeptides for use in producing antibodies or for rationally designing inhibitory or stimulatory compounds. Other uses for the isolated nucleic acid molecules of the invention can be determined by those skilled in the art.

As used herein, the term "nucleic acid molecule" refers to both deoxyribonucleic acid (DNA) and ribonucleic acid (RNA) molecules, and can optionally include one or more non-native nucleotides, having, for example, modifications to the base, the sugar, or the phosphate portion, or having a modified phosphodiester linkage. The term nucleic acid molecule includes both single-stranded and double-stranded nucleic acids, representing the sense strand, the anti-sense strand, or both, and includes linear, circular or branched molecules. Exemplary nucleic acid molecules include genomic DNA, cDNA, mRNA and oligonucleotides, corresponding to either the coding or non-coding portion of the molecule, and optionally containing sequences required for expression. A nucleic acid molecule of the invention, if desired, can additionally contain a detectable moiety, such as a radiolabel, a fluorochrome, a ferromagnetic substance, a luminescent tag or a bindably detectable agent such as biotin.

The term "isolated" in reference to a nucleic acid molecule is intended to mean that the molecule is substantially removed or separated from components with which it is naturally associated, or otherwise modified by a human hand, thereby excluding nucleic acid molecules as they exist in nature. An isolated nucleic acid molecule of the invention can be in solution or suspension, or immobilized on a filter, glass slide, chip, culture plate or other solid support. The degree of purification of the nucleic acid molecule, and its physical form, can be determined by those skilled in the art depending on the intended use of the molecule.

The term "comprising" or "containing" in reference to a nucleic acid molecule of the invention, is intended to mean that the nucleic acid molecule can contain additional nucleotide sequences at either the 5' or 3' end of the recited sequence, or branching from an internal position within the recited sequence. The additional nucleotide sequences can, if desired, correspond to sequences that naturally occur within the gene, including intron or exon sequences, promoter sequences, coding sequence, or untranslated regions. Alternatively, the additional nucleotide sequence can correspond to linkers or restriction sites useful in cloning applications; to other regulatory elements such as promoters and polyadenylation sequences that can be useful in gene expression; to epitope tags or fusion proteins useful in protein purification; or the like. Those skilled in the art can determine appropriate sequences flanking the recited nucleotide sequences for a particular application of the method.

The invention also provides isolated oligonucleotides containing at least 15 contiguous nucleotides of a nucleotide sequence referenced as SEQ ID NOS: 1–261, or the antisense strand thereof. The isolated oligonucleotides of the invention are able to specifically hybridize to nucleic acid molecules associated with invertebrate geotaxis or with modulation of a mammalian vestibular system under moderately or highly stringent hybridization conditions and thus can be advantageously used, for example, as probes to detect DNA or RNA of a gene associated with invertebrate geotaxis or with modulation of a mammalian vestibular system in a sample; as sequencing or PCR primers; as antisense reagents to administer to an individual to block translation of RNA in cells; or in other applications known to those skilled in the art in which hybridization to a nucleic acid molecule associated with invertebrate geotaxis or with modulation of a mammalian vestibular system is desirable.

As used herein, the term "oligonucleotide" refers to a nucleic acid molecule that includes at least 15 contiguous nucleotides from the reference nucleotide sequence, can include at least 16, 17, 18, 19, 20 or at least 25 contiguous nucleotides, and often includes at least 30, 40, 50, 60, 70, 80, 90, 100, 125, 150, 175, 200 or more contiguous nucleotides from the reference nucleotide sequence.

As used herein, the term "specifically hybridize" refers to the ability of a nucleic acid molecule to hybridize, under moderately or highly stringent conditions as described above, to a desired nucleic acid molecule, without substantial hybridization under the same conditions with nucleic acid molecules that are not the desired nucleic acid molecule. Those skilled in the art can readily determine whether an oligonucleotide of the invention hybridizes to the recited nucleic acid sequence under moderately or highly stringent conditions by performing a hybridization assay in the presence of other nucleic acid molecules, such as total cellular nucleic acid molecules, and detecting the presence or absence of hybridization to the other nucleic acid molecules.

Depending on the intended use of the oligonucleotides of the invention, those skilled in the art can determine whether it is necessary to use an oligonucleotide that specifically hybridizes to the recited nucleic acid molecules. For example, when there are a large number of potential contaminating nucleic acid molecules in the sample, it may be desirable to use an oligonucleotide that specifically hybridizes to the recited nucleic acid molecules. However, when background hybridization is not considered detrimental, when there are few contaminating molecules, or when the oligonucleotide is being used in conjunction with a second molecule, such as a second primer, an oligonucleotide of the invention can be used that does not specifically hybridize to the recited nucleic acid molecules.

If desired, the oligonucleotide containing at least 15 contiguous nucleotides of a nucleotide sequence referenced as SEQ ID NOS: 1–261 can further be capable of specifically hybridizing with a reference nucleic acid molecule. Such a reference nucleic acid sequence can be any predetermined sequence such as a ployA sequence, a sequence containing a restriction site sequence or a sequence that uniquely identifies the invention oligonucleotice (e.g. a "zip code" sequence).

In one embodiment, the invention provides a primer pair for detecting nucleic acid molecules associated with invertebrate geotaxis or with modulation of a mammalian vestibular system. The primer pair contains two isolated oligonucleotides, each containing at least 15 contiguous nucleotides of one of the nucleotide sequences referenced as SEQ ID NOS: 1–261, with one sequence representing the sense strand, and one sequence representing the anti-sense strand. The primer pair can be used, for example, to amplify nucleic acid molecules associated with invertebrate geotaxis or with modulation of a mammalian vestibular system by RT-PCR or PCR.

The isolated nucleic acid molecules and oligonucleotides of the invention can be produced or isolated by methods known in the art. The method chosen will depend, for example, on the type of nucleic acid molecule one intends to isolate. Those skilled in the art, based on knowledge of the nucleotide sequences disclosed herein, can readily isolate the nucleic acid molecules of the invention as genomic DNA, or desired introns, exons or regulatory sequences therefrom; as full-length cDNA or desired fragments therefrom; or as full-length mRNA or desired fragments therefrom, by methods known in the art.

One useful method for producing an isolated nucleic acid molecule of the invention involves amplification of the nucleic acid molecule using the polymerase chain reaction (PCR) and oligonucleotide primers specific for the desired nucleic acid molecule and, optionally, purification of the resulting product by gel electrophoresis. Either PCR or reverse-transcription PCR (RT-PCR) can be used to produce a nucleic acid molecule having any desired nucleotide boundaries. Desired modifications to the nucleic acid sequence can also be introduced by choosing an appropriate primer with one or more additions, deletions or substitutions. Such nucleic acid molecules can be amplified exponentially starting from as little as a single gene or mRNA copy, from any cell, tissue or species of interest.

A further method of producing an isolated nucleic acid molecule of the invention is by screening a library, such as a genomic library, cDNA library or expression library, with a detectable agent. Such libraries are commercially available or can be produced from any desired tissue, cell, or species of interest using methods known in the art. For example, a cDNA or genomic library can be screened by hybridization with a detectably labeled nucleic acid molecule having a nucleotide sequence disclosed herein. Additionally, an expression library can be screened with an antibody raised against a polypeptide encoded by a nucleic acid disclosed herein. The library clones containing nucleic acid molecules of the invention can be isolated from other clones by methods known in the art and, if desired, fragments therefrom can be isolated by restriction enzyme digestion and gel electrophoresis.

Furthermore, isolated nucleic acid molecules and oligonucleotides of the invention can be produced by synthetic means. For example, a single strand of a nucleic acid molecule can be chemically synthesized in one piece, or in several pieces, by automated synthesis methods known in the art. The complementary strand can likewise be synthesized in one or more pieces, and a double-stranded molecule made by annealing the complementary strands. Direct synthesis is particularly advantageous for producing relatively short molecules, such as oligonucleotide probes and primers, and nucleic acid molecules containing modified nucleotides or linkages.

In one embodiment, the isolated nucleic acid molecules or oligonucleotides of the invention are attached to a solid support, such as a chip, filter, glass slide or culture plate, by either covalent or non-covalent methods. Methods of attaching nucleic acid molecules to a solid support, and the uses of nucleic acids in this format in a variety of assays, including manual and automated hybridization assays, are well known in the art. A solid support format is particularly appropriate for automated diagnostic or screening methods, where simultaneous hybridization to a large number of genes associated with invertebrate geotaxis or with modulation of a mammalian vestibular system is desired, or when a large number of samples are being handled.

In another embodiment, the invention provides kits containing two or more isolated nucleic acid molecules or oligonucleotides. At least one nucleic acid molecule of the kit contains a nucleotide sequence selected from the group consisting of SEQ ID NOS: 1–261, or modification thereof or at least 15 contiguous nucleotides of a nucleic acid sequence referenced as SEQ ID NO: 1–261. An exemplary kit is a solid support containing an array of isolated nucleic acid molecules or oligonucleotides of the invention, including, for example, at least 3, 5, 10, 20, 30, 40, 50, 75, 100, 265 or more isolated nucleic acid molecules or oligonucleotides.

A further exemplary kit contains one or more PCR primer pairs, or two or more hybridization probes, which optionally can be labeled with a detectable moiety for detection of nucleic acid molecules. The kits of the invention can additionally contain instructions for use of the molecules for diagnostic purposes in a clinical setting, or for drug screening purposes in a laboratory setting.

If desired, the kits containing two or more isolated nucleic acid molecules or oligonucleotides can contain nucleic acid molecules corresponding to genes that are upregulated in invertebrates exhibiting negative geotactic behavior, or are downregulated in invertebrates exhibiting negative geotactic behavior. Additionally, the kits containing two or more isolated nucleic acid molecules or oligonucleotides can contain nucleic acid molecules corresponding to sequences identified from Drosophila screens or other invertebrate screens, from rat screens, from screens in other mammals, or any combination thereof.

The invention also provides a vector containing an isolated nucleic acid molecule associated with invertebrate geotaxis or with modulation of a mammalian vestibular system. The vectors of the invention are useful for subcloning and amplifying an isolated nucleic acid molecule, for recombinantly expressing a polypeptide, and in gene therapy applications, described further below. A vector of the invention can include a variety of elements useful for cloning and/or expression of nucleic acid molecules associated with invertebrate geotaxis or with modulation of a mammalian vestibular system, such as enhancer sequences and promoter sequences from a viral, bacterial, invertebrate or mammalian gene, which provide for constitutive, inducible or cell-specific RNA transcription; transcription termination and RNA processing signals, including polyadenylation signals, which provide for stability of a transcribed mRNA sequence; an origin of replication, which allows for proper episomal replication; selectable marker genes, such as a neomycin or hygromycin resistance gene, useful for selecting stable or transient transfectants in mammalian cells, or an ampicillan resistance gene, useful for selecting transformants in prokaryotic cells; and versatile multiple cloning sites for inserting nucleic acid molecules of interest.

A variety of cloning and expression vectors are commercially available, and include, for example, viral vectors such as a bacteriophage, baculovirus, adenovirus, adeno-associated virus, herpes simplex virus and retrovirus; cosmids or plasmids; bacterial artificial chromosome vectors (BACs) and yeast artificial chromosome vectors (YACs). Such vectors and their uses are well known in the art.

The invention also provides host cells that contain a vector containing a nucleic acid molecule of the invention. Exemplary host cells include mammalian primary cells; established mammalian cell lines, such as COS, CHO, HeLa, NIH3T3, HEK 293-T and PC12 cells; amphibian cells, such as Xenopus embryos and oocytes; and other vertebrate cells. Exemplary host cells also include insect cells (e.g. Drosophila), yeast cells (e.g. *S. cerevisiae, S. pombe,* or *Pichia pastoris*) and prokaryotic cells (e.g. *E. coli*). Further exemplary host cells are cells publicly available through sources such as ATCC (Manassas, Va.). Methods of introducing a vector of the invention into such host cells are well known in the art.

The methods of isolating, cloning and expressing nucleic acid molecules of the invention referred to herein are routine in the art and are described in detail, for example, in Sambrook et al., *Molecular Cloning: A Laboratory Manual,* Cold Spring Harbor Laboratory, New York (1992) and in Ansubel et al., *Current Protocols in Molecular Biology,* John Wiley and Sons, Baltimore, Md. (2000), which are incorporated herein by reference.

The invention further provides transgenic non-human animals that are capable of expressing wild-type nucleic acids, dominant-negative nucleic acids, antisense nucleic acids, or ribozymes that target nucleic acids, where the nucleic acids are associated with invertebrate geotaxis or with modulation of a mammalian vestibular system. Such animals have correspondingly altered expression of polypeptides associated with invertebrate geotaxis or with modulation of a mammalian vestibular system, and can thus be used to elucidate or confirm the function of such polypeptides, or in whole-animal assays to determine or validate the physiological effect of compounds that potentially modulate a mammalian vestibular system. The transgene may additionally comprise an inducible promoter and/or a tissue specific regulatory element, so that expression can be induced or restricted to specific cell types. Exemplary transgenic non-human animals expressing nucleic acids and nucleic acids that alter gene expression include mouse and Drosophila. Methods of producing transgenic animals are well known in the art.

The invention also provides an isolated polypeptide having mammalian vestibular system-modulating activity, or fragment thereof, containing substantially the same amino acid sequence as an amino acid sequence encoded by a nucleic acid sequence selected from the group consisting of SEQ ID NOS:1–261. Isolated polypeptides of the invention can be used in a variety of applications. For example, isolated polypeptides can be used to generate specific antibodies, or in screening or validation methods where it is desired to identify or characterize compounds that alter the activity of polypeptides that with modulate a mammalian vestibular system.

The isolated polypeptides of the invention can be prepared by methods known in the art, including biochemical, recombinant and synthetic methods. For example, invention polypeptides can be purified by routine biochemical methods from neural cells or other cells that express abundant amounts of the polypeptide. An invention polypeptide having any desired boundaries can also be produced by recombinant methods. Recombinant methods involve expressing a nucleic acid molecule encoding the desired polypeptide in a host cell or cell extract, and isolating the recombinant polypeptide, such as by routine biochemical purification methods described above. To facilitate identification and purification of the recombinant polypeptide, it is often desirable to insert or add, in-frame with the coding sequence, nucleic acid sequences that encode epitope tags or other binding sequences, or sequences that direct secretion of the polypeptide. Methods for producing and expressing recombinant polypeptides in vitro and in prokaryotic and eukaryotic host cells are well known in the art. Furthermore, invention polypeptides can be produced by chemical synthesis. If desired, such as to optimize their functional activity, stability or bioavailability, such molecules can be modified to include D-stereoisomers, non-naturally occurring amino acids, and amino acid analogs and mimetics.

Also provided are antibodies that specifically bind polypeptides encoded by the nucleic acid molecules of the invention. Such antibodies can be used, for example, in diagnostic assays such as ELISA assays to detect or quantitate the expression of polypeptides of the invention; to purify polypeptides of the invention; or as therapeutic compounds to selectively target polypeptide of the invention. Such antibodies, if desired, can be bound to a solid support, such as a chip, filter, glass slide or culture plate.

As used herein, the term "antibody" is used in its broadest sense to include polyclonal and monoclonal antibodies, as well as antigen binding fragments of such antibodies. An antibody of the invention is characterized by having specific binding activity for a polypeptide associated with invertebrate geotaxis or with modulation of a mammalian vestibular system or fragment thereof of at least about $1 \times 10^5$ $M^{-1}$. Thus, Fab, F(ab')$_2$, Fd and Fv fragments of a polypeptide-specific antibody of the invention, which retain specific binding activity for the polypeptide associated with invertebrate geotaxis or with modulation of a mammalian vestibular system, are included within the definition of an antibody. Methods of preparing polyclonal or monoclonal antibodies against polypeptides are well known in the art (see, for example, Harlow and Lane, *Antibodies: A Laboratory Manual,* Cold Spring Harbor Laboratory Press (1988)).

In addition, the term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be produced or obtained by methods known in the art, including constructing the antibodies using solid phase peptide synthesis, recombinant production, or screening combinatorial libraries consisting of variable heavy chains and variable light chains.

The invention provides diagnostic methods based on the newly identified and characterized genes described herein. In one embodiment, the invention provides a method of diagnosing a graviperceptive disorder in an individual. The method consists of determining an expression profile of the individual, and comparing that profile to a reference profile indicative of the graviperceptive disorder. Correspondence between the profile of the individual and the reference profile indicates that the individual has the graviperceptive disorder. In one embodiment, at least one of the genes profiled is a gene containing a nucleic acid sequence substantially the same as one of SEQ ID NOS: 1–261. Typically, at least one of the genes profiled is selected from the group consisting of α-tectorin, gp 390, PIN, SV2, PROX1, actin-binding double-zinc-finger protein, SCA2 and APP-binding protein.

The methods of diagnosing graviperceptive disorders have numerous applications. For example, a variety of different types of graviperceptive disorders are known, many of which are extremely common in a given population, some of which are more rare. Appropriate diagnosis of a graviperceptive disorder will allow more effective treatments: using currently available mammalian vestibular system modulating compounds or methods; using compounds identified from the screens described herein; using the therapeutic methods described herein; or any combination of these treatments. Likewise, the methods of diagnosing graviperceptive disorders are applicable to monitoring the course of therapy for the disorder, such that appropriate modifications can be made if needed.

Furthermore, the methods of diagnosing graviperceptive disorders are applicable to screening for graviperceptive disorders among the general population, or among populations in whom graviperception influences the safety of the individual or the general population (e.g. transportation workers, individual operating heavy machinery, and the like). Additional useful applications of the diagnostic methods of the invention can be determined by those skilled in the art.

Appropriate laboratory animal models of human graviperceptive disorders of interest are known in the art or can readily be developed by transgenic and knockout methods that alter expression or activity of genes associated with invertebrate geotaxis or with modulation of a mammalian vestibular system, or by pharmacological, surgical or environmental manipulation.

The diagnostic methods of the invention can also advantageously be used to characterize previously unrecognized graviperceptive disorders, or to newly categorize graviperceptive disorders, based on characteristic patterns of expression or activity of genes associated with invertebrate geotaxis or modulation of a mammalian vestibular system. Such newly characterized or categorized disorders are also encompassed by the term "graviperceptive disorder." The diagnostic methods of the invention can also be advantageously used to identify the specific genes most closely associated with, and thus likely to play a causative role, in particular graviperceptive disorders. Such genes are targets for modulation by gene therapy methods or by selective targeting of the encoded product with therapeutic compounds.

In a further embodiment of the diagnostic methods of the invention, there is also provided a method of determining sensitivity of the vestibular system in an individual. The method consists of determining an expression profile of the individual, and comparing that profile to a reference profile indicative of a predetermined sensitivity of a vestibular system. Correspondence between the profile of the individual and the reference profile indicates that the individual exhibits the predetermined sensitivity of a vestibular system. At least one of the vigilance genes profiled is a gene containing a nucleic acid sequence substantially the same as one of SEQ ID NOS: 1–261.

Those skilled in the art understand that the methods described above for diagnosing graviperceptive disorders and determining sensitivity of a vestibular system can readily be applied to methods of screening for novel mammalian vestibular system-modulating compounds; to methods of validating the efficacy of mammalian vestibular system-modulating compounds identified by other methods, such as by the invertebrate screening methods described above; to methods of determining effective dose, time and route of administration of known mammalian vestibular system-modulating compounds; to methods of determining the effects of mammalian vestibular system-modulating compounds on homeostatic regulation of graviperception; to methods of determining the molecular mechanisms of action of known mammalian vestibular system-modulating compounds; and the like. Such methods can be performed in laboratory animals, such as mice, rats, rabbits, dogs, cats, pigs or primates, in veterinary animals, or in humans.

Thus, in one embodiment, the invention provides a method of determining the efficacy of a compound in treating a graviperceptive disorder. The method consists of administering a compound to an individual having a graviperceptive disorder, and determining an effect of the compound on the expression profile of the individual. A compound that modulates the expression profile of the individual to correspond to an unaffected or normal profile indicates that the compound is effective in treating the graviperceptive disorder. At least one of the vigilance genes profiled is a gene containing a nucleic acid sequence substantially the same as one of SEQ ID NOS: 1–261.

As used herein, the term "treating" is intended to include preventing, ameliorating, curing, and reducing the severity of the graviperceptive disorder or symptoms associated with a graviperceptive disorder. Those skilled in the art understand that any degree of reduction in severity of a graviperceptive disorder can improve the health or quality of life of the individual. The effect of the therapy can be determined by those skilled in the art, by comparison to baseline values for symptoms or clinical or diagnostic markers associated with the disorder.

In another embodiment, the invention provides a method of determining the efficacy of a compound in modulating a mammalian vestibular system. The method consists of administering the compound to an individual, and determining an effect of the compound on the expression profile of the individual. A compound that modulates the expression profile indicates that the compound modulates a mammalian vestibular system. At least one of the genes profiled is a gene containing a nucleic acid sequence substantially the same as one of SEQ ID NOS: 1–261.

The genes to profile can be determined by those skilled in the art, depending on the type of mammalian vestibular system-modulating compound it is desired to identify or characterize. For example, it may be advantageous to examine the effect of a compound primarily on single genes such as α-tectorin, gp330, PIN, SV2, PROX1, actin-binding double-zinc-finger protein, SCA2 and APP-binding protein; or only primarily on a gene substantially the same as an invertebrate gene whose upregulated expression or activity corresponds to negative invertebrate geotaxis; or only primarily on a gene substantially the same as an invertebrate gene whose downregulated expression or activity corresponds to negative invertebrate geotaxis.

The compounds so identified that alter an expression profile can, for example, increase or, decrease graviperception as described above in relation to invertebrate screening methods. The effect of these compounds on graviperception can be corroborated, or further evaluated, in either invertebrates or mammals. Compounds that beneficially modulate the sensitivity of a mammalian vestibular system can be administered as therapeutics to humans and veterinary animals.

Once genes associated with graviperceptive disorders are identified, the expression or activity of such genes in humans or veterinary animals can be selectively targeted in order to prevent or treat the graviperceptive disorder. The diagnostic, screening and validation methods of the invention are useful in determining appropriate genes to target and appropriate therapeutic compounds to use for a particular indication. Additional genes associated with invertebrate geotaxis or with modulation of a mammalian vestibular system can be identified by the methods described herein or by other methods, including differential display, arrays, and other forms of expression or activity analysis in invertebrates and mammals; genetic methods, such as by randomly or specifically targeting genes in model organisms such as Drosophila or mouse, or by mapping genes associated with graviperceptive disorders or from screens for genes associated with other behaviors or molecular pathways that are subsequently determined to be associated with graviperception.

Thus, in one embodiment, the invention provides a method of treating a graviperceptive disorder in an individual. The method consists of administering to an individual having a graviperceptive disorder a compound that modulates the expression profile of the individual to correspond to a normal expression profile. At least one of the genes profiled is a gene containing a nucleic acid sequence substantially the same as one of SEQ ID NOS: 1–261. In one embodiment, the modulated gene is a gene containing a nucleic acid sequence substantially the same as one of SEQ ID NOS: 1–261.

In a further embodiment, the invention provides a method of modulating the vestibular system in a mammal. The method consists of administering to an individual a compound that modulates the activity or expression of a gene that modulates a mammalian vestibular system. In one embodiment, the modulated gene is a gene containing a nucleic acid sequence substantially the same as one of SEQ ID NOS: 1–261.

The therapeutic methods of the invention involve determining the effect of the compound on an expression profile. Thus, the therapeutic methods of the invention are not intended to encompass administration of mammaliam vestibular system-modulating drugs which inherently may modulate expression or activity of one or more genes associated with invertebrate geotaxis or with modulation of a mammalian vestibular system, in the absence of a determination that such drugs predictably modulate invertebrate geotaxis or predictably modulate expression profile of one or more genes associated with invertebrate geotaxis or with modulation of a mammalian vestibular system. The effect of the compound on the expression profile of a particular individual to whom the compound is administered need not be determined, however, if the effect of the compound on expression profile in other individuals has previously been established, and such effect on expression profile can be shown to be reproducible across individuals. Of course, it is understood that the expression profile of the individual can, if desired, be determined prior to administration of the compound, and/or monitored during the course of therapy, using modifications of the diagnostic methods described herein.

A variety of compounds can be used to modulate the expression profile in individuals having a graviperceptive disorder or in whom modulation of sensitivity of the vestibular system is desired. Compounds can be determined or designed to alter gene expression or activity by a variety of mechanisms, such as by directly or indirectly increasing or decreasing the expression of a gene. For example, a compound can directly interact with a gene promoter; can interact with transcription factors that regulate gene expression; can bind to or cleave a gene transcript (e.g. antisense oligonucleotides or ribozymes); can alter half-life of the transcript; or can itself be an expressible gene associated with invertebrate geotaxis or with modulation of a mammalian vestibular system. A compound can also act by increasing or decreasing activity of one or more encoded polypeptides. For example, the compound can specifically bind to a polypeptide and alter its activity or half-life; can bind to a substrate or modulator of a polypeptide; or can be a polypeptide associated with invertebrate geotaxis or with modulation of a mammalian vestibular system or active portion thereof.

The type of compound to be used can be determined by those skilled in the art, and will depend, for example, on factors such as the severity of the disorder; the time period over which treatment of the disorder is desired; the cellular location of the molecule to be targeted; whether the compound is administered in a clinical setting or by the individual; or whether an individual is presently experiencing symptoms of a graviperceptive disorder or anticipates experiencing symptoms of a graviperceptive disorder.

Compounds can be formulated in pharmaceutical compositions in such a manner to ensure proper distribution in vivo. For example, the blood-brain barrier (BBB) excludes many highly hydrophilic compounds. To ensure that the compounds of the invention cross the BBB, they can be formulated, for example, in liposomes, or chemically derivatized. Methods of introduction of a compound of the invention include, but are not limited to, intradermal, intramuscular, intraperitoneal, intravenous, subcutaneous, oral, intranasal, intraspinal and intracerebral routes. A compound can also appropriately be introduced by rechargable or biodegradable polymeric devices, which provide for the slow release or controlled delivery of drugs. Appropriate formulations, routes of administration and dose of a compound can be determined by those skilled in the art.

If desired, the compounds of the invention can include gene therapy molecules that modulate expression or activity of a gene associated with invertebrate geotaxis or with modulation of a mammalian vestibular system, including genes encoding polypeptides or active or inhibitory portions thereof; genes expressing antisense molecules that block expression of genes associated with invertebrate geotaxis or with modulation of a mammalian vestibular system; and genes expressing ribozymes that target genes associated with invertebrate geotaxis or with modulation of a mammalian vestibular system. Such methods are advantageous in treating graviperceptive disorders or for providing long-lasting prophylactic effects to an individual. Methods of introducing and expressing genes in animals, including humans, are well known in the art.

Gene therapy methods can be performed ex vivo, wherein cells (e.g. hematopoietic cells, including stem cells) are removed from the body, engineered to express a polypeptide associated with invertebrate geotaxis or with modulation of a mammalian vestibular system, and returned to the body. Gene therapy methods can also be performed in situ, in which an expressible nucleic acid molecule is placed directly into an appropriate tissue, such as the brain or CNS, by a direct route such as injection or implantation during surgery. Gene therapy methods can also be performed in vivo, wherein the expressible nucleic acid molecule is administered systemically, such as intravenously. Appropriate vectors for gene therapy can be determined by those skilled in the art for a particular application of the method, and include, but are not limited to, retroviral vectors (e.g. replication-defective MuLV, HTLV, and HIV vectors); adenoviral vectors; adeno-associated viral vectors; herpes simplex viral vectors; and non-viral vectors. Appropriate formulations for delivery of nucleic acids can also be determined by those skilled in the art, and include, for example, liposomes; polycationic agents; naked DNA; and DNA associated with or conjugated to targeting molecules (e.g. antibodies, ligands, lectins, fusogenic peptides, or HIV tat peptide). Gene therapy methods, including considerations for choice of appropriate vectors, promoters, formulations and routes of delivery, are reviewed, for example, in Anderson, Nature 392:25–30 (1998).

It is understood that modifications which do not substantially affect the activity of the various embodiments of this invention are also included within the definition of the invention provided herein. Accordingly, the following examples are intended to illustrate but not limit the present invention.

EXAMPLE I

This example shows the measurement of geotaxis scores for strains of Drosophila that have varying geotactic behaviors. This example also describes preparation of sub-lines of a Drosophila strain that have homozygous sets of chromosomes.

Established Drosophila lines that had been subjected to divergent behavioral selection for positive or negative geotaxis, called 'hi' for the negatively geotactic line, 'lo' for the positively geotactic line, and 'hi5' for the most recently re-selected 'hi' line were obtained from Dr. Jerry Hirsch, Department of Psychology, University of Illinois at Champagne-Urbana and are described in Erlenmeyer-Kimling et al., J. Comp. Physiol. Psychol. 55: 722–731, (1962); Ricker and Hirsch, Behav. Genet. 18: 13–25, (1988), and Stoltenberg and Hirsch, J. Comp. Psychol. 110:252–259 (1996).

These strains and a standard laboratory wild-type strain (Canton-S, obtained from the Bloomington Drosophila Stock Center, Indiana University at Bloomington) were then tested in a geotaxis maze constructed according to the design of Hirsch (J. Comp. Physiol. Psychol. 52:304–308 (1959)) as modified by McMillan and McGuire (Behav. Genet. 22:557–573 (1992)), shown in FIG. 1.

The geotaxis maze was fashioned from plexiglass and the maze chambers were hollowed out as semi-circular depressions in the slab, such that when the two slabs were bolted together a circular tube was formed in maze. This design thus made it possible to observe the entire time course of the assay. Additionally, this maze is easy to clean and standardize.

For each strain, a geotaxis score was determined. In separate measurements, twenty to thirty flies of each strain were loaded into a starting tube on the left (see FIG. 1). The maze was set upright in front of a light source on the right, and, after turning on the light, each strain was scored according to the distribution of the flies in the nine collecting tubes on the right. A perfect score for positive geotaxis would be 1, for negative geotaxis, 9, and for an even distribution, 5. The geotaxis measurements were repeated 3–5 times for each strain (see Table 1).

TABLE 1

| Strain | N (20–30 flies in each) | Geotaxis score | SEM |
|---|---|---|---|
| Canton-S | 3 | 5.53 | 0.61 |
| lo | 5 | 4.19 | 0.26 |
| hi | 5 | 7.25 | 0.59 |
| hi5 | 5 | 8.37 | 0.17 |

A control assay was carried out in which the maze was placed flat on the table so that all nine collecting tubes were chosen by the flies at the same level with respect to gravity. The control assay yielded a random distribution through the maze. Thus, the flies have retained their selected phenotype, even to the extent of showing a lower variance for the recently re-selected 'hi5' strain than for the older 'hi' strain (Stoltenberg and Hirsch, supra, (1996)).

In order to decrease the genetic heterogeneity of the 'hi5' line, sub-lines were derived that were homozygous for a set of chromosomes from the 'hi5' strain. This was carried out by mating flies of the 'hi5' strain to flies carrying multiple balancer chromosomes according to the method of Greenspan, Fly Pushing: The Theory and Practice of Drosophila Genetics, Cold Spring Harbor Laboratory Press, Cold Spring Harbor, N.Y., 1997.

TABLE 2

| Strain | N (15–25 flies in each) | Geotaxis score |
|---|---|---|
| hi5-3a1 | 2 | 8.45 |
| hi5-3d | 2 | 8.19 |
| hi5-1a | 2 | 7.03 |

These results show that the essential phenotype of the selected lines can be captured in homozygous sets of chromosomes and thus can be characterized as a combination of homozygous alleles. The sub-line 'hi5-1a' falls short of the score for the original strain, demonstrating that it contains a subset of the relevant alleles.

EXAMPLE II

This example demonstrates the dramatic change in geotaxis score that occurs in mutant Drosophila that do not synthesize histamine or wild type Drosophila treated with a histamine receptor antagonist.

Several mutants were tested for alterations in geotactic behavior as judged by being consistently more positive or negative than the unselected wild-type strain Canton-S. A mutant with abnormally positive geotactic behavior was the $Hdc^{P211}$ allele of Histidine decarboxylase, an enzyme in the histamine biosynthetic pathway (Burg et al., EMBO J. 12:911–919 (1993)), as shown in Table 3. Those whose geotactic behavior was similar to Canton-S included $for^s$, a hypomorphic allele of the dg2 locus encoding cGMP-dependent protein kinase (Osborne et al., Science 277:834–836 (1997)), and Appl, a null allele of the gene encoding the Drosophila homolog of the amyloid precursor protein (Luo et al., Neuron 9:595–605 (1992)).

TABLE 3

| Strain | N (15–25 flies in each) | Geotaxis score |
|---|---|---|
| Hdc$^{P211}$/Hdc$^{P211}$ | 2 | 7.51 |
| Canton-S | 3 | 5.53 |
| Canton-S fed for 2 hr on 20 mg/ml hydroxyzine | 1 | 8.50 |
| for$^s$/ for$^s$ | 2 | 5.35 |
| Appl/Appl | 2 | 5.20 |

Extreme negative geotaxis is induced after interference with histamine, in both the histidine decarboxylase mutant Hdc$^{P211}$, which fails to make histamine, and in Canton-S flies fed with the histamine receptor antagonist, hydroxyzine. The geotactic behavior of the Hdc$^{P211}$ mutant and hydroxyzine-treated wild type is particularly significant given the long established role of anti-histamines in the treatment of motion sickness and vertigo (Brand and Perry, *Pharmac. Rev.*, 18:895–924, 1966) and the ability of histamine to modulate activity in the vestibular system (Yabe et al., *Exp. Brain Res.*, 93: 249–58, 1993).

These results show that an anti-histamine compound that modulates vestibular system activity can also change fly geotaxis, and that a genetic mutation effecting histamine synthesis can result in geotaxis similar to that caused by the anti-histamine compound.

EXAMPLE III

This example demonstrates the identification of nucleic acids that are differently expressed in Drosophila that exhibit negative geotaxis in comparison to Drosophila that exhibit positive geotaxis.

To examine the molecular basis for the behavioral difference in response to gravity between fly strains, differences in mRNA levels between the 'hi5' and 'lo' strains were measured. The assays were carried out using microarrays containing 8,800 unique cDNA EST (expressed sequence tag) clones from the Berkeley Drosophila Genome Project and made available through Research Genetics (Huntsville, Ala.). This number of cDNA clones represents approximately 65% of the Drosophila genome (Rubin et al., *Science* 287:2204–2215 (2000)). The microarrays consist of DNA samples printed in a high-density array onto treated glass slides which can then be hybridized with reverse-transcribed, single-stranded cDNA that has incorporated a fluorescently labeled nucleotide, Cy3- or Cy5-conjugated dTTP (Schena et al., *Science* 270:467–470 (1995); Shalon et al., *Genome Res.* 6:639–645 (1996)).

A previous control experiment has determined biological variability by taking animals from different vials and preparing polyA+ RNA independently from each (White et al., *Science*, 286:2179–2184, 1999). In this previous control experiment, no gene was differentially expressed more than 2.5-fold; so 2.5–3-fold was set as the cut-off criterion for a significant difference in expression in the present experiment. Threshold was arbitrarily set at signal intensity of 1000. The value of 1000 is typically between 2 and 3 standard deviations above the mean background value in microarray experiments.

In reciprocal experiments, PolyA+ RNA from ~500 isolated heads (mostly brain) from 3–5 day old flies of the 'hi5' strain and the 'lo' strain was fluorescently labeled with Cy3 and Cy5, respectively or Cy5 and Cy3, respectively, according to the method of Schena et al. supra and Shalon et al. supra. In each of the reciprocal experiments, microarrays were simultaneously hybridized with 5 μg fluorescently labeled RNA from both strains. Averaged results from the reciprocal experiments indicated that 25 genes exhibited a 2.5-fold or greater differential in 'lo' relative to 'hi5' (SEQ ID NOS:1–23), and 240 genes exhibited a three-fold or greater differential in the 'hi5' strain relative to the 'lo' strain (SEQ ID NOS:24–258).

The majority of differentially expressed sequences were unidentified ESTs. Some corresponded to previously cloned Drosophila genes and others were homologous to genes cloned in other species. Examples of genes with particular significance for human gravity response are shown in Table 4 below, and a complete list of all differentially expressed genes is included in the sequence listing.

These results demonstrate that at least 265 genes can be differently expressed in flies that demonstrate negative geotaxis relative to flies that demonstrate positive geotaxis.

TABLE 4

| Expression difference | Drosophila genes | Mammalian genes | Other organisms |
|---|---|---|---|
| up in 'hi5' vs. 'lo' | protein tyrosine phosphatase (Ptp61F) | tectorin-α (mouse) | DnaJ |
| up in 'hi5' vs. 'lo' | non-muscle myosin heavy chain (zip) | glycoprotein 330/megalin (human) | α-tubulin |
| up in 'hi5' vs. 'lo' | cysteine-proteinase-1 (Cp1) | protein inhibitor of nNOS/PIN (rat) | |
| up in 'hi5' vs. 'lo' | serine/threonine protein kinase (nemo) | synaptic vesicle transporter/SV2 (rat) | |
| down in 'hi5' vs. 'lo' | croquemort (macrophage receptor protein) | actin-binding double-zinc-finger protein (human) | hemocyte protease-2 |
| down in 'hi5' vs. 'lo' | cryptochrome (cry) | spinocerebellar ataxia type 2, SCA2 (human) | |

EXAMPLE IV

This example demonstrates determination of the effects of gene expression levels on geotaxis behavior in flies by artificially manipulating expression levels of genes previously identified to differ in expression level between 'hi5' and 'lo' strains.

Expression of prospero (SEQ ID NO:15) and Pigment-dispersing-factor (SEQ ID NO:3), were both found to be reduced in the negatively geotactic 'hi5' strain compared to the 'lo' strain. Flies containing pros[17] which is a mutant allele of prospero (SEQ ID NO:15), which has been described in Doe et al., Cell 65:451–464 (1991), were obtained from the Drosophila Stock center at Indiana University at Bloomington. Flies containing Pdf[01] (SEQ ID NO:261) which is a mutant allele of Pigment-dispersing-factor (SEQ ID NO:3) and flies containing a transgenic chromosome bearing a copy of the Pigment-dispersing-factor (SEQ ID NO:3) locus were obtained from Dr. Paul Taghert at Washington University, St. Louis and are described in Renn et al., Cell 99:791–802 (1999). Flies containing pros[17] and Pdf[01] (SEQ ID NO:261) were tested for alterations in geotactic behavior as described in Example I. Results of geotaxis assays are shown in Table 5.

TABLE 5

| Strain | N (20–30 Flies in each) | Geotaxis score | SEM |
|---|---|---|---|
| Canton-S | 4 | 6.023 | 0.240152 |
| Canton-S/Pdf$^{01}$ | 10 | 6.471 | 0.066273 |
| Canton-S/pros$^{17}$ | 12 | 5.901 | 0.064508 |
| Pdf$^{01}$/Pdf$^{01}$ | 6 | 7.908 | 0.197879 |
| Pdf$^{01}$/Pdf$^{01}$/Dp | 6 | 7.413 | 0.138604 |
| Pdf$^{01}$/Pdf$^{01}$/Dp/Dp | 4 | 6.793 | 0.27834 |
| Pdf$^{01}$/pros$^{17}$ | 8 | 8.178 | 0.108689 |

As shown in Table 5, geotaxis score increases as the copy number of the mutant Pdf$^{01}$ (SEQ ID NO:261) allele increases. Geotaxis score decreases as the copy number of the normal Pigment-dispersing-factor (SEQ ID NO:3) increases. Further, as shown in Table 5, flies bearing both the Pdf$^{01}$ (SEQ ID NO:261) and pros$^{17}$ alleles have an increased geotaxis score compared to flies bearing a single Pdf$^{01}$ (SEQ ID NO:261) allele or single pros$^{17}$ allele.

These results demonstrate that artificially manipulating the expression levels of Pdf, can convert a normal, geotactically neutral, lab strain (Canton-S) into a negatively geotactic strain. This example also demonstrates that titration of the gene dosage of Pdf titrates the geotactic phenotype such that lower amounts of gene product produce increasingly negative geotactic behavior. These results further demonstrate that prospero and Pigment-dispersing-factor operate in a network influencing geotactic behavior in invertebrates.

Throughout this application various publications have been referenced. The disclosure of these publications in their entireties are hereby incorporated by reference in this application in order to more fully describe the state of the art to which this invention pertains.

I claim:

1. A method of identifying a compound that modulates a mammalian vestibular system comprising:
   (a) administering a test compound to an invertebrate in an effective amount and for a time period that modulates geotactic behavior of said invertebrate, and
   (b) measuring a geotactic behavior of said invertebrate, wherein the measurement is selective for a perception of a force vector, a compound that modulates the geotactic behavior of said invertebrate is characterized as a compound that modulates a mammalian vestibular system.

2. The method of claim 1, wherein said compound increases the geotactic behavior of said invertebrate.

3. The method of claim 2, wherein said compound increases or decreases the sensitivity of a mammalian vestibular system.

4. The method of claim 3, wherein said compound decreases graviperception in a mammal.

5. The method of claim 1, wherein said compound decreases the geotactic behavior of said invertebrate.

6. The method of claim 5, wherein said compound increases or decreases the sensitivity of a mammalian vestibular system.

7. The method of claim 6, wherein said compound decreases graviperception in a mammal.

8. The method of claim 1, wherein said compound decreases the symptoms of a graviperceptive disorder in a mammalian subject.

9. The method of claim 8, wherein said graviperceptive disorder is selected from the group consisting of motion sickness, vertigo, labyrinthitis, Meniere's disease, acoustic neuroma, multiple sclerosis, syphilis, trauma, infection of the middle ear, exposure to ototoxic agents and epilepsy.

10. The method of claim 1, wherein said invertebrate is an insect.

11. The method of claim 1, wherein said invertebrate is *Drosophila melanogaster*.

12. The method of claim 1, wherein said mammal is human.

* * * * *

SEQUENCE LISTING

<160> NUMBER OF SEQ ID NOS: 261

<210> SEQ ID NO 1
<211> LENGTH: 502
<212> TYPE: DNA
<213> ORGANISM: Drosophila

<400> SEQUENCE: 1

```
acaaattgaa aacccgcgac aaccgaaagc gccacaaaga gctctttct  ctcccggtcc      60 ggttgactaa aaaaaaatta aaagatacaa ctccaacgat aacagcctaa ggcccactaa     120
caacaaggct ggtgcaggag gcgggaacgg aggcgcagca gtgcgtccgt cggcgcaggg     180
cgtctacaac aacacgtttt tcatgcactc ggccacggcg ctggtgggca gcgttgtgga     240
ggtgcgcctg cggtcgggca atatctacga gggcgtattc cgcacattct cgggcaactt     300
tgacatcgca ctggagctac cggcgtgcat taagtccaag aatctgccgg aggagggcaa     360
ggtgccaaaa cacattatat tcccggccga cactgtggtg accatcatgg ccaatgactt     420
tgactcgcaa tacgccaccg taggcgcttt tcaaacggat ggcgccattt ctgacaagtg     480
caacggtgcg cgttctgact ag                                             502
```

<210> SEQ ID NO 2
<211> LENGTH: 634
<212> TYPE: DNA
<213> ORGANISM: Drosophila

<400> SEQUENCE: 2

```
attcaatcga ttgcttgtgc atttagcaaa tcaaagccac aacaaccaaa ccagaatcaa      60
tatgaagttc ttctcagtcg tcaccgtctt tgtgttcggt ctgctggctc tggccaacgc     120
tgttcccctg tcgcccgatc caggaaatgt ggtaatcaac ggggactgca aatactgcaa     180
tgtgcacggt ggaaagtagg aaagtaggaa agtaggaaag tactcgcctt aatttcgaag     240
atgggccaaa acttacctca aatccaaagc accatattta tactctcact cttgtactaa     300
aatgaaaact agtagtaaaa aatacatcgc caattacaaa taaataaaa  aaaaaaaaa      360 aaaaaaaact cgagactagt tccctcaatg agagtcaagt caaaaccaag tcaagtcact     420
aggccagtca gtcagtcagt cagccaacca gtcagtcaga cagtcagtcg tttggttctt     480
aatgccattg cctatgttta acatacattt tcaaacagat taacaattga gtaattaact     540
```

```
ttaagaaagt tgtttgcatt tcgctgtgta tttcaaattg aagaatggaa tagtttattg    600
taagaacaag tcgcctcaaa actaaaaaga aacc                                 634
```

<210> SEQ ID NO 3
<211> LENGTH: 1080
<212> TYPE: DNA
<213> ORGANISM: Drosophila

<400> SEQUENCE: 3

```
actgcataac caaatatttg cgtggctcca actcgactcc gtatttgcct gggctgaagg     60
accgccgctg cctgcggatg acatgtattg gtcctgcgga tgacaccgat actgacgctc    120
ttgggttgcg tggtcgggcg gtctcccgca gtgggttatc cagtccaggt tgctatataa    180
gtcgaggatg cgccaaccga cgttcattcg caagtctcct gctgcaggtg ttccgtgctc    240
agttcctgct cctggccacc ctttcagctc ctcggactaa tggctcgctt cacgtacctt    300
gtcgcccttg tgcttctggc catttgctgc cagtggggat actgcggcgc catggccatg    360
ccggatgagg agcgctatgt gcgcaaggag tacaatcggg atctcctcga ctggttcaac    420
aacgtgggcg tgggacagtt cagtcccggc caagtggcca ctctctgtcg ctatccgctg    480
atcctcgaga actccttggg cccatccgtg cccatcagga agcgcaactc ggagctaatc    540
aactccttgt tgagtctgcc aagaacatg aacgatgcgg gcaagtaaga acggaaaatg     600
ctgaaggatt aggacgaccc accactgaaa gttggaacct ggacaagaac ttattatttg    660
atgttatcgt atgattttt ggtgcgtcga aggaaatga aaatccgcag ataaaagccg      720
gtgtagtcat ctaatagaga gaaaagaccg tataactttt gttgctttaa acctaaatag    780
aaaaatatac aagtagccta ttgtagaaat gttgtatatt attaggctta ctgctgaaat    840
aaacgttttc tggattgttt cgacttgaaa tctggtacaa caactagtca ggattttat    900 tcttaatcac agatactaaa gctagttaaa gatattggtt atccccgtaa agggcgaacc    960
aatgaaagcc aaaggtgttc tcaaagtaga ttttgttcaa tgctacgatt ggaataaata  1020
gatgtttcta gcttagaata gcagccccat ttcgtttatt gacttcattt attatgctat  1080
```

<210> SEQ ID NO 4
<211> LENGTH: 647
<212> TYPE: DNA
<213> ORGANISM: Drosophila

<400> SEQUENCE: 4

```
gcaggtgcag gtggcaggtt gcaggttgca ggtgaagcaa tccgtgcggc aatcgcgata     60
agtgcaccaa caaatggttg gcaaatctgg agcactcgca aagtccacaa acaatgtgca    120
aaaggtcgcg cgagttgggg acttacaagt ttaataaagt catatacacg cactcccgat    180
ggccaagatg ccaatacaca taattgtaag gatgtgtgta tatgtatgaa ttgtaggggc    240
cacggctcag tctgactttt ccggcagaat gaccgacgaa cgaaatgtga ccgaaataca    300
ccatcaattt ttaatatcta tttaacattt caatcagcgg aatcgcagcg ctcgccgctc    360
gattcgtatg caaattttaa ttaatattta attttcatt cattgtattt ctgtgttttg     420
cctgcaattt taatgacgca tcgcggagcg ctaataaaat taaatggccc aaacaacaca    480
ggaccgatcc actcacacag atattccggc actcacacac tctcacacag gcacactcga    540
ccgaatgagt tgtgctttag cttccttttt cgtttggctt gcttgcttgt tttgtgggtt    600
ccacgcgcta cggtcttctg ctcaacgata cgcgaaaatc caatccg                  647
```

<210> SEQ ID NO 5
<211> LENGTH: 686
<212> TYPE: DNA
<213> ORGANISM: Drosophila

<400> SEQUENCE: 5

| | | | | | |
|---|---|---|---|---|---|
| gaacacaagc | atcctaatcg | tggccctggt | ggcacttttc | gccattaccg | aggcacttcc | 60 |
| cacaacagga | cccattcgcg | tccgtcgcca | ggtgctcgga | ggttccttaa | cctccaatcc | 120 |
| cgctggtggg | gctgatgctc | gtttggatct | gaccaagggc | attggcaatc | ccaaccacaa | 180 |
| tgtggtgggt | caggttttcg | ccgccggaaa | cactcaaagt | ggtccagtca | caactggcgg | 240 |
| aactttggcc | tacaacaagt | gagttctcta | aactaagaga | ttactagagg | atatattaac | 300 |
| tctattctat | tcatttttga | agtgctggtc | atggtgcctc | tttgaccaaa | acacacacgc | 360 |
| ccggagtgaa | ggatgttttc | cagcaggagg | cccatgccaa | tttattcaac | aatggcagac | 420 |
| acaatctgga | tgccaaggtc | tttgcttcgc | aaaataaact | ggccaatggt | ttcgagttcc | 480 |
| agcggaatgg | agctggtctg | gattactccc | acatcaacgg | acatggtgct | tccttgacgc | 540 |
| acagcaactt | cccaggaatc | ggccagcaac | tcggcctgga | tggacgtgct | aatctctggt | 600 |
| catcgcccaa | tcgtgctact | accttggatc | tcacgggatc | ggcgagcaag | tggacgagtg | 660 |
| gaccgtttgc | caaccagaag | ccaaac | | | | 686 |

<210> SEQ ID NO 6
<211> LENGTH: 619
<212> TYPE: DNA
<213> ORGANISM: Drosophila

<400> SEQUENCE: 6

| | | | | | |
|---|---|---|---|---|---|
| tttctatata | tttctccagc | ggtgaggtca | acgttgtgcg | cttgggtgaa | ctggagttcg | 60 |
| ataccgacac | ggatgacgcg | gaacccgagg | actttggcgt | gctcgtctg | aaggcacatc | 120 |
| ctggcttcga | gaacccgcaa | ctctacaatg | acattggcat | agttcagctg | gatcgcgagg | 180 |
| tcaagttcaa | taggtacaag | catcctgcct | gcctgcccct | cgacgacggc | gagcagcacg | 240 |
| agtccttcat | cgccatcggc | tggggccaga | agaagtttgc | ccagaaggag | tcaaagaagc | 300 |
| tgttgaaggt | gcagctccag | ggctataagg | accgatgtgt | cagcagtgtg | gatgcgaatg | 360 |
| atgagttgcc | caatggctac | gagcccaaga | gccagctgtg | catcggatca | agggacaaca | 420 |
| aggacacatg | caacggcgac | tctggcggtc | cagtgctggc | ctatcacaag | gatctcgcct | 480 |
| gcatgtacca | cgtaatgggc | atcacctcag | ccggcatcac | ctgctccacg | cccgacattc | 540 |
| caagtgccta | cacgcgggtg | cactacttcc | tcaactggat | caagggcgaa | ctggccaagc | 600 |
| agacgcaagg | aatgaaatg | | | | | 619 |

<210> SEQ ID NO 7
<211> LENGTH: 567
<212> TYPE: DNA
<213> ORGANISM: Drosophila

<400> SEQUENCE: 7

| | | | | | |
|---|---|---|---|---|---|
| ggaaatcaat | aaaagcagcg | cacaaattaa | gcacctttg | cgcttttccc | cctgccagtt | 60 |
| agttgcttta | ctttgctttt | ccaggccgca | acgtgaattt | aataggatta | tgcggcaagg | 120 |
| atgggccgac | ggggagaaag | gagacttatg | caaagtcctt | ccactctgcg | ccactgcaat | 180 |
| cctgaaaacc | ctttgcgccg | ccacacaata | tgaacctaat | tgtcgtgatt | ttcgcctgat | 240 |
| ggcaactttt | cacactccca | ttcacagaat | tgtgggtcgt | ggaggacctc | cgcccaagtt | 300 |

```
ttgttatgcc aaaaacaaac ttcggcaatt tatgataatt caacgtcagc tgggacagtt      360
cagggaagta catagagggg aaccgtcatc acggcaaact caactcgact ccgctcaagt      420
catctgaact cagctgaact gacagctggc tagcaaaggc cttggaatat gctcgcagca      480
cacattaaac ttatttctca cccccactcg aagcgccact aatgcccggc atcgtgtaca      540
gatttactcc gaagcagacg tacagca                                         567
```

<210> SEQ ID NO 8
<211> LENGTH: 652
<212> TYPE: DNA
<213> ORGANISM: Drosophila

<400> SEQUENCE: 8

```
cgaagataaa gaaataaatt gtttaatcca atttagccca gcaaactgca agtttgcagt       60
ttatctttct ctgcttgccc tcttcggcaa cgcgaaagtg ccttttttt agttggatag       120 cagctttcag atcaattcca aaggcgcttc ccacgcttga gtttagctgt aaaagtaata      180
agaagggaag tctgacaatt tgaatccctt tcgtacggta cttttgcgat tccaggcacc      240
aaaggtaaag ggactaagcg atcatcgaag cgggaagtcc cagaaaaata aatttactcc      300
gaactatggc ataataaatg tcaaggccaa agcaaaacaa taacagagcc atcagaagct      360
aatgctaaaa gacgtagttg tgtgtgagat aaaagatgca actaactgcc tagggctgga      420
ttattcccac cttggctatt ccttaaaagc gtgaaccttt ggaatcctac gtatccacca      480
tgtgctgcaa gtgctgcggg gaaactcaac gaaaggtctg ggtcttcggc ttgggatcgg      540
ttttcctttt gctgggaata ctaatcgtgg tcttctggcc gggtattgca gataaccttg      600
tagaggatgg ccttaccctc aagcccggga ctgatgccta tgaaagctgg ct             652
```

<210> SEQ ID NO 9
<211> LENGTH: 565
<212> TYPE: DNA
<213> ORGANISM: Drosophila

<400> SEQUENCE: 9

```
ccgtagttct cccttcgttt tcgtcccctt ttccccgcaa acaggtaaac aaaaaatcta       60
ctgtgcgaaa tgcacgaaga agtgctccgg cgaggtgctc cgcgtggcgg acaaccactt      120
ccacaaggcc tgcttccagt gctgccagtg caagaagtcc ctggccaccg gcggattctt      180
cacaaaggac aacgcctact attgcatacc ggactatcag cggctgtacg gcaccaagtg      240
cgcaaattgc cagcagtatg tggagggcga ggtggtcagc accatgggca agacctatca      300
ccagaagtgc ttcacctgct ccaagtgcaa gcagcccttc aagtcgggca gtaaggtgac      360
caacaccgga aaggaggtgc tttgcgagca atgcgtcacg ggtgctccag tgtcgcccag      420
tcgccaggcg acgggtggag gcgtctcctc gccagctcct ccggcggaga gtccgacgag      480
agccactgcc caccagcagc acggcagtgt gatctctcat aaggcgcacc tcaaggagga      540
ctacgatccc aatgactgtg ccggc                                            565
```

<210> SEQ ID NO 10
<211> LENGTH: 685
<212> TYPE: DNA
<213> ORGANISM: Drosophila

<400> SEQUENCE: 10

```
atcgtcgaga tgccgagatt gttgagcaag tgcagcgtgt ttgccctttg ggcgcctgca       60
```

-continued

| | |
|---|---|
| gtgctcctct ttgttttggc ttgcgaaaag ggattagccg gagctcagac cttaatcgaa | 120 |
| actataacca ccactactcc agcgtcctct ggcggctact gtgcggctgc actttgtgag | 180 |
| ctgtacaatg gaacgcattt ggtgcatgtg ccgcataccg catgtggcaa caatggcagc | 240 |
| ttttcacccg cctgtggacc ggaacccaag ctcctggaaa tgagcgagag gcgacgtcag | 300 |
| ctcctgttgg acatgcacaa tttggccaga tcgaagatcg ccagcggaaa tctggatggc | 360 |
| tatagaagcg ccgcacatat gccgcttctg cgttgggata ccgaactgga gcaaatggcc | 420 |
| gccttgcatg ccaaacgctg ccaattcgcg cacgacaagt gccggaatac accgcgtttc | 480 |
| aagtttagtg gtcaaaatat tggttacttt tggattggaa gagagttcaa atcgcattcg | 540 |
| cgacgcatga aatccttcgt gatcaactgg ttccgcgaac atcaggatgc caatcagagc | 600 |
| ttcatcgata gatatcatcc acatccgcaa ggcaagaaaa ttggtcactt cacattactt | 660 |
| ggttcggatc gagttaatcg cgtcg | 685 |

<210> SEQ ID NO 11
<211> LENGTH: 522
<212> TYPE: DNA
<213> ORGANISM: Drosophila

<400> SEQUENCE: 11

| | |
|---|---|
| cttaagttct cctcgtcggg atcggccaag tgcgcaagca ggaagtagca caagtgttct | 60 |
| gtacaaatag gaaactttaa agcttaatcg gacttcttca actactaata tactaataga | 120 |
| cagcaaccta ccctgctccc cttccacggc gtagaaaagc ggtgggtttc cgcccctcgc | 180 |
| ctcggatgca ttgatgacat cccgcttatg tgcacggttc tttagcaacg tcttgttcag | 240 |
| ctccagccgt tcgcaggcac gatcgtagta cttggcgaag cccttctcgt cccactcatt | 300 |
| cggattcgct gcctccaggg ttctcctgta caccgtttcc cccagctcgc gctcgtctat | 360 |
| actatcaagg attgcctcga caacaaggaa ctggttattg cgcactgcca ggtgcaaaac | 420 |
| tgtataacca tcatcgttgg ttagcagaag actgttcaaa tcgattctgc gcaacagcag | 480 |
| cctaatggac tctatattta tatggtttat caccgccaga tg | 522 |

<210> SEQ ID NO 12
<211> LENGTH: 636
<212> TYPE: DNA
<213> ORGANISM: Drosophila

<400> SEQUENCE: 12

| | |
|---|---|
| agactgtcga gtatgggtca agaacccatt gcatgacgct ctatgcacga tgcacataac | 60 |
| acttgtggcc ctcatgggtg cactgtgcct ggaatgtgcc tacgacttgg atgatgccgt | 120 |
| aaacaactac tacgttgttg gactcctgaa cgtcaacaat cacggagcga acacatgcca | 180 |
| acgatggagc cctagatgtc cagaacttca aagagttaa cggcgcaagg tgtgagctc | 240 |
| gcaggccact ttgaccgccg ccgaggcaac cgttaaggag aacttggagt gggctacggc | 300 |
| caagctgggc gttttccgca gctatctggc caactatcgt agtggaagcg ccatggtcaa | 360 |
| cgccttcagc gccatcagcc ttttgatggt ggccctggtc accatgctgc gtaactaagc | 420 |
| agggattagc tcctactgga gtcaggtgcg atcgagtcac gagtgctcct taggccataa | 480 |
| agtatttgta cgcaagagca cccaataaag taacacctt tttaaaatt tcaacagtga | 540 |
| acatcttgtg cagaacacag accaaatatt ccaaaaatgt ctctcgttgg caagaagtac | 600 |
| aagctggaca agtccgagaa cttcgatgag tacctg | 636 |

<210> SEQ ID NO 13
<211> LENGTH: 628
<212> TYPE: DNA
<213> ORGANISM: Drosophila

<400> SEQUENCE: 13

| | | | | | |
|---|---|---|---|---|---|
| agcgtccatt | gcgactgatc | atatccaccg | ttccgaaaga | tttgtgataa | ccacttgata | 60 |
| accaaccagc | cagtctagtg | tctaataaag | ttgttattga | atttgcccat | ttacaagatc | 120 |
| cataaacaag | ctgtcaagta | atctttcaat | catgggtttg | acgcgcgtgc | tggtgaagga | 180 |
| tggcggtttc | ggcacccaga | tgaccgtcca | tgtgggtgac | tctgtggatg | gggatccgct | 240 |
| atggagtgcc | cgcttcaatg | ccaccaatcc | ggcggccatt | atcagcaccc | acctggactt | 300 |
| tttgcagaat | ggtgccgata | tcattttgac | caacacctac | cagtccagtg | tcgatggtta | 360 |
| catggagtac | ctggagctgg | acgaggagca | gagcatcgag | ctgataaaga | cacggtccg | 420 |
| cctggcccac | atcgccaagg | aacgctatct | caccgagtgc | tatcaggcgc | actgtcggtg | 480 |
| caggagggat | acctttgat | cattgcctcc | attggaccct | tggggccca | cctgcacgat | 540 |
| ggctccgagt | acaccggtag | ctatgccgac | tttgtgccgg | ccaaggagat | tacggactgg | 600 |
| catcgcgtga | ggatcgaagc | gtgcttgg | | | | 628 |

<210> SEQ ID NO 14
<211> LENGTH: 566
<212> TYPE: DNA
<213> ORGANISM: Drosophila

<400> SEQUENCE: 14

| | | | | | |
|---|---|---|---|---|---|
| tcgtggatac | aacccacag | ttaaattcaa | tgtacttact | atttttgatt | ttagttatcc | 60 |
| tatcagcctt | ttaacctggc | cttaaaactt | tatcagtttc | acaaagatc | gttgaaaaga | 120 |
| cttacatgag | tcgagccaat | gatttagaca | aaatctaata | gaaactacac | caaaaaggta | 180 |
| caagtgcgat | tacatcgcta | aaaggtacat | acatggaatg | gctaaactta | accatatcca | 240 |
| taaacaatat | tagagatgct | tttgataaat | cctataaatg | tattaataaa | accgcgctga | 300 |
| tcaaaactca | gacgcttatt | tttcacataa | aggtattgat | aacacaatac | aacacattac | 360 |
| aaaacctaat | agtaacaaac | aaaagcaaac | tcactgaaga | acataaagtc | caatgcttca | 420 |
| aagttctcag | ttcatttggt | aaaagactac | ataataccag | cgttagacac | agtattataa | 480 |
| tagaagtccc | aacagaacta | accaaaatag | cagaattcga | cgaaagccag | ttaagagact | 540 |
| tggacgagtc | gcagccgtta | gaagat | | | | 566 |

<210> SEQ ID NO 15
<211> LENGTH: 562
<212> TYPE: DNA
<213> ORGANISM: Drosophila

<400> SEQUENCE: 15

| | | | | | |
|---|---|---|---|---|---|
| cccgcttcgt | ccaccaacgg | cggctgttca | gcaagcaagc | ggactccgtg | accgcggctg | 60 |
| ccgagcagct | gaacaaggac | ctgctgctgg | cttcgcagat | cctcgaccgg | aagtcaccgc | 120 |
| gcaccaaggt | ggcggacagg | ccccagaacg | gacccacgcc | cgcaacacaa | tcagcggctg | 180 |
| ccatgttcca | ggcgcccaaa | acgccacagg | gcatgaatcc | ggtggccgcc | gccgcgctct | 240 |
| acaactcgat | gaccggaccc | ttctgcctgc | cgcccgatca | gcagcagcag | caacagaccg | 300 |
| cccagcagca | acagtccgcc | cagcagcagc | agcagagctc | gcagcagaca | caacagcagc | 360 |
| tggagcagaa | cgaggccctc | agcctggtgg | tgacaccaaa | gaagaagcgc | cataaggtga | 420 |

-continued

| ccgatacgcg catcacgccg cgcaccgtca gccgcattct tgcccaggat ggcgttgtgc | 480 |
| cgtccaccgg aggcccaccg tcaacccccc agcagcagca acagcagcag caacagcaac | 540 |
| agcagcagca acaacagcag ca | 562 |

<210> SEQ ID NO 16
<211> LENGTH: 631
<212> TYPE: DNA
<213> ORGANISM: Drosophila

<400> SEQUENCE: 16

| ccagacaggt aaaaaaatta atagatgatg aatagttga accatcaatg tctgaatata | 60 |
| atagtccatt acttttggtt ccaaagaaac cacttccgaa ttccacggaa aaagatggc | 120 |
| gattagcagt tgactatcgt caaataaata agaaactatt atcagacaaa tttccacttc | 180 |
| caagaataga agatattctt gatcaattag aagagcaaa gtattttca tgtctcgacc | 240 |
| taatgtctgg attccaccag atagaactag aaaaaaggta tagagatata acgtcatttt | 300 |
| caacagccaa tggctcatat cgcttcacgc gattaccata cggactgaaa gtagcaccaa | 360 |
| actccttcca acgtatgatg acacttgcat tttctggtct tgaaccatcg caagcatttc | 420 |
| tatatatgga tgacttagta gtaataggtt gttcagaaaa acatatgctc aaaaatttga | 480 |
| ctaacgtatt cgagctatgt agacgacata atttgaaact acatccaggg aaatgttctt | 540 |
| tctttatgaa agaagtaaca tatttgggtc acaaatgtac cgataaaggt atactcccag | 600 |
| atgacaccaa atatgaagtt atagaaaaat a | 631 |

<210> SEQ ID NO 17
<211> LENGTH: 581
<212> TYPE: DNA
<213> ORGANISM: Drosophila

<400> SEQUENCE: 17

| cgagcgaatc gtgagtgcgg aaaaaagaaa atcttttcat cagctggaaa actgttcttc | 60 |
| ccgatcaaaa ctgggattcg ggagatttt gaagcccaaa agcagggaac tcctcactga | 120 |
| tggccacgcg agggcgaat gtgatttggt ttcgccatgg attgcgcctc catgataatc | 180 |
| ccgctctatt ggccgccctc gccgataagg atcagggtat agccctaatt cccgttttca | 240 |
| tattcgatgg agagagtgca ggtaccaaga atgtgggtta caatcggatg cgtttcctcc | 300 |
| tggactcgtt gcaggacatc gatgatcagc tacaggcggc aactgatgga cgtggacgcc | 360 |
| tcctggtctt cgagggcgaa ccggcttata tcttccgccg gctacatgag caagtgcgtc | 420 |
| tgcacaggat ttgcatagag caggactgcg agccaatttg gaatgagcgc gatgaaagca | 480 |
| tccgttctct atgtcgggag ctgaatatcg actttgtcga aaggtatca cacacgcttt | 540 |
| gggatccgca attggtgatt gagaccaatg gtggcattcc a | 581 |

<210> SEQ ID NO 18
<211> LENGTH: 229
<212> TYPE: DNA
<213> ORGANISM: Drosophila

<400> SEQUENCE: 18

| attacctacg agacagtgga ttcctgccat ggatccagac ccctgattgt ggacggcacg | 60 |
| ccggcggaac ccaaggaatt tccatttgcc gctcgcctcg gccatcggaa aactaacaat | 120 |
| gaaataaaat ggttctgtgg cggcaccttg ataagcaatc gcctggtgct cacagcggct | 180 |
| cactgctttt tttccgaaca cggtgaggtc aacgttgtgc gcttgggtg | 229 |

<210> SEQ ID NO 19
<211> LENGTH: 632
<212> TYPE: DNA
<213> ORGANISM: Drosophila

<400> SEQUENCE: 19

```
cgagcgaatc gtgagtgcgg aaaaaagaaa atctttttcat cagctggaaa actgttcttc      60
ccgatcaaaa ctgggattcg ggagattttt gaagcccaaa agcagggaac tcctcactga     120
tggccacgcg aggggcgaat gtgatttcgt ttcgccatgg attgcgcctc catgataatc     180
ccgctctatt ggccgccctc gccgataagg atcagggtat agccctaatt ccgttttca      240
tattcgatgg agagagtgca ggtaccaaga atgtgggtta caatcggatg cgtttcctcc     300
tggactcgtt gcaggacatc gatgatcagc tacaggcggc aactgatgga cgtggacgcc     360
tcctggtctt cgagggcgaa ccggcttata tcttccgccg gctacatgag caagtgcgtc     420
tgcacaggat ttgcatagag caggactgcg agccaatttg gaatgagcgc gatgaaagca     480
tccgttctct atgtcgggag ctgaatatcg actttgtcga gaaggtatca cacacgcttt     540
gggatccgca attggtgatt gagaccaatg gtggcattcc accgctgacc taccaaatgt     600
tcctgcacac ggtgcatatt attgggcttc ca                                    632
```

<210> SEQ ID NO 20
<211> LENGTH: 617
<212> TYPE: DNA
<213> ORGANISM: Drosophila

<400> SEQUENCE: 20

```
cgaatcgtga gtgcggaaaa agaaaatct tttcatcagc tggaaaactg ttcttcccga       60
tcaaaactgg gattcgggag attttttgaag cccaaaagca gggaactcct cactgatggc    120
cacgcgaggg gcgaatgtga tttggtttcg ccatggattg cgcctccatg ataatcccgc     180
tctattggcc gccctcgccg ataaggatca gggtatagcc ctaattcccg ttttcatatt     240
cgatggagag agtgcaggta ccaagaatgt gggttacaat cggatgcgtt tcctcctgga     300
ctcgttgcag gacatcgatg atcagctaca ggcggcaact gatggacgtg gacgcctcct    360
ggtcttcgag ggcgaaccgg cttatatctt ccgccggcta catgagcaag tgcgtctgca    420
caggatttgc atagagcagg actgcgagcc aatttggaat gagcgcgatg aaagcatccg    480
ttctctatgt cgggagctga atatcgactt tgtcgagaag gtatcacaca cgctttggga    540
tccgcaattg gtgattgaga ccaatggtgg cattccaccg ctgacctacc aaatgttcct    600
gcacacggtg catatta                                                    617
```

<210> SEQ ID NO 21
<211> LENGTH: 573
<212> TYPE: DNA
<213> ORGANISM: Drosophila

<400> SEQUENCE: 21

```
aaggcctgcc aggcggtgct caatggggag tacatgggca agacgcggt gccctactgc       60
gagaagtgct accagaaggg attcggggtg aagtgtgcct actgcagtcg cttcattagc     120
ggcaaggtgc tccaggcggg cgacaaccac cacttccatc cgacctgtgc ccgctgcaca     180
aagtgcggcg atcccttcgg cgacggcgag gagatgtacc tgcagggcag tgccatctgg     240
catccgcgat gcggtccggg tccctccgag tccggcataa ttttgaacgg cggcggaggc     300
```

| | |
|---|---|
| acttcgtcgg tggtcggagg tgcctccaat ggcaacttca cagacactga atgcgaccgg | 360 |
| atgagctcca gtgcccttag cgagatgtac atccgctcca gaactccgag ctttaatggt | 420 |
| tcactttatt cctctagccg caagcactac cgaacggtga gttcgggtct gatactccgg | 480 |
| gagtacggac gacccaatgc cgaggacatc tcgcgcatct acacctacag ctatctgacg | 540 |
| gatgcgccgc actatctgcg caagccgatc gat | 573 |

<210> SEQ ID NO 22
<211> LENGTH: 614
<212> TYPE: DNA
<213> ORGANISM: Drosophila

<400> SEQUENCE: 22

| | |
|---|---|
| tgcaagccgg gctttgttat cgcacaaatt ttatgtaaac aaaagaaaac ttcgatctgc | 60 |
| tccatgatca ccttagcccc tctgatcgtc ctagtcctcg cttgcctggg aaacacggcc | 120 |
| agcgagaagt tgcccaacat tctgctgatc ctgtccgaca tcaggatgt ggagctgcgc | 180 |
| ggtatgtttc ccatggagca tacgatcgaa atgctgggtt tcggtggcgc cctgttccac | 240 |
| aacgcctaca cgccctcgcc catctgctgt ccggcgagga cgagtctgct gacgggcatg | 300 |
| tatgcgcaca atcacggcac ccggaacaat tccgtaagtg gtggatgcta cggaccgcac | 360 |
| tggcggcgtg ccctggagcc ccgggctttg ccatacatct tgcagcagca cggatacaac | 420 |
| accttctttg gcgggaagta cttgaatcag tactggggcg ctggggatgt gccaaagggt | 480 |
| tggaataact tctacggcct tcacgggaac tctagatact ataactacac actgcgcgaa | 540 |
| aataccggca acgtgcacta cgagtcgacc tacctatccg atctgctaag agatcgcgcc | 600 |
| gctgactttc taag | 614 |

<210> SEQ ID NO 23
<211> LENGTH: 613
<212> TYPE: DNA
<213> ORGANISM: Drosophila

<400> SEQUENCE: 23

| | |
|---|---|
| caaaaatgat gcagtgcagc cgaatgacga cgacgttgaa gatgacgaac cttctgctag | 60 |
| cagtggcctg cgccgccgtg ctgatgggat cggcgacggc ggacgaggag gaggggtcca | 120 |
| tgaccgtgga cgaggtggtg gagctgatcg agccctttgg cgacgcctgc acgccaaagc | 180 |
| cgtcgaggga gaacatcgtc gagatggtgc tgaacaagga ggacgccaag cacgagacca | 240 |
| agtgcttccg ccactgcatg ctggagcagt tcgagctgat gcccgaggat cagttgcagt | 300 |
| ataacgagga caagacggtc gatatgatca acatgatgtt cccggatcgc gaggacgacg | 360 |
| gcaggcgcat cgtcaagacc tgcaacgagg agctaaaggc cgagcaggac aagtgcgagg | 420 |
| cagcccacgg gatcgctatg tgcatgctgc gcgagatgcc ctcttcgggc ttcaagattc | 480 |
| ccgagatcaa ggaatgaggc catggagctg ctcgctggcc caccattgca tgttctccct | 540 |
| ccctttttt tttgttagtg attcagttcg atttaattac caaagctaga gaacttggag | 600 |
| tggtttccca aac | 613 |

<210> SEQ ID NO 24
<211> LENGTH: 631
<212> TYPE: DNA
<213> ORGANISM: Drosophila

<400> SEQUENCE: 24

| | |
|---|---|
| ccgagtggcg tgcgaaatac taattctagt ccgaggttcg cgatcgaacc cttgaaaata | 60 |

-continued

```
ggaagaatgt tgccccgcg agtggctgtt ctcctggtgg cctgtgtgtc cttggcctcg      120
gcaggaactc ggcaactgtc tgtggatgtc cagccgccgg cgacgctcgc caccgagcta     180
aatgaatacc gcctggccga gcacatcacg ccggttaact acaacattac gctgcgtccc     240
tatttgctgg agaccgatgg caacaagagg ttcaccttcg atggcgaggt ttggatcgag     300
gtgatttcca accagaccac caacgacatc tatctgcact cgaaaaacct cacatattcg     360
gtcagggaat actggcaaaa gccaaccacc gaagtggcca atcctacggt catccaaatt     420
agtgccacca atacaacgaa ctatgatacg gatattgtaa agctgacggc gtcaactgct     480
ttgaccgcca atacgacata tatactgcat ttcgtgtaca ccggtctgat ggaggacgat     540
atgcacggtt tctatcgcag ctcctatgtg acgataaca atgttaccaa gtggctggga     600
tccacccaat tccaaaccca tcacgctcgt c                                    631
```

<210> SEQ ID NO 25
<211> LENGTH: 635
<212> TYPE: DNA
<213> ORGANISM: Drosophila
<220> FEATURE:
<221> NAME/KEY: misc_feature
<222> LOCATION: (1)...(635)
<223> OTHER INFORMATION: n = A,T,C or G

<400> SEQUENCE: 25

```
tccttggcct aacataacat attttcgact attttcggct ttgtaaaaca aaatttggta      60
aaaaggttca atatgttgcg aatgttgcgt cagaaatgtc gttccctcgt agatcggagc     120
atgccgtgcc tggagtcttt ggtaaatgcc tgttctctat tcaaggtcga ttggtccaag     180
aatctgagcc aaatcaaaac cccggccgac tgcgttggcc ccagtgtgct ccggcagcac     240
ctgttacgcc gcaactacag cagtcagtct tccgccgatg attgcgggcg gccaaaggat     300
tgcgatcagg tatcgacctc caagggctgt ggtcctgctc ggttcaaggg caccatttgc     360
gatgcagtca agggcggtaa gcgcaagaag aaggaagagc caagaagga aaagtccaac     420 aagccgaagc tgccagcaaa gatgaggtcc atgtggtata cccgactg cgagtacgtg     480 ccaaagtgcg atgtgccagt gcggtacgac atccagcact accgcatatc ggacaaagag     540
gcccgccagt accaggtgac gtggaacgag tgccccggt tggtgatcaa gcccaagaag     600
gtgtgcatcc acgcaaagcg accgcgtncg aagcc                                635
```

<210> SEQ ID NO 26
<211> LENGTH: 749
<212> TYPE: DNA
<213> ORGANISM: Drosophila

<400> SEQUENCE: 26

```
ctaaattcat acgttttcat tcgtttcgtt ttctatagtt atttgaataa aaacatcaaa      60 attttttcaaa aaaaaaaaaa acagtatcaa aattttgtcc aagtccgtat tgcttctttt    120
tgttctccca ttttgtgtga accatctaga agaaagtaaa gtaaaacgg tggccctgtg     180 aaaattgttt tgatatatga gaagagtacg ataacgaatt cagaaaaaaa cattgcgaaa    240
agaaagagga agtagtgaaa caggcgccaa acccattacc aatcgagaag ccaaaatgac    300
tgagagcatt gtgtgtcaca agtgccagga ggccatcacc aagcgtatga tcaccgccct    360
gggcaagacg tggcacccgg agcacttcct gtgccaccac tgcgatgagc agatcctgga    420
tgccaccttc aatgttcaga gcggagaacc agtgtgcaac aagtgcttcg tggagcggta    480
```

```
cacctacacc tgtgccggct gcaagaagcc gatccttgaa aaaaccatct gcgccatggg      540
ggagagctgg cacgaagatt gcttttgctg cggcggtgcc tgcaaaaagc cgctcgccaa      600
tcaaacgttc tatgagcgcg acggcaagcc ctattgcaaa aaggattacg aggacctctt      660
tgctgccagg tgcgccaagt gcgagaagcc tataacggac tcagcggtgc tcgccatgaa      720
cgtgaagtgg catcgcgatt gcttccggt                                        749

<210> SEQ ID NO 27
<211> LENGTH: 375
<212> TYPE: DNA
<213> ORGANISM: Drosophila

<400> SEQUENCE: 27
aaatttgaat cgcatgctca aaatgtttcc cggcgactat cgcatattcc ccaaaacctg       60
gctaatgcca accgatgcct acgatgtagc catttatgcg aacaaacaca agcgcacttt      120
tatcctaaag ccttattcgg cgggccaagg acgtggcatc tggataacca ccgatcttcg      180
tactgtgggc aaacgggaga agctcatctg ccaaacttac atagaacggc ccctacttat      240
agatggctac aagtttgatc tgcgcgtcta cacacttgtc acctaggtgg atccactacg      300 cattttgtg tacaatgagg gttctggcac gctttgccac ccagaaattt gtgccaccaa       360
caacgggtaa tagcc                                                       375

<210> SEQ ID NO 28
<211> LENGTH: 373
<212> TYPE: DNA
<213> ORGANISM: Drosophila

<400> SEQUENCE: 28
caagttagtg ggatcctggt caaatgtttt aacaaggcca ttaaaggtca tggcggctgg       60
cggctgttga gtcaaacgtt tctggcgcgg cggtggcttt atgtttagct gcacgtgctg      120
caccttcgaa cattcaatag gttcatttaa atcacattcc actggcgcag ggagcttggt      180
atccagcacc ggcttatccg tcagtataga cacattttg tcataaacct tgctgatctc      240
atccagcaaa agtttccct tacatatcat gtgctcgtaa tttccgcagg tattactgct       300
ttgtttcgac atttcttctg ctgggctcct cttgtggttc ttctgaagaa tctctgccgg      360
cagccagtta tcc                                                         373

<210> SEQ ID NO 29
<211> LENGTH: 323
<212> TYPE: DNA
<213> ORGANISM: Drosophila

<400> SEQUENCE: 29
aaatctgaga aaaattcaat gtgtgtagat tgtccaggtc ttttatcaaa tcacaatcgt       60
tgttgcaaga aacttagcca ccgtcctcgc atcgacccac cgtaatggcc gagcttctgt      120
cccgcgagaa ggagctcttt aagataaacc aggagctgaa tctcctgacc ctcagtccag      180
ctgccgacgc catgtatccg gcaaagggt catccaaatc cacggcggtg gcggtgccgc      240
gcttcgccac cttccagaaa caaaggggc cgagcagcct gctccggaaa aagggtgctc      300
ccacggcgtg cacgaaggca gcc                                              323

<210> SEQ ID NO 30
<211> LENGTH: 509
<212> TYPE: DNA
<213> ORGANISM: Drosophila
```

```
<400> SEQUENCE: 30
tttgtcttcg caatagagtg taatagatat aaagcgatcg gaaattcaga acgataagtt      60
tgccccaccg ccgttggcca tgcaaaacga caagtatcca gcgccaatag gcttttatcc     120
accacaagga cagccgggat atccacaacc agcgtcacag ccaggatacc ctcagccagg     180
gcagccgcaa cacatcacac cggcggagac atacggacca caaccaccgc caatgccacc     240
gcgggatcca cacaccagag tggatccacc aggaggatgc tttcagcgca accaaaagaa     300
caaacctcaa tccaatgctg tgggcgcagc tggtctcatc tttatctctg gaggtatgaa     360
catagcgtgg gcgattggct tccaaggacc aatctattac caaaccacca agcacaatta     420
cattgcctgg ttcataggcg ccattattgg agctttggtt ccgatggcgc tgaccaacaa     480
ggtggccaaa aaatatattc tgcaatttt                                        509

<210> SEQ ID NO 31
<211> LENGTH: 465
<212> TYPE: DNA
<213> ORGANISM: Drosophila

<400> SEQUENCE: 31
aaccatgggg tgatgtgaga tcgtcagata gccagcttac cctgaagcag agtgagagcc      60
gggagacgat aagaccattt gggtatgagt tagctgatcc atccgagctt agctcctacg     120
acattcacct gggtcttcta gtagagaagg gtttaattga cattaactca ttggacaagc     180
cctcgaacga ggaccttaca gactatccgg actatccggg tcttttgtcc aggtcggcgg     240
atcgtagtgg aattgctgag atagtcaaag aaatgcgaaa cgaattcatg acaagctga      300
cctctaaggc taagagcttc aaagaaatcc tgattaagaa aggcttaatg gagccaaagg     360
acgaaaatcc tgctatgcag aagaatgact ctgagaataa agcaaagacc aaagacgatt     420
ctcagattcc agatcgtaaa gacaaagcgg gaaaacctct aagag                      465

<210> SEQ ID NO 32
<211> LENGTH: 598
<212> TYPE: DNA
<213> ORGANISM: Drosophila

<400> SEQUENCE: 32
aactctcgga cctttcgttt cggccagctt ctaaattttc caaattccaa attttcttc       60
caaattaatt tgaccaaata gacgctcgac gggctcaaga tgtgtgacgg atgtggatcg     120
ttggagccgc gcggatgccg cagtcgggag ttacgatgcg gcatcatgta caccacttgc     180
gactgcgtga agcggaacgg tctgcaggac aagtgcccgc ggtccgcctg ccagggccga     240
ccggcctgcc tgtgcttccc cttccccacc tgcggtccgg cggcattccc gctgcgctac     300
gctaacatga tgatgggcgt gaacaataag cgtatgcgct gtgccgccac tggagcacca     360
aatggcggtg ccggatgcgg tggacgcgtt gccggcggct gctgtggatg cggtccctgc     420
tgctgagctt tatgcccact acgctgatcc gtcaacaatg atagcatgtc ctgggctttg     480
tgagcgtaga ggtaggatcc atgaccaaa tgctgttgcc aggccccaaa tccttcatga      540
cccttttgacc tccatccgca tcctgtcgcg tgtggcttat aagtatttcc tggcaagt      598

<210> SEQ ID NO 33
<211> LENGTH: 552
<212> TYPE: DNA
<213> ORGANISM: Drosophila
```

```
<400> SEQUENCE: 33
cccagtgcta gtacacaacc ttttgtaaac ctacaaaaaa aattccacca aaattcaaaa      60
ttcaaagttt ttagttttg gcctttcagc acaagtgaaa aattaagtag tatgcgctta     120
tttggcagag taaccaacat tttacagata tctagatgcg ttagctacca tgctccgcta    180
taccgaccgc gcagcctact ccatgcagaa cggttgaggc aactatgcac cagtgcctcc    240
tccggatcaa agtctagccg gaggacgaat catccgtgtc gcgtccgggt gcagaggtac    300
tcccaaaagg gtagcaatgt gttctcggtc agcgataacg tggatatgct gcgcaaacgg    360
attagctttt ccggcaactc gagcaatgcg cccaagatca tgcccattgg actgattaca    420
ccggaaacgg gtgatggcaa ggatctgaag atagtcattg tgcccttgga tctgtctggc    480
atggatggca acgaactcaa ggacacgctg gaaaccatca acaagttgcg cttgtacgcc    540
aaccacatcg ag                                                         552

<210> SEQ ID NO 34
<211> LENGTH: 684
<212> TYPE: DNA
<213> ORGANISM: Drosophila

<400> SEQUENCE: 34
tcgatcacta gatccccaca taaaccacca actctatacc cacacgtgcg ccttgaagcc     60
tagggtcat tgcacttgcg aactatgtga cagtggcact acggaaacag cgccagggcc    120
gggtttacca ctgcgtctcc ggagcaccag gatccggaaa cgcaacctaa gattaagacg    180
tcgctgaaca caggatccga ggaccaacaa ccgatccccg ggcgatcaaa acccggcgc     240
catggccatt cacgagcaga tcgacaacct gaacatctgg tggtttccgc gcgacttctg    300
tcagtcgcga ttcggggagt tccagcggag cggcaccaac tcctgcacca tcatttccct    360
aatactggcc gacaaggtgg ccaaggcgga cagattctat cacagggtct ccgatctgcc    420
gctgcgggga tgggagctct tcggcaacgc cattaacgac ggaaacagcg tgtaccacaa    480
tgtgattaca actaatacgc cgcacgccag gaatctcaac ctcaacattc cggatgctat    540
cgccgccatt cggtcgcagc acaagatgaa cttccggctg gaggagtggt tttacacgca    600
catggaggcc gatcccagca atcccatgta caaccggaac gttgctgtgc agttgtcgcg    660
ggttttccag ataacactcc agat                                            684

<210> SEQ ID NO 35
<211> LENGTH: 675
<212> TYPE: DNA
<213> ORGANISM: Drosophila

<400> SEQUENCE: 35
cggggagagt tccgtccaac gcggttgtgc caaaatgatt atcttgtggc tgattctggc     60
cctaagtgcc ctgctctact ggctccacag agccaacaag gattaccaca tcctgtcctt    120
cttcaccaaa agaattcgat taaaggatgg aacccctgtg gagatcatcg ctcccatagc    180
caagggaaaa acaatattcg gcaacaccct tgacttgtat gggcgagatc acgctggtgt    240
ttcaattac tcgcgtgagc gtgctaagga aatgggtact agctacatag aatatgtctt    300
tggaaaggcg atttacaaca ttatcgatgc ggatagcgcg gaaaatgtgc tgaatcatcc    360
gaatctcata accaagggc tcgtctacaa cttcctacat ccattcctaa ggacgggctt    420
gctgacatcg actggcaaaa aatggcatgc tcgccgcaag atgctcactc cgacattcca    480
tttcaacata ttgaaccagt tccaggagat ctttaaaacg gagagtcaaa agttcctgct    540
```

| | | |
|---|---|---|
| acaatttgag ggtcaagatg aggtaaccat aacgttacac gatgttattc caagatttac | 600 |
| tctaaacagt atttgtgaaa ccgccatggg tgttaagctc gacgagatgg ccgagaaggg | 660 |
| ggatcgatac cggga | 675 |

<210> SEQ ID NO 36
<211> LENGTH: 560
<212> TYPE: DNA
<213> ORGANISM: Drosophila

<400> SEQUENCE: 36

| | |
|---|---|
| cacagtttgg acacttatat taccaaaatt tctgttaaaa ttatttgata aaaaattatt | 60 |
| cagttcaatc atgttcaaag tgcgcagctt ggcgctcatg aaattgagtg aaggcgtttt | 120 |
| cggcgcacga ctaatggcca atcgccgaaa ggattcgggc aaggattctt gcaagggtgc | 180 |
| cgattccaaa agaagaaag acaaaaagaa aaggatatg tgtggcagaa ctgttgttcc | 240 |
| cacttcacca cgttgcaaaa acaaacccgg cggctcagac aaatccaaag atgagtgcaa | 300 |
| gaaaaagtag cagagttcga ataaatcatt tcagccccct aaacaaaatc acagcaggcc | 360 |
| tttaaacaaa cttcaagctg ctttggccta agtcaaaatt aaagttacaa agaaaaaaa | 420 |
| aaaccatgtc ccgactttg ctgcagtgcc gcagaacttt gctgatcctt cgccatcaaa | 480 |
| cggcggtgga aaatgagaaa ggactctttg gcaaactgct gggaaagtgc cagtcctttg | 540 |
| gcaaggatga aaaggatctt | 560 |

<210> SEQ ID NO 37
<211> LENGTH: 529
<212> TYPE: DNA
<213> ORGANISM: Drosophila

<400> SEQUENCE: 37

| | |
|---|---|
| aaaagtactc ggtcggcaaa acggcaagcg gcgaaaaaca gtgaaaaaaa aagggggaaa | 60 |
| gcgaaaagac gtgctcagga actgcggtcg aagtctttgt gagtgtgtgt gggtgcagct | 120 |
| gtcgccaaac aaatgaaaag cgcctggctt gcattaaaat cgaaaagtgc attgcatccg | 180 |
| aaaagcgaat atccagtatc caatatccat tatccgaaag cagctaatta ccgacagaca | 240 |
| aggaattatt tagagatcgc cgccaaaatg tcggaggaag tagatcgcaa cgatccggag | 300 |
| ctcaagtacc tctcggtgga gcgcaaccag ttcaacgatc cggccacgca ggccgagtgg | 360 |
| acacagaagc gtctggtgtg ggtgccacac gagaaccagg gcttcgtggc cgccagtatt | 420 |
| aaacgggagc atggcgacga ggtcgaagtg gagttggccg aaaccggcaa gcgggtgatg | 480 |
| atcctacgtg acgacataca gaagatgaat ccgcctaagt tcgacaaag | 529 |

<210> SEQ ID NO 38
<211> LENGTH: 593
<212> TYPE: DNA
<213> ORGANISM: Drosophila

<400> SEQUENCE: 38

| | |
|---|---|
| aaaatattac actatattat ggattattta caaaatgttc ctgttttgaa gtcatttcac | 60 |
| cccgaatccc cacttcgaac cgtccagagt ggtggtggtg accccgaccg tcgtccaacg | 120 |
| gctgctcaat caatcaatat tgaaggttcc cacaccgcag gcgaggcact ggaactccat | 180 |
| gggttccacc cccttcctc gccagtgtgt tggccatttt gtttgctatt tctgtttggc | 240 |
| tttttcttgt gctgaccgct aaatataacg ttggacggct aagccgcgga ggtgtggagg | 300 |

```
gtcgaccggc ggtgcaataa tctgtgaggg gaaaagaggt tgggatgaaa tcggatacgg    360
gccaagtagg aagttacctt gagtgcattt ctatatatct gtatcgacag tgacaatgcc    420
cgcccaagtc caagttgcag ttcattcatg gtttcagtcg gttcgttttt tcgttctctt    480
tccgagtttg gtgtaaacag gttcacaggc tcacggcaca gaaaccgcac aagttttttcc   540 cggctgctca tcctcatcct cggcctcgtt caccttccac ttttcctcag cca           593
```

<210> SEQ ID NO 39
<211> LENGTH: 598
<212> TYPE: DNA
<213> ORGANISM: Drosophila

<400> SEQUENCE: 39

```
cttattcgga aatacgcgcg gcgtagttgc acaaaaccaa caagaacaac agcgacggaa     60
aagagcaaca actaaagcaa taactacaac acacacggc taatttcaca aatcaaaaaa    120
ctgaaacggc aaaaattata aatattata agtgcgcatc gccttttttag agataagagt    180 aaagttttgc ttttgcactg caaacacaaa aacaacgac agtaagaaag aaactcaaca    240
gtcggccagc tcaaacaatc aaacacaaaa tgcacagcaa caataatagc agcagactca    300
acaacaacat aagcaacaat tattatcaac aaaaacaatc gcttatacgc tatttggatc    360
gagctgctgt tggtctgaac ggtgtcgagt tcgagggcag caagctgcat gccgagcagc    420
tggacaagaa ccagcggcgt agccagcgta accagcgcaa tccgtatccg ggtatgcccg    480
gtcccggacg ccaggcggac tttccgctgc gcattcttgt gcagagcgaa atggtgggcg    540
ccatcattgg tcgacagggc agcaccatca ggacgatcac acaacagagc cgtgctcg     598
```

<210> SEQ ID NO 40
<211> LENGTH: 557
<212> TYPE: DNA
<213> ORGANISM: Drosophila

<400> SEQUENCE: 40

```
tgctctggcg cgatcgaatt tgcctggaat tcgggagtca acataatatt ttcgaaagtc     60
accagctata gcgaaaatag tcgcggattt tcaacaaaga gcaatcatag tgatggtata    120
aaagagggga aggacgaaag caaagagagc aaaccgaaaa cagttactct gcccatgcgc    180
acagctgacc cagaacctgg cataacggta agtaattgt gtcgtacaac aagcgaaact    240
tgacagcgaa agggaaccgg aagtcgccta aaatcgcgga gcggaaagga atcagtccg    300 ccaaccgcgg gagctgaaaa tcgaaatcac aacccacaaa agcgattcca aagtgctatc    360
ttggtgctac tcccatacaa aatgttccaa gtcctgcccc gtccgtcaag atccacgttc    420
cactgcatag cggcagccgt tgtcacagtc gtcctaatgt catgggcccg accgctgggc    480
gtgctattcc tgggactact tggctactgg atctactgga cgcgctgcag cttccgcgtt    540
gtgcctacgg acgagct                                                  557
```

<210> SEQ ID NO 41
<211> LENGTH: 550
<212> TYPE: DNA
<213> ORGANISM: Drosophila

<400> SEQUENCE: 41

```
aattcgctac ctgaattta ttctatttaa gttcacaacc atactgatac cacggaatac     60
atctttaagg tacaggatta tcaccatacc gactagaaac taacccgaac atgggcacgt    120
caaatggata atatagaaca agtgaccgag cacataaagg acactgaatt ttcacacaga    180
```

```
cacgtattat cgggatgtcg cggatccctc gtcaagtata aattaaagat gcattatttg    240
caggccatct ggtagaggaa ctggatgatc gatcgagtcg gacgaccagt catgcaatcc    300
ttgagcaaat acggaggaac tccgtgctta gccagcattc cggtgccgtg ggtatccagg    360
tgcacccagt cggagcaggg aaccagttcg taaaggatag cagccgccaa gcaggaggat    420
gcgtgtccct ctcccgtgct gcatatatcg taggatgcac gggggccac taatttgcgg    480 aagtacctcc atagggcat gcgccacaaa cgatcgccgg tgagagctcc ggccttttgg    540
aaattcttcc                                                          550

<210> SEQ ID NO 42
<211> LENGTH: 643
<212> TYPE: DNA
<213> ORGANISM: Drosophila

<400> SEQUENCE: 42
aaaagaatcc accaattgtt ttttttattt tactgataac attcaaaaat ttggacaaat     60
gatacacttg gaatttggag agggttagtt ttcgcgccac taatagttgc gcttcatttg    120
accggtggca aagagcacgt cgaggatttt caggaactcc cggtagttga actccatgca    180
catgcccttc ttcacgccga agcacttgca gatcgcttgg aactcgcggc tgctcagcat    240
tacatgcatg tcgcgcaccg tgatgccgcg caggaattga ttctgcgtga tcgagccgca    300
ctgttcgcga tcgaagtcct tgaacagctg actcagattg agatctcgt ccggtttgcg     360 ggccaacttc atcagggcct gcgagcagat ggttcgctcg tcgaagctca ggaagcagtc    420
gacgcagtcc agattgggca aatggagcag tggcacggcg gtcaccacct ggtcacccat    480
gttcgtgtcc agttggatga agatctcgtc gagggccttg cagaaatcgc gatagcgaat    540
gcaggacacg cgattcggtg aacggaagat gttgcacaag atgttagctt cctcttcctt    600
gatgattaca cttgagttat ccagggctcg cttgaagtcc gat                     643

<210> SEQ ID NO 43
<211> LENGTH: 627
<212> TYPE: DNA
<213> ORGANISM: Drosophila

<400> SEQUENCE: 43
attttttcat acgctctggt cgcgcttaca cattacgatt tctatctctc cgctcttctt     60
cattttactt gatttccatt tgtcgcttcc tccgcttttt tttgtatttc gctggcgaga    120
tttctttcca cgttgaattt atactatatt gcatttatat tattgcgctt atcactggcg    180
ctttgttgct ggcttcttgc ctttcgctct tttttgggct caaattaaat ttacaatttg    240
tttggccaaa tgcaaaaagt tcaaccaaat gctgatatcg ggacaaagaa aaatggctgc    300
actgcgagtg aaaaaacgag ttaaagagta ttttttgaaca aaggaaccgg aaagatgcag    360
tactcttgtg actattttga aatttaagat agcaaccaaa tacgcttctg attaagttgt    420
agtttatata tgcagatatt tgtaatattt taattcttaa agcgaaagaa aggtcaacgc    480
ctgtacttac atgccctaaa gttgcgggtt tgtattttc ttctgttcaa aatgcctttt     540
ccatatatat cataaataca tatacataca tacgtataca ctactgcagt tatcgctgtt    600
ttattttagt atttgtgaac ttagttt                                       627

<210> SEQ ID NO 44
<211> LENGTH: 595
<212> TYPE: DNA
```

<213> ORGANISM: Drosophila

<400> SEQUENCE: 44

```
aactaaattc atattgttgc tcacacaaaa gacacaaaaa gcattaaaca aattctggag      60
ctgcagtcaa aagtaatttt ataaaattaa catagtgcgt ttagacgaat caaatgcaac     120
cgaaaactgc aatgccgcct tctaagctaa attgccaatg gaaccgccgg cggtatctgc     180
aacaccatgg aggtgacttt tcggatgagg aggaggatcc caggctaagg ggcatcctgc     240
ggagaaccag ctgccagcgt taccgtgaac gattgcgttc gaaccgccta tcacagctcc     300
tccatggact ttccatcgtg gcgacggtaa cactgggggt tgtcctgatg ttcttccttg     360
gaatgaagtt atccacggag cagatggatt atcccgcacc acgtgaggaa ggcctttggt     420
tgggtttcct cagactgctt ggcttggagc aggaggatta tctctcagga gacttgtatg     480
tgcataataa agatactttc tgcagtcccg aggctctgaa cttggaacgg atctttcgat     540
atatgggcag ggtggttctg aatcaggagc aggcactgtc tcgcatggaa agggc          595
```

<210> SEQ ID NO 45
<211> LENGTH: 618
<212> TYPE: DNA
<213> ORGANISM: Drosophila

<400> SEQUENCE: 45

```
atgactgtgc cgtgggtgga gggaccactg tggaggggcg gttaacctgg atctgatctc      60
ggcttacgat caaacccagc ctgtggcaca gctccttaaa ggctttgtga gaaactatgt     120
cttggtagcg agttgattcc gtaaaggtga aaaatttctc aaaagccttt atgcactcga     180
tttggttttc gatttccagc tccgtatagc tgcgatttga gcacagggtg catctgggac     240
acacggatcc atcgccaccg tattcatact tctcgttcaa aagatcgttg acccggatga     300
ggaattgggc aattagaacg gtctcaggtc tgttcgccaa cttcgcctga tcgcccacag     360
ccagctggag gcactgttta ctgtggttta ctagagtatt tcggtccaaa ggctgcatct     420
gatcgtgctc tttggtggtg aaagtcatac taagaccttg tcctcctggt aatacaccaa     480
ccgcgatctc ttccagaggc atttgctcgt ctcccagttg acttagggtg tcaaagatct     540
ggcgctcgag aaaaatccca ttttcaacac gattcacggc atcaccaacg acctcgggac     600
gcagcaatgt tgtagttg                                                   618
```

<210> SEQ ID NO 46
<211> LENGTH: 550
<212> TYPE: DNA
<213> ORGANISM: Drosophila

<400> SEQUENCE: 46

```
cttcgataca cttctaaatt tctctgatca aattttataa gaaacaaaaa acaaaaatta      60
acttttact ctttcggttt attctagtcg aaacttaaaa tgtgctctcc gtgcggtcct     120
tgtagtccat gcgatccctg ctgcggtccc ttcgagtgct cacccaagtg ctacaatgcc     180
gcccaattgg aggccttgcc acaatgtgct ccacgtattc caccacccct cccaaatgc      240
atcaccgtgc agcaaccacc acgcatgatc tgcaagaaac gcgttgtgtt cacggagaag     300
attgtgccgg agccaatggt ggttaaccga tgcaggcaga tcaccattcc aaaggtcgtt     360
gatgccacgc gggtgatcaa ggtgcccaag ctgatttggg tgtcgcagat ggtgcgagaa     420
cccagagtaa tctactaccc ctcgatgatc cccgacccct atgtggtgtg ctatcccaag     480
cgcgtctgcg aaccacgtga ggtgtgtcag tcgatcctct gccagccgaa gccccaaacc     540
```

```
atcgacattc                                                              550
```

<210> SEQ ID NO 47
<211> LENGTH: 560
<212> TYPE: DNA
<213> ORGANISM: Drosophila

<400> SEQUENCE: 47

```
cacatctaaa acaaaaaaat gcggtgcggt cagtagttaa attgcgaaat tgaaatcgaa       60
gtaagctcgt ggcgtcttac cagttttacc caaaattatc tcgttttgat ttgaagactc      120
gctgcaaaat aattttaatc aaacaaaatt aaaatgcttg ccaaaagcaa accgctgatt      180
ggcatgtctc acttgctgca aaagcaggtt ttaggctttc tgcctccgtc ttcgtttcgc      240
cactttaact ccgagggcaa tttgtactcc caggatggct gggagagtgg ctatccggcg      300
cccttgctgc cgcgcaagga cctaaagccg ttggagaaga aagacagatc aaaggtatac      360
gatgcctgtt ggcaaacgac gcggcggacc gaatacaagt gccgttcgga tccagagttt      420
cagatgcacg cctttatcga ttcgcgcaaa agttgtttag aagaccctg cgccaccgag       480
atgttggcca tcgatctcac ccactataag ccctcggaca tgggcaaacg aaagtatccg      540
cgcacctggt tcgaatgtgt                                                  560
```

<210> SEQ ID NO 48
<211> LENGTH: 593
<212> TYPE: DNA
<213> ORGANISM: Drosophila

<400> SEQUENCE: 48

```
aacaacatcg ttcttccaaa attaaaaaaa aattatataa taattataaa aagtgaaaaa       60
catagtaaaa ctctcacaaa caagaaacga tgtccaacgt tattaagaag gtgattccca      120
tgctggaccg cattctaatc cagcgtttcg aggtgaagac caccaccgcg ggcggcatcc      180
tgctgcccga ggagtcggtg cccaaggaga tgcagggcgt ggtggttgcc gtcggacccg      240
gagcccgcaa tcctgctgga gctggacact tgtccgttgg cgtcaaggag ggcgatcgcg      300
tgctgttgcc caaatacggt ggaactaagg tcgatatgga cgacaagcgc gagtatgttc      360
tgttccgcga gagcgatatc cttgctaaac tggaatagat ttgcaacact ttccgaaaca      420
tcaaagccga tatacacgat atacatataa tgctccaagc aatactcatc ctcctatctc      480
gtcacttatc ttcggtggag actgtcattt tgcttccgaa ttgcgttcga aactaaatga      540
ttataatgaa atgttatatt tgggaaatgg ccaatctaca cactccacac act            593
```

<210> SEQ ID NO 49
<211> LENGTH: 662
<212> TYPE: DNA
<213> ORGANISM: Drosophila

<400> SEQUENCE: 49

```
ttcaagcttc gattttccca cttacgccca cgtaaccagt agccaaatca gaaccggaac       60
gatcgccacg atgccggagg acgtaatggt gcccgctggg gactacaagc tggtcaagca      120
gatacgccgg aaccaggaga cacgtcgcaa gaaggacctg ccgtggtcga agaggatatt      180
cgacatagac gagcacaaat tgttcggacg cacagctctg ggttggatgc gtatcactgg      240
cttctacctg gtactatacg ccctaatcgt gtgcattgtg gcctttggt tgggcatctt       300
tatgctggcc atcattgatc cgaataagcc gcgctggctc aagggtccgc cgggtctgtc      360
```

-continued

| | |
|---|---|
| gatggtgccc aaccagaatc gatccgtgct ggcctacttt acgcacatca tgagtgaggt | 420 |
| caatccgatt gcggaccgca tcgacgattt cctgaacaaa ttgaacgaca atgccattga | 480 |
| cttcttcgcc gatttcaacc aggacactac gtggggctac gccaccgaaa agccgaccgt | 540 |
| cttcatcaag ctgaacaagg ttattggcta tgtgccggag acctacgaca cgccagatga | 600 |
| cttgcccaag gaggcgccag cgagccttca ggacaccgtg gcaagctgg gcaacacgcc | 660 |
| ca | 662 |

<210> SEQ ID NO 50
<211> LENGTH: 489
<212> TYPE: DNA
<213> ORGANISM: Drosophila

<400> SEQUENCE: 50

| | |
|---|---|
| aaaagcggag gtaacggaac aggaagatcg tagtggaact cgatgcacta gcttacgagg | 60 |
| atccacgttt aaattttgct ttgaaagttt aacactctcc aaatcgacat ttcgctacac | 120 |
| ttacacaaaa atggtcaagc catccaaggc acctcgttcg atgacagcca gcggtggccg | 180 |
| cagtggtggc cgaagcggaa gtttcagctc caaggattcc gaccaggtct attgcgtgct | 240 |
| gctccacgtg gtcgaggcga taaacttcat tggacgcgat gccacagatc ggcagcagat | 300 |
| agtgatgaac gccgctctga acagtgtgga ctttgaggtg gagggcaccc agtcggagga | 360 |
| gaccattatc tttaacagca actgtatctg ggagtgtgac ctggctggga ttaagcggct | 420 |
| caaaaccgat caccgtcccg tcaaaatgac cttctatgcc tgtcgtggcg gcggagcgga | 480 |
| acgaaagaa | 489 |

<210> SEQ ID NO 51
<211> LENGTH: 604
<212> TYPE: DNA
<213> ORGANISM: Drosophila

<400> SEQUENCE: 51

| | |
|---|---|
| cactttagta taacaaattc tcgccaagat atgaagccgt atttagattc agattattcc | 60 |
| atcagtcgca atttgcgtca gagacataga aaaaaaggag tttctaacga atactcaaat | 120 |
| tatttagatt ccgaaaataa aaaaaaaggc agaaagaaat gtcaaaatag cgcatatgat | 180 |
| gaatacggaa atattcgctc aaacggtctg acatatgcg actgtatgaa tcaagaatgt | 240 |
| gatggttgct ggtataattg ccgaagttgt ggctctacca ggtgtggtcc ccaatgtcgc | 300 |
| tcgaatcgaa agttttttta tgaggacata acatatgacg gtaaagattt aaatattcaa | 360 |
| aataaatata taccaagata aagttaagca atcacatgt attaattaaa tatttgtaac | 420 |
| ttaatataag tattaatgaa cagccaaacg agcattaaac tatcattcag acgaaataca | 480 |
| tcacatataa caattcttaa caaagttatt gcttcagaaa aatacattat gtgctaattg | 540 |
| aaaggaaatg attccaaaat aaagtaaatt cttcagcagc tatggtgaag acttattgta | 600 |
| cttg | 604 |

<210> SEQ ID NO 52
<211> LENGTH: 536
<212> TYPE: DNA
<213> ORGANISM: Drosophila

<400> SEQUENCE: 52

| | |
|---|---|
| ttcctgctgc catgccataa cgaagtaacg cgaatccgct atagttgtgt atatgacatg | 60 |
| cggccattcg ctaaataacg aaagttgtag gttacgtcat tgaatttatg catactgcgt | 120 |

-continued

```
gatagtcctc accaattgac agcatccaag tgcacagagt gcatacgggg tcgtagttcc      180
tcctcgcaga agtaatacac attcacatgt agcgaggtta gcttcacctc cctcttgtga      240
tggtccagcg gcctgcttcg catttccagg tacaccggcg tcgaattgtg cacgcaaatg      300
cggctgccaa acggcgtaaa gatctctttc tctgtaatgc atcaaagagg ctagaaagat      360
tcgtaaagtg tataaatgat cataacccac cgctagtcag gcgccgcact ctgcccaggt      420
aaacccatcg cgggcccatt ttcaactcct gctcgacgtc tttgggctcg cgcgaaggtg      480
tttgaggcag cttTggagat ggagatTttc tggcgccatc aaaggaggga ttatgt         536
```

<210> SEQ ID NO 53
<211> LENGTH: 683
<212> TYPE: DNA
<213> ORGANISM: Drosophila

<400> SEQUENCE: 53

```
atcactcgtt tagcatttgt tttatacatt cgaacgggaa atgttgtctg ccgcacaaaa       60
tgcagaaaaa taaatctttt cgttgttgtt acccgagttt tggatggaaa ttaaaacaga      120
gaatcacgcg aaaacgagct gtgcggaaat tgcgccactt actggtgaag tacaatatcc      180
aaattgagaa ttgaaggctt tcggaattga gatttcagct tgagcctagt gaataattgt      240
attgacttac acactcaatc actcaaccgc acaacatggc caagaagagg ggaagaaagg      300
gcaagaaggg caagaagcca aagtcgact gcaagttcaa gatcaccaat gagatgctca      360
agcccatgaa cgagaatgtg gacgactgtg atggctgctg tcagtgcgcc tgcgattgcg      420
actgcagtcc ggagttggct ccctgcttca tccagccgac caagccggat ccgggtccgg      480
aggcgtacga cgagttcgag gcctgcctca atggcagcgg tctgaccata cgcgtactca      540
agaacaccca aaggtggag agcgtgatgg atggcagcga gactgcgccc aatctgggcg      600
catgcgatga tccctgctat cgcgatgacc ccaatgactg cgagcccgca aaggagtcct      660
gcctgcacga tatgctccag cgc                                              683
```

<210> SEQ ID NO 54
<211> LENGTH: 647
<212> TYPE: DNA
<213> ORGANISM: Drosophila

<400> SEQUENCE: 54

```
gaagctgccg atcttgtagt ttattgagta acttgcgaag gtaaacaaa gtgggatcca       60 ccgccactaa tcaaaattcg tgtataatgt gtagtagtaa aattaaaatc attttgcggg      120
cccagcaacc gaggcgatct cctcccgtcc tcctgcacca gtcgtcccca taggtcttgc      180
atgcatttca gcgtgaaatg gcgatggact aacgaatgtg agagcgctcc aaggaattct      240
aacgactgcg ccccgaatcc tgcggatcga tattggacac ccattgcacg ggattgatgt      300
aaatgttgga tatggtaccg cgcagcgtgt caaagccctg attgagggga accggcttgg      360
cccgcttgtc cacctgtttc atccagttct gccaggcgcc ttggcggcgc tgacggcgtt      420
cctcctccag tttctgcttg ttgcactgca gtcggatcag gcgttgtttt tcctgttgct      480
gctgctcccg cttggcttgc tcccacttct gcagacggtt cttTgtgttc tcgggagaca      540
ccttccttgt agggggcggtg ctaaagctgg aaaccgatcc caaactggag ctagaggtcg      600
aggatttctt ttgcttttgc cgctgctgct gctgctgctc ctccttg                   647
```

<210> SEQ ID NO 55

```
<211> LENGTH: 586
<212> TYPE: DNA
<213> ORGANISM: Drosophila
<220> FEATURE:
<221> NAME/KEY: misc_feature
<222> LOCATION: (1)...(586)
<223> OTHER INFORMATION: n = A,T,C or G

<400> SEQUENCE: 55
cgtgttttta aatgaaagaa caattatttt atttcctctt tttgattaac atctgaataa      60
ggctgctctt cgcccatgtc agtactgtga gaagtataag gttaactact taacctgaca     120
aattgtttag cagcgcttgg ctttctcctt gtagtttcga ttgaacgttt gaagatgagt     180
tcgacgttga ctgcgacgat gaatgtgacg atgattgaga cgacgactcg gacttcgact     240
ccgactgagt cttggagctc gattgatcta gtagcaaggt atttcgattg ccagcctcct     300
gtcgttgtgc ttcagactgt gatgcctgcg atgactgtga tgacgaactc tgcgagtttt     360
gtgagttact gtgcgagctt gaagaagagg ttttctgatc attttccgtc tgaattcgca     420
gttgttcctg ctccttcaat cgctgaagag cggcgctttg agatgcagaa ctttctgtgc     480
cttgtaggga actantctgc aggccantgg atccagcttg aagaccctgc tgtgagcctt     540
gagctccagt actttgtata tcttgctgta acttggtctg agaact                    586

<210> SEQ ID NO 56
<211> LENGTH: 541
<212> TYPE: DNA
<213> ORGANISM: Drosophila

<400> SEQUENCE: 56
aatcgtcggc cacgtcactg ccggaggcca agggatgcac tgccaccgaa aactgccagt      60
tgctagcgca agaggcggaa acaaagaacg ccagcaacga acaaggtgga ttgggcaaaa     120
tgtcggttag cctgccgcaa caaaactgga acgctaatca atcgtcggcc acgtcactgc     180
cggaggccaa ggagatcagc tccaaagagc aggcgatcat ctactggcgg cgtcttttcg     240
atggtatcca caagcgccag cgtggcgaaa gaaaagttgc agcaatgcag cccgaaaata     300
ccacagatgt cgtgctgacg tccaagccaa acctggcatt gcgctacaag ccctcccatg     360
agtcgcttaa aaacaagcgg atcaaggacc tggctcctga acgatgcccg agcacgtccc     420
ggggatcaac gtcctgcaaa ctggtatcgg acctcaagat ggagacgttc agcctgccgc     480
cgcagcagac gtgtgtggtg cgcgaggtgg agcctcggtt tggccagcgc cgacgcatgt     540
t                                                                      541

<210> SEQ ID NO 57
<211> LENGTH: 587
<212> TYPE: DNA
<213> ORGANISM: Drosophila

<400> SEQUENCE: 57
taaaatgaaa gccatcaccg tttgccttt ggttctggtt tcggccacct gtctgctgac       60
cacgcgggcc aatgcaatag aattgctgga gaacgagaac ttcgactatg atttcgactt     120
tgaatcggaa ttggagcagt tgctggatga actggacaat gacactgact acatggatgt     180
ggaggcacag ggctttatta gaacatgcct taaaatcctt cgcaaggcat tgaaaacggt     240
tcgaggcacc aactgtatta tcaaggaggt gacaaacatc cttagttcat gcaccagcta     300
tgtggatgct attgatgcct gtggcactgc cattcccaag gatgtggcca agattgtgga     360
ctccgttaag gagattatca aaatctgcga cgatattttg catctgcatt cgaaactttg     420
```

```
tgccacggat aagtccgtgg gctcgttcat caaaaactcg gccaaatgct tctggaaatt      480
gttcaaggca ttcatgaggc tgacccgaaa gatcaattaa accctaaaac tgattgccaa      540
attgccagcc gataccagtt cctgctttgt aaatgccacc aataaag                    587
```

<210> SEQ ID NO 58
<211> LENGTH: 581
<212> TYPE: DNA
<213> ORGANISM: Drosophila

<400> SEQUENCE: 58

```
tcgcgtctgc gccgttctac gtcggacatc ggattacgga tagctgaata cggaatacgg       60
atttccggcc tggcttcgcg aaaaggatcg taataagagc ccatcggaaa tggcaacgga      120
tgtgcaatct ttttacaaag acaaaactgt cttcctaaca ggcggcagtg gattccttgg      180
aaaagtgacc attgcgaagc tgctctgcac caccgaggtg aagcgcatct atgtgctgct      240
ccgtgccaaa cgcggccagg aaatgcggga gcgatgcgcc gcatgggata aggatccggt      300
attcggtaat ctaatgaaaa caaatcccga ggctctgaag cgcgtggtac cttgtggtgg      360
cgattgccag gagccggatc ttggcctgag caacagcgat cgtcaggttt tgatagatga      420
ggtgcagatt gttatccaca cggcggccac tgtgcgtttt gtggagccgc tgcacatcgt      480
cctggcttgt aacacccgag ccacccgact catgattcaa ctggccaagg agatgtccca      540
cttggagtcc tttgtccatg tgtccaccgg gtactcaaac t                          581
```

<210> SEQ ID NO 59
<211> LENGTH: 450
<212> TYPE: DNA
<213> ORGANISM: Drosophila

<400> SEQUENCE: 59

```
atgaaagtgc tcgtagtctt cgccctggct ctggccaccg cctccgccgg tctgctgccc       60
cagcaggtgc cgatccaccc ccgtgacctg ccgccgtga ccaatatcga gggtcgcatc       120
accaacggca agaccgccac ttctggccag ttcccctacc aggtgggact cagcttcgcc      180
agcaccagcg gcagctggtg gtgcggtggt tccatcatcg acaacacctg ggttctcact      240
gctgctcact gcacttctgg tgcctccgct gtgaccattt actacggagc caccgtgcgt      300
actagtgccc agctggtcca gaccgttttcc gccgataact tcgttcagca cgccagctac      360
aactcgattg tgttgaggaa cgacatttcc ctgatcaaga ccccaacggt tgccttcacc      420
gtccttatta caaggttga gctgcccgtc                                         450
```

<210> SEQ ID NO 60
<211> LENGTH: 647
<212> TYPE: DNA
<213> ORGANISM: Drosophila

<400> SEQUENCE: 60

```
aatcgagcag gcaacacaca ctttaaaatt taatgtgagt tcagagcttg atttggggaa       60
aacagttcaa gctctttaag cgtgatggac gaggaattct ctaatcagcc catcgatcca      120
agcatcgctc ggagtgacta ctcccggagt catttcgtta accagagctc catgacattg      180
agtcgcggat tggactccac ccgactgctt ttcgtaggcg aaaacttcca gcagacgcgc      240
agcgaacagg acttatttta cgactgtcaa ggtccgggtg aggactcgcc aaaggagggc      300
cgtagtgcca ccagccggtg caagttcgat gatccggctg cgatacggga tgccctggaa      360
```

-continued

| cgggcggcca atgccacaca gatgctactc aagaattttg acaagtcagg tggttggaat | 420 |
| cagccatgtg ccgtcaccct ggagttgacc gctcggttgg tggacccaa gaagggtcgc | 480 |
| gctggttgtc cgttgcacgg aaagcccgtc accgtccaga tgccgctgga gttcaatccg | 540 |
| cagagcggca agatggtcaa gtgtcagcaa agaaacaac cggtcaccag gcatcggaaa | 600 |
| gagtccatct gccagtgccc gttcgcaagc agtatatgcc gttcccg | 647 |

<210> SEQ ID NO 61
<211> LENGTH: 550
<212> TYPE: DNA
<213> ORGANISM: Drosophila

<400> SEQUENCE: 61

| ttgcactcac ttcgtgtctg agatcaaacg aaaaaatatt agaaccaaaa gttttgaaag | 60 |
| tttttttttt attatagttt caaacttaag tgcaaaatgt ttcggtcgtg tgtgcccaag | 120 |
| gcgattacct ctagtcgctg tttcgcgcgg atgtactcga aggacgtgcg ctttggctcc | 180 |
| ggagtacggg caatgatgat ccgggggcgtt gatattctgg ctgatgccgt tgctgtgacc | 240 |
| atggggccca agggtcgcag tgtgatcgtg gagcgaccat ggacctcgcc gaagatcacc | 300 |
| aaggacggct tcacggtcgc gcgctcgatt gccctaaagg accagcacat gaatctgggc | 360 |
| gccaagttgg tccaggatgt ggccgataat acgaatgagt cggcgggtga cggcacgacc | 420 |
| acagcaacag ttttggctcg agcgattgcc aaggaaggat tcaatcagat taccatgggg | 480 |
| gctaatcccg tggagattcg tcgaggtgtc atgttagctg ttgacgtcgt aaaggacaag | 540 |
| ctgaaggaaa | 550 |

<210> SEQ ID NO 62
<211> LENGTH: 628
<212> TYPE: DNA
<213> ORGANISM: Drosophila

<400> SEQUENCE: 62

| cctaaattta aaaaaaaagc ctgttttatt ttggttccca gattgagctt aaccgtattt | 60 |
| aaccattaaa caatattgga cccgaatcgg ataaacactc caagcttggg gaataagacg | 120 |
| ataccgcaat gatgggcaca cgggctgcgg agccccgagg atccaggagg tccttggcag | 180 |
| gtcaaagcat tcaagagctc tctgtgtgcc aggaacccga cccgctaaac accttttttgg | 240 |
| agaaaccact taccctgtat cagtggatgc ggtggcgcaa ctgcaagacc cataagccgc | 300 |
| acctagagga aacatacccc agcattctac cgcctatatc caaatgtgac gatgccaaga | 360 |
| ctctgaagta cgttgaaaat gccatggagg ccaacaaatg taaagaatac gtcaaggaag | 420 |
| acgtgctgac cgtgtggaac tacagtcccc aaaaggaatc cttggtgtgg tatggcgtta | 480 |
| aatcgcagta cccgtctcca caggccgtcc tctatgaccg cgctttgaaa aagagcctaa | 540 |
| aggcggctag tcttgctcca aaaccgccga agaagtccaa cataaagcct aaatggcaac | 600 |
| ttcagaagaa gccccccccag cctggcgc | 628 |

<210> SEQ ID NO 63
<211> LENGTH: 494
<212> TYPE: DNA
<213> ORGANISM: Drosophila

<400> SEQUENCE: 63

| tggcgcaaga accgtcgtcc caacggatac cgcaacgaaa gtggagattg ctacggcatt | 60 |
| gacatgaacc gcaactttga ctaccactgg ggaggtgccg gctggaacat cgatgagccc | 120 |

```
tgcgatcact ggttcggtgg tgaggagccc aacaccgagg tggagatcat ctcgctgcag      180
aactttgtga gctccttcga ggatggctac atccgatcgt acatggccta ccatgcctac      240
ggacagtatg tcctcctgcc ctacggacac tccaacaccg agttcccgcc caactacgag      300
cagatgaagc gcattgccgc tgcattctcc gatgctgccg ctgatgtcta tggttccacc      360
ttcacctatg gagctagtgg tctgcttaac tatgtcgttt cgggagctgc caaggattgg      420
gcctatggcg taaagaaaat cccattcacc tgcaccgtgg aactgcgtga agggcacc       480 ttcggattct tcct                                                        494

<210> SEQ ID NO 64
<211> LENGTH: 703
<212> TYPE: DNA
<213> ORGANISM: Drosophila

<400> SEQUENCE: 64
tcacgagaac atcggatact cgacccgatt ttgtacagaa cattttcatg gaaattttc        60 taaacatatt ttaacacttc tttgtcaaac tcttctttcc ttaaaaatca aaatttaatt     120
ctactctaaa agccccatat cattagaaat tatcatagct cgcggagatg gagaagcaac      180
taacagagca catggtggaa agcatgtcca ggtgcaggga ctatgccaag gccttgaagt      240
tgaatttctg taactgcggc ctgaatgaca taagtctctg cctcaagatg ccgtacctgg      300
aggtcctttc gcttagcatg aacaagatca cttcattgaa aagccggtg agatgcactc       360 gactgaagga gctgtacttg cgccagaacg agatagcaga ctttgatgag ctgaaatatc      420
tagtcaatgc caaatccctc acatccctct ggctgctgga caatccatgc tctattgccg      480
ctggctccaa ctatcgggca tctgtgctac gaatgctgcc gaatctaaag aagctggaca      540
acgtagatgt tgccgaagag gagctggaat ccgctttgcg atacgattac tacccggacg      600
tagggagtgc gatccttaat cctgttttgg atttaagcaa ctgcagtccc gatgacatgg      660
cataccgcga tatgatcgaa cagtgcgatc ggacgatccg tca                         703

<210> SEQ ID NO 65
<211> LENGTH: 609
<212> TYPE: DNA
<213> ORGANISM: Drosophila

<400> SEQUENCE: 65
ataaattcca ttaattgggc gcacaatgga aatctataac taacttagga tctacgtttt      60
agaatagctt ggcggccaga aggcaggcaa ggattgccaa aatggaggcg ttcagggcgg     120
agctgccgct gcggaatccg gcgacccagg tcatcagggg atccctgttg gaagccagcc      180
acgcgtagtt ggcattcacg ttgctatcca cgctatcctg cagagtgctg gcacatact      240 cagaacccctt gacagtgtcc accaactctt gcaaggcatc cttctgcttg tcgttgacgg     300
tataggcgga aatacccaca atgtcgctgt acagaggatt tacgccacca agccggaat       360 ttagctgacc atacttttcc cagttcttct gcaggaactc aatggcgacc agcagaccca      420
cctcgccgcg ggagtagacc ggactcagca ccgtgatcct ttcctgatcc ctcaaaccct      480
ctggctcaat gctgctgtac acgaacttct ctagctgggc agtgttctgg gagcagccca      540
gggcggagat cagaagacga cgctcggcct gatcggtgga gttcagcagc ttgttgaaca      600
caaagtcaa                                                             609

<210> SEQ ID NO 66
```

<211> LENGTH: 638
<212> TYPE: DNA
<213> ORGANISM: Drosophila

<400> SEQUENCE: 66

```
tgagcacagt gtggaaatga ttcggctact caagacgctt ctttattgcc tgctcctcat      60
ctcccctgct gatgtgctgg gccggcttaa tgccagaaag tcggcgaacg aggcgagtct     120
ctatagcgat acagacaatg tgattatgtt ggacatcgaa tcgctgaggc cagctctaaa     180
cttgaagaac agcaagctgg ttcagttcct caacagcttc tgcggtgact gtcatcgctt     240
cgcaccggtc ttcaagaccc tttcccgcga cctctacaag tggcgaagaa ttctccggat     300
ctatgccgta gattgtgccc aggagagaaa tgctcaactc tgcagggaat caatatccg      360
ccagacgcca tcattgcgat tctttggtcc cgacatgagg aagaacgatg atgttcttgg     420
agcggtaatc ccaggccaag atcccgagtt cattagctca acactggccg aattggtatc     480
ccaaaatgac tatgacccg gccagccaaa ctttcgtccc ctaaaagcaa cagactatga      540
aattttccaa gatcaagatg gggaaactcc gatacaattt gtggctcttg tccttcagcc     600
aaaaaattca aagatcggca gggacacgct gctagaac                              638
```

<210> SEQ ID NO 67
<211> LENGTH: 597
<212> TYPE: DNA
<213> ORGANISM: Drosophila

<400> SEQUENCE: 67

```
caaacctgct gaattcctga attacacaaa tataaattaa aaatatatat attttttgag      60
ataggaatcg agaaattgaa atagtaccaa caaaatggag gagctggata taacaagcgt     120
gggtcaattc cagaccctgg tgcgctacaa caacccggtg ctggtggtga agcacccgga     180
caagaaaggg ggtgctccgc tcacagagat agagatgaaa aggccccaaa cggcgggcgc     240
tttgctagat accaaagggg aaactgagga aattctaaat tctatattgc caccgcgctg     300
ctgggaggag gatggccagt tgtggcagca gtctgtgtcc agtactccag caacacgcca     360
ggatgtgatc aatttgcagg agatgcttga tactaggctg cagcagaccc aagctcgtga     420
gacaggtatt tgtcccgtgc gccgcgagct gtactcacaa tgtttttgacg agatcattcg     480
ccaggtcacc attaactgtt cagagcgtgg cctgctactg cttcgcatcc gcgatgagat     540
cgccatgtca atggaggcct atgaaacatt gtactgcagt tccgtagcct ttgcatg       597
```

<210> SEQ ID NO 68
<211> LENGTH: 680
<212> TYPE: DNA
<213> ORGANISM: Drosophila

<400> SEQUENCE: 68

```
ggaattttag tcatatctaa aatttcggca acataagacc ttccaatttt tgtttgtaaa      60
taagaacgtt ttttaaattt aacttcggtt tttgttctgt tgggtagtta gtttccgcac     120
tcgaaacacc gacaaaaacc atgtttcgca atctttcgat gctgaggaat cagctggcgc     180
tgcaccgtgt ccgtgtggcc cgctcgacct tgcactccaa aatgtctact ggtcttactt     240
gcctcaccat tgaccgtccg cggaacatcg atggcgtgac cgtgatagat atcaatataa     300
atgagatggc caagactgac gtagagttta atcgcaattt cgtcaattcg ctgacattga     360
tggaccatac tccattcaaa gaggtgacca acatagtgga cgcggatgca gttgagtcgc     420
caccagcaga gaatccgatt tctggagata ccgtggagat cctgcctact ggcgcaccta     480
```

```
gttccgtcgt aggcgtcgac ggcaacccca ttgtccccat cgagattgat ggctggaacc    540
aggacgagga ggatcccacc gtgcaaaaga acgtccagga cgtggacatt ggtaacgatg    600
acgagtacaa ggccgagatg gagctgcggg tgccggaggt catggaaggt cgaaccgagt    660
acaagggcat caaggtgacg                                                680
```

<210> SEQ ID NO 69
<211> LENGTH: 495
<212> TYPE: DNA
<213> ORGANISM: Drosophila

<400> SEQUENCE: 69

```
aaaaattgaa ggcaaacgtt gaagcaaact tcgctaaaaa aaattcgaaa aggcaaaaaa     60
aattcctttg tctagacagg gttgtgaata aagagaaaaa aaatcaaaaa tgtcaattat    120
accactgctg cacttggccc gggagttgga tcatgactac cgcaccgact gggggcattt    180
gctggaggat gacttcggtt ttggcgtcca tgcccacgat ctgttccatc cgcgtcgcct    240
gctactgccc aacaccctgg gactgggtcg tcgtcgctat tcgccgtacg agaggagcca    300
tggccaccac aatcaaatgt cacgtcgcgc gtcgggaggt ccaaacgctc tgctgcccgc    360
cgtgggcaaa gatggcttcc aggtgtgcat ggatgtgtcg cagttcaagc caacgagct    420 gaccgtcaag gtggtggaca acaccgtggt ggtagagggc aagcacgagg agcgcgagga    480
cggccatgga atgat                                                     495
```

<210> SEQ ID NO 70
<211> LENGTH: 434
<212> TYPE: DNA
<213> ORGANISM: Drosophila

<400> SEQUENCE: 70

```
ttagccagaa tgtaacggcg cctttcccgc tccaattgga atccgcgtgt aattttgtgt     60
ctcgtgttaa ttgtattatt tcccccgctt ttcggatttc cgcataaaaa gcgatgagtc    120
tacaggacga gagttttccg acggacgagc tgtttgacca gctgaacaat ttgagtagca    180
gtggcgccag gaatacctgg ttcgcggagc accataagcc cgcagtcttc gagcgggata    240
cagcgccatt tttggagatc tgctacgcgg atccagactt tgatgcggat ggggatgtgg    300
ccaacaagag cgccaagaca tgcgtaagcg atcccgtggg tcgtgatcag gaggatgagg    360
acgactatga tgaggatgtc gatggcgatg atcataaact gggttgcgag aaggctccat    420
tgggcagcgg gcgc                                                      434
```

<210> SEQ ID NO 71
<211> LENGTH: 525
<212> TYPE: DNA
<213> ORGANISM: Drosophila

<400> SEQUENCE: 71

```
tggtggtgcg tgtcctcgag ggtcacgagc ccgtggagtt taagcgtctc tttgccaact     60
ggttaaatgt ttggcaggag aacaccaggg gacataagcc agtgtccaca aagtttggaa    120
agctagatgc ccattcccta tgcgaacgcc ctaaaatggc tgcagataca cagctcgttg    180
atgatggcag gggtgaaaga gtaatctatc gtgtcttcgg agatcaggtg caagaggtgc    240
ccatctcaaa aacggttgtg ttcaccacca atgccagttt cgtggtcaag tacagcgtgc    300
agtgcgccac cgttgttccc gcagatttgg cctccgttgg cattaaaaca atcatctacc    360
```

```
agtggaatgg ttcggaggcc tctgtagagt ccatttcccg gcggacaag ttcgccaagg      420 ccagttttga tgggctcaag gagcctgtaa tgtttgtaca gctctatgag ttcgatgaac      480
caccgcactt ccttcagatc ttcgagggaa aacttattat catgc                     525

<210> SEQ ID NO 72
<211> LENGTH: 631
<212> TYPE: DNA
<213> ORGANISM: Drosophila

<400> SEQUENCE: 72
aaacagaacc acttaaaaat ctagttagga tttccactta tatagttagc acacatagtt       60
gcatatttcg ttacgcgata aaaatgtttt cgtttaaaat tatttcgcag tcctggagac      120
gtattaagca ctttaattag cggagctgca acggattgct gcaggaagac gtcacattgt      180
ttggagttgg atcgcgctcc cgctgtcgct gcctgctgga tctgtatgcg gatgatcagt      240
caatatcagt tcaggaccac gaaaccagcc tactatccag atcgccagcg ggaggcgaag      300
cgaacgtcag cgggagccac gcctcaacag gtgtcatctc cggctgttaa gtacccgcaa      360
agccgaggca tgcccaagga ctactactac aaagtgttag cgtcaacag gcacgccacc       420 atccagcaaa tcagatcggc tttctatgcg ctggccaagc gctatcatcc cgactcgacg      480
cactcggaac aaaagctgaa gcacttccag gagctgtcca acgcctacaa catcctaacc      540
gacgagacga agcgcttgga gtacgatcag ctgggcggga ttaaggatga gcgcgctttt      600
cttgaacagg cgggcaatcc cctaaatgtg g                                    631

<210> SEQ ID NO 73
<211> LENGTH: 698
<212> TYPE: DNA
<213> ORGANISM: Drosophila

<400> SEQUENCE: 73
ctaaaagtca caatcaagca tgcgtttcct ggtagtctta gcctgcctgg tggccgtttg       60
tgccgccggc actctgccca acgaggtgga gcagcgtctg ttggagctgg cggatcagaa      120
tggtgacatc gatctggtcg cggagcccca ggagggagtt gaagttgccc cccagtttat      180
tgtgtcctgg caggcgcgtc gcttcatccg caagctccag aagcagatgg agtgcggatg      240
gccccagtat ggcattcccg tgctggctcc tcttcgcatc aacgaattcg acctagacta      300
caaaaagggc attttcgaga ccttgaacca tgtgttccgc ctgaagatcg ccggtctgaa      360
tgacttcaat atccagaagt tcaagctgaa cgtgatcacc agcaagatta ccttcgattt      420
tctgttcaag aacatcgata ccaccgtcca gaagtacgac actgatacgc tgatcgatgc      480
cctgcgccag ttgggtctgt ccgtggagta cgagggatcc ggagagctgt tgttcgattt      540
ggtcaacctg cgtattgctg gcactctgaa gtacaagctt cccatgctgt ggggttccgc      600
caagatcacc tcgctgaaga ccaccatctc gttggagtct gtgacttcgg acatcactgg      660
attcatgggc aacggcaaga tcaaccgggc catcaaca                             698

<210> SEQ ID NO 74
<211> LENGTH: 591
<212> TYPE: DNA
<213> ORGANISM: Drosophila

<400> SEQUENCE: 74
atagaaatgc gcaacttcgt gatcatattt agcctatctc tggcatttgg catcgcctcc       60
gccaccgatt attgcaaaaa gagctgcgga agcaccaaga atctgggatg cgacaataat      120
```

-continued

```
ggagcctggg cctcaagctg tcccagtgac gccaccctgt tgaccctctc cagcgctgag      180
aaggatgcac tggtggccag gacgaacgag tatcgcaacc acatcgccgg cggactgaat      240
gccaatctga gtgccgcctg tcgaatggcc acgatcaagt ggaacgatga actggcttac      300
ttggccagtt tgaacgtgaa aagttgtcaa atgaaacacg acggctgcca caatacggat      360
gctttcgact ggtctggcca gaatctggcc tggatgggct actacaatcc gctaaatgtt      420
acacactatc tagaatgggg cgtcgatatg tggtacgatg aggcggtgta caccaaacag      480
gcctacatcg atgcctatcc gtcgaactac aatggtccgg ccattggaca tttcacggtg      540
ctcgttgccg atcggaatac ggaagtgggt tgtgccgcgg ccacgtactc c              591
```

<210> SEQ ID NO 75
<211> LENGTH: 643
<212> TYPE: DNA
<213> ORGANISM: Drosophila

<400> SEQUENCE: 75

```
agcgttcgcc tgtacagacc aaaatttcgt gtctctcaac ctgccacagc accggttcca      60
atccaaaacc tccgtttagt tatgtttctg gccaaaagtt catcaatact tcgcccgcag      120
cttcttaatg aggtgaaggg actagtgaag tcacaatttc tggctctgtc acaggtcgac      180
cgacgctttg cccactcgga cgataggtgc gccaataaga aatccaggaa gtgcgagcag      240
agcccaccca agggtgtagg tttgccccc  cgggatcgaa gacattctca tacgatggc      300
gtcagtgata agtgcgcgaa gaacaaaaaa gataagcggg agtgcaagaa gtttgagtcc      360
gagaatgcca aaagccgga  atgcaaaccg cccgttgtcc gtgctccaaa atactacaag      420
cagctaaaac cgtgcaagac cgacaaggag ctctccgagc tgcatcccaa gtatctgggt      480
gtatggggc  gttgcgacat accctacaag ccagagcccg attgcaccga tccctgtgat      540
ttggccgtac gtttggatga caagtactac aaacccagca atcgctgga  ccgcgaattc      600
gaccagtact gggtggagtg cttcttcgga agcagaaacg ctg                       643
```

<210> SEQ ID NO 76
<211> LENGTH: 606
<212> TYPE: DNA
<213> ORGANISM: Drosophila

<400> SEQUENCE: 76

```
agcggattca gttcgttaca cgccgcctct ttggaagcag gctacatttt ggcattccaa      60
tactaaaact tacacaattc cctaattctt ttaataaaat ttctaaaact gtaaaaaaaa      120
aaaaaatatc ttccgagaat ggttaacatc cacggtggca ctcggatgat ggtgaaccgt      180
tgcatcgagc tcctccgtgc gcggatcgaa tgcgcctcaa cgcgtcacat gccaggcgt       240
tcccagcggc ccagagtggg cagccaatac ctgccagaca tcagatact  cagggagcgg      300
gagaaagcgg atgtgtacaa gaagaacaag cgacgctcca tgtgggagca ggacgagggc      360
cacggacgca tctcggtcgg ggacgatcag gaacgcttcg ataacgagca gtaccatccg      420
cgcgaactgg agaagcgcaa gtacgagtgc acctgggtta atttcccgga cagtgtggcg      480
accaaacgaa atcgtagacg ggactttctg gagtcgatgg aaactgaggc tcctcgacgc      540
cgccgagccc aggaagaaag accgagtacg gcaaagccat gtgacgacga ggcccgtgcc      600
tttatc                                                                606
```

<210> SEQ ID NO 77

<211> LENGTH: 592
<212> TYPE: DNA
<213> ORGANISM: Drosophila

<400> SEQUENCE: 77

```
acattataaa atgtatattt attaattatg attatcatta ttcattacta ttataatgaa      60
ttaagtaccg aaaattttgt atatttccat agaaaacctt tttccctaga tatcaccgaa     120
tgctgccttg actggcaagt ccacagaaaa cgaatgtatg acttttctat gaattaggat     180
agcaaaaagc aagtaaatgc agtaaaacac gatagaaaat atgcccacgg agcgcctggc     240
gaaaaatccc agcgtcgtgg accatagaag agtggaaaac acacccaggt ttagaaaaat     300
gaatgcattt aagccgtaat tgcccgtttg gttagcttcc gagaccggga ggccaaatag     360
attcttgaca tgcatcacag tgctggcgga catgacaacg gtgaagaagg gtcctccaat     420
ggctgaggcg taggccatcc tgggatatcc gtgcaatgcc atcgccacgt tggcaattag     480
tggacccaga cttcccgtac aagccttcac cgttgcgccc ataaagtcgt cctccacctt     540
caggatgtgg ccaataactt ccaggacctt gtctatttcc gtcgcgcaaa tg            592
```

<210> SEQ ID NO 78
<211> LENGTH: 588
<212> TYPE: DNA
<213> ORGANISM: Drosophila
<220> FEATURE:
<221> NAME/KEY: misc_feature
<222> LOCATION: (1)...(588)
<223> OTHER INFORMATION: n = A,T,C or G

<400> SEQUENCE: 78

```
aaataaattt aaaaatcata gttcggttta tttctagtct gaattttacg cacggtagaa      60
aagttacttt aactggatcg gtttggaata tttaggtcaa cggaacaaga tactgagcgc     120
tgggattagg attcaaacag cactatggaa ttaagcccta ctgcccccgc agtttggctt     180
ccgtggattt ccttcgaact tcttcagctc acgaatcagg tcacaggatc ttggaacatc     240
tatgcagttg cattcaacgc cccgaggctt gcgaagacga gagcggctgc actcggagaa     300
ggaaggatan ggggccttga ctttgacgca ntcggtctta cttctaacga cgtggcaaga     360
gacgctgtct acggccttac agccgggcat cttgattcta gggcagggtc ctccctccgt     420
ggggcattcg acattcgtgg gacactcggc ggatgtcacg aacttcttgc gcttgcgcct     480
tgggatcggc ggacgaattc ncgcctcgta ncagcagatc ttcttgggct ttatctttat     540
gggcggacac tccacccagg tgacctgtta cttgcgcgtg gccttgtc                 588
```

<210> SEQ ID NO 79
<211> LENGTH: 669
<212> TYPE: DNA
<213> ORGANISM: Drosophila

<400> SEQUENCE: 79

```
ccccactgtt ctaaatttcc cattcggcta acatcatttt tctgattttt tttttggcgt      60
aaaattaaca cgttattaga gggaccctgt gattgcgcgg acatctaatc cataatcctt     120
tgaagatgtg cgacaagccc gcctgccccc cgcctccgcg atgctgtcct ccgccaccgc     180
ctccctgtcg cccgccgccc accttgtggc agaaattgaa ctgcgttccg tgcaaccgtt     240
ttgtgttctt catgatcggg gcgggcatcg gattattctg ggaccatatg aagaaggagg     300
cccagaaggc ggccgaggag gccgcgaaat cgcccaagga gaaggagaag gaggccaagg     360
agcgcgagaa gaagcagaag gaaaaagaga aggccgaaaa ggagaaggcg gagaaggaga     420
```

```
agaaggagag ggagaagaag gagaaggaaa agaaggagaa ggaaaagaag gagaaggagg    480
ccaagggcaa agagaagggc aaggagggca agtaacgact atagaccccc aaacggacat    540
gtcaaggagc aggatgtttt cccccaaaat tctcatcgaa tccatatcgt ttctaaactt    600
caaaattttc aagtgcatta tatggcatac ctaacgataa ctattggtca gtccattgcc    660
gcgttgatg                                                            669

<210> SEQ ID NO 80
<211> LENGTH: 412
<212> TYPE: DNA
<213> ORGANISM: Drosophila

<400> SEQUENCE: 80
ttaacacctt tgaaaatagt ttgtgtctta cgttttccgg tacctatttt ggtggttcta     60
agatcctatt tctgtaaata ggccaaattc cacttagctg ccctttaga aggaaattag    120 gatacccctga acgcttttcc ccaagacaaa ataaaatcga agatcatgtg ctgcggaccc    180
tgtggacctc gctgctgcga tccgtgcggg ggatgctaca actgctgcgt ggaactctgc    240
tgtgtaccct gcaccccagc ctacatccag tgctcattta tgccctgcgg accaagaggc    300
tgttgctgaa gtggggatgt gccaggtgcc gaaacacgtt caaccatatt gtacctgaaa    360
cactcgtaga tacccaacat gtcccaataa acgaattta taaatgttaa aa             412

<210> SEQ ID NO 81
<211> LENGTH: 523
<212> TYPE: DNA
<213> ORGANISM: Drosophila

<400> SEQUENCE: 81
cgtacgggtc acagatcagc tggcaataga aatacgaaac aaaattctca gtgttaacaa     60 aaaaatttg tgaaaaaata cgcgcgtgac caaatttag agttacgtgg ctcggaggtg    120
accaacaaac gtattaatat tatagaaaca ttgcgagtta tacaaaattt cctattcgtg    180
tgttcattgt aattctcaat ttgatattga tattgaagaa tgccttcgta caagaacatg    240
tctttggtgc gcgctggcct gcgtatggtg cgccaaaatc gttctggaca atctgtgata    300
ccgtcatatc gccgctatgc gacatcctgc aagagtccca agggtgttgt ggttggtgtt    360
tataccaagg atggcgataa gccatcgaaa accaccgcaa atgcagtgac cttggatgat    420
gctctgggtg gcaagctgtt gaccctgatc cgtgaacgtg aatggacgg cactcccgga    480 aagggtctgc tcttcagtgg cttcgagggt aataccagg cgg                      523

<210> SEQ ID NO 82
<211> LENGTH: 638
<212> TYPE: DNA
<213> ORGANISM: Drosophila

<400> SEQUENCE: 82
caaagcaaac cggcaaaata atctacgact ttccatggcc aaaaagtacc gaattatagc     60
ggaacttgga ggaaccatgg ccaagcgctt ttcttgccaa tgaaagactt cgcgcggtgc    120
aagaaaccgc gactggatgt tagcgttacc cgcggatcag cgcgacccag tccaccgagg    180
aacaatttcg atgggattct ctgggacgac gatgacgatg tcatcctgat ggccacccag    240
ctggcggaag cggaaatcga ggcggaggag cggaaaaaga agggcggaac agaagtggac    300
atcggcaaca gcgaggtcac cttcagcgaa tttgcaccca cttttcaggg ctcaaccagc    360
```

-continued

```
acacagcaaa tgtttccgcc gccaccgacg ccacaaaaga agcctacttc cctggatatg    420
gatgcgattt tcgcggatga tgatgatttc gattttctgg ccgttaccct catggacagt    480
gagccacaaa agatgccgga gccgaagacc agcacaagta ggataactac cagcagcata    540
agtgttcagc agaaaaccac gaccacgacg accatcaatg ccacgcaatc ccgccagcag    600
gagcatcaac taaagtttct catggataag attgaagc                            638
```

<210> SEQ ID NO 83
<211> LENGTH: 631
<212> TYPE: DNA
<213> ORGANISM: Drosophila

<400> SEQUENCE: 83

```
attttagcaa cgaaagccga caacacattt cgttcggtcc ttttttaaat atacatttta    60
cgttcgcaca tgaaacattt ttgaaacatt ttctcttttt tttttttttt tgggcacctt    120
gcaaaacttt tgaacgtggc tggtcaaaat tattagagac agttcgagag accaacattc    180
atacacttcg agagttgccg taaattgtaa aaacacacaa cagtcgtcaa aattgggcag    240
ataatagctc gcgtatatag tgcggtaaac ataataatac tatatactat gcgtggacaa    300
ctgttgctga agggacccgc attggcgagg agcttgagcc ggtgccgcgt aagtgccgtg    360
ccccaaattg gatctgttcg tcatgtgacc gccggctgtg cagctggtga taccgtcaag    420
ggcggcaaag gaatcgtctt gggcctctac gaaaaggagt cgggcaaggg acctcgatta    480
acgcctgctg gcgaaaagtt tgacgatcgt gtgcagggca agctatcgga attggtttgc    540
gaaaccaaat taactggacg attgggtcgc ggcaaggtct tcaacaatgt ggacagcgag    600
ttcagatcca tttgcgtggt gggcgttggt c                                   631
```

<210> SEQ ID NO 84
<211> LENGTH: 614
<212> TYPE: DNA
<213> ORGANISM: Drosophila

<400> SEQUENCE: 84

```
aagtgaaaca cgcacacact cggagaactt ttgaaacaca cataccaaaa caaaattatc    60
gtattggtct tccaatggac gaatttagag tacccaaaaa ggttaaccgt aacgttttca    120
aggccattag cattcttcaa tcttcccgaa ccgattttgt ctgcgctaat gcaatcgtcg    180
accaggtaaa gttccaaatg cggaaccgca ttccggtcga gcatatagat gaggccataa    240
aacagtcgct ggccaacttg accatgctgg gcatagtgcg gcgtctggga tcgtctaagt    300
attcgcttag caccatagtg tatggccggt tgggaatgcc caatcccatt gcacatccgc    360
cgggcaatcc tggtagacca catcggcgag ctgcgcagaa tgcgcgtcaa aagcgacctg    420
tcgggcgctt ggatccttgg aaatcggtca gcaagatctt gagtgaggac tctctgtctg    480
gaactgagat gaccaagatg cgcaagcgga tgcgcaccaa cacaaagcgc gttgtcaaga    540
agaaacgaat ccccaaccgt cgactatctc gagccaggaa gtataaagaa acagaaatgg    600
ccaccaccag tatc                                                      614
```

<210> SEQ ID NO 85
<211> LENGTH: 564
<212> TYPE: DNA
<213> ORGANISM: Drosophila

<400> SEQUENCE: 85

```
cggaactgaa acataggact agctcagtct tatttttatt cgtttcgagg ttgaacacgt    60
```

```
acacactttt agctagtctg ggtgaaaaaa tttcatgaat tattttgaag cggcacagaa      120
aatcgaagag aaagttttca atactagtag taatattatt cagcattcat caaagtttta      180
agttaaactt caagcaaaat gtttcggttt tctcgcaatg ccataacccg ggcgtgtagt      240
ctctccattc gtcggccgga ggtgatccgt catcgcaggt acgcctcgca ggcgatcaac      300
cagatgctgc agctgcagca gatggagatc tgcgcggatc ctccgtcgcg tggcttggtc      360
gttggagtct acgccgacga ggaggacaag aacgacgctg gcatcctgac gccaaccggc      420
tggaagtaca atgtgcagaa gacgcacggt cggttgctag aagtgctgcg aatgtccgga      480
cccatgccca aagggggaga gacccgcctc ctgttcgccg tggagccgga gcgcgtgccc      540
tactattcgg cggtggcagt tatc                                            564
```

`<210> SEQ ID NO 86`
`<211> LENGTH: 683`
`<212> TYPE: DNA`
`<213> ORGANISM: Drosophila`

`<400> SEQUENCE: 86`

```
ctgtacgata cgtacatctt tgtcagcacc gatcgcctga gccacagcat cctgctggag       60
ctgctgggtt acctgactaa tgagcagcag tatgctcctt ggtccactgc caacactatt      120
ctgaccgtct acgatcgtta cttgcgtggc gatgattctt actacaactt ccaagatttc      180
gtgaagcgcc tgatcgatcc catcttcgat aaaatcggtg taaacgagat tcccggcgag      240
cattatctga caactatctg cgcatcgtgc tggtcagctt ggcctgcca ggtgggatcc       300 gatgattgct ataaccagtc ggccaataaa ttatccgagt acctatacaa tggcacagcc      360
attgaggcca ctctaaagac tcaagcctac tgtgctggtc tccgatcgac taccaatgaa      420
atctatagca gagtgcagtc cgatttgctc agttcctcag attccaccga tcgcagcctg      480
ttcatctcct cgttgggctg ctctggaagt acgagccagc tgcttgattt cttgagacta      540
tccctggaca ccaacaatag cttgagctac tcggagcgca cttcccttct aaactcggcc      600
tattcccgca gtgaaatcgg tcttaccgct agtttggaat tcctggagag caactgggag      660
gcatatgcca acctttcaga ctc                                              683
```

`<210> SEQ ID NO 87`
`<211> LENGTH: 617`
`<212> TYPE: DNA`
`<213> ORGANISM: Drosophila`

`<400> SEQUENCE: 87`

```
aagaaaagca atccataaat ataacgtcat gaaactgtta atatggttgt gcctcctcgg       60
cttcctggcc agtgcctatg gcattttcct ggacaagatt accggtcgag gggattcatc      120
tggaaacggc tactagacg atatctttgg actcgaaagac tcggataaca gcagccacaa      180
caaaacctcc caacatgcat tgccagcgtc gggaattttt actccggtta aagtagctgt      240
tgacgttatt caaaatatat gggatgaatt ttctaaggga gttttaggcc ttatgggcag      300
ttttggtacc ggtgatgatg gaggcgaatc accgccgtct gggaatacag cgcctgtcac      360
aacagagtct agtttgccat cgcaagaaac cacaacgact agaacaacgc cgtttacaac      420
aacggaatcc agaacggaat cggtcttgga acaaccaca acagattcat ccacgagtac      480
tttgccgcca taaggagaaa ttctgtcgcc taaccttcgc atcggatatt gcttgtcatt      540
gtttgtttcc cagctgcttt ctgtctggtg tatttaaaca acgagaatgt aaatataagt      600
```
accagccacg cttaaaa                                                  617

<210> SEQ ID NO 88
<211> LENGTH: 448
<212> TYPE: DNA
<213> ORGANISM: Drosophila

<400> SEQUENCE: 88
ctcagtcggt tcagatcggt tcgttttaca attttccccg ctacagactt cgtaaacaaa    60
ttgtatgaaa atctgaattt gaaaatcaat ttttggctat ccacactcga gctacacaac   120
ctctcgtcaa aacttttaag tttacatcgc gacaaacgga acaacaggga atcatgagat   180
ccagcaaagt tcgtggggc aacgccagtc gattggctga cgcggaggga cagtggggaa    240
agggatgcct gggttcccag cactcaatta tcaagaatca cgggcgtggc ctttcatccc   300
aaactcccac gcaatttggt ggattctcgc cgtcgggaca gcagtatcct gccgtgtact   360
cgcagccagg attccgggcc gatggtaagc tgaaggtcac gcccaactcg ctgctccagc   420
agcagcaaca gcagcaacag cagcaaca                                       448

<210> SEQ ID NO 89
<211> LENGTH: 634
<212> TYPE: DNA
<213> ORGANISM: Drosophila

<400> SEQUENCE: 89
tttcgtagag ttaagaactc atcaaaaaaa atttaacgta aaaaaattgc ttattgcact    60
agaccccatt tcgactattt gttatttcca atttattgga aacaaatttt acgaacgat    120 aaattcatag tttttttttt ctctcgattt tggaacaaca ttttttttgaa gggtactta    180 cgtgtgcaga agtactggga caatgttcgg aaaaactcgt cagttgctat tcagcgtttg   240
cattcggtcc ccggtgtgcc gacgatatgt cccgaagttc atcaagcgtt catacgcctc   300
gcaggcggtt aaccagatgc tgctgctcca gcagatggac atctgtgcgg atcagccgtc   360
gcgagccttg gtcataggcg tctatgcgga tgaggaggac aagaacgatg ccggcattct   420 gaccccccgcc ggctggcgtt ataatcttca aaagacaaat ggtcgtctga tagaggtgct   480
ccggatgtcg ggacccatgc caagagagg cgaggcccgt cttctcttcg ccgttgagcc    540
ggagcgtatt ccctattatt ctgtggtggc ggtcgttggt ctgggtaagg agtgcttggg   600
ctataatccc tatgaggtcc tggacgaaca gaag                                634

<210> SEQ ID NO 90
<211> LENGTH: 474
<212> TYPE: DNA
<213> ORGANISM: Drosophila

<400> SEQUENCE: 90
ttctccaggg cacagacgac caggttcgag acaaaaatgc aaagtggccc actctaggag    60
tcgcgatgct atcaaaaatt ctacgtaaat atggtacaca gaacatattc ggcaatcacc   120
atccgcataa cacccatacg cgcaatccga gctgcccttg gaagtcggag tgcggatgcg   180
ggcacggatg cgtttgtggc gacgtccccg gcgattcgca ggtgatctgc gcggaatac    240 acgactggga tcggcgcagt gcggcacacc acgagcgccg taagatcatt ccgaaactgg   300
tgtatttgca caatccgtgg aagtacctgg tgaccaagtt caatctgtgg aagcttaagt   360
ggctctggga tcgggagttt agcgagcctg acttcttgga gggcgccaag caggcgggca   420
tcgtgatgac ggacatcatc cgtcagcaga gggccgataa gattagcgag tata           474

<210> SEQ ID NO 91
<211> LENGTH: 348
<212> TYPE: DNA
<213> ORGANISM: Drosophila

<400> SEQUENCE: 91

| | | | | | | |
|---|---|---|---|---|---|---|
| cgcttttaag | gcacaatatt | ttgggaattg | aacaaaaaat | ctttaatgaa | atgtttcaag | 60 |
| atttcccttg | agattgtcga | cataacatct | ggatatatat | ttatatacaa | tattttaatg | 120 |
| tttgtcaggg | ctgacttgtg | ataatgattt | tgagtaagaa | accaagcaat | tccgttcatt | 180 |
| atatatttat | atatttattg | tgaaaaaagg | agtgcgtcat | atatttatac | cagttctgtt | 240 |
| ttggatatat | gtatagggtt | agataagtgt | attctattca | acggttttgg | tttaattact | 300 |
| atgcatcctt | cacatgagta | ataactatca | gaccattcgg | ttacgggg | | 348 |

<210> SEQ ID NO 92
<211> LENGTH: 600
<212> TYPE: DNA
<213> ORGANISM: Drosophila

<400> SEQUENCE: 92

| | | | | | | |
|---|---|---|---|---|---|---|
| ctgcgaaggc | tgcgttggct | aaagctccaa | tagaatctga | ggagatgccg | gaagacgagg | 60 |
| acaaggagga | acttcattcc | gtggaatcgg | gcggagagga | ttccgaagat | gactttgaag | 120 |
| atataaaggc | catccttaac | gaaaagcccc | caagcgttgt | cgtcgaagag | gaaatcgaag | 180 |
| aggatctcga | ttcggaaggc | agctttgatg | agcccttgcc | caggctggga | gtgtccataa | 240 |
| agagtgagtt | tatccgcgga | tttgaaagtt | tgccaagcat | atcggatata | tcactcgatc | 300 |
| cggagccgga | accagaacct | gaaccggagt | taagcgctca | ggacaaatcc | gacaccaagg | 360 |
| cggacacaga | tgatggtgta | tttcacaaga | tggcacaga | tgccggcgag | ggcgagtcgg | 420 |
| ggagctcttc | gggttccgat | aaggatgcta | gcactgctat | aaatgcggcg | gctgagtcgg | 480 |
| aagaagacga | cgattccatt | ttgatggatg | atctggcgga | tgagcaagag | ccgacagaaa | 540 |
| aacgggtcgt | cattggggag | gaagtggaca | ccatggccat | gttaaccgag | gccgtcgatg | 600 |

<210> SEQ ID NO 93
<211> LENGTH: 533
<212> TYPE: DNA
<213> ORGANISM: Drosophila

<400> SEQUENCE: 93

| | | | | | | |
|---|---|---|---|---|---|---|
| aaactctaga | gccctaaaac | gatgcctaaa | agtagttatt | taccaaaaaa | catgcaaatt | 60 |
| ggttctgctc | gctaggtatt | aatcatttag | ttcatatgta | tacatataat | ttgccgtttg | 120 |
| caccgttttt | ccgtcttcct | accatccatc | tgtatataat | gcttatttga | tctgtgtata | 180 |
| tatagaattt | ctacttatgt | tccataatat | tcgttgtgtc | agattttac | tataagttac | 240 |
| gttttggatt | tccttctcaa | acctttgtt | tttgttttct | tgttcttac | gcctcccaat | 300 |
| cttcgttcag | taaagttgc | aacttggaga | gattttggaa | tagttcagat | tataagtgag | 360 |
| tagatataag | tgtgtgtgta | tataactgct | tgaagaagat | tctattgagt | tgagatccat | 420 |
| catcatcatc | gtcatcgtca | tcattatcat | cgtgatcatc | tgccatttaa | agaactactc | 480 |
| cgctagtaag | ccgatttcta | gactagattt | tggttgttta | taattctcat | ttg | 533 |

<210> SEQ ID NO 94
<211> LENGTH: 647
<212> TYPE: DNA

<213> ORGANISM: Drosophila

<400> SEQUENCE: 94

| | | | | | |
|---|---|---|---|---|---|
| ctctattgat | agttcaggtc | gatcgcttca | ggctcaagtt | atctataaat | tgcttacttt | 60 |
| tatgtgaatt | ctcgtgacgt | agcccgtgcg | cttttttaaa | attatttgtg | caagaaaaat | 120 |
| tttagactcg | tggacgaccc | tatatcgatt | gctaaccggc | caggatggag | aagtacgagt | 180 |
| gcaagccaga | gccggtggag | aagaaggaga | agccggtgga | agagctaatg | aactgggatg | 240 |
| cctactacaa | gaaccgcgga | ttggtcagca | cccgattggg | cagctgcaaa | gcggactaca | 300 |
| tgcactgctc | cacgtaccag | gagaagggta | atgcccagga | gaaggacaag | aagggtaagg | 360 |
| gcgcgtgctg | ttgctcctcc | tgtccggttc | gaaaccggga | agaggtatac | cagcccaggt | 420 |
| gcccggctcc | cggccagaag | ggcaagccca | acagggacta | catgcgctgc | tttgccgcca | 480 |
| aactgatcgt | tcagaagctc | aacatgcccg | gtagggactt | cgaatgccag | gataagctgc | 540 |
| agattaaggc | aaacgtgtgc | cgcgggtgca | agatctgcct | tggttccagc | agcatcaatg | 600 |
| tcaactgtct | tccactgaat | ccggacaaga | cattccagat | ggaagcc | | 647 |

<210> SEQ ID NO 95
<211> LENGTH: 532
<212> TYPE: DNA
<213> ORGANISM: Drosophila

<400> SEQUENCE: 95

| | | | | | |
|---|---|---|---|---|---|
| tttttttca | ttgaaatagt | ttattaaaaa | actaaactat | atcttctttg | atgtatttat | 60 |
| acagaaaaat | tattcatata | ccgatcatgt | ttaaaaatta | atcatacaat | ccaagatgtg | 120 |
| tatataatat | acaaattttc | aactttatgc | gaaattacaa | taaataaaaa | taagggtatat | 180 |
| aagaaatgaa | atctttcgcg | atatatgctc | acctcatgca | agtttaaggg | tatgtatata | 240 |
| ataattatgt | tagtgagttg | cgtgtggatg | ggtgtttgta | tatagttttt | tttaggtaca | 300 |
| ttggatgcgt | cgttaggtat | tttaagtggg | ctgtagcggg | tacaaaaagt | tagaaactaa | 360 |
| ctaatttaaa | agcgaatttt | cggatagaaa | tagtagattg | tgtagatgtg | tagagtagag | 420 |
| gtgtaaatat | aaattcaaaa | caatttcaaa | attttaacac | ttcgtttaaa | gttaatcctt | 480 |
| tttttggttt | ttttttttaag | tttcaacaca | cattactttg | ttacaatgtt | ag | 532 |

<210> SEQ ID NO 96
<211> LENGTH: 724
<212> TYPE: DNA
<213> ORGANISM: Drosophila

<400> SEQUENCE: 96

| | | | | | |
|---|---|---|---|---|---|
| agatcaaaca | gaccaaattt | ctcgttaaaa | aaaaaaaaac | tactaaaaaa | aattgttttg | 60 |
| gccaattagt | tttgtagatt | tcgttatcaa | gatgatgcta | tcaacctatc | agcacgacta | 120 |
| tgtcccgccc | agtgccaaac | ggtacgagtt | tctaacgcgg | cccaggggcg | ccgaggctca | 180 |
| cagtggtccg | caggtcaagg | agtgcgaatg | cgtcgacgag | tccaagatca | tgatgccgcc | 240 |
| gaacgcgtct | aaggactgtg | gcggcgtcga | gtggacgggc | atagcgccaa | tgggaaagct | 300 |
| ggtggatccg | cgtatcatac | ccacccagct | gactcaggac | caggtggaca | agatggcctt | 360 |
| ctccgcggaa | acagattgct | ttaagctgca | acccaaccgc | tttctcaaga | tcttacgtac | 420 |
| agtctacccg | gatctgtatg | aacgcctgaa | ggtcatgccc | aaggaggagc | tgagccgcag | 480 |
| gctggagacc | aaccgtatga | acaccaccta | tcagatcgat | tactgtaaca | tgaacgagta | 540 |
| cccggagggt | atttatgaga | gcctaaagac | ggaggacgag | tccaagaacg | ccaacaagct | 600 |

```
gatgagcgaa cgtggaccct gcaacgagtt ccgctcgaac gtgatgaacg aactggagcg    660
ggaggcgtcc gctggctacg agatgtctag cgacgagtgc caaaagaact acaagccatt    720
caag                                                                  724

<210> SEQ ID NO 97
<211> LENGTH: 611
<212> TYPE: DNA
<213> ORGANISM: Drosophila

<400> SEQUENCE: 97
tgtagaccca gaaatcgata gtgtatactt tagaccttta cagcttgcca cttctcctcc     60
agttggacca agatcagaat ggagaggcga agaccccgaa agtcctcgcg taaatacgtg    120
tgctccaaat caaactcttc agttggagga ggagtagagg aagacagtgg ctcatcattg    180
cctgccaccg ccaaagcgtt actcctccag ccggacggta ataaagcacc aaccatgaca    240
tcccttctgg gcgaacgact cagaagagtt tctcgcatcg caagagctcc gcacagccta    300
caagttaccg aaaatccaga agaagtggaa gcaccaatcg taccactaag agaatccggc    360
gcatcggaag tgtcagaagt aaatccgggg gttatggtca ttccggagtc ggccagtccc    420
cggggatcgg cggtgcatgg acaacacgct agcttggtct tcagtgctga agccagggat    480
tcggacagta cgcggatatc ggaggaaatg gtggaagtgt tccaaacctc ttcggcgaga    540
accacatcca atgagcccgc aggggcaat  ctgcgctttg aaaccactcc cgtggctgta    600
agcgaaagta t                                                          611

<210> SEQ ID NO 98
<211> LENGTH: 603
<212> TYPE: DNA
<213> ORGANISM: Drosophila

<400> SEQUENCE: 98
tgaattccgg aacgacaccg tgacgctcag aaacgcggcg caaacccag  agtggatttg     60 caggtttatg ttgcagttta cggctgaccg gactcgtata tgacgaaatt cgcgcagcgc    120
agcaaaaaga cgtgcgaaat acgcgggaca atggatgtgt gtgtgtgtgt gtgtgtgtct    180
atgtggaagg aaatttgtga gacctgcgac cgggaggcga aggagaagca gttcagcacc    240
tcggaatcgg aacgccacac gaaccgcggc ctgaatcgct atcgggatgt gaatccgtac    300
gatcattccc gcattgtttt gaagcgcggc agcgtagact acatcaatgc gaacctggtt    360
cagctggagc gcgccgagcg ccagtacatc ctgacccaag gaccgctggt ggacacagtg    420
ggccacttct ggctgatggt atgggagcag aagtccagag cagttctcat gctcaacaag    480
ctgatggaga agaaacagat caagtgccac ctctactggc ccaacgagat gggagccgac    540
aaggccctga aactgcccca cgttaaactc accgtggagc tcgtccgtct cgagacctac    600
cag                                                                   603

<210> SEQ ID NO 99
<211> LENGTH: 613
<212> TYPE: DNA
<213> ORGANISM: Drosophila
<220> FEATURE:
<221> NAME/KEY: misc_feature
<222> LOCATION: (1)...(613)
<223> OTHER INFORMATION: n = A,T,C or G

<400> SEQUENCE: 99
```

-continued

| | | | |
|---|---|---|---|
| ccagccactt | cggacagact | gatttccaca | tcaccgagtt | attataaata | aatcagaaag | 60 |
| acatctaaaa | tgggtttcga | accctctgag | gataaggcaa | ggcctggagg | tcttggcgtg | 120 |
| cgacactggc | aggcggttct | tctgttcgtg | ggcatgatga | tcaactactt | ccagcgggtg | 180 |
| aacatctcgg | ctgccattgt | gcccatgacg | cagtccaccg | cggggctcc | gttctacacc | 240 |
| tgggatacgt | cggacaagtc | cctgatcctc | agcagctttt | tctggggcta | tgtggtctcc | 300 |
| caggtgccgg | caggactgct | tgccaagcga | tttggagcca | agttagtgct | gggcctggcg | 360 |
| actgcaatcg | gaggtatttt | gtgcttcttc | catcccattg | cagccaaaag | cgggtggcag | 420 |
| agtatctgcg | ttctgcgcgt | tcttaccggt | ctggtccagg | gcacggttta | tccgtgtgtc | 480 |
| cacacgctgc | tggctaagtg | ggtgccacgc | actgagcggn | gactgctaac | cactggcgtt | 540 |
| tattcgggag | cacagttcgg | aacggctgtc | atcctggtca | ccagtggctt | catcttcgaa | 600 |
| tccagcatgg | gtt | | | | | 613 |

<210> SEQ ID NO 100
<211> LENGTH: 360
<212> TYPE: DNA
<213> ORGANISM: Drosophila

<400> SEQUENCE: 100

| | | | | | | |
|---|---|---|---|---|---|---|
| cgctgggaaa | aagattcgcg | aaagaagcg | aaaaaagcga | aagccaaggg | aaaactatga | 60 |
| taaaactatc | ctttccatgg | ggaggagtcg | tcgaaaatct | tccagaagta | gaaggcgacc | 120 |
| aagaagaaca | tggtggaatt | ggatcaggag | cagaacttgg | agcccatttc | actgtctcgc | 180 |
| aactatctaa | aactggaact | caactggcac | agatggaaaa | tagtatggat | atcaaaattg | 240 |
| aaaattttga | tatttcggca | caaggaaagc | tgttattcga | taaagcgagt | ctgacaattg | 300 |
| tttacggaag | aagatacggt | ttggtcggac | ccaatggaat | gggaaagact | actctattga | 360 |

<210> SEQ ID NO 101
<211> LENGTH: 917
<212> TYPE: DNA
<213> ORGANISM: Drosophila

<400> SEQUENCE: 101

| | | | | | | |
|---|---|---|---|---|---|---|
| gaaattcgcc | tgcgctacgg | ttctgctctt | ggccaccatt | cttggggccc | aggctgtgga | 60 |
| ctggaattcg | gtcaagaacc | tgaacatcga | gaccccgatg | cccaaggtcc | atggcgagac | 120 |
| cctgcccagc | ggtaggatta | ctggaggaca | gattgccgag | cccaaccagt | tcccctacca | 180 |
| ggtgggacta | ctgctgtaca | tcactggagg | agctgcctgg | tgcggaggca | ccatcatcag | 240 |
| tgaccgctgg | atcatcaccg | ccgcccattg | cacggacagc | ctgaccaccg | gagtggatgt | 300 |
| ctacctgggc | gcccacgatc | gcaccaacgc | caaggaggag | ggacagcaga | tcatcttcgt | 360 |
| ggagacaaag | aatgtgatcg | tgcacgagga | ttggatcgcc | gagaccatca | ccaacgacat | 420 |
| ttccctgatc | aagttgccag | tgcccattga | gttcaacaag | tacatccagc | ccgctaagct | 480 |
| gcccgtgaaa | tccgacagct | acagcaccta | cggcggagag | aatgccattg | cctccggatg | 540 |
| gggcaagatc | agcgactctg | ctaccggagc | gaccgacatt | ttgcagtacg | ctacggttcc | 600 |
| catcatgaac | aacagcggct | gctctccctg | gtacttcggt | ctggttgccg | ccagcaacat | 660 |
| ttgcatcaag | accaccggcg | gaatttccac | ctgcaacggc | gactccggcg | gtcctttggt | 720 |
| cctggatgac | ggcagcaaca | ccctgattgg | agccacctcc | ttcggcattg | ctctcggctg | 780 |
| cgaggtggga | tgcccggtg | tcttcacccg | tatcacctac | tacctggact | ggatcgaaga | 840 |
| gaagagtggt | gtggtcaaca | acggcgacta | agcgttgatt | ttgatcttaa | aataaacgtt | 900 | tattttttggg ttacaag 917

<210> SEQ ID NO 102
<211> LENGTH: 619
<212> TYPE: DNA
<213> ORGANISM: Drosophila

<400> SEQUENCE: 102

```
acaattgttt tgcagctcta tcggctacgt gcctcgcata cgtgtatttt tcatattttt      60
tgggtttcgt ttaaaccatt tgacttaata aatactagaa taaagaaaaa aaatcacact     120
acatggctac gaaaaaaaag tatagatagt ggtaaaagta ggagtactaa aaaggtgaaa     180
agcacaaaca gttgcgttga atagttggtt aaaaggatat atagtatata cgtatacatt     240
atatagggc accactcgct aaagaccaac aaacaaaaag gtattaatca aatataaaag      300
taacgagtta aaaaacgaaa gaaaaattaa ttgactctct ggctggcttg tgcgttgggt     360
tcttattcgg tgttttagat ttataaattc gtcatcaagt tttcggtttg ggatattcat     420
cggtattcat catctatata cagggctgga ttccggtttc gggttcgggg ttgcgtgtgt     480
gtaatcgggg tcctagattt ctggattcta ggccaccgtg gcgtactgac gcttctccaa     540
cgagacattt aatccattct caagctttag gatgatgtca gcctgcagct tgaaatctgc     600
ctccgtgtcc gtggagtgg                                                  619
```

<210> SEQ ID NO 103
<211> LENGTH: 650
<212> TYPE: DNA
<213> ORGANISM: Drosophila

<400> SEQUENCE: 103

```
agacaatcgg tttgaaaaaa agaaaagcca aaaaattatt tcgtttaaca gtgtctatac      60
agcttcctcg ttcatacgcg ttcctctaaa aataaaaagg ttaagagaat ggcattttgc     120
ggccacgtta cttcctctgg acaaatagtc ctgcgggatg agatcttcag cagcaggact     180
tgcattgcgc gctccccgtc atccggaggc tcactaaact ccatgtcttc gccgagctcg     240
ctcgcccaga acaccacacg cacatacttc ttcaaggacg acggtggaaa tccttcgccc     300
caatctacgg acaactggtc gctcggcgga ctcaagcgat cggagatcca gagcaacttg     360
gtgccctcgc tgtgtctcag ctcgcaggaa agctccctca actatctcag ccactgcaag     420
ggaattaagg tggaccgcca accagaggcc gcctatcaga actggtactc agccaagcag     480
cagcaattac tagagaagca gcggcgaatc aaggaggagc aggagttcaa gcagcagcgg     540
acggaggagc gcaagcagct ggccaggatg tgctacgagc agtggctaaa ggacaaggcc     600
cgccaggcgg caaacttgca gctggagagc cacatccaag acgcggccat                 650
```

<210> SEQ ID NO 104
<211> LENGTH: 657
<212> TYPE: DNA
<213> ORGANISM: Drosophila

<400> SEQUENCE: 104

```
gattatgttc agaaccttcc gcccggagtc atcgaagtgg gtggtctcca catcaagaac      60
cagaccagcc ctttgcccac gtatatacaa gaattcacgg agaagttctt cgacggcatt     120
gtgtacatca atatgcccta tattgagtat atgaatgacc agggattgaa ggctatgtat     180
acgatgattc acggaaatcc caatgttgcc ttcatttgga atgtggagca actagagcag     240
```

| | |
|---|---|
| ttgccggcca agaaaccaaa tctgttgacg cttcatgtga atcaatcact acagcaagac | 300 |
| atcttggcta tgcagtacgt caaggggttc ctgaatcatg agatagtttt cagtcttcag | 360 |
| gaggcaattc actatggagt gcccgtcgtc gtgcttcccc ttaaactaga ggaatttaat | 420 |
| aatgcccaac gtgtaatgga acgcaacttg ggtgtgatgc ttcaggtcaa ggaatttaac | 480 |
| caaagctccc tgtcggatgc ccttacgcga atcctggatg aggagcgttt cataagtgct | 540 |
| ctccaccagg cccagttgaa gttccggacc cgtccgcaat ccgcctgga attggctgta | 600 |
| tggcatgcgg aacaacttat cgccgaacca cgactattta acattttgc acaaact | 657 |

<210> SEQ ID NO 105
<211> LENGTH: 556
<212> TYPE: DNA
<213> ORGANISM: Drosophila

<400> SEQUENCE: 105

| | |
|---|---|
| cctgtacaac atgtgctccg ggttggtgta caacggcttc ctaagcacct accaaacgca | 60 |
| tccagccgac ctttgtcacc gccttccaga gtccatcagc atggaggcgg gtgcctgac | 120 |
| gcagacacta gcactggggt gccaggcgtg cttcaaggcc aatgtcacgc ccaccagcaa | 180 |
| cgtcctcatc ctgggagcct gcccaacggc tgtggcggcc ggcatatgcg caaaggccat | 240 |
| cggggccaag cgtgtggcca ttgccggatg tatggctccg gctctggatg tggtcgcccg | 300 |
| ggacttcggc ttccaagcag tcgagttcga tagcaacgca ctgttcggag aggtccttga | 360 |
| agccatctac agcaagttcc gggattggcc ggactgcgta atcaactgct ccatctctgc | 420 |
| aatgacgatg aatctggcgg tcatggctct gcagccatgt ggggtgtgtg tgctggccga | 480 |
| gtgcgattca gagtgtgcca gcttcaatgc tctggacgta ctgatgaaga acatccgcct | 540 |
| agtgcccagt tttcgt | 556 |

<210> SEQ ID NO 106
<211> LENGTH: 629
<212> TYPE: DNA
<213> ORGANISM: Drosophila

<400> SEQUENCE: 106

| | |
|---|---|
| aagcaataac atgcagtctt ttacaattct aacccttttc accatcgttt tgatggtcca | 60 |
| aaattcaaga gctggaactc tcagcattgg gtccctgatg ggagatgtgt cccaagtggc | 120 |
| tgttgctggg gagaaggtca tccatcaact ggaaaacgct gtggccagct ctcaatcgga | 180 |
| ttttgtccag ccaaccactt tgaacattct aagcgacatg ggaaacgcct gggtgatct | 240 |
| ggctaacgcc cttactagtt taagagtgga taacgattat atgcaacccg aggccaccaa | 300 |
| tctcttgggc aatgttctgg gtggagtggg cactggtctt ggagatttgg ctaatgccat | 360 |
| taccagtctt agtgttcaga tgacgaacgc acctcaggct cgcagtcttt cgtccaatgg | 420 |
| tgcttctatt atagccaaag gaggagccgt gagtgcgaag actattgccg ctgctgcaga | 480 |
| tgcagctgcc cctatataa agcagctaaa tgctggccta gcgatctgg ctaatgccct | 540 |
| caccaacctc tgaagaactt tggagcagtt caattaacaa ataaatattc aatcgcgcaa | 600 |
| agagcttaaa aaaaaaaaa aaaaactcg | 629 |

<210> SEQ ID NO 107
<211> LENGTH: 639
<212> TYPE: DNA
<213> ORGANISM: Drosophila

<400> SEQUENCE: 107

```
tccatccgta attcagaaat aagaaaacga tgtctcgtcg ttcgaccgtt ttatcaactg      60
gtaaggagag ctccaaggag gaaaagaatc gaatgtccca attggacgtt attatcggtc     120
aactgaagac gatggcggtt ggaaaccgga gggccggaaa tctatccgag gccaccatca     180
catatatatg ccaggcgagc cgagagctgt ttctatccca gccgatgctc ctcgaactga     240
gtgctccggt aaagatctgc ggggatctgc acggtcagtt caaggatcta ttgaggatat     300
tccagcagtg cggtgtgcca ccgctttcaa actacctatt ccttggggat tacgtggatc     360
ggggtcactg ctccatcgag actttatcgc tgctgttgac ctataagctt cgctatccgg     420
agactttctt cctgctgcgc ggcaatcatg aatcggcgga tttgaatcgg tatatgggt     480 ttttcgacga gtgcaagcga cgatatagca tcaagttgtg gcgctccttt gtcgattgct     540
atgactgcat gccagtggcc gccatcatag ccgatcgcat cttttgcgtc cacggcggac     600
tgagtccgga tctgaataac ctggatgaca tccggcggc                           639

<210> SEQ ID NO 108
<211> LENGTH: 575
<212> TYPE: DNA
<213> ORGANISM: Drosophila

<400> SEQUENCE: 108
cgattggagg attctccgcg agatattcgc atctacagtt ccgatcgcca aaagtgcaat      60
gtgaatccgt gcaggatcaa caacggcgga tgtgcccaga gctgtcatcc tgccccgaat     120
ggcaaggccg agtgcaagtg cgacgatagc accaaggtgg tgaacgaggg aaggatgtgt     180
gccccgcgaa acaatacttg cgaggccagc aaattctact gcaagaacgg cagatgcatt     240
tcgagaatgt ggtcctgcga tggcgacgac gactgtggcg acaactccga cgaggatccc     300
aactattgtg cctatcactc ctgctccccc aacgagttcc gctgcaacaa cggacgctgc     360
atctttaagt cgtggaagtg tgatcacgag aacgactgca aggatggttc cgatgagctg     420
ggctgcgtct atccaccatg tgtggatggt gagttcactt cgccaatgg acggtgtatt     480 ccacaggctc aagtgtgcaa tggtgtgaat gactgcaagg ataatgccac atcggatgat     540
acgcacgaac ggtggtccat gaacaccact tgtcc                               575

<210> SEQ ID NO 109
<211> LENGTH: 563
<212> TYPE: DNA
<213> ORGANISM: Drosophila

<400> SEQUENCE: 109
tcaaaccatt actcctacaa ttattgggtt ttcccaagcc aaacaacaca tgcttttgag      60
gattttagat cagagtctca ctattccatc gcgatggaca gggattcctg ccaaaatttc     120
tcattagact ccacgagcag ttcccatttt gctcctccgc cagtttgcgc gcccagaagg     180
aagaagccgg agaagcccgc agctgaggag gcatctcccg aatgctccaa cgtcacatcg     240
tcatcctcgt cctcgacaac caccatatcc ataggcgcct tcgattcgca atgcaacctc     300
cacaacgccc ggaatcccga ggccccgaac attggctatg agttgaacgt ggccaagtcc     360
atattgcaga agtatagcac cctcagtggg acaacttgt tcgatcatct tagtgacatc     420
ataaagaggg tgattgacga acgtcctccg aatgtgatag acttcttcga ggaatttagc     480
cgaaatgttc gcgaacagaa gttccacttg ccagaacgct ttccgccag tggcgtgttc     540 gatgaggtgc gatctttccg ggt                                            563
```

<210> SEQ ID NO 110
<211> LENGTH: 472
<212> TYPE: DNA
<213> ORGANISM: Drosophila

<400> SEQUENCE: 110

| | | | | | |
|---|---|---|---|---|---|
| cagacattgt | atttcgatta | aaaaaacaaa | aaaaatgcca | gttttgaaac | ttaatgctta | 60 |
| tttcaccaaa | ttcttcccat | cctcgatggt | gcgttccaag | gagttggtgc | gaagaaggta | 120 |
| ttcgatgaag | gtcgcgcagg | tgcgaagatc | ttacaacata | aagttcaatg | aagatccaga | 180 |
| attcgaatgc | gatgccacag | tcacgaatat | gccccaatcc | ttgaagacta | tgattaagag | 240 |
| gaaactgctc | tcaaagcgtg | tgatcggtac | ctttcgacta | agattccata | gcaattcgtt | 300 |
| taagaaaagg | ctcgagatca | cagccacaat | aaccaaccca | acagttccgt | cggacacaga | 360 |
| tctcgctccg | gaggatgagc | agctgtacga | gctgtacata | tgcagtagcc | agggtcaatt | 420 |
| gctgggcaag | attcccttcc | tggagagcga | ctaccggcgt | gcagctcgcg | ag | 472 |

<210> SEQ ID NO 111
<211> LENGTH: 529
<212> TYPE: DNA
<213> ORGANISM: Drosophila

<400> SEQUENCE: 111

| | | | | | |
|---|---|---|---|---|---|
| aatagcctgc | cgaccttcag | atcggtgggc | ggtgcttatc | gtctgcttgc | tggcaaggat | 60 |
| cagaagaggg | attccgcggg | gcacaagacc | agacagccgg | aaaagccacc | acaagataag | 120 |
| cagaagagta | aggtgctag | tgcaaacca | tagagtgctg | ggtcaactga | ctccgacaag | 180 |
| aagaccacca | aggttaccct | gatcaacggc | gagggcgtgg | gacgcgagct | gatggacgcg | 240 |
| gtgcaagagg | taatctgtgc | tgtgaaggcc | ccaatagagt | gggatgtcca | cgatgagttc | 300 |
| aaggccaagg | acagcgatga | tgtgtacccg | gaggttctta | agtccttgcg | agccaataag | 360 |
| gctggcatca | atggacccgt | ggatagtcat | cactggcagc | gcctgatccg | caagcagttc | 420 |
| gaccaggtcg | tctacgtgtc | attgcgctcc | cacatcgacg | gactggactc | gccctacggt | 480 |
| gacttcgacg | ttgtgatcat | ccaggaccag | atggagggcg | actactttg | | 529 |

<210> SEQ ID NO 112
<211> LENGTH: 881
<212> TYPE: DNA
<213> ORGANISM: Drosophila

<400> SEQUENCE: 112

| | | | | | |
|---|---|---|---|---|---|
| cagagaactc | aaaatgaaac | aattcgcggt | tatattcgca | ctggctctgg | cttcggtttc | 60 |
| ggccatttct | gtccctcagc | cgggattccc | cgaaggtcgc | atcatcaacg | gctatgaagc | 120 |
| ggcgaaggga | gaggcgccct | atattgtgtc | cttacagacc | acatccaact | cgcacttctg | 180 |
| tgcaggaagc | ttgctcgatg | aggtgaccat | tgtgaccgcc | gcacactgcc | tgacctacaa | 240 |
| tcagggtcag | gcagttgccg | gtgcacacag | ccgcactgac | caggagaacg | ttcagattag | 300 |
| gaagttcacc | aatgcccagt | acgtgatcca | cgagaactac | ggtggcggtg | tgggacccaa | 360 |
| cgacatcggc | ctaattctcc | tcaaggaaga | ggatgccttt | gacctgaatg | ccgttgcccg | 420 |
| tgatggcagc | aatccggttt | ccgcagtaag | tcttccttca | aagacattcc | aaggcactag | 480 |
| cgatggatat | ctgtacggct | ggggccgcga | caactcagga | ttgctgccgc | tgaaccttca | 540 |
| gaaactggac | gctatcattg | ttgactacaa | cgaatgcaag | gcggcgttgc | catccaacaa | 600 |
| ttcgctggca | gaaaccaatg | tatgcaccca | cacccccgga | aaagccgacg | gatcctgcaa | 660 |

```
cggagacagt ggcggccccc tggtctcgca atccagcagt cgaggagccg agctgattgg    720
catcgtctcc tggggataca caccctgttt gtccacaacc tatccttccg tatacacatc    780
agtgtcttca tttttgcctt ggatcgatga gaaccgtaag gcgaaataga caaaaaccta    840
ttctcttata taaccactta ataaacgaac attctgtact c                       881
```

<210> SEQ ID NO 113
<211> LENGTH: 500
<212> TYPE: DNA
<213> ORGANISM: Drosophila

<400> SEQUENCE: 113

```
cttaagctct atggcttagt acattcgttt ttcgttaccg atttcaaaca attgaacttg     60
taaaaataaa agtattaaag ctaactaaaa attttaagta tatacaactg ccgcagtaac    120
gcaggatacc aataacccat tgacgtaatg cattcagccg gtaggagcag tgggcaaagt    180
gcgggctcaa caccccgagg tggaggaccc aacaccatct ccggggccac agtgcgttcc    240
aagttagcgg cacctctatc gacgcagacg gcgggaacac ggcgaactgt tcacggcgga    300
gcgggcgatg ggggaaccga tgcggcttgg aagcagaccg gtcgtcgcct tggcaagcat    360
aatccacctt tcggctggt ccagcccacg gtagcctctt cgctgagggc cagcagcaac    420
aggcagacgg ccaagcagaa gttcgagaga gcgagaggac atgagaagtc cagattagtg    480
gtgcccttgg ccaaggacac                                                500
```

<210> SEQ ID NO 114
<211> LENGTH: 507
<212> TYPE: DNA
<213> ORGANISM: Drosophila

<400> SEQUENCE: 114

```
gttcagttgc gggtgaaaat agagtctttg acgtacgttc aagacaataa ttggacacat     60
aacccacttc ttgtttgcac aagtgaacca ttctgtgttc ccagttgaaa gggaaacccc    120
aataagtgca gaatgacgag tgcaagtcta ttgtcgcgtt ccctgctaac agaagctccg    180
cgttctaaga atcgctcggt gtttaccttg attgctggtt tggtggtcgg ctactgcctg    240
gctcaaatct tctccagcat tgcgccgcac gagagtctct atccgtatct cagcagacgg    300
ttcagcgatt cccaggtggc caccggtggt caattggctc cggagcagag cgggttgaag    360
catgatcatc gcaacgacaa cgtcagcgtg gccgagcagt tgaagaagga ggtacgcatc    420
ctctgctggg tgatgaccaa tcccacaaac cacaagaaga aggctcgcca tgtgaagcga    480
acctggggca agcgctgcaa catcttg                                        507
```

<210> SEQ ID NO 115
<211> LENGTH: 575
<212> TYPE: DNA
<213> ORGANISM: Drosophila

<400> SEQUENCE: 115

```
aagatggcca ttaagtgtct gattttgctt acttccctgc tgggaataag ccttgcagcg     60
gactattgtg ctctgcccac gtgcctggac aagcacatag cctgcaacaa caagggaaat    120
ttcagtgaaa attgtcccaa ggacgtgcgt gaggtgaaga tcgagccgca tcacaaactc    180
atcctcaatc tcttcaacga gctgcgcaac aacgtggctg gaggcaaaat agaaggacta    240
cccaaggctg ttcgcatggc caagatgtcc tggtgcgagg agctctccca tctggccttg    300
```

```
ctgaacgtaa agacctgtga gtccctgcca gataaatgtc gcagcaccga gagattcgcc    360
tacgccggcc agaacaacgc cttgttccag tacagcggag ccgagacaga gtacaccgat    420
gcggaaataa taaggagca gatcgagaac tggtttgctg agcgctcgaa tgcatctccc    480
gagatcctcg ccagcttccc ggaggagctt cccaacaagg cggtgaccaa gttcaccatc    540
gcggtggccg agaagaacac ccatgtggga tgtgc                              575
```

<210> SEQ ID NO 116
<211> LENGTH: 609
<212> TYPE: DNA
<213> ORGANISM: Drosophila

<400> SEQUENCE: 116

```
gtagccagca taaaaacttc aaaatcgaga cctattgtac ttttcaataa aatttccgaa     60
gccttggtta acttgtagaa aaataataac attcccggta cagcatgaaa atagaatctt    120
agatttcgag gacggtagta cggttgcgga ttgcaggatg gaaaccttcg ccgtcaagga    180
ctgcaatgta tcagcgggta ccaccttctg cgccagcgcc aacctgagca caacaactct    240
tctctggcat ggtcgcccat gcaacaccc agcctggaca cttggaccca gtcaccatga    300
tcgacgaagg aatgctcgtc accaacgatg taacgataaa tatcaccgac gaaaagggaa    360
taagccataa tatcaggaac ttacctggta tcatataccg aaaaaattaa aataaatggc    420
acccattacg tcaacaatat ccgaacatca agaagaaag cctcagtttc agctatggcc    480
caagtaaacg ttctgagaca tctagagcgt cttagtctgt catcaattca cggaatgagc    540
gttaaaaatc tgcaacacat ccaccttcaa tcccgactgc catcaggcaa cacctggatc    600
ttttgctct                                                            609
```

<210> SEQ ID NO 117
<211> LENGTH: 611
<212> TYPE: DNA
<213> ORGANISM: Drosophila

<400> SEQUENCE: 117

```
ccaacagagc aagagccgga tagacagagc cccaaacctt tgcgcagata acagcaaga     60 gtgataatcg aatcgagaca agatgtcgga tcgcaaggcg gtgatcaaga acgctgacat    120
gagcgaggag atgcagcagg acgctgttga ctgcgccacc caggccctgg agaagtacaa    180
catcgagaag gacatcgccg ccttcatcaa gaaggagttc gacaagaagt acaaccccac    240
ctggcactgc atcgtgggcc gcaacttcgg atcctatgtg acccacgaga cgcgccactt    300
catctatttc tacctgggcc aggtggccat tctgctcttc aagagcggtt aaacgcatct    360
cgacgcctga tagccgctct accatggcgc ccaccaaagt tttccggagg agtcgccaaa    420
cactattgtt ccttgaattg taaactcatg cacacttacg aatccacact cacacatacg    480
cactgcactg cattgacaca cgcacacttg acctcgcgtt gattcgtttt ttcccaaatt    540
ccaaaaactt cgctgtgctg acttagccac tctgctgcca aataaatcaa atactggtcc    600
tgacttcaaa a                                                         611
```

<210> SEQ ID NO 118
<211> LENGTH: 567
<212> TYPE: DNA
<213> ORGANISM: Drosophila

<400> SEQUENCE: 118

```
cattttcctt tgccattgtg gagcggtatt tgcacaaagc cttggattga ataatgatgc     60
```

```
cggcgggatc agaggcaaac ggagaaggaa tagcttattt ccagattgaa attctcttgt    120
tggcaaaaat tttgaaacgc ttagggcctt agcaagtgat agatacaggc aactgggata    180
gtaagggcac tttgttcatt cttttaaaaa attccctctc gcaaagtttg aaatttcatt    240
tttgtaagaa aaaaattgct ggtaaagaaa gcttctaaat taaatcaaat taaatataaa    300
ttaaacccat aattcttaag catggcaaag ttttccgtg attttccag cacttgcctg      360 caagttgaac ccctaatcac tgcccttcgc ccaaattgca gcagcgtcat ttcagcgctg    420
ggttgccaat tgacgtggcg gtaagtcacc tctattgcat aacacctgac aaatgcaatt    480
caggcaaaat gcttcgacga tgccgatgat gatggcctca agtgaaaaac actcacgcaa    540
acacgcgacg cactttgagc tctggat                                       567
```

<210> SEQ ID NO 119
<211> LENGTH: 465
<212> TYPE: DNA
<213> ORGANISM: Drosophila
<400> SEQUENCE: 119

```
ccaagcaagg cgaatttatt tatgccacta agcgtggtat tgtccgtaaa gcgtctccaa     60
gagacaggaa tgtcgatcga atttgacaaa gcggtgtaa ccatttcgaa aaatgggtta    120
atggttgtca aaaattcaga gaatcaactg gctgacatat ttacaaaacc gttgcctgct    180
gcgagatttg tggagttacg agacaaattg ggtttgctgc aagacgacca atcgaatgct    240
gaatgaaatt tttatatata tttttcaaat ttaaattcct gtaaacatat tttgttacaa    300
tgatctgatc gggtttttct gggttttccc cgtatcctcg cagcaaatgc tggatcagtt    360
aacacttccc agaatgcaca ccacccacat ttgataggta ctaatgaata ttattggtat    420
gtttttaatt atagacgtta tttttgaggg ggcgtgttgg aatat                    465
```

<210> SEQ ID NO 120
<211> LENGTH: 528
<212> TYPE: DNA
<213> ORGANISM: Drosophila
<400> SEQUENCE: 120

```
ccgacgttag ccactggcaa cgatgacaac gaccacatca cctagagaaa ccacacagac     60
cacatttacg gttcgcaaga tgacgggccg gcgaatgtca aagctatcca cagtcctgct    120
gttctgcgcc gccttgctgc tgaccaagtc ctgcggcatc ctggcgctca gcggcgacgg    180
tttgccccaa tcccaggatg tgggccaggg ggagctatgg agcgatgatg ccaccaccac    240
catcatttcg cccagcgagg agaacagcgg ttccggtggc tgggaactga ccacggaggc    300
ggacaccacc ataccgagtg aggaaactac tgcgggcaat gaggaaacca ccgtttccga    360
agaggagacc tccacggacg cctctggaga tgtagagacc accactgctg cgccggaaac    420
ttcaccagct gaccaggaga gctcttccgc tcccgaagag accacttccg ctcccgaaga    480
gaccacttcc gctcccgaag agaccacttc cgctcccgag gagagctc                 528
```

<210> SEQ ID NO 121
<211> LENGTH: 639
<212> TYPE: DNA
<213> ORGANISM: Drosophila
<400> SEQUENCE: 121

```
ttgaatcaca ctttaaagac aagggatata cccctaaaat atcacataga acactatgca     60
```

-continued

| | |
|---|---|
| ttggtatgca atcctccaag gattcctcct gggaatatca tcgataatca ttttatgggt | 120 |
| acaaggagtc gttggcttgc cattggctac aaccgatctg gagtcacttc caatcgtctt | 180 |
| ggcagaggat gttccggtgg agagagctcc aaggcaagta aaaccagatc cgtcgacgtt | 240 |
| cgatattttc aaggtggatc aaagctccaa taaccaaatg cagcagaaat ccgacggctt | 300 |
| cagagtgttc gcaaagaaac tacaggatga ttatcaccgt agagctggct acaatgaaac | 360 |
| taatccgcca ccaattactg tgacccgagg aagcactact gctcctaaga aaatccataa | 420 |
| aagtggcatt cgactatttg cttctccaca agatccacct ccgcctgaag ctgcggcgcc | 480 |
| agctgatgga gctccagcgg cggcaggagc ggctgaagga ggtgccgccg aggaaaagg | 540 |
| aactgaacca cccaaagagc tgaccgtcag tattcaacaa ttcgttacaa accaatatgg | 600 |
| tgagaaggaa tacaatgctt ggggcgtcac ttttggtag | 639 |

<210> SEQ ID NO 122
<211> LENGTH: 596
<212> TYPE: DNA
<213> ORGANISM: Drosophila

<400> SEQUENCE: 122

| | |
|---|---|
| atttcaaaag taaacacata atattcacaa tagtgtatca ctttaataaa attttttggtt | 60 |
| accatggcga tggaaactat tttggggatc aagggaccag actttgtgat gctagcatca | 120 |
| gatacaatgc aggccaaatc gctggtcttc atgaaagatg accaatcaaa aatccaccga | 180 |
| ctatcagact tcaatatgat ggccacggtg ggtgatggtg cgataccat tcagttcacc | 240 |
| gacttcatat ccaaaaattt gcatctgtac aagatttccc acggatacca tctaagtgcg | 300 |
| aagtcagctg cccatttac caggaaaaca ctggcggatt atataaggac caacaccaga | 360 |
| taccaggtgg caatgctcct ggcaggatac gatgcggttg agggacctga cctccactac | 420 |
| atcgactcct atgcgctgc tcagtcaatc aatcatgcag gtcatggttg gggcagcatg | 480 |
| ttctgtggca gcattctgca gagatattgg aactcgaagc tcagccaaga ggatgcctac | 540 |
| tcgctgatga agaagtgcgt cctggagatc caaaggcgac tgatcatcaa ccagcg | 596 |

<210> SEQ ID NO 123
<211> LENGTH: 535
<212> TYPE: DNA
<213> ORGANISM: Drosophila

<400> SEQUENCE: 123

| | |
|---|---|
| gttctagttg ggagcacaca ctttctgaaa ttgttaacgc ataaatcctg ctgttttacc | 60 |
| taaacttttg caaacataat ggccttccgc tcggtggtta cgatggagaa gccgctccag | 120 |
| cacatttcgc tgacggactg gtatgcccgt gtgaaccaga tgcggaatgt ggcggatgcc | 180 |
| cggaggtcgg acgccttcgc catccgccac tcatcccgat ccttgaggaa cgagacgcgg | 240 |
| atcgagggcg actgggccaa ctacgagaca atgaggctc tgaccgatcg catctccgag | 300 |
| ttgaatcgct ggcgggatat catttccaag tccttcgaga agatcgagcg cgagatattc | 360 |
| atgctgcagg aggagaagaa tgccacggaa cgggagctgg aggcgttggc aggtccgatt | 420 |
| tccgtgatag ccgagtgcct gaccataagg gacggtcgcc tcggatcgga gatcacctac | 480 |
| gatgaggccg acaccgagat caagaacgaa ctggtcgtgc tggagaacaa ccagc | 535 |

<210> SEQ ID NO 124
<211> LENGTH: 544
<212> TYPE: DNA
<213> ORGANISM: Drosophila

<400> SEQUENCE: 124

```
gatgatatga ctatgccatc atttggaaga tcttacggag gacctgctac taatgaatgt      60
cttgaggata tatcgatgcc ttcatgtggt gaaaatacag gatcgtctat aggatttagt     120
ccaatgcctc tagaaagcac aagacgcgga gcgttgatgg tgcaccgatc cagacgaggg     180
acgatgacta acgaacggct ggatgacatg acgatgccct ccttaggtag ttcagaacat     240
ggacaagcta caagtgaatg ccttgaagat atttcaatgc cttcatatgg agcgaattca     300
ggaatgtcta aaagaaagtg ccctacacca ccgaaaagaa atactccgaa tgttacaaca     360
gagtgtttga atgacatgac catgccatcg tttggtgatc caagtcatgg aaacggattt     420
ggtgaatgtc ctgagtcctt cagattgatt acagataaga agttacaatg cccgatgacc     480
agcgaaaact tggataatat gactatgcca tcgcttggta ctttaggcca aagtcaagcc     540
taca                                                                  544
```

<210> SEQ ID NO 125
<211> LENGTH: 507
<212> TYPE: DNA
<213> ORGANISM: Drosophila

<400> SEQUENCE: 125

```
agagcgcgag tttcttacct tcagcaagac gggactgact ttccccgaag acaccacatg      60
gattctgaca atcaactacc agggacatct gcgcacagac aacggaggat tctacctatc     120
cacatatacg gatgaggagg ggaacaccaa gtatctggcc accacccagt ttgagtccac     180
tgacgcacgg cacgccttcc cctgctacga tgaaccctcg aagagggcgg agttcactat     240
caccattaag cacgatccaa gctacaatgc catcagcaat atgccagtcg attcgagcag     300
cacctctgga gtcaccgtct tccaaaagac cgtaaatatg ccatcctacc tggtcgcctt     360
tattgtgtcc gagtttgtct ctcggaggg tgagctaaat ggcttgccac agcgcgtctt     420
ctcccgcaat ggaaccgaac atgagcagga gtgggctcta accaccggaa tgctggtgga     480
gaagcgtctg tccggctact ttgatgt                                         507
```

<210> SEQ ID NO 126
<211> LENGTH: 615
<212> TYPE: DNA
<213> ORGANISM: Drosophila

<400> SEQUENCE: 126

```
ccacaacgtg cgggagttcg tgaaagttta gctagcgtta ttagtcaatg atgtcggggc      60
gttgtgcact cgaattgata gccgataatt cgcccggact gccgccgcgg cagtgaccag     120
atagatggcc atggccaact gaacggaagg agagcgcgag accagaaaaa agcgagccac     180
aagcaccaaa cagccaccaa gtgatggcct cctccacatc ctctgcgcgt gggaacaaca     240
aagcagccac caccaacacc accgcagcca ccgctcccgt ctccaccgcc tcgtcggctg     300
ccgtttccgg ttccggtgcc acctccgcgg cagctactgc ctccgctccg ccagctgtga     360
ccctaagcga gctgattggc cagcagctga agcacctgaa cgccgatgag ctgctgcaca     420
aggacgagct gcagctgctc ctgctcataa cgcctgtgca acgccagaaa ctgagccgca     480
atctggagga tggcgatctg gaggccagca cctcggcggc gccactttcg cgtcccgaaa     540
acggcgagga ggatgacgac ctgattgggg cggtgggcgg actcggtatt ttgttcccaa     600
ctacgaccaa agagc                                                      615
```

<210> SEQ ID NO 127
<211> LENGTH: 833
<212> TYPE: DNA
<213> ORGANISM: Drosophila

<400> SEQUENCE: 127

| | | | | | |
|---|---|---|---|---|---|
| catcaatcaa | aattttaagt | aattttttt | agactattta | ttattttatt | tttcgcgata | 60 |
| ccaactaaat | tgttgaagta | aaccatgctg | gataagccag | ccccagtggg | ggcctcatgg | 120 |
| tacaccaatc | tgtccgactt | ccaggtgcag | gccgtcgagg | cactggcctt | ctcgattcgg | 180 |
| gatgacaatg | cggagggtac | tgtgtaccgc | acccagttct | gtctcagtcg | cttgggagtc | 240 |
| acgcccatgg | taaagacccg | gatgttgcgg | aagctaattg | ggatttgtcg | cggcagcgac | 300 |
| ttggcattcc | tttactttct | gatggaggcc | tgctataagg | gcacaggatc | tgcgtacagt | 360 |
| gaacggatcc | tgatgtccgc | catcaccttt | ttggatctgg | agatgaccat | gagggaactg | 420 |
| gacaaaatac | tgccgccggg | agtggaacgg | ctgaataaga | aagagtcgat | agctccgcca | 480 |
| gtggattatc | gctccatgtc | gttgccaaca | cctttaccga | ccaaacggga | atcggatctc | 540 |
| cgaaaggtcc | gctcgcccta | ctttaccccg | ttgcccaaac | caaagctacc | caagggtggc | 600 |
| gagaagttca | ctgccaagag | accctgcctc | gtggtctcct | ttccattctg | gcccgctggc | 660 |
| gagaggccca | actacaaggt | gaacgaggag | aaccgctggt | tcgccgctta | caggttccag | 720 |
| ccggtgaagc | ggatgctctt | caagatggtc | ggcgacatca | tgaccgacta | ctggacaaag | 780 |
| atagatggta | ctcaaccggc | ggagaacgaa | gcgatgccca | tgtgcgagtt | cca | 833 |

<210> SEQ ID NO 128
<211> LENGTH: 550
<212> TYPE: DNA
<213> ORGANISM: Drosophila

<400> SEQUENCE: 128

| | | | | | |
|---|---|---|---|---|---|
| aaccgctgaa | caagtacgga | gtttgtaaaa | tacttaatat | tagctaagtc | cgtgcgagcg | 60 |
| tagccaaaca | aggaaactaa | ttccaacgct | gccgtgacac | aaacttccgt | acgaaattga | 120 |
| aagtcaaatg | aattctgtac | aaaactgtgt | gtgtgcgtgt | aattcaagcg | tcaatttgtc | 180 |
| gatgataaaa | tttgcctgcg | cctaatgtac | acatgtctgc | gtcttcgttg | agcatatgag | 240 |
| cctgtgaatg | tgtgcgtatc | ggtgtgagcg | tcgagcataa | gaaagcagca | caaaacaaca | 300 |
| acaacggcag | cagcagtaac | aacaacagca | agaaggcaac | gacgctaaga | gaaagagaga | 360 |
| aggaagggaa | gagcagagca | taatcggact | ccattttaca | aggcgaaaaa | aggagtagga | 420 |
| aagagcgcac | catggccagt | ttccagatcc | accaagacat | gagcaacaag | gagaatccgg | 480 |
| gaaagttcag | gtcttccgtg | acgtcagaaa | tcttaatgtt | gatgagaatg | tggagtacgg | 540 |
| cgccaagaaa | | | | | | 550 |

<210> SEQ ID NO 129
<211> LENGTH: 480
<212> TYPE: DNA
<213> ORGANISM: Drosophila

<400> SEQUENCE: 129

| | | | | | |
|---|---|---|---|---|---|
| cgcaacaata | tagcaattct | gaacttggtt | cgagtgtttt | tgcagcacga | attgataata | 60 |
| tgccgtaggt | gcggcccagc | gcggatcatc | agcagcagca | gcgatggcct | acatcaacat | 120 |
| cgccgagtgg | acgcccgacc | aggtcaccga | ctggataaaa | ggtctggatg | agtctatgaa | 180 |
| ggggtatttg | tacgagttct | ccaagcagga | gatcggcgga | cgggcgttgc | tcaacatacg | 240 |

```
gccatacgag ctggagaatc tgggcatgct gcgcattggc catcaggaga tcgtgctgga    300
ggcggtggag aacttaagaa acttccatta tcacctgaaa aacgacaatc tgcagttcat    360
ggccttgcat gtggccacgg cagctaagaa tctgcatcgc gaactggcca ggaatcatgc    420
ggagagcact aagatcgata cccggatact gcacgatatt accaggacga tagctactct    480
```

<210> SEQ ID NO 130
<211> LENGTH: 738
<212> TYPE: DNA
<213> ORGANISM: Drosophila

<400> SEQUENCE: 130

```
taacaccttc caaacacaat tcatagcgcc tggagctaac tcaaatctat cattcgttca     60
cattttgtat acgactaaaa tggtggttgt acagggaatg tacgaagtca cggagctggt    120
ggctggcagc gtgggatgcg tgtgtctata catcgccgga tgcaatgtgc tgcccatgga    180
gcatattccc gatcttccgt cggcgctgtt cgtcctgacc gccgtgcttt ttctccatca    240
tctgagggta atgaattgcg caccgctgca gaagctttgg cttttgctgc tggaactgtt    300
ggtcttctat atgtgcaccc aggtcgtggt gcttgtgtgg ctccagttgc tcagccatat    360
gaataaactg cgggacaatg cagttaatac tcgtaccggc atgtaccttt ttgaagccta    420
tccaaaagtc tttatgtttt tgcgccaaga tgtctactat ttggggcagc ttatcatgtc    480
cgtggcgtgc acctacaagg cgataatggt cactcatgcc ctggactacg ccctaccaaa    540
tcgccggacg tacagatact atgagacaga tgagaactta tgcgatggtc cgcggcgtcc    600
tacccgaaag agcaaccagc gatcaacacc caagaagagc accgtgcgtg gtcgcaaaaa    660
atagaagctg tcgcagaaac tggatcaatc aaatcgccca atctaaacac agttttcta    720 tgctttcgat cattgaat                                                  738
```

<210> SEQ ID NO 131
<211> LENGTH: 528
<212> TYPE: DNA
<213> ORGANISM: Drosophila

<400> SEQUENCE: 131

```
ccctttgaaa ttctcaagcc cgtcgccaca gtatggcaat acaaaatttt agtaatcctc     60
ctctaggtat ttggcaaaaa tcaggagatc caagatggtg cgagtgatcg aagacatgtt    120
cggcatcgcc gtcaacccga tgacgcagaa gactgaccgt gtccggcgct tcacgctggt    180
cacagagcgc ggcatgtcgg tgtcgatcct gacgatgggt gccataatcc agtccttgaa    240
ggttcccgac ttcaacggaa agctggagga cgtgtgcctg ggctacgacg acgtggcagg    300
ctactaccgt aaccagcaat acttctttgg agccaccatt ggccgggtgg ccaatcgtac    360
agcacacggg cgcttcaagc tctgcggcaa ggaggtcagt gtgagtcgaa acttgcggga    420
taggcatcac cagaacggcg ggttcgtggg cttcgacagc gtcatctggg acgtggtagg    480
ggtgcacaag gacggtgtca ccctgcagca catctcgcca gatgggca                 528
```

<210> SEQ ID NO 132
<211> LENGTH: 516
<212> TYPE: DNA
<213> ORGANISM: Drosophila

<400> SEQUENCE: 132

```
aatacgtata aaaaaccaac aaaattttca acactgcaag tcgaattcca ttatgtccgg     60
```

-continued

| | | |
|---|---|---|
| tattggcatc aatggctttg gccgaatcgg tcgcatgttt gcccgccagg ctctagttcg | 120 | |
| caaagatgtc aagatcgtgg caatcaacga tccctcactg gatcccaagt atctggccta | 180 | |
| catgctgcga tacgactcca ctcatggaca gttcaatcag aagatctctg tcgacgggaa | 240 | |
| caatcttgtt gttaatggca agaagatcca gctgcttaag gagtcggacg tcaagaagat | 300 | |
| taaatggtgc gacctgggcg tgcatacggt ggtggagtgc tccggtaggt ttaccaccct | 360 | |
| gaaagcctgt caaggtcact tggatagtgg ggccaaaaag gtggtcatat cggcaccatc | 420 | |
| tgccgatgct ccgatgtttg tgtgcggagt gaatcttgag gcatacaagc cgggcacagc | 480 | |
| aatcatctcg aatgcctcat gcacaaccaa ttgcct | 516 | |

<210> SEQ ID NO 133
<211> LENGTH: 550
<212> TYPE: DNA
<213> ORGANISM: Drosophila

<400> SEQUENCE: 133

| | | |
|---|---|---|
| ccaacaccta atattgggtt ctaaattttc aaaatagatt ttctttctaa tattgcacaa | 60 | |
| aactaacaaa aatggcggtg cgaccttttg gccctggacc cggcgtttac atgctgcccc | 120 | |
| ccactgtggg ctatgataag catgacaacc gcaaacagcg gttgccgcag tactcttccg | 180 | |
| gcatgcgcac ccgtgctcct ggtgaggatc tgggtcctgg tccaggggcc tacaaggtgg | 240 | |
| acaagttgac tcgctatggc acgagcaagg gtttggagtt ctcgatggcg cccagaacca | 300 | |
| atgtcatcga taagcgaagc agtcccggtc cgggagcaca cgatgttcat aataggccat | 360 | |
| tctttaaggg ggttaatgct ccttcgtatt cgatgggcct acgaacggac tttaacttca | 420 | |
| agaaggatgg tcccggtccc aatgcctaca agtacgaggt caatgccgtt cgtcctggag | 480 | |
| tcccgagcta tagcatggga ctacaaacaa agattttgaa caagacgaat tctccgggtc | 540 | |
| cggctgcata | 550 | |

<210> SEQ ID NO 134
<211> LENGTH: 626
<212> TYPE: DNA
<213> ORGANISM: Drosophila

<400> SEQUENCE: 134

| | | |
|---|---|---|
| aatcgaaaag ccaatcaaaa attagaaaaa aatagtttgg ctttccgaca caaacacaag | 60 | |
| aaattaccac atcctggccc ataccttcta aaatttaatc cgaatcagga aattgccaac | 120 | |
| ctgtctaccc aacatgtttc ctgatgactt cgacgtagaa cccttcaatc cattcaatgt | 180 | |
| gggaccaccc aatagtggag cccgatctga attcaaaata cctacatgcg ttacgtatcc | 240 | |
| gccaccggta ttcgtaccca agtccgaata tgtacaacca tcagaggagt tggtttcccg | 300 | |
| gaagagcaac caaagtatag gcaagtcgac tatcggcgag gtggacattt ccaaggccat | 360 | |
| caatgaagag atggccgtgg ccaagaagca ggccgaagtt ctcaatgaaa aagatcgcat | 420 | |
| tgatgcgggt ggtgtttcaa caacgaagct gtccaaggta tctcaatcaa aggaagcggt | 480 | |
| ttcaaaggac tctttgcgca ccctaatgcc aataaggtca aaccgtcagg tcagtggtga | 540 | |
| tggtagagca aattccaaat tatccatatc acaattcagt gcggcatcca agacgagctg | 600 | |
| cacaaataag caaagtgagg gtgacg | 626 | |

<210> SEQ ID NO 135
<211> LENGTH: 542
<212> TYPE: DNA
<213> ORGANISM: Drosophila

<400> SEQUENCE: 135

```
ccccattaca catttatcac taaacattca aagaattttc caaacttta ctctgtttta        60
aacacgatga cgtccatgct gaatacccg atagtctcca tcttcgattt gatggtggaa      120
cgtcacatca ggctgcgcag ggaactgaat ggaaatcttc cgccagttcg tcggcctaaa     180
gcagcacgtg gagctgccga cggaaagaaa cctttcaaat acaaaccaag tccgatggag     240
tttcccttgc cagaaacact ggaattgatg tctccgccag cggcaaatgc cattactgcc    300
gcgcatttga cccaaaaaca cactttcctt aagatccagc caccgagcga gaagaacgca    360
attaagaagc tggtggagaa gatgtcccat ggacgaggca agaccaagac cgtgtcgcca    420
aggcactccc tgtccagcaa gaagaccagt gccaattcct ccaagacggt cggcattcag    480
cctcgcaaaa agaaagtaac cgggcaggga tcattccgtg ctcagccaaa gctcggcaag    540
ac                                                                    542
```

<210> SEQ ID NO 136
<211> LENGTH: 580
<212> TYPE: DNA
<213> ORGANISM: Drosophila

<400> SEQUENCE: 136

```
cagcaaatgg taggcaccat gtctatgtat atgggcaaag ctctaatgat gttcttcgac     60
agcgagaagc tgcactaaa gtcccagatc caggtagagt ttgacaagaa tgtgggcgaa     120
aaaccaccca agcctgttag aggagttcaa cgtagcagcg gtggaaccgc tggtaattcc    180
ccagacaatg aggacgatga tggtggggca gccggagaag aggagcccat taatatggct    240
gatcttctac cacgcgttga tattgctcca cagattacgg aggcattgct gaaggagatg    300
tccgacaagg actggaaaac tcgcaacgag ggtctgacta agctgcaggc tattatttca    360
gaggcgcggc taatcaaacc cagcattggc gacttggctc ctgctctggc ccaccgtctg    420
gtagattcca atgctaagat tgcccaaacg acacttgcca tttgcgagca gcttgccaca    480
gccatggggg ctggttgtcg aaatcacgtg cggaacttgt tccctggctt tttacacgct    540
ctgggtgata caagagttt tgtaagagcc gctgcccttt                           580
```

<210> SEQ ID NO 137
<211> LENGTH: 691
<212> TYPE: DNA
<213> ORGANISM: Drosophila
<220> FEATURE:
<221> NAME/KEY: misc_feature
<222> LOCATION: (1)...(691)
<223> OTHER INFORMATION: n = A,T,C or G

<400> SEQUENCE: 137

```
ctacacatac acaaacacac acgcacacca cacacgagat gaacaagccg caaaagccca     60
tcaaggtgaa gcgcgccaag cggaccggat gctccaggat tcagccgcag gaattcgtgg    120
aggctcaggt ggagaacgcg cgcagggcgg tggagcgcaa gctgatctac ctgtccgagt    180
cgaacagagc cagtgcatcc actcgggcgg ccaagcgaag cacggctggc gcaggcggag    240
gagcagggcg ggaaggatcg agcatggctg gccatgccca tggtgagcgt cgcaggcgca    300
gcaagaggag tctgctacac gctccagctc aggaagagac cgacgaggag gagagttcgc    360
cgctggagaa gacgaacaac tacgataaca gaagacgcag cagttgcaat ctattgctat    420
ctcctcgtcg caatggcctc acgccccgga actacgaggc cgaggccgag gcagcggaaa    480
```

```
tggaagccat tatggccgca cagcaagcct ccaacggaac gacgaagccc gatcatgatg      540
aaggagatgg cggngagtat cagggcggac cgtttggccg actgcagctg aagccgctgg      600
gcagctatgc cacggaccag cagctgccca gctactcgtg cggcgtgtgc ggtgccaagt      660
ttcacatccg atcgctgctg ggcgcccacc g                                    691
```

<210> SEQ ID NO 138
<211> LENGTH: 521
<212> TYPE: DNA
<213> ORGANISM: Drosophila

<400> SEQUENCE: 138

```
agctggcgaa ccggttgaaa ttcgtgctcc gccccataac tacaatggcc acgtacgaac       60
aggttaagga tgtgcccaac catccggatg tgtatcttat cgacgttcga cggaaggaag      120
agctccagca gacgggcttc attccagcca gcatcaatat accettggat gaactggaca      180 aggctctaaa tctggatgga tctgctttta aaaacaagta cggaagatcg aagccggaga      240
agcagtcgcc aatcatattc acctgccggt cgggaaatcg agtcttggaa gcagagaaaa      300
ttgccaaaag tcagggatac agcaatgtgg tgatctacaa aggctcctgg aatgaatggg      360
ctcaaaagga gggactttga cgataaacgt cgctatattt ctgaataaat gaagattaat      420
attaattaat taattaatta ttaatagcta aaaaaaacag aaaactttaa ttatttgtta      480
atattaagct gtatttttca tatatctcaa gttcttgact a                         521
```

<210> SEQ ID NO 139
<211> LENGTH: 618
<212> TYPE: DNA
<213> ORGANISM: Drosophila

<400> SEQUENCE: 139

```
tcgaagtgac agaaccacct ggaaaacagt atcagagtta aacacattcg aattcgagtt       60
cactcaaact aaaattctta tatttctttt actatatttg aacaattaaa aacgtgcaaa      120
aatgccagtc catttggatt taaccctaga ggaaatgacc aggattgctt tgggtgtgcc      180
cgagttaacc cacgtaaatg tggctgtact ccaaagtctt ttgaatgtcc ttctcaagaa      240
actgaactgt cagaatgata tggtaaggat aagtggcttc gagggcaagt gtatggagcg      300
cattctcgag caatccaaaa tatctccact gcccttcgac gtggaggcta ttgttccaat      360
ttccgagcaa ttggataaag ttcaagagtt ggacaaacgc atcaagcagc tggagtgcaa      420
gttggagtgt cactttcagc agattcgcat ttgcaacaag gccaaggaca agaagtacaa      480
gatcaaccag gccgaacagt acgcctctcc ttgcgaggat ctgtgcaccg tttgcgatga      540
ggacaacaag atcgcatgca gtctgctggc caacatggac ttcatgaaaa agctaatgcg      600
acgtatagcc acacccat                                                   618
```

<210> SEQ ID NO 140
<211> LENGTH: 650
<212> TYPE: DNA
<213> ORGANISM: Drosophila

<400> SEQUENCE: 140

```
taccttattc caccaggtat tcctggctat aattatccac ttggatggcc ccttcgttat       60
ccattaggtc cttattggcc taatcgacca ccatggctac caattaattc tccaccgata      120
cgtccaggtg gactttccc tggtggacct tccctggtg gaccttcccc tggtgaacct      180
tcacctggtg aaccttcacc tggtggacct tccctggtg gaccttcccc tggtggacct      240
```

```
tcccctggtg ggccatcccc tgtggacct  tccctggtg gaccttcccc tggtggacct      300
ttccctggtg gatctccacc ttcaccaggc ggaccacttg gaccatggca atttccatgg      360
atactaggtg gtcctcggcc gaaccgtcca ggaagacctt tccctggtgg tatccttcct     420
ggtcatttag acggttcggt agttccaaat agtgtgctaa atgttgctgg cggaatcttt     480
ggaaacggtg gactgttcgg tacgggaatt ttcggacaac atggactttt cggaactgga     540
tttcttagtg gaccttcgtt agaccccttt ggcatttttta ctccaatcgg aaatttcttt     600
ggatcactag gaaacttatt cggatttagt tcacctagtc aaattattcc                650
```

<210> SEQ ID NO 141
<211> LENGTH: 550
<212> TYPE: DNA
<213> ORGANISM: Drosophila

<400> SEQUENCE: 141

```
cgaaagtgtc gtgtacctag tcccgttttg gaaaacatag aaaaaaatca ctaaagtttt     60
catcaaaatt ttttgtcgta tttcgtgtct tgtgtttcat gtttcgtgaa aaaaagttt     120 tttgcttgca atttaaacgg ctgaatcgca atacgccgc ataacgaaag taaatacgaa     180
atttatagta gtaacaaaat ttggatcgcg cacacataca agttgataag aaattaagaa     240
ttcaaaatga acaaactacg taatgttctg aagtcagtag tccagcgtcg tctgcccgtt     300
tcccatttga tccaaatacg taccgcctgc ggtggtgaat ccaagtcctc caagggtctt     360
gtggtcggtg tttatcagaa ggagaacgat aatgacccaa agctaacgcc agctggcgaa     420
aaggtcaatg atcggctgca tggcaagttg caggagatga tttgccagag caaaatcact     480
ggccacttgg gcaggggcaa gatattcaac aacatagatc cagagtttcg cagtatggca     540
gtggttggtg                                                           550
```

<210> SEQ ID NO 142
<211> LENGTH: 600
<212> TYPE: DNA
<213> ORGANISM: Drosophila

<400> SEQUENCE: 142

```
agtagactag aaaccaagag aatgttcaag accatcgctg tagtagtgct cctggcagcc     60
ctggccagtg ccgagctcca tcgcgtgccg atcctcaagg agcagaactt tgtgaagacg     120
cgtcagaatg ttttggccga gaatcctat ctgcgcacca gtaccagct gccctcgctt      180 cgcagcgtgg atgaggaaca gctgtccaac tcgatgaata tggcttacta cggagccatc     240
tccatcggaa ctcccgctca gagcttcaag gttctgttcg actcaggctc ctcgaacctg     300
tgggtgccat cgaacacctg caagagcgat gcctgcctga cccacaacca gtacgactcc     360
agcgccagct ccacctacgt ggccaacggc gaatccttct ccatccagta tggcactggc     420
agcctaactg gctacctgtc caccgatacc gtcgacgtca atggcctgag catccagagc     480
cagacctttg ctgaatccac caacgagccg ggcaccaact tcaacgatgc caacttcgat     540
ggcattctcg gtatggccta tgagtccctg gccgtggatg gtgtggctcc tccgttctac     600
```

<210> SEQ ID NO 143
<211> LENGTH: 626
<212> TYPE: DNA
<213> ORGANISM: Drosophila

<400> SEQUENCE: 143

-continued

```
ataaacccaa aattttgaa aacggcttaa atatttgact taagttagat actcccaaaa      60
ttcttggtga atgcattgcc caaactatgc cctacagaag cagcagctaa gcaccgagct    120
ctaagaacca tcttcagcca tgctaatcaa tgatgccact agagatcgtc ccatctatca    180
ggatatccag cgtcttacag atgcccaact gagtaccatg tgcaaaagcc acggtctcat    240
tctgggtccc ataactttc aaaatagacg catggcagag cgcaagctcc atatagcaat    300
gatcacagag cgggccaagt accgggccca tcagcagttt gccctggagt gcaacatgaa    360
aacccaagtt ccgcctgcgc agcaaaacta cggcttagtg gacgtactgc cccagaacta    420
ttaccaaccc atgccaccac aaacttactg gccatctccg ggcaccaatt tgcgcagccc    480
acctccgcct agttggaata cccaaaatcg tcgggagcga acggacccgg tgctcgagcc    540
acgtcagtac gttagttgga ggcaacagaa caggaaccaa aaaaatactg aaaattctgg    600
taataatttt ctgggtttca agatgc                                         626
```

<210> SEQ ID NO 144
<211> LENGTH: 658
<212> TYPE: DNA
<213> ORGANISM: Drosophila

<400> SEQUENCE: 144

```
caaccgttaa caactattac tataagataa attcatttcg acctagccgt ttttcacct     60
ccaacagtcc aaaatgtcag aagaagaagc cccaggatct ccgggtgagg ctgttgaaga    120
agaagatacc actacatccg atgctgatac aaccacagct ggtgcccgca tgatgatgat    180
ccacccatgg ctgacggccg ccgcagtggc catgtatgcc accaaggtca tgtgggtcaa    240
gttccgtgag atcggcctgg ctaaacagga aaaacggctc aaaaatcaac tggcgaagca    300
gtctaagccc ttgcagacta ttgatgaaga tgtttccgaa tctgatgcag aatatgatgc    360
agaatctgat gcagaatctg atgcagaatc agatgcagag gacgaagacg tcgtcgggcc    420
ccaagtcgaa gatgcagcag agggaccggg attcgagcca aaccgtgtgg atatatgcca    480
tcgcccgatc gaagtctcta ctgactgctg atgttcgaat cggggatgaa ggaccgcgga    540
aggatgaaca tgcacacaca cactggacaa ctacactaat tgttgtaatg cttgcgtttt    600
ccgtagggga ggatccacgg acaatgtttg acatgtacca ccacattggg ggaccaca     658
```

<210> SEQ ID NO 145
<211> LENGTH: 350
<212> TYPE: DNA
<213> ORGANISM: Drosophila

<400> SEQUENCE: 145

```
agaatcctga ctgggaagac gccatgctgg ggcacatcgc ccagctgccc aagatgaagg     60
gtcccaccag caagggcctc ctggacaact gtgcctgcta cgagaagctg aacgaacgtc    120
acgagcagtg gtgtcccaca tcggagttgt ccaagcgact gctgcccctc ttcaatctct    180
gcaagatgca gactggcaac atagtgctga tccttagatt ggtgtgcaat ggtccgacca    240
ttgtgtccac gttcccccttc agcaaggtct gctcccgcaa tcccaagtgc ccggagccct    300
gctgcggtcc ttgtggcccc tgtggtccct gcggcccctg cccaccacct                350
```

<210> SEQ ID NO 146
<211> LENGTH: 549
<212> TYPE: DNA
<213> ORGANISM: Drosophila

<400> SEQUENCE: 146

-continued

```
aggacgcatg tgcagacaac ggagcggata cgcagcgtga acgtgaacga agacatcaag    60
tacgagcatt aaggtttacc cctgttaggc atccgataat ccgtgaatca gagagaccat   120
cgtcgtcatt agggcaacca attagccaag tcagtgattg tgataatgct taaaggtgtt   180
cccacgctag ccggtcgaaa ccttcgtctc ctgacgaccc aggcacaggt gctggtccat   240
caacgcgcca aagcgtccgc cgccgagccc gtcgaggact tgaccagga cggatctt    300 ttgaagcgcg ccaagttcgg acacacgggc aaacagctgc agcagaaaat aatcaatgag   360
aaaaatctgc cgcgctccacc gcttatgaac ttggtgtttg ccaatcggaa gttgtccttc   420
tacgatacca gttccactcc caagaccaaa gaggataatg ccaagctcag tcagagacgc   480
cactattcga tgcggcccca tcgcgagcag gagcagcgaa atgcggagga tgtgctattc   540
gacatgttc                                                          549
```

<210> SEQ ID NO 147
<211> LENGTH: 528
<212> TYPE: DNA
<213> ORGANISM: Drosophila

<400> SEQUENCE: 147

```
ctaaccaaca gaaacattcg catcctgaaa atttttacaa aatttcggta ttacgtaaaa    60
tgataggcat tcaaaaaaag cgaccagccg ccggagagta cgtagtgcca aacaattcgg   120
ctctaaatct gcagaataag cccagtatat acgatcaaac gcccaaccaa atggagaaga   180
ccaccaagtg ccgctattgt gagaacatgg ccaagaactt tctgtacctg gagagcctga   240
tccggaacaa caaggataac gacaagaaca acaagtgcag cttgtgcaac tcgtcgctaa   300
agtacttgga gtatgttaac cgcaatattc gccaggtttt cggcaacttc gattcaattg   360
tccaggcgga tcgtgctctg caatccaagc cggccatgat gcccaaatac tcggtgggcc   420
cggctccgga aaaagctgat ctgcgctcca agggtggcgc cattgtctcc cagcaaaggt   480
cggcaaaaag cctcaagtcc aagagcctaa atcccttaa atctaagt              528
```

<210> SEQ ID NO 148
<211> LENGTH: 538
<212> TYPE: DNA
<213> ORGANISM: Drosophila

<400> SEQUENCE: 148

```
cacaaatctt ggccagaata tgtctatctc agtgaagcgg aaaacggtga tttcaccgca    60
ggaactcctg aagacactcg agctgtccgg cgaagaggac ctcgatctgc agatcaagaa   120
ctgggtgatg tgggaccgca acgaggcgac gctccagcag gtgactgagg cagtcaggga   180
tcaggattgg aaggcgttgc gggtgagact gtgccatagg atcacctatt tgacaactgg   240 cttgaggga gtgatgcgcg caggcttcga ctctttgaac gatgtggtga tcatcgaagt   300
ggcccagggc atctgcgcct acctcgtcga tgcctatcca agcatccaga gaggcaaac   360 acagggcgtg gtcgttggct acgatggcag gtacaatagc aagcggtttg cccaactcat   420
cgccaccgtg ttcctgaaca cgacttcaa ggtgttcctc ttcactcgga tgattccgac   480
accctttata cccttcaccg tcgtcacgct ccagtgcctg gcggggatcg tggtcact    538
```

<210> SEQ ID NO 149
<211> LENGTH: 439
<212> TYPE: DNA
<213> ORGANISM: Drosophila

<400> SEQUENCE: 149

```
taactgatgt ttttaatata tgtaggaaat ataacctaaa gttgcatccg gaaaaatgtt      60
cattttcat gcatgaagtg acattcctag gtcacaaatg cacagacaaa ggagttttgc      120
cagatgacaa aaatatgac gtcatcaaaa attatcctgt ccctcacgat gcggacagcg      180
caagacgatt tgtagcattc tgcaactatt atcgtcgatt tataaagaac ttcgccgact      240
attcacggca cataactaga ttatgtaaaa agaatgttcc ttttgaatgg tcaagcgaat      300
gccaaaacgc attcgaatac cttaaagaaa agcttatgca ccccacatta ttacaatatc      360
ctgattttcg caaagaattt tgcatcataa cggatgctag taaacaagct tgtggagcgg      420
ttttaaccca gaaccgaga                                                  439
```

<210> SEQ ID NO 150
<211> LENGTH: 650
<212> TYPE: DNA
<213> ORGANISM: Drosophila

<400> SEQUENCE: 150

```
ttcaatacaa attaataaaa caaaaatatt aagttttgtc gatcatgcaa cctcaagagg      60
aagtgaaggc cattttcaag ctgattctaa tcggagacgg gggaactggg aaaaccacat      120
tggtcaagcg acatctgacc ggcgagttca agatgcaata caatgcgacc ttgggtgtgg      180
aggtcgagca attactgttt aacaccaaca gaggagtttt ccgcatcgat gtttgggaca      240
ctgccggtca ggagaggtac ggtggcctgc gcgatgggta cttcgtccaa tcacaatgtg      300
ccataataat gttcgatgtg gcctcgtcaa atacatataa taatgtgaaa agatggcacc      360
gcgacttggt gagagtatgc ggcaacatac cgattgtcat ttgtggcaac aaggtggata      420
tcatgcataa aaagacttgg aaaaagggtg ttgactttga tcgcaagaca aacatttacc      480
tcattgaaat gtccgcaaag tcgaactata cgtggagaa gccattcgtc tatctattgc      540
gaaaattggt gggtgatccc agcctgcagt tagtccagag ccccgctata cagcccccaa      600
aagttgtttt taccgacgag atgagccgtc aagtggaaag cttattcaat              650
```

<210> SEQ ID NO 151
<211> LENGTH: 656
<212> TYPE: DNA
<213> ORGANISM: Drosophila

<400> SEQUENCE: 151

```
aatactcaga catacatagt tagtcagtga tcatttagtt agttagtttt ttccttaaat      60
tgtctgtgat acattacata ttacggataa ttcacgatga tctgggactt ctttacctt      120
atacgcggag ccaccgagtt cagtgccact gcgctactga ttttgctcgg ttgcatggga      180
gactcaacga accaaggtgg tgagagcaaa ttcttggtgg ccagcgttca ctatggcctg      240
acggtgatgg tggtgatgca cgtgtttggc ttcgtatccg gagcccattc gaatccatgc      300
atctcgatct catgctactt gatgggctac atcgccctgg aagtgatgat gatgtacgtg      360
gtgtgtcaga tggccggtgc tttccttggt tacttcctgc taatgcaact gctgcccaag      420
gagctggtgg acaaaagcaa gccaggcatt tgcctggtac aaccgatgga cactctgtcc      480
acataccagg tcgtcatcat cgagtgcctg ctgaccgcgg tcctcgtgct cggatggtgc      540
tccttgtggg acgtgcgaaa cggaaggttc ctcgactcgg tcgccattcg catgggtctc      600
ctcgtgatcg cttgcagttt cgcagggatt caactaactg gagccagtat gaaccc         656
```

<210> SEQ ID NO 152
<211> LENGTH: 583
<212> TYPE: DNA
<213> ORGANISM: Drosophila

<400> SEQUENCE: 152

```
ccaaaagcag actgggtgaa aactgctttc gaacttctgc aataaaacgg ctcctaaccc      60
gtccttagag gcatctgtat gaagttcggt ttctgcttct cacacggttc agcatcgaac    120
acagtaaagg ggttggactt caccctcgttt ttctaatgag tcgtaatcaa aacgaaagca   180
acctccttga tatcaatgaa gatctgcctt ttgctcttgc tctgcccccc gtctcaatgg    240
attcgttgca gctgaacgca gacggcaata gccccgagga caagacgctc ggtattggcc    300
gtaaaaccat tttgaatgcg cacacaaaat ctttggctcc cattgtgagt gacgaggccc    360
tgaacacgct aaatgagctc cgcgagcaaa atcttctctg cgacgcccag atttctgtgg    420
gggaggatgt gttcaacgta catcgtgcaa taatgtgttc atgtagctca tactttcgag    480
ctcaattcac agggtttaac gctgacactc ccggatgtgt agatgggtca gatgcaaaaa    540
aaacaataa ttttattcat atccccggcg tgagttcatg tat                       583
```

<210> SEQ ID NO 153
<211> LENGTH: 507
<212> TYPE: DNA
<213> ORGANISM: Drosophila

<400> SEQUENCE: 153

```
ggcactgtgc tacaggagta cggaacgttt tggagcgaca ttgtgaacaa agtgcaggcg     60
gagcggccat aactgaaatt atgtacttac ttttaaggca gccgggcaat aaatcttaaa    120
aaccctaatt agtcaaaacg aaattgttgt ttgaggattt tttttcgact gccattcacc    180
attccgacgt cttggacgtc ggacgccaaa ggcgccccat tgagctgtgc aatcaacatt    240
acagggcaaa attattggct ttttggctca gcgcttatga atgaccagcc cacatcccag    300
cgcccaacga ggcgaaccag ttcccgtcgc ccaccacaga cagcaccttg ccacccacat    360
ccgcccacat cctcccaccc actccactcc aagtccgaaa tggaacgcac gagccgagca    420
cgttttgggtt tccagacacg ttggccagct tctcatagga aattcgtttt gggcgccccg   480
gcaaattgga aactctaagc acctttc                                        507
```

<210> SEQ ID NO 154
<211> LENGTH: 558
<212> TYPE: DNA
<213> ORGANISM: Drosophila

<400> SEQUENCE: 154

```
gtagcagaac caccaaataa aaaaccaaaa aaaaaaatac aggaacaaaa tgatgcagcc     60
gagactagtg attttgggtc tgatcggatt gacggcggtg ggcatgtgcc acgcccaggg    120
acgcatcatg ggaggggagg acgcggacgc cacagccacg accttcaccg cctccttgcg    180
ggtggacaat gccatgtgt gcggcggtag cattctctcc cagaccaaaa tcctgaccac    240
cgcccactgt gtgcatcgcg atggaaagct aatcgatgcc agtcgcctgg cgtgccgcgt    300
gggcagtacc aaccagtatg ctggtggcaa gattgtcaac gtggaatcgg ttgcagtgca    360
tccggactac tataatctga acaacaacct ggccgtgatc acgctgagct ctgagctgac    420
ctacaccgat cggatcactg ccatcccgct ggtcgccagc ggagaggcac tgcccgccga    480
gggatcggag gtgatcgtgg ccggctgggg acgcaccagc gacggcacca actcctacaa    540
```

| | |
|---|---|
| gatccgtcag atatcgct | 558 |

<210> SEQ ID NO 155
<211> LENGTH: 550
<212> TYPE: DNA
<213> ORGANISM: Drosophila

<400> SEQUENCE: 155

| | |
|---|---|
| cgaaggcgac tactttatgc acagtgagaa atattcaaaa gtgaggaaac caatagtcat | 60 |
| ataccaaagg tatcaaaaac taaaacgatt gcatgccaag acgctgaaga atatgaacta | 120 |
| atgtagtgta tctaccctca ctataactct actctacata tatataagta acgtacatac | 180 |
| attgtgacac tttgttgcaa acacaaataa acataattca catcaaagac cacatgcact | 240 |
| tacataaaca ctccagccaa tgaaatacga tctaacgctt atacataagc cgatcgcgga | 300 |
| gcgtgagaat gctgagcatg cacttagcag ctcaagtggt caagccatac ataacatatg | 360 |
| tatgccttct gcatacacat gtatatgtat atacaatatg tacaatatgt aagaacacca | 420 |
| tgtacgggta gctgtaccca agacagcaa catagattca ttcaaataaa acgattcaaa | 480 |
| cggaacagac gctctgagct gttcaatatc tattgcactg agctattact taatacttat | 540 |
| tacatggcga | 550 |

<210> SEQ ID NO 156
<211> LENGTH: 562
<212> TYPE: DNA
<213> ORGANISM: Drosophila

<400> SEQUENCE: 156

| | |
|---|---|
| ccatttccaa tccggatgag aatccactta acgccctcaa tagtggggat tcccattcac | 60 |
| ctgatagcga gggcagtaag gagagctctc aggatagctg cacaaagaat aacccaccag | 120 |
| gcgattctga gttggaggcg gaaaccgagg cgaacaagca caagcagcgc cattcgctgg | 180 |
| actctgccat ggacgaaaac tgccgttcgt tgagcacact cactgaaagc acggatcaga | 240 |
| gtgcacccat caacttcgat atgtcaaata gggcaaagct gccaagggc attgaaaaca | 300 |
| ttcggccgca tttggaacag gttgacaatg tcccactgca agtatcgctt tttacggact | 360 |
| gctcagcgga agccacgcgt cagatgctgg acatcatgca atcctacggc gagattgttg | 420 |
| tctgccttgg aagttcggcc agtaatgcca atgcggacat ttttctgcag gccgactgta | 480 |
| gtatagccgt ggagccgttg tatccgcaag tgtgccagga tgtggacgcg tacacggaag | 540 |
| ccaatatcca gaacaacaaa ct | 562 |

<210> SEQ ID NO 157
<211> LENGTH: 834
<212> TYPE: DNA
<213> ORGANISM: Drosophila

<400> SEQUENCE: 157

| | |
|---|---|
| attccgagca ccagacctaa atgggatagt tttgttttcc ggcttttttg tttttcggtg | 60 |
| tgagtttgtg agcttgtaac cgttcgaaat tttgtgcttt aagttttgt tggacaagtc | 120 |
| gctgccatgt ttcaccatga attcgaacga gatcagtgca tcatcgagga ataccaaaga | 180 |
| cgccccaaaa acgatgtcct ccaatggtag tggtgcggtg gacggcgtaa gtccttgtca | 240 |
| tctggccgca actgcggttg tttccactgc cagaggaggc gtcagagaaa cgagcagagg | 300 |
| acataaggct atccgtgtat ttttggatca ccacggtggt taggaaatcg cgttgctcta | 360 |
| aaactcgcta atcctggcca ctgcaaaaat taacttttcg atgaacacat ttttgggagc | 420 |

-continued

```
tattattgga ttcagattat aatagctctc atatgctggg atacccaaca ctgggatatc    480
ctacactggg taacctatac tttggtaccc tataccttgg taccctataa tttggtaccc    540
tatagttgga tacccttcac ttggatgccc tacacttgga taccatacac ttggataccc    600
tacccttgga taccctaccc ttggataccc caaagcttgg ataccccaaa gcttggatac    660

cccaaatatg gataacgatt gactaggatt cgaaatatat aggataggtt tctaggatta    720
acttggatac cccatatttg actgttatta ggacggctgt tcccaaactc aagaatgaat    780
agattattta aaacgtcaat ctacgttgat taattaaaga ctttaataag cgtc          834
```

<210> SEQ ID NO 158
<211> LENGTH: 550
<212> TYPE: DNA
<213> ORGANISM: Drosophila

<400> SEQUENCE: 158

```
attcccagaa tttgtggcat tttgtgtggc gtcttattat cggatattta gattttaact     60
gtaataagaa cagggataac acgatgctga gccgcaagcg ccgggcgagc agcatatcca    120
gccggcagga cgaggatccg ctgcagctgg acgactcgac gccggagcag tcaccggtgc    180
agcagacgac gacacaatcg gcgcgaaaaa agcgccgtct cgatcccaca gaactgtgcc    240
agcaattgta cgattccata aggaacataa agaaggagga cggttcaatg ctgtgcgaca    300
ccttcatccg cgtgccgaag cgccggcaag agccctcgta ctatgacgtg gtggtcaatc    360
ccattgatct gctcaaggtt cagcagaagc tgaaaaccga ttcctacgac gatttggatg    420
atctgatggc cgacctggag ctgcttattg gcaatgccaa ggccttctac ataccgggca    480
gtagcgagca ccaggacgca gtctctctgt ggcagcacat tcattcgcag agacagcgca    540
ttatggaggc                                                           550
```

<210> SEQ ID NO 159
<211> LENGTH: 566
<212> TYPE: DNA
<213> ORGANISM: Drosophila

<400> SEQUENCE: 159

```
aaaacaaaac acacacacac attaacacca aaaatgtccc agaatcatgc ctctacggaa     60
gaagtcttgc acgtggtgga ggccatcgag gcaggtgaaa aatccgaggt agacactgtt    120
ccagtggttg tgccaccaga atcaacagct gagcccgaag tgatctccaa gccagaggag    180
ggcaaccaac cagctggcga tgagccgcgg gaggagaagc cacagatcga atctggcgca    240
attaccgccc aggtggcgac ggaggaggga caggaagcgg aaaccaccga acacgtagct    300
atcgaagcaa ctgagcttgg taatgaagtg cagcaaacgg aagcatcaga tgaactatcg    360
ccagaagaaa agaaactgaa gctgaagaag gagcgaaagg agcgtttgaa gaatttcgca    420
accactcgct ttgcaccgac agcaatcgag agcccagttc attttacacc ggaatatatg    480
gaagagatca gggataatga ggtagaggaa gaagagcagg aacaggtagt cacctttgat    540
gagcccacca ttggagacgg ggagtc                                         566
```

<210> SEQ ID NO 160
<211> LENGTH: 633
<212> TYPE: DNA
<213> ORGANISM: Drosophila

<400> SEQUENCE: 160

-continued

| | |
|---|---|
| caagaccaga ctctaaatct tatcgtaaaa aagtttacta aaattccaaa tttaacaaac | 60 |
| atatggtgca ataagatttt gcaagacaaa tcatttgtgt atatctagaa tcatgcagcg | 120 |
| ttcgtcttat cctctatgcc acactgtgcg acccagcttg actgggcttt taggcggcgg | 180 |
| atggattgac cttcgaagga ctatggcctc agattcgtgg ggacgggggtg acggcaatag | 240 |
| ccagcccaat tcgccaaggg ctggcgtttc gcgtgccagt gccacatcga cggtgataag | 300 |
| tgatgccagc tcctattcgc gtggcgtcaa cactggtgct ttcgagcgac gcatcaatcg | 360 |
| ggaggataat atgtggaggg atcagagcta tatcgataca aaatggttaa atcctcgcga | 420 |
| tcccaatgcc tatcgaccga atttccgtca aacagagccg acatcgttgc gcaagcaatt | 480 |
| catgcgcagt ccggatgaaa tatcccgtga ggtgatgggg cgtgattggg aggaaacggt | 540 |
| caggacatat aaacgcaacg cccagagcaa acacagtgtg gcgcgcacag aggagcggca | 600 |
| atcttcggat aatacacgta atcgccagca aca | 633 |

<210> SEQ ID NO 161
<211> LENGTH: 600
<212> TYPE: DNA
<213> ORGANISM: Drosophila

<400> SEQUENCE: 161

| | |
|---|---|
| aaagatttga atttgtttcg agcaataaag tcaagaaatc gataattgga atttttatcaa | 60 |
| ctctggtatt tcctagtcca atgccaagta ttcaaaaaaa cacttttcgg aacatcgatc | 120 |
| aggaggtcta tggcgagcca ccggatgaga gcatcagtca tgcggccaag atatacggac | 180 |
| ttagtgtgat cctggccgcc atcgcattga cacagtggat cattataggt tacacccata | 240 |
| tgctgagcca cagcagatcg gaggagcgct acggctggtg gcttctgtgt acctttttcg | 300 |
| cagtcgccac tttatcgtgg accaagctag gacgcaaggt gcccttaaac tacatcatta | 360 |
| tcgcagcgat cgtggaaagc tcaactattt atatagccat ggaacagaag cacaatgaga | 420 |
| atagactcgt caacttctac gccggcattg tagtggttgc cttgatgttg gcctcgatat | 480 |
| tttggggcgc ctactttccc atgttcattg ttcccggtga tctgctgctc agctgtttgg | 540 |
| tggcaatagc caacattatg atgatcatat tctttatcaa tgtcctattt atcaactacc | 600 |

<210> SEQ ID NO 162
<211> LENGTH: 510
<212> TYPE: DNA
<213> ORGANISM: Drosophila

<400> SEQUENCE: 162

| | |
|---|---|
| cgccgagcaa aatggacgaa atgccaacac agaaaccaaa aattgcacgc ctctccttgt | 60 |
| tcgttcgcca actggaggtc gatcaggaga gctgtctgaa gccggattac gtgaagcctt | 120 |
| tccgcacaaa ggatgaggcg gttaaaaggc taatcaggta tcattgcatg catgagaacg | 180 |
| acgttgagtt gccttctgac gaagacgagg aatttgagtc cactgctctg gaattccagg | 240 |
| acaaattccg ccaactgaac ggcaagttcc aggaaattct gatgcaggag tcaacgctgc | 300 |
| cacaccgaac ttctgagttg ctacaaatgc agcagctgat gatcgatgat ctcaaaggcg | 360 |
| agatcaatga gattcgaacc gctgaaaagg agttagagca gcagctaaag gaggagcaga | 420 |
| ctagcgaaaa atcgacggcg gaaagcgatg tactttcgga ggcgaaagtt aaggaggaga | 480 |
| ttaaacagga accaatagat aagtctgctc | 510 |

<210> SEQ ID NO 163
<211> LENGTH: 646

```
<212> TYPE: DNA
<213> ORGANISM: Drosophila

<400> SEQUENCE: 163
ccactatctg tcattacaga cactcgattt taaactataa tagtgctata tttagatatg      60
tttaacacgt ttatcagctc tacacagaag ataacatata gataaataca tcccctctaa     120
taaaatggaa tgtcaggaac tcaagctcgt cacggataaa gaactcattg ataagaatct     180
tgaaaaagag gagcaaacat gcaacttagt cccagcctgg agccctagga atcccttgga     240
aaacagcatc gattgccgcg agaagtcaat tgtggaaaaa ataaatgcag accaggatgc     300
cattgccaaa atccaatatc ttagttcgga acatgccaag ctggataaat atttagataa     360
tcaggagcag gatgaatcac ttcgcaaata tcttgtcgtt ggagttcatt gggtttctct     420
gctcacggaa catgtgttga gccatccgtt tctagtattg cgttggcagt gtcaggttta     480
taatgcctcc aagtgttacc acttgcatcc ttttaccctg ctgccctgta ttgtccactt     540
gcacagacgc caaggactaa cgacactatg aagggaatg ggcagctgct tgcttgttcg      600
tggaatgtcc tgcgccattg acgatgtaat atcgaaactc agcagt                    646

<210> SEQ ID NO 164
<211> LENGTH: 565
<212> TYPE: DNA
<213> ORGANISM: Drosophila

<400> SEQUENCE: 164
tcagagctgc tgaagaacgg acaagaaaat ggcagaccac agatggatgc acttcagcaa      60
cggcagcgtg ccgccgaatg ccgtggtggc tggtcacgat tcggacgggg acaccatcta     120
cgtgggccgt gccttcttct ccaacgacat gctgccggcg aaggtgattc ccaacaaggg     180
caaggcctac gtggcgtatg cgcgcgagga gcacgagctg gagaactacg aggtgctttc     240
cggctacaac tacgagtggc tgtcggcgga gaacggggag gtgccgccgg cgccgtcaa      300 agttggtcgg aatgtggacg gcgagtattt gtatgcgggc aggggttatc atgccggcag     360
cttaaccatg ggcaaggtgc atccatccca cggctgcctg tatattccct acgattccga     420
tgaggttaag atctttgcct acgaggtgct gtgccagccg aacgttgga tcgacaccac      480 cgcaacaaat attccggatg gagctctggt tgctgggcac gattccaacg gggacaccat     540
ctacgtgggc agggtgttcc gcaat                                           565

<210> SEQ ID NO 165
<211> LENGTH: 900
<212> TYPE: DNA
<213> ORGANISM: Drosophila

<400> SEQUENCE: 165
gaaaccgaac actagattga cttttaaaag ctgtgccgca gtgtgccgaa cttttcgat       60 agtctgggca tcttcggcgt cttaaactgg cacatatgca agataatcat gtaaagaaat     120
cgtcacacga atatgtgctt gtgctggttg gcagcgatgt aaataaaatt taagctgctc     180
ccgagtaaaa tcttgccgca aagtaaaaaa acttaaacgc cgaagtgcca cttgtagcaa     240
aagttcgcgg acagcgaagt ctcagcacga accgtagaga actgagcgtg ggtctgcgag     300
ttctccaagt ccaaccgcca agacgctaag atgcatgcat cctccgcggc ggccactgca     360
cttgtggagt actcggacgt cagctcagag gacttctcgg atcaggaggc aggggacttg     420
gatgcggacg ccggcaaggg tgccggaaac atcaaaaaac cgaagccagc tccggataat     480
```

```
cagttctcca aaggtcgtct tgatgccaag cccgataaag agggttatga taactacaga    540
agtagaaggg cggaagactc aagcgaccca gtggcggccg gatcgaggca acgtctagc    600 agcgaggcca cgaatccgcg ggaggaacct tcgcaggcat ccaacacctc gaaggacgag    660
ctgtggggca gagagatata catgtccagc gattctatcg acaccgatga gctggaggcg    720
gaaatgaagc ggcagaagcg caaaaagcag aaaaaggaaa aacacaaaca caagtcgaag    780
aaaaagtcca agaagcgcaa aagaagcgg gccaagtcat actccagcat cgattcgatg    840
tcagacaatg acatcaatgc cttactggac cggcgctata ctccgccgac ggctcctagc    900
```

<210> SEQ ID NO 166
<211> LENGTH: 635
<212> TYPE: DNA
<213> ORGANISM: Drosophila

<400> SEQUENCE: 166

```
ttgatggtga ctacatacgt cactcgcgtg acaacacggc agttgcacaa ctgtgctgtt    60
ctgtgcttct agcactttcc atcgcccaa cccagcaagc tggcaatcag tattcattct    120
aatctatagc gttcgttcgt ttgtgtttcc cctatatttt cagctgagag atgggcaaag    180
acttctacaa gattctgggc ctcgagcgca aggccagcga cgatgagatc aagaaggcct    240 accgcaaaact ggcactcaaa taccatcccg acaagaacaa gagcccacag gcggaggagc    300
gcttcaagga gatcgccgag gcgtacgagg tgctgtcgga caaaaagaag cgcgacatct    360
tcgacaatta cggtgaggat ggattgaagg gcggacagcc gggaccagat ggcggcggtc    420
agccgggagc gtacacttac cagttccacg gcgatccgag ggcccacattt gcccagttct    480 ttggatcgtc ggatccgttt ggcgcgttct ttaccggcgg cgataacatg tttagtggcg    540
gtcagggcgg caataccaac gagatcttct ggaacattgg cggcgacgat atgtttgcct    600
ttaatgccca ggcacccagt cgcaagcgcc agcag    635
```

<210> SEQ ID NO 167
<211> LENGTH: 683
<212> TYPE: DNA
<213> ORGANISM: Drosophila

<400> SEQUENCE: 167

```
tggtgtgtac gctagtactc ctagcaaaca cactcattct acaaatgtca accgttgttg    60
gtttaactca catgcctttc caattccatt ccattccttt aacctacaca tcacacaaca    120
aataaattcc tgaacataaa gatcattttt gatacctgaa atttccacac gaaatttcta    180
cacgaaattt tctgaacatg gccggagaaa cagagcagct aacgttgctt agtgaactga    240
acaatattgg aggtggcgag ttcgagtcgg gatactgcct gaatgagaaa cctattctgc    300
cgccagtgat gactgactgg aagagactgg aaatgatgcg actgcgcttg tgcgccttaa    360
ccaaggaggt ggtccagaag aggaaccaga ttacaaatcc tgaacggagg gatgcatcta    420
ccaatacaaa atcgcaacaa ggatttggtt gtccggtcat aatgggacgc ttccgccaga    480
gattacagca atcggagaca atgatctatg atcacacagc cgagatgacc atgcagattt    540
ctgctccgcc tagcatgcca attgggatga cttctcagct ggtaatggag atgcttctc    600 tgactccgcc gcaaagagtt gttgtcacgc tgacacccgt gaagttggcc acagcagaga    660
gtgtttgggt gaccaagttg gat    683
```

<210> SEQ ID NO 168
<211> LENGTH: 500

```
<212> TYPE: DNA
<213> ORGANISM: Drosophila

<400> SEQUENCE: 168
gcaacacttc ctctacgaga aggaactcaa atttaagttc accagccatg ctcaactctt      60
tggccaagag aattgtgctt atgcccagcc ttatagcact ggaggatact tgtcgaacta     120
ttcacgttac cgccctaatg gcgaggatgg gaaaggattt ctgtcccgtg agtgaggttc     180
ccgactgcaa agtggtgaag aagcgaccgt gcagtcccac ggatccacct gttcgtcctt     240
gcagcgagga gggctgcacc cagccgcgat actcatgttg cgtgagtacc ggcatttcgg     300
cgaatccatg cgctgatcca agcaagaaga ccaagttcgt ttcgatgtgg aagagataca     360
aggatgatgg tagtaatcgg ccagaagcta tgtggcacta cccggaggag tgctgtccaa     420
agtgtgatga tacgcgattt gacgttttgt actatacacc gtcggacaag tgccgggagt     480
tccagcgcac ctggtgggaa                                                 500

<210> SEQ ID NO 169
<211> LENGTH: 575
<212> TYPE: DNA
<213> ORGANISM: Drosophila

<400> SEQUENCE: 169
cgctcccttg ttcgtgttat tgcagcgcaa ttaaataaga tacgttagtt gtggccagtg      60
ctgcaactta ccaccacccg gatacaccat tccctagcgc gatgtcacag gtttacttgc     120
tgccggtgct cacgttcctg atattccagg tcacctttct tggcacgtac atcttcgccg     180
tgctggaggg gcatgtggtg cccacggttc cctacatcag cgatgcggcc acctactcgc     240
cggaaagctg tgtgttcggg cagcttatca acataggcag cgttctgctt ggaattacca     300
tctacgtacg ctaccgtcag gtgctgcagc tttatgaaca ccatccggat ttggacgggt     360
cggtgctgcg ccagaaccga ctagccttgt ggttcggact ggtgtcctgc ctgggcatta     420
gcttcgtggg caactttcag gagacgaacg tgcggattgt ccacttcatc ggagccttct     480
gctgcttcgg ctgcggcacc ttgtactttt ggatgcaggc gctcatctcg tatctgatct     540
tccccatgtc gggtacccgc attaacgctc acttg                                575

<210> SEQ ID NO 170
<211> LENGTH: 600
<212> TYPE: DNA
<213> ORGANISM: Drosophila

<400> SEQUENCE: 170
cgacagttca gttcacaaaa tttcggtctt taattttttgg agttaaaaat ttgtagctaa     60
caaaattgaa aattcaaaaa ttcagttcgg agttttattt tcagacaaca ccctctcgtg    120
cacgcatcaa aattttttagt tctgaaaagg gagttcaatc caagacgagt caatagcaag    180
atgaatacca cttttaaaat ggctcgaacg agcctgaatc attcttggcg gtttgttagt    240
aacaaagcca agggcaatt ttccagtttg cgacgattac cagcagttac cagccaaaat    300
cgtcgctacg cagaccgata taccttcgac gaccagactc aagcacaaat ccagggcatc    360
aagaagatga aagagatgtc cgcggtgccc cgggagtctc cttggcgtga cagcgaatgg    420
tctcccgatt tcccgagcg tttggatgag ttgggctacg agtcccactg caacgatcgc    480
ctctatatag ccaagaacaa aatccgtcac gagcaacaaa aatatgaatt ggaacgtgaa    540
gagcgtcgca agcaggccca acgaagaatc aatagtcact tcgctaaagg tcaggcagaa    600
```

<210> SEQ ID NO 171
<211> LENGTH: 600
<212> TYPE: DNA
<213> ORGANISM: Drosophila

<400> SEQUENCE: 171

```
atcttaacta aatttctatt ccttacatct ttaaaatggc aaacgaagag gttaaagaca      60
atggccaact taaggcaact atggtaaact gcaatttgaa ccccagtgtc gcggatgatt     120
ttgctgagtt cgaggcaacc cttgcgaaga tcgattgtat actgcagaac aaggcaccct     180
gtgacgatga agattcaaag gcaggtggcg atgccaagga agatcaac tttgacaact      240
tggatgtgga taaggtgcgg cttaaagtga agaaaatcg aacagtcatc aacagaaagt     300
ctctagaaga agacaatgag aagcaagtca aggatatgaa ccagaagagt ttcatggagc    360
aggtggagaa ggatgccaat gatcgtgcag aggcacgtgc caaagccgaa tacgaagcag    420
aactacagag aagtcaggga acgaagcat ttcgcagcca gaagtacgag aaggcaatcc     480
tacattatga caaggctatc atcaaagtta aggacacgcg tattacatat tgcaatcgcg    540
ccttgtgcta cattaagcta cagaactata agcgcgccct caagggactg cagtacgtgt    600
```

<210> SEQ ID NO 172
<211> LENGTH: 624
<212> TYPE: DNA
<213> ORGANISM: Drosophila

<400> SEQUENCE: 172

```
aaattcaacg tgagcaatcc aaaccagatt ggacggatgg atagctcggt gccatccgga      60
gccgaaagcg gtcttatcaa ggagtacaag gactttgcca atgcctgga cgaactggag     120
ttcaagaccg atgagctgct aatcgatgct aaaatggtgg atcaggagtt ggccaactgc    180
cacaagtttc gcgaggatca gctgctgaag catctgacgg agaagaacga cgacgacgag    240
cagatgcagt tgctgcggga aaacatcgag ctcaaggcga ccggcgttga gttccaacac    300
ggcattgagc tgatcatgga agtaccgt gagcacagcg aagggacat gttaatcgat       360
acctaccaac tgagggagca ctacctggcc ggtttgtcga aggtggtcga agagcaggat    420
gcccgcatcg agcgtatggt tgatgtgatg aagctaactg tcgacttcga ggaccggagc    480
agtgccgaga accagcagat catttgccag ctgactgatg aaaatgagca gttgcgtcgt    540
cagttgcaga tcagtaccac cgatgagctg ttccgccagg gagcactgag ctccagcgaa    600
agtagcactc agatcggacc aaac                                           624
```

<210> SEQ ID NO 173
<211> LENGTH: 594
<212> TYPE: DNA
<213> ORGANISM: Drosophila

<400> SEQUENCE: 173

```
ttgctacacc gatcaaaacc aaagcgcttg aaaacaaaat tgtattcaac gaaataagtt      60
gtgcatttat aaatatctat atatatatat attttttact gcacacgcac gcactataaa     120
cgttaaatct caaaatcgtg tcaaaccaac caacctacca accgaccaat ccacgaacaa     180
taaccaattg tgtctgttga atcgtatcgc gtcagtcttc cgcaatatga gcacaagacc    240
agacaccaaa gaaacatccc cacgcgtatc cttgtgtccc ccagaaccgg ctcgaaccga    300
aacgccaatt ccaccggctg acgacgccct atccattgat aactcgtgcc gagatagcga    360
agttggagac gtgccggcag ataacagcac agtcacaaag tccgatcagg tgaacgaggg    420
```

```
ctgtcaaact cggcgagact ctggaaataa tcccgaacag ccatactcgc tgaacaagat        480
ggcaggcgtg agcaatgtaa aggagcccct tgggctctgt ccaaacgaga ttaatgagga        540
gcagcaggcg tgctccaaac tcgattcacg caatccgatc acggtcctcg gcct             594

<210> SEQ ID NO 174
<211> LENGTH: 631
<212> TYPE: DNA
<213> ORGANISM: Drosophila

<400> SEQUENCE: 174
cgacttgaag cggcaacatc gtcggatcaa gcaacatata acaactttcg tgagtgccac         60
aagtgcccct tttttacgat taactgcagt aaaaggagcc agagacattt gataattgag        120
tgtgtgccaa ttttttgtaaa aacaagacaa ttgacaataa ttacaactcc caaccgaggc       180
tccagattaa aattgtgata ccaaacatgc tacggctgtg ggcctgcctg ctcctcctgg        240
gatcaatcca gatccaggcg gttccattct acggcgacag cggatacgac accgagttcg       300
tgccactgga gcaccagcag cagccgcagg acgccagga cggcggcc accgttcccg         360 ctcaaacccc cagcggtgtg gagcagaagc cgttcaatgt ggacaccatc accacggatg        420
tgaattcccc aaatccggcc atcttcttcc agcaatcgtt ccccttcttt ggcaatgagt       480
tcttcaattc gttcggaggc tttggctttg gagctgccca ggagccctgg tggaagggac        540
ccaatgtgtg caccgaaaag gaggaagacg agactgtggc cagtgaaacg gaggcagaag       600
aaaccgtgga cacctttggc caggaacgtg a                                       631

<210> SEQ ID NO 175
<211> LENGTH: 579
<212> TYPE: DNA
<213> ORGANISM: Drosophila

<400> SEQUENCE: 175
aacacatcta gttttctaac atcattttca ctttcgtaat tttatgtaat gcaaaacgta         60
aatcaacaca acatgggaa ttctgcgtcc cgtcgcagaa tccttggttg gataaacaac        120
aatcttggca ccacttacgt acgtttagag gaactgcgaa ccggcgcgga atattgtcga       180
atgcttcata agctgcaacc ttcggcgatt aggttgaaaa gggtcttcaa ggaaccaaag      240
agccattatg aatgtgtgca aaatatgaaa ttgctgcaaa agagcctctt aaaacagggc      300
gttgagaagc aaatacccat tcagcggcta gtttctcgtg gtaatagcga gagtttggag     360
tttgcccagt ggttcaaggc attctatgat cataaccacc agctgttatg cccgaaaag      420 accgaagatg caccgaagcc cctagaaaaa ttcgacgaaa agcctgacag tttcgtggat     480
accggaaaat gcaggtatgg agcaagatgt agtcatagat tagattcgac tgtaagcagt     540
cgacattcaa atcaatcagg gaagaatttt gaaaactac                              579

<210> SEQ ID NO 176
<211> LENGTH: 628
<212> TYPE: DNA
<213> ORGANISM: Drosophila

<400> SEQUENCE: 176
ataaatcgaa atgaaggacc tggacggctc cttggacact ctggagaatg cccgcttcaa         60
ctacgtgtat atgaaggaca ttgctcgcct ggcaaaggac tcgatcttct cgcataacga       120
gctgattagc attgtaatgc tctaccataa gtttgtgctg gtcaatgggc cgagagcaaa       180
```

| | |
|---|---|
| gtacatgacc attcagcaac tctctgcgct gatggagctc ttgtttgaga tcgtggatcg | 240 |
| cgatctcatt gcgaccattg tgtatagaat agcccataca ccaggttcca ggcctcctga | 300 |
| cttctttttcc gacaagcata tacacttgga gtcctttgtg cggcttttca ccgtatactt | 360 |
| caccaaagat cttcagctga aaatggaatt cgcattctcg gtctacgata aaagcgattc | 420 |
| caagcagttg aatggcgagc aagttgggtt cttcgtcggc aagttctttg agagcgagga | 480 |
| tgaagacgaa tccattgagc tgcgcttgga catgaaggag atgctgttcc tcaaattcga | 540 |
| cttggacaag gataccaaca ttggggttga tgagtactac gaggtggtcc gccgacagcc | 600 |
| catgctgctg gagtgctttg gtcgcgtg | 628 |

<210> SEQ ID NO 177
<211> LENGTH: 600
<212> TYPE: DNA
<213> ORGANISM: Drosophila

<400> SEQUENCE: 177

| | |
|---|---|
| taaacaccgt tcagcggagc aaaattttgt acaactttta tttggtcaaa aaaaaaaaaa | 60 |
| tcgaaagaaa aactgtttct ttttcaccac tttcccaaat tatttgtatt taggatttac | 120 |
| tcaaccgcaa ctcacaatat gtcgaattcg ttttcgtact ggaatggcca gccgttgaat | 180 |
| gctcccgttt atccgcagat gggtgacttc atgcagcact ctgccgctgg agcagccgct | 240 |
| ccaccaccac tatcagcaac agcagcagca ccaggattag gatcagccgg cggactagga | 300 |
| ggttggccta gccagggcgc agctcaggca cactccatgc taccatacgc cggaggagcc | 360 |
| ggtggcatgc cggctgccat gccgggtgcc atgccgggcg tcatgccggg tgccatgtcg | 420 |
| ggtgccatgc cgggtgccat gccgggtgcc atgtcgtgtg catgcccat tacaggagcc | 480 |
| cagcatatag tgccgccacc cgtggaccgt tcaatatatg gagacatacc cggacgaaat | 540 |
| gaaccgtgca tcgacaatgg cgaagccttc tgcgcctaca acggcatgga catgagcatg | 600 |

<210> SEQ ID NO 178
<211> LENGTH: 658
<212> TYPE: DNA
<213> ORGANISM: Drosophila

<400> SEQUENCE: 178

| | |
|---|---|
| ataacataaa atctaaatta cctttttttt tgcgaattct ttcactatgc aaaaaaccaa | 60 |
| taactacaaa agcttcaaaa tcttcttcaa gaacgttcca tttcgttcat atcccgactg | 120 |
| caagaatggt aaaggttcag gcctaaaagc caagttggca aagaaaattc ctatagaacg | 180 |
| tgaaaagttt ttgggtataa agtgtctgca cggcaagaag ataattggcc agatcagtgt | 240 |
| taatagcgtg attggaggaa tgcgaggact tccacttttg ttttgcgaga catccagctt | 300 |
| ggacaaaaac aagggtattt attaccgtgg aaaactgctt aaggatgtgt gtgccaaact | 360 |
| gccacgggtg caagagggca cacaagaggg cactcccgaa ggatgtttct tcctgctgac | 420 |
| cagcggatcg atgcccacga agaaggaggc acaggaagtg accaacgagt ggctgaagcg | 480 |
| gggctcagtt ccgcgctact gcctccggat gatcgactcc atggacaagc gggtgcatcc | 540 |
| gatggcccaa ttgtgcgccg ccagtgcctg tctcaatccg cagagccagt tcgtcgaggc | 600 |
| ttacaccaaa ggggccagac gtgcagacta ctggaaatac tcctacgagg attcaatg | 658 |

<210> SEQ ID NO 179
<211> LENGTH: 764
<212> TYPE: DNA
<213> ORGANISM: Drosophila

<400> SEQUENCE: 179

```
tagaggtgct cgaattcccc cagatccgga cggtggccat catcgctgaa ggtattccgg      60
aaaacatgac tcgcaagctt attattgagg cggataagaa gggagtggca atcattggac     120
ccgcaaccgt gggtggcgtt aagcccggtt gctttaagat tggcaacacc ggcggtatgc     180
tggataacat cctgcactcg aaactgtacc gtccaggcag tgttgcgtat gtttcgcgct     240
ccggaggaat gtccaatgag ctgaacaata ttatctcaaa ggccaccgac ggcgtgattg     300
agggcattgc cattggagga gataggtacc caggctccac ctttatggat cacattctgc     360
ggtatcaagc cgatccggaa accaagctga ttgtcctttt aggagaggtt ggtggaaccg     420
aggagtacga cgtttgtgcc gctctgaagg acggacgtat taccaagcct ctggtggcct     480
ggtgcattgg tacctgcgcc agcatgttta cttcggaagt ccagtttggc catgccggat     540
cctgcgcgaa ctccgaccga gagacggcta cggccaagaa caagggtctg cgagatgccg     600
gcgcctacgt tcctgattcg ttcgacacgc tgggtgaact catccaccac gtgtacggcg     660
agctggttaa gactggtcga gtagtgccga aggaggaggt gccaccacca actgtgccca     720
tggattattc gtgggcccgc gagctgggtc ttattcgcaa gccc                      764
```

<210> SEQ ID NO 180
<211> LENGTH: 650
<212> TYPE: DNA
<213> ORGANISM: Drosophila

<400> SEQUENCE: 180

```
ttaattctag agctgttaaa tttgaaacag tgttccacaa cttaaaacca ttgggttcat      60
agcccacaaa aatacttta atgatttat catcaaactt tccttgtttg tttttaatat       120
gcacataaac agttgcacca aacactctca aatgttttaa gtatggcttc ttattgtgcc     180
acatctcata tggggtcttt gaactatcaa caagtgctct actaggaatt ctgttgatta     240
aataagtagc agttaatact gcttcgcccc aaaagctttt atctagcttt gcaccactaa     300
ccatggttcg agcttttttcc gtaatggtgg aggtcatcgc gagagatcaa ttgaaattaa     360
gcattaaatc acatcatgag cttcttgcgc agtgccctgc gctatgccca caccaatggc     420
tacacgggac tcctttacac tccgcgcggc gagttcatca tcacgtgcgg cacagatgga     480
gacatccggc actggacctg cattagtgac gacgatccac gctcaagttg cctgggcgag     540
ttcgtcatgt gcatagccca cacgggaacc cgtttgctgg cctcgacgga tcggaatacg     600
atccatgcct acacctttcc cgagatggac agcgatggca tcctcatgcg                650
```

<210> SEQ ID NO 181
<211> LENGTH: 547
<212> TYPE: DNA
<213> ORGANISM: Drosophila

<400> SEQUENCE: 181

```
taagggtct tggacgtatc gagcgaatcg ttcgccagag ttgccgcaat acataattac       60
gaactgtgaa gtgaaattga cggataatat aaaaccgaaa aaatagtaga ggtaaccggc     120
gcgaaggacc aaacaatcct atcgcctatc gatagagaaa tcggaaatca gatcgtcgac     180
aaaaaagcca gcacaacgga gaccgaaacg gaaacggaaa caatgggcgg cggtgaagtg     240
aaggtcgcta ccgtcgacgt cgagggcggg gacaatatgg ccaccttgcc ggtgtcccgc     300
tcgcataccg ccggcagcac cgacagcgcc gagaagaaca acgccgccaa caaggagatg     360
```

-continued

| | |
|---|---|
| gaactcaaga acgtcatgcc gcagccgctg cagaggacat cgctgttcat cgtgaccagt | 420 |
| ctggtgtacg cgatccttct gatcgtcgtg tgcattgcat acgttatcag cgatgtaacc | 480 |
| acccaccgac tgccggtttt gtactacgag acattcttca catatctata cggcgtcagc | 540 |
| atactct | 547 |

<210> SEQ ID NO 182
<211> LENGTH: 600
<212> TYPE: DNA
<213> ORGANISM: Drosophila

<400> SEQUENCE: 182

| | |
|---|---|
| agttttcggc tgtgctggct gctctacgct gcgatctccg ttctccgttc tccaatcttt | 60 |
| gtaatatctg tttagatata catagttata gtatatacat acatatattt cgtgtgctca | 120 |
| gtggagcgtc ttccgcgttt tgtggctgcg tcgcttaatt ggcccaaaag tatctcaagt | 180 |
| gtgtgattgt gaaagttcct gaagcaaaat gtacgtgaga cgagctctgc tcttggcctg | 240 |
| cctgctgtgc ctccagccgc tgggtccatc tatggccagc gaggatgagt ccaatccgct | 300 |
| gctggacatg gcctccatgt tcttccagga ggcgctgtcc aaccagaacg gtggcaacaa | 360 |
| tggaggaggc ggtgctggtt tggcgggtgt ggcctcgcta attggcacct tcatgcaagc | 420 |
| gagtggcaaa tctggaggcg ccggagcagg aggcggcggt gctggtggcg ccatgcagat | 480 |
| cctctcgggc ctgggcagtc ttctgtccaa gagtcagggc ggtcagagcg gtggcttcga | 540 |
| tccctccatc attggcaatg tcctcgagat gttcacccag ggcgatgacc aggaagccac | 600 |

<210> SEQ ID NO 183
<211> LENGTH: 600
<212> TYPE: DNA
<213> ORGANISM: Drosophila

<400> SEQUENCE: 183

| | |
|---|---|
| ttgaggtagc cttacgaaga gttgcgctta taattattag gaataatatt aacctatcga | 60 |
| aatgtggaag aaaataattt tctgtgtggt gcttgtggcc tttgtggttg tgccgtttgc | 120 |
| caactcactg acctgctcca agtgcacatc gccgtctgga tgcaaaagtc cttcctccga | 180 |
| aacctgctcc aattcgacgg ccaatgccaa taaggaattt ctggaaggat accatagtaa | 240 |
| tgtgcccacc gttaatggca gtctgagttt ttcgtgtgcc aatctcactt actatcatgc | 300 |
| agcaaactac actcacacct ttgagttcct gggctgcgtc ttcaacgaaa cgaatgtctg | 360 |
| caatctttcc ctgaacaaca ccgcgagtgg atggagcaag aagtgcctcc aatgcggcac | 420 |
| cgactactgc aatccagctg gaacctacag cagcagtgtc tatacaatcg tgggatccgc | 480 |
| cattgccgtg attttggcca aagttctaag ctaaacttat aatctgacga cggagctaaa | 540 |
| cagtatttca actacctttt gattgtacaa tatttatttg aattaaaaat aaaatcattt | 600 |

<210> SEQ ID NO 184
<211> LENGTH: 480
<212> TYPE: DNA
<213> ORGANISM: Drosophila

<400> SEQUENCE: 184

| | |
|---|---|
| gcatatattg gtttattaca cctcaattcc atccctacga ctctttccat cggacaactg | 60 |
| gtccaaagct atctggatgg gcttattgag aaagctgtgg acatattcgg taatacggac | 120 |
| tatttgcggg cgaagaatct ggacaaaata ctccctcgta acgccgagca gcagatccta | 180 |
| catcaacgaa tcccaacgga gtcggtactt gggtgcccta acgaattgg atcattggct | 240 |

```
taacaggaca cgacaggctg agcagatgca cctggctgaa aggaacgac tgctgtcgga      300 attggagcgg atgcaacgag aggacaacga gaagatcgag aggctggcgg agatcttcac      360
aaggacttta ctgcgggaca gccaaccgtc tgaacgcctt cgctttgtaa cggaaaccgg      420
tcttaaacac atgagagcaa aacgcgatgc gttgtctgcg acacgactga ttttgatcat      480
```

<210> SEQ ID NO 185
<211> LENGTH: 691
<212> TYPE: DNA
<213> ORGANISM: Drosophila

<400> SEQUENCE: 185

```
ctaacccaca aaaatctaa aaatataaa attaaaattt caaaaaccta caaaaaagca      60
tccaagaatg actcagttaa gcgagttcgc cctggacagc cactttgcct ccgagctgcg      120
cagcctgcag ttgtattcca aggagcaccc tgtcagccaa gatgaccacg ataagtca       180 gcgttggatg cagcacttcc aaaacgccaa gggtttggat aaattcgcac gaaactgcat      240
gctgctgatg atgtgcgaac agttgcgaga tcttggccac ttgagcaaac ccttcaccga      300
actgaagaac ttgagtcgcc ccatggacga tttgctgaac gagtaccatg ggacgactac      360
tgtggaggag gggcaaatgt cgccggttga agatattgag gactcggaca ccaatgtctc      420
caactatggc agtggcagta gttctttctc ccctggggtg ccctatccca tttccacgcc      480
cgagttcgag agcattaagc ggtctaacca ggatctgctt aaggaaatcg actcgctgca      540
ctgtcgcacg gtggaagcgg aaaagctata ccttagcagg agccaaattc tggagaagca      600
gattgccgag aagtcggcgt tggccaaaac gaaacttccc caggagggta tctatcaatc      660
ctgccgtgcg gcctgccagc ttctgaaaaa t                                     691
```

<210> SEQ ID NO 186
<211> LENGTH: 497
<212> TYPE: DNA
<213> ORGANISM: Drosophila

<400> SEQUENCE: 186

```
caaacgtttc tgtggcgctt cttttcagat gccgtcaatg tgtcgttcgt attgcatcgt      60
cgcctcacat atcgactagt gggtaaagta caagtcctga tggagctgag gaaatctaac      120
gtggtgctgg tgcaccttct gctgctgatc tgcataatgc gcatctttta tcagtccgga      180
ccactgtcgc agctggaacc gcagaagaca ttactggata tgggtgtacc accagctgcc      240
gatcgcctgg tggctttact tatcgaatga ctccgcacgg acacgttatt tcggacaac       300 tgcagtgggg ctgtctacat acgggatata atcctgcgcc aggactagt cagcatatct       360 taaactagtg ttccaactat gacccgatct gctgaagtag ccctattcgc tggattcaat      420
ccgatgccat ccatattgcc tacctctaat ttcgatacca ttttcaatcg cactttggct      480
ctcgacaagg gtgcgtt                                                     497
```

<210> SEQ ID NO 187
<211> LENGTH: 644
<212> TYPE: DNA
<213> ORGANISM: Drosophila

<400> SEQUENCE: 187

```
cataactgcc acaaaactaa attgaaaatt tatacattta atgcatcact tttaacctga      60
tccaaggtca tgtccttgca gtggcaaaat gaggtggtgc ggattacgcg ccaagtgaag      120
```

-continued

| | |
|---|---|
| cgcaatctac cgcaccgaaa tttccgagag attaactttg atcgcgagac cataaggcaa | 180 |
| ggaatcaccc ccctgaccta cgatgaggcg cgccgtctta agggaccagt tttcgaggct | 240 |
| ctggaggatg agttgcgtcg agcaggatgc accatgctgc cggagtttct ccactgcctg | 300 |
| gccaccaagg agaatgctct tttcgagagc ctaaatatcc gggaacgtct atccgatgac | 360 |
| tcggaattgc tctacggaat ggtggatcga ctccgggatg ccgaactggc tgtttgcctg | 420 |
| aacaagcacc ggggtctcaa aaagtgtttt ggcctattct tcgagaccat gcagctgctg | 480 |
| gagccgtatc gtcagaaata cgcatacgcc tggtggccc tcaatgagca catcatctcg | 540 |
| ttgtgccgca acattgccgg ccaggaacat gatgccgccg agtacatatc ccgcatctac | 600 |
| tacatctatt ccatgtacct ggtgaacaca ggccagcgaa cctc | 644 |

<210> SEQ ID NO 188
<211> LENGTH: 614
<212> TYPE: DNA
<213> ORGANISM: Drosophila

<400> SEQUENCE: 188

| | |
|---|---|
| tacaaaaccg agccatattt tattgtaaat aaaattcgat aaaatttcgg tggacatatt | 60 |
| ggacgaagat gtccagtctg caagatattc cgcttgccga ccccgagggc ctgtctgtgg | 120 |
| aaggtcccga ggtggccccc gctccaaagt ccaattcctt gaagcgcttc tttaagatca | 180 |
| gcaagaagcc aatgatgcgc gaccaagtgg aggatgacga cgagacatcc tcccaggaca | 240 |
| acaaggacct gggaaagtca aacactataa gtcgcttctt tacccggatg aagggagcca | 300 |
| ataaggatgt tcaagatcct tcgagctcgg tggtcgaacc cgtggagcag gataagccgt | 360 |
| tgccgaatgc aaagcccacg attaagacat ccatttcatc ctactggaag atactgttca | 420 |
| accggcagaa gagccagcgc caaaacgcag ctttagggca gaccaatgcc aataaagagg | 480 |
| ataacgagtc tgaagaagtc catgaactgc aaccagtaag ccaagatccc gataccgatc | 540 |
| ctcagccgac agtcaaggat gagcacgatg aaatggaacg tggcacagat ccggagccac | 600 |
| ccaacccgaa gccc | 614 |

<210> SEQ ID NO 189
<211> LENGTH: 493
<212> TYPE: DNA
<213> ORGANISM: Drosophila

<400> SEQUENCE: 189

| | |
|---|---|
| aatgtagttt ggattttcat ttgaaatttc gattcgatgg gcagcaaggg caaggctggt | 60 |
| ctggacttct ccggcaaagt ggtgcttatc acgggcgcag cctccgggat cggggccgcc | 120 |
| gcggcggaga tgttctcgaa gctgggtgcc tgcctggccc tggtggatcg ggaggaggag | 180 |
| ggcctcatat gtgtgatgaa acgctgcatg aagatgggcc acgagccgta cggcatagcc | 240 |
| ggagatctgc tcaagcctcc ggagatcgaa tgcattgcgc ggaagaccac ggagcgctac | 300 |
| gagggcaagc tggatgtgct ggtaaatggg gctggcatca tgcccacggg aacgctgcag | 360 |
| agcacggaac tggcctgctt cacccacgtg atggaggcca atgtgcgttc tgggttttat | 420 |
| ctgaccaagt tgctgctgcc ccagttgctg cagtgtaagg gcagcattgt caacgtgtcc | 480 |
| agcgtctgcg gac | 493 |

<210> SEQ ID NO 190
<211> LENGTH: 550
<212> TYPE: DNA
<213> ORGANISM: Drosophila

<400> SEQUENCE: 190

```
ctcgtttcca accatacact ctcaattcac atctcttttt cccaaacata cttattatat      60
cttccaattg tcctgttcca catggcgctg gtttacgggg ttgaaaagaa gacggtaccc     120
acccacatga aattcgtgat gggcggaacc tccggaatgc tggccacatg cattgtccag     180
ccgttggacc ttctcaagac ccgaatgcag atatcaggaa ctttaggcac acgcgagtac     240
aagaactcat ttgaggttct atcgaaggtt ttgaagaacg agggatatt atccttgtac      300
aatggattga gtgccggact attgagacag gccacgtaca catcagccaa gatgggtgtt     360
taccagatgg agttggattg gtatcgcaag aacttcggaa attatccatc tatggtggcc     420
agtatgacga tgggcattgt ggctggcgcc tttggagcca tgtgtggaaa tccagcggag     480
gtggccctga tccggatgat gtccgataac cgcttaatcc cggaggacag gcgtaattac     540
aagaatgtgg                                                            550
```

<210> SEQ ID NO 191
<211> LENGTH: 570
<212> TYPE: DNA
<213> ORGANISM: Drosophila

<400> SEQUENCE: 191

```
aaaggaaatt aatggttaaa attaagatat gacacatgtc cggaaagggg gagatcatcc      60
agatccacat tggccaggcc ggtgtgcaga tagccaacgc tgttgggag ctcttctgtc     120
tggagcacgg cattttggcc aatggaagac taacccagtc gcccatggac gactcgttcc     180
tcacgttctt tgagttcacc agccatcagc cgtgtgtgca acctcgactc gtcatgatcg     240
acacggagcc cacagtgata gatgaaatcc gtaccggctc ctaccgcaac ctctttcatc     300
cggatacttt gatcacgggc aaggatgaca gtggcagtaa cttcgccagg gctacaatc      360
tgatggccag cgagctgttg gatcgctcca tgaacgccat tcgtcgcgtg gcggatcgtt     420
gcagaaatct caggggtttc ctggtctttc gagcaatcgg cggaggttct ggttccgggc     480
tagggactcg catcatggag agactggtcg aagactctgg caagaagatg actgttgtgg     540
agttccctcg ttattcttcg gcttcaatct                                      570
```

<210> SEQ ID NO 192
<211> LENGTH: 620
<212> TYPE: DNA
<213> ORGANISM: Drosophila

<400> SEQUENCE: 192

```
actcgacaag acccaaaata tattcgagct caaaagttta caatttcgaa caaagtcaag      60
gcttcacaaa attttcacat aaaattcacc gttgaaaata acttttcgtt ccgctctttt     120
ttcgttcctt ttctgtttaa atatacaata tatattgat taaacggcgt acggacccac      180
tgagttacaa tgcaacgttc cattttcaag agtagctgtt ccaggacact gatcctgctt     240
aactccctga atccatgca ccacaagagc ctgcacgtgg agcaactgtt ggaggcagct      300
ccagcgccca aaaccgctg cctggatctg ttgggtcgct tgatccatgg ccgattgagt      360
ctcttgggcg tcgtcctgt cccgcccaga ttcttaccgc tattggcggg tgatcgaagc     420
ctgtacttta atgcggacga ggacgaagag tttcgtaagc gtttggccat gcagctgaag     480
gagttgcgag agaccctgca agaaaaacag gaacttcgcg agggacaaga gcaggacttt     540
caggagctgg agcaacagga cgaggaggag gatcagccgt atgtgcccag atctcgggag     600
```

```
atctccatgg aggatctcac                                                    620
```

<210> SEQ ID NO 193
<211> LENGTH: 643
<212> TYPE: DNA
<213> ORGANISM: Drosophila

400> SEQUENCE: 193

```
tcacatcaat caaattaaac agttcgatac agtaaaacag catgaacgac aaataggcgt    60
agaatccatc aggtgtagga gttctcaaga atcggcgagg gtctaatatt gggaatgtcc   120
aggcgggttt ttggcctcag tataaaatca ttccgattgt tccgaagaac tccgatccat   180
cccccagcat tccagcattt ttctggtggc gtctttcgaa cttcctttag gagtttctgc   240
gattgtcagg aacaccgaag aatggatcta ccagagggaa tacttatggg ctttggcaac   300
cccctgctgg acatcacctg caccgttgag gataatgtga tcctggagaa gtacggcctg   360
gaagcaaatg ctgcgatcat tgctgatgaa aagcacgatg ccctgtttga tgagttgatg   420
aacatggaaa atgtcatcta ttcggcgggt ggagcctgtc agaactcgat gcggatcttc   480
cagtggatcg tgcagacacc atttcgagct gtgttcatag ggtcagtggg caaggataag   540
ctaggtgatc gcatcgaaaa gagggccaaa tccgatggcc tgctaacact ttatcagctg   600
aaggaagagc tgccgacagg ctcttgtgct gtgatcatca acg                      643
```

<210> SEQ ID NO 194
<211> LENGTH: 706
<212> TYPE: DNA
<213> ORGANISM: Drosophila

<400> SEQUENCE: 194

```
cctcttcctc agtaactgcc aacgatcgga acactcgat tgaaaattgt taaattattt     60
gtagtacaac aaaagttttt gctatttcaa atcttcgta aaatggccaa ccgtatgaga   120
ggaggagcct gctgtccttc aagatgtcag cccgcctgtc caccatgtcc gccacctggt   180
ccgccctgcg atgcacctct ggtgcgactg ataaactgt ggccggagcc ctacaatcct   240
tgctccttca agaattgcct gatctttggc ggtcacgatg agccctatat tcgacccttt   300
gatcctaagg gttgtacacg aatgcgtcgc aatgatatcg accgatcgtt gggctatccc   360
ataggcgtag tgtctggtac gactgttata aagtcgggca ttccgaatca ggagagcgtc   420
cggtttgctt caaatcttaa ggcatttgct cattcctatt acacgcggcg cgatgaatgg   480
aaaccggata cgatcgatat ggtggtgaac gagggtcagg ttttgtttaa cgattccgag   540
aacatggacc ctccgaatgc atcagactcg ccggatatct acgatgaaaa tgagcaaaag   600
gtgacgcgcc actttaagat caacgatatc gagtttgcca tggagttgga ggcgcccttt   660
gaggtctatg gctacgaaaa cgtcatacgc aatctacgca gaatct                  706
```

<210> SEQ ID NO 195
<211> LENGTH: 642
<212> TYPE: DNA
<213> ORGANISM: Drosophila

<400> SEQUENCE: 195

```
acgctcacat gtattccgtt caatttgaat attccggctt tttaaataga caaaattcaa    60
aacaaattaa actatggaat gatgtggata caccggttgc tgatggacaa gtgcaccogc   120
tatggtcatg tgctgcggca tttgattcgg gcttccaggc gaactgcgac ctcaacggga   180
catcaccaga gtgcttcggg aaaggatgtg ccaatggtgc aaataagtcc gccgattga   240
```

```
ccaccaagtt ggctctcctc cggctgaagc tcctttggga ctgggacttc tccgagcaga    300
agttcattga gaattcgagc caggcagccg ccgttttac ggacttcgta aggcgccgcc     360
gcaatcggaa tgtggagcga tgcagtacgc ctatgggttt caagcagatc aagcacgatc   420
tgttggatga tccgcccgac tggaggctca aaatgatgcg cttcgagaag gagcacttcc   480
ggcgggccat tccgctcaag gtgcagctgc tgcggcacta cgaccatcgt ttcgccttcc   540
tggacgtggt cttcgtggcc ctgcggagat ccaatgactt tcgctcgccg gcggaactta   600
gtgagatgac ggagctgcta aaggagttca tagatcccgc tc                      642

<210> SEQ ID NO 196
<211> LENGTH: 537
<212> TYPE: DNA
<213> ORGANISM: Drosophila

<400> SEQUENCE: 196
tttcggagcg ttcggtggtg gagagcagct gcatttgtgc atttcgcatc gaacattcat    60
cgtgatccca agcgcacgaa gttgttgttt tgttttggtt tttgtcgcca aatttcgcgg   120 gatttttcg tgaacgtgtg tgtgcgcgtg catttatttc gcacactgtc gacggggcaa   180
taccaggatc tgtcgcctgt cttcgcctca gacttctcct ccggatcctg cggagcggag   240
cgtacgtatt tgtggcttca actccgtgtg tcgtatgtgc ccgtgtatgc ctctgtgtgt   300
ctgtgtgtgt ggcgtaccgg cataccgtct ttgttgttgg ccaccattgt aattgcagtc   360
agtgtggcac tggcaacgcg gcgtatactt gacatcttcg ccgccaaatt gtgcgatttc   420
ttcgactcgt tcagctctcg cgctggctcc ttgaatgcgg ctccttgtga cattggcgtg   480
aagacgtgaa gagccctcaa aatccgctat tccactgtgt tcgcaatcca tttgcct     537

<210> SEQ ID NO 197
<211> LENGTH: 599
<212> TYPE: DNA
<213> ORGANISM: Drosophila

<400> SEQUENCE: 197
aaggcgaagc cagatgccac ggtgatcttt ataccacctc catccgccgc cgagggtatt    60
tgcgcgggta tcgagagtga aattggcttg attgtggcca tcaccgaggg tattccccag   120
gcggatatgg tgcggatatc gcaaatgctg aattgccagg agaagtcccg cctgctggga   180
cccaactgtc cgggaatcat ctcgccggat cagtgcaaaa tcggaataat gccgggagat   240
atccacaagc gaggagtggt gggcatagtc tcgcggtcgg gaaccctgac ctacgagtcc   300
gtccatcaga ccaccaacgt gggattgggt caggctcttt gcgttggcct cggcggggat   360 cccttaacg gaactagctt catagacgcc ctcaaagtgt ttctgtccga caaggagatc   420
aagggcattg tcatgattgg agagattggc ggatccgccg aggaagaggc tgccgatttc   480
cttaaggaga gaacactgg ctgcgaggcc aagccagtag ttggcttcat tgctggacag   540
actgctccac cgggtcgtcg aatgggtcac gccggcgcca tcatttccgg tggcaaggg   599

<210> SEQ ID NO 198
<211> LENGTH: 537
<212> TYPE: DNA
<213> ORGANISM: Drosophila

<400> SEQUENCE: 198
cccgcgagca cacgggtgac atcgctaata ccccaaaaaa aacaaaatac actacaaacg    60
```

| | | | | |
|---|---|---|---|---|
| acgaaaggaa | cttaatggga | gaaccgacga | agaataagca | tacaggatgt cgggggctgg | 120 |
| agaacactca | gatgaagagt | cctatggaga | ggagtccttc | gaggaggact cggagtcgga | 180 |
| ggtggaggtg | gaggaagaag | agattgagta | tattgagcca | gaggagtcaa aaccaagtga | 240 |
| cgctcttctg | ttgggggaga | gcgacaccca | aagcgagagc | gatgtgaaag aagagtttct | 300 |
| tagcggcaac | ccacacgccc | gtcgctattt | gggcgcccga | gtggtgtcct acctgagttc | 360 |
| ctcctctgac | gacgaaagcc | aagtggtcat | caccaagacg | gtagccgagg taaatcaact | 420 |
| aagtctgcga | gtggacacgc | ctccggagga | tgagacgccc | tcggtgcgca ctctgatgcc | 480 |
| aggcagtgcc | cattctcggg | ttaaggatga | ggacgaggct | gaagacgagg atgatga | 537 |

<210> SEQ ID NO 199
<211> LENGTH: 623
<212> TYPE: DNA
<213> ORGANISM: Drosophila

<400> SEQUENCE: 199

| | | | | |
|---|---|---|---|---|
| cgcgcgagga | ctttcactaa | atcgagactt | atcacagcag | cgatataaag ttattaaata | 60 |
| ttgatttaaa | ttttaggtga | acattccgcg | atggaaactg | ataaggaaaa acaaagcgat | 120 |
| gagctcatga | atcgcattcg | gaacgagctt | acagctatat | tatctcaaga ggctgctgat | 180 |
| gattccgaca | aggaggcgtc | acaggaactg | ctcctgagtc | ccaatccgct gcccattttc | 240 |
| gggcccataa | ggaaaacaag | gaaagcaaaa | tcgaggagtt | ccaagaagaa caatagtaag | 300 |
| gcctcctcct | cgtccgctgg | cagtacaaag | agttcgtcgt | cgggtaccag atcatctgaa | 360 |
| gatcgtttaa | ctggaggtgg | agcccaggag | aagccatcgg | atccggtctc cacatcctcg | 420 |
| agctattcgc | taagatcagg | atatgacgct | ccgcccgtgg | aggccagtgc ccgtgccgac | 480 |
| ttccttgaat | cgcaagcggc | caaaagcatc | gacgaagatg | tccggaagat gcagctggag | 540 |
| ctcaagcaga | gctacgaact | cttccagggc | attggcgaga | aattggagtc ggttagcttc | 600 |
| acgggcttga | aggaccgcat | acg | | | 623 |

<210> SEQ ID NO 200
<211> LENGTH: 521
<212> TYPE: DNA
<213> ORGANISM: Drosophila

<400> SEQUENCE: 200

| | | | | |
|---|---|---|---|---|
| ccccgattag | tcactttttt | tgtacgtttg | taagctgccg | ccagttttca gagtggcgcc | 60 |
| acggggatac | gtggaatagc | gtgttgtgct | ctacgtatat | ttttatatca tcattgcgga | 120 |
| accacaaagc | tctcgactac | tttctaactg | aggaactgaa | tcaaaggact ctccttcaga | 180 |
| cgcagtacaa | tctccgactg | gccgtcgata | gcgaaacgcg | gcggtcgatt tgaggcaacc | 240 |
| aagctgatta | gtgtgaataa | tatgtccgtg | agtcgagtga | ctatgatgcg aaagggccac | 300 |
| tccggggagg | tagcacgcaa | gcccaacact | gtggtggtgt | cggttccacc gctggtgaag | 360 |
| aagtccagca | agagccgctc | gttccacttc | cgctatctgg | agctgtgccg ggccaagaat | 420 |
| ctgacgccgg | tgcggaaaat | ccgcagcaag | tcgaatgcga | ccaccacctt tctggagctg | 480 |
| tgcggcgata | agctggcggt | cagcgattgg | cagcttctaa | c | 521 |

<210> SEQ ID NO 201
<211> LENGTH: 585
<212> TYPE: DNA
<213> ORGANISM: Drosophila

<400> SEQUENCE: 201

-continued

```
aagacccgc ggctatgtgg tcatagacgc acctgtcacc gattccagtg aggatgagga      60
tgagctcgat gatgagttca aggtatccga tgtagccgga accacgagtg ccgacagcga     120
ttctgccgat tcggatgaca gtgagaagga gaaaaagaag cccggaccac gtgggcgtcc     180
tcgaaaaaag ccactcaaga gaggcacgga cagcgatggg gagccttcca gcgcccaaaa     240
gaagaaatac cagccctctt cgacggcttc agtgggccca ttcgagtgtc ccaactgcga     300
cttgacgttc tcgcgcaaac aatcctatgt gctgcatcgt aagactcacg agagaataga     360
gcatgcctgt cccatctgcg gcaagaagtt caaggtggag tgggcctata aaacgcacat     420
gcaacggcac gagcaggagc gcgcccattt ccgctgcgag ctgtgcccca agatattccg     480
actgcgcgcg gaactgaagc accatatggc ccagcgacac gacgagcatg gcttcattta     540
cgagtgcaag cgctgccagc ggacgttcct cacccagcag cgact                    585
```

<210> SEQ ID NO 202
<211> LENGTH: 543
<212> TYPE: DNA
<213> ORGANISM: Drosophila

<400> SEQUENCE: 202

```
ctcaacactt ccgggctgta attttatcaa aatttcagtt gaccatgtcc ggcaattggt      60
tcaaatggac tgctcttcac gggcggccaa gaactgtcgg cttaaacact aatggaagaa     120
ttctacggct tttggacgat gccgtagttc gatttcggca gccattctac gaatcttggc     180
ggcgtcgtag gcgccttgaa gacattgaaa agagagaaat cccagtgcga cagcaagttc     240
caaggatacg gcacaatcgt tgtccagggg cgaaggaaaa tccttgccgc aaaatgccca     300
gtgttcttcc tgggaagggt gaagtgcttg ttccctctcg cattcaaccg gcacggaatt     360
caatgggttt ctcagttata agattatttg gaagctccac taatgatggg ggttccggtg     420
aaccaccgga aaatcgcgaa ggaaagctca ttaagtttac agtgggttct cgcatagcca     480
aacccaaaac gggcaagatt gaaatatcaa aaaaaggacc attaggtttt gagacaacta     540
aac                                                                  543
```

<210> SEQ ID NO 203
<211> LENGTH: 600
<212> TYPE: DNA
<213> ORGANISM: Drosophila

<400> SEQUENCE: 203

```
agaaagtcaa ctagactttt aactcattct ctattcggcc ctgtatttaa aattttgttt      60
cataacaaaa cagtttgtgg aggctgtaat aggaaaatgc cgagcctggt gaacacggaa     120
attgaagccg cggtcaaggg cttcctgatc gaccaggaga agatgaccga ggtggtggag     180
cgcatgacca aggagataaa gatgggcctg ccaaggaca cgcatgcacg agcggtgatc      240
aagtgcttcg tcagccatgt gcaagatctg cccactggca aggagcgggg aaagtatttg     300
gccctggatc tgggtggctc taatttcagg gtgcttctgg tgaacctgat tagcaactcg     360
gacgtggaaa ccatgtcgaa gggctataat tttcctcaaa ctctgatgtc cggatcggga     420
aaggcgcttt tcgacttcct tgccgaatgc ctgtcggagt tttgtcactc ccatggcctg     480
gagaatgaat cactggctct gggcttcacc ttctcgtttc cgctccagca gcagggactc     540
tccaagggta tccttgtggc ctggaccaaa ggattcagct gcgaaggcgt ggtgggcaag     600
```

<210> SEQ ID NO 204

<211> LENGTH: 617
<212> TYPE: DNA
<213> ORGANISM: Drosophila

<400> SEQUENCE: 204

```
aaaaaacatc cgtgaatatt ttctacacac caaacttaaa atcaaatctt ccagacttgc      60
ttattacaga cttgaaact gaggctccgc ccgcatcttg gtttttacat ttcttttttt     120
ggacattaac tgattttagt tctactaaca atgtgcacta agacaaacga acgtgccact     180
cgacttcatg aacctggaag ggtttgcagg gagttgttgt acctcaggtc gaaggtgcca     240
gtacgtgaag ttcccgcctt cacttttcag gcactgcagc ctaatactgt ggtgaaacct     300
cctccaaaga tcgacatttt caagcggaag ccagtgaagg agaccgtatt caagatctac     360
ttcaatcgcg gcgacattcc gtgtgtgatg tccggcagga gcagcaaaca ggatccgacc     420
aaggagcgtc cggtgaagtg gcactgtgtg ccggagaatc tcgactattg ctactatctg     480
cccatcttcg tggacggact ggcggacatg gactacgaca cccggttgct agcggtcaac     540
ggagccattg acctcatcat gcggtccccc aaaaaggtgc tacccgtgct gcccaagctc     600
attcttcctc tgaaacg                                                    617
```

<210> SEQ ID NO 205
<211> LENGTH: 670
<212> TYPE: DNA
<213> ORGANISM: Drosophila

<400> SEQUENCE: 205

```
cccaccgagt gcaaaccgtt tacaacgagg ttgcttttaa atcttttgta cgtgacttga      60
acaccaatct gcgggacatc ctgggcacat gtcgcgaaat ctgggtcaga tttgacccca     120
ctcagatgtc gcagggcctg ctgtttacct tcctgccgtt gttctttatc ttccttgtgg     180
taaacaactc tcggccagcg gattttccgc acatcttcaa agccaaggag gtcttctatg     240
tatacctaat caacttggcc gctggagtat ttggatatcg gtatttcaag acattctcct     300
ttaaaacaga ggagcaagga gtgatcttct ttacggcaat atccagtgct gtcatcctgg     360
cttttccatac actacgtcac tggaccagca ttgccacgaa ttggtcagca gtcaagcgat     420
ttggacacat gcccacgcgt ctgctgcttt tcggttccat ggcggtgttc ttctcgaaca     480
gcttcgtcat ccaggaggcc aagatcttat cgtacctctt ggcagcagcg atactactgc     540
tctcccacga acttcttcgg ctgagtgccc gtttggattt taggacaaaa ttcaaggcat     600
cacaatttct gcgctccaca gcgttaagat tgatcctggc cagcgttttg gcgatatgct     660
taatacgatt                                                            670
```

<210> SEQ ID NO 206
<211> LENGTH: 477
<212> TYPE: DNA
<213> ORGANISM: Drosophila

<400> SEQUENCE: 206

```
atgtgaaaat cgtcgcagct cgttccgtgt tttcgccact cgagcgggaa atcaaaaaaa      60
tatttctacg ctcaacaaaa taattaatt gaaattgatt tttcaagcaa cagaaatagt     120
tctagaagaa ctataaatcg aggaagtcat ttttgtttta tcaaatttca agtgcaatgg     180
gttcattgtg aaatcaatct aaagtgtgtg tgtgtgtgtc attcgaataa ttactattat     240
taaaaaagaa ataaatacgc agaaagagag agagagatcg aacgaggcag agtgaaagag     300
agagatagag aaaaaagcga gagatccgga gatctctcga gaatctttaa acaacagcgc     360
```

```
taaagttacg gatctaatt  caaacagttt aatttacttt taattttct acaaaacaac    420 aaacttcaaa aagaaaaata cgaaccagca aaactcaaag caaaaaacga tctcata      477
```

<210> SEQ ID NO 207
<211> LENGTH: 714
<212> TYPE: DNA
<213> ORGANISM: Drosophila

<400> SEQUENCE: 207

```
ttaagcacaa ataatttagg ctactgtaag tttagagcga caagatgatc gatattttgt    60
cgctgccgcg gcgaaataag gtgtccggaa acccggccct gctaaagatg atctcctaca   120
agactggact acccatcaac agtctacccg gatgggagct gatccctctt aattgcaagc   180
tgccaatgct caaatgtccc ggcaatcagg tcatattctc caagaacaag atcggacagg   240
acttcaagag cggtaaacag gagtttgagt gttccgttac cgaacacatc ccggagtaca   300
atccgctaca cgactccaac ctaaagacgt tctactccaa tgagcgtaat ctgaagcggt   360
tgagggaaaa cggtgagata acgcaggaca acgatgtaat atgcaatctg aaggacttca   420
atcagcatcg ccaggagctg cacaaatcgc agttgtacta cattttgcag gcatacaagc   480
ggcgcgagtc ggagcaatat gatcgaatgc tgatcgccaa cgcggagtcc atcacaaaaa   540
aggatcacca gaatctcgca gcccgtcacc agtgcactga ggaggttctt gccagaaaga   600
aactacagga gcaggaacgc cacgaaagaa aggtccatct gctgaatatc acatatgaga   660
agtttaagcg cttagagaac ctggccacca tgcagaatat gttgctggag cacc         714
```

<210> SEQ ID NO 208
<211> LENGTH: 549
<212> TYPE: DNA
<213> ORGANISM: Drosophila

<400> SEQUENCE: 208

```
ccgtacatcg cgaatctgtg tctcagctcc cggatcagca agcaagttaa acagtatgct    60
tgtgaagtca ttcagatcgg ccctggttgc ctgcctgatc acccttgtgc cttgcggaag   120
tgctcaagca tacatcgcga agccgacatc tccgcaggga tatcaggatg tcaacggcgt   180
gtggcaaagc tctttcgttt gtcaaacagg atatcaattg aaagcggatg gaaaatgtta   240
tccacagact aacaaaacgt gcgggcctgg atactttctt agcattgatg aactatgcta   300
tcgtacgaat cctgagcctt gccgcttga atcgacgacc actactacta cgacaacaac    360
aacaacaaca acagagccca ctaccacaac aacaacggca gagcccacta ccacaacaac   420
aacaacagag cccactacca caacaacaac aacagagccc actaccacaa caacaacaac   480
agagcccact accacaacaa caacaacaac aactgcgcct cccgtcatta cagaactgac   540
tcgctgtcc                                                            549
```

<210> SEQ ID NO 209
<211> LENGTH: 368
<212> TYPE: DNA
<213> ORGANISM: Drosophila

<400> SEQUENCE: 209

```
cacaggttgc gcacttttcg accgtatcac aacactgatc taccctagta ttcacaggaa    60
gttgcatcct tggcatccag aagcctctag aagtttctag agacttccag ttcgggtcgg   120
gtttttctat aaaagcagac gcgcggcgtt tgccggttcg agtcttgaaa aaaatttcgt   180
```

-continued

```
acggtgtgcg tcgtaacaac aaacagcgtc tgaaaagttt tgtgaatttc caattctata    240
caaagcaaag tgaaaatatc tgtatttta cctttattct gtgaatagaa cgaaaaacat     300
acatacaagg tgagtaatgc aattacaaga aaagagtgaa tagtttatca gtggctatgg    360
ccaaaatg                                                             368
```

<210> SEQ ID NO 210
<211> LENGTH: 600
<212> TYPE: DNA
<213> ORGANISM: Drosophila

<400> SEQUENCE: 210

```
ccgtgcacgc catccaggaa ttcgaggtgg gcactcacct gaagttgtac agcaaaaagg     60
attactatca gggcaacaac tcggacatcg tggccaccga ttcgcagaag aacaccgtct    120
atttgctggc gaaaaagcat ggcatcgaaa gtcccgagaa gtttgccctg ctcctggcca    180
agcactttat taacaaatac tcacatgtgg aggaggcgca cgttcatgtg gaggcgtatc    240
cctggcagcg agtttgccag gaggagacca ggaccaacgt caatgggaag tgcgagaacg    300
gagtccaagg gaactgcgac ttcagctcca ttgacaacag atcactgcac aatcacgctt    360
ttatattcac gcccaccgct cttcactact gcgatgtggt tataaggaga acaggttaag    420
tcaaacatta cttaagcaat aatatttaaa actatttaat catcaccttc tttaatgttt    480
tagatcccaa acaacggtc atcacgggca tcaagggtct ccgggtgctg aagacgaccc     540
aatcctcatt cgtgaacttc gtgaacgatg agttcagatc tctgccagat cagtatgatc    600
```

<210> SEQ ID NO 211
<211> LENGTH: 600
<212> TYPE: DNA
<213> ORGANISM: Drosophila

<400> SEQUENCE: 211

```
atcgctggaa tagtttaaac gtaaactgta tataaaaaaa aaaatgctcg tcaagttgtg     60
cgctatcctt ttggcccttg gccttagtca ggccattgcg tatccgcccc tgcaacttag    120
taatccgcac cagaacctag tgcagttcct gatacaatca cgtgatctcg gcaacgatgg    180
tggacatacc cttgaatgct tggattatta tcttcccctg ctgaacgacg ttgtggagac    240
ctacaaggct gatttaaatg cgtgtttgga acagctagt caggaggtct cacagatcaa     300
cgacaatacc aaggaagaac gagatgccat cgatgcctca gccaagagct cctgcgatgc    360
cctcaccgca tgtagtacaa aggaagcggc catagattac ttccagtgct acagtgaagc    420
cggctccaac aacaccaaaa ccatgttcac catctccgct aacgcttcgg agctgctggc    480
tgctgtggag gaggaagtgc gtctcatcaa ggtgaatgaa gaggtgtgca ccaacaagac    540
ccagagggcc tatggagaga gctacggtca gctgtacgcg gatttgggtg attgcattgc    600
```

<210> SEQ ID NO 212
<211> LENGTH: 550
<212> TYPE: DNA
<213> ORGANISM: Drosophila

<400> SEQUENCE: 212

```
gaacacatcg ggaaactttt cgttgtctag tgtctttgca aaattattct ttagtcgttt     60
cggcagtgtc aagtctactc aatcgtttct cccagctccg agcaaacaaa attatttcca    120
ttgacaattt tccagttttc gtcagctcca catcgccgtg tcggtttgtt tgatttcaag    180
tttctggagg ttattgtccc ataatcagcc atgtccggtg attgcaacac gtattgccaa    240
```

```
aatgcctgcg atccctgcca ggcgcccacg gatttctcgc cctgtccgcc gaattcaacg    300
tgtccgcctt gcgactgcgg cgactatgca ggatgctgct accagcagcc gccgcgcacc    360
atgcccatcc tgcccaagtc gcacttcatg cgctccacag cgccgctgga cacggacacc    420
atataccgac gatcgttcta tgctaactgt ggcgacaaca ttagggcccg acccgtaatg    480
ccgtgctccc aaatacgagc atccacggcg ccgctggaaa agtgcaccat acagaagtta    540
tcctacatgc                                                          550
```

<210> SEQ ID NO 213
<211> LENGTH: 181
<212> TYPE: DNA
<213> ORGANISM: Drosophila

<400> SEQUENCE: 213

```
ttgttgtttc aactattttc ctgtatttgt ttttattgtt cgctgctggt gctggtgttg     60
gttttgggta tgttagacaa caaagttta atggtattag caagccaaat ataacacaca    120
caaaatgtta ccaacaacaa tgttgaattt gaagcgagaa gagtaacaca cacagtaata    180
t                                                                   181
```

<210> SEQ ID NO 214
<211> LENGTH: 563
<212> TYPE: DNA
<213> ORGANISM: Drosophila

<400> SEQUENCE: 214

```
tcatcagctc cagaaactcg aggcgctgga ggatcagttt cccgagaata ccctggatgc     60
accttatcat ctgcgatacc ccttcaccga catctccatc aagccgaatg gtgtgggctc    120
ggagttggag ttcttcaagc atcgcatcca tctggagcgg gattcggtgc gtcgggccaa    180
ggaatcgcta aggacacagc gcacaaattt ccgccttaga cagcgggaga tcggccagca    240
gcggaagata accgcccctat cgccgaaaca ttccattgat cagctaatcc aggaggagaa    300
ggaactgacc gagatggagg tgaatctcca tcgcactcgt tccctgctgg gcgagaaaat    360
aatacgactg cgacatttgg aacagagtct gctgaggatc tacgagaagg agaaatcgat    420
cctggacctg ggcaccatgg acgatgcggc cacacttagc gatctatcgt cgcactccag    480
ttctggcttc agtagcaccg atttggccag tgccgcggat ttccacaaga agaaggacta    540
ctaccagcag gagtcgaacg agt                                           563
```

<210> SEQ ID NO 215
<211> LENGTH: 620
<212> TYPE: DNA
<213> ORGANISM: Drosophila

<400> SEQUENCE: 215

```
ttcacactgc actttacgca tagccggtcg tcccagaaat ttgaagagcc aaacagttga     60
taatggcaca ttcaatgctg aaactgggga tgatgtgtgg aatactccac ctgctgacct    120
ttggagtcat tgccgaggat cagctgaaaa acaacacaat agtggtacat actcctctcc    180
agaactacga tcaacccaat ctccaggact acgaggaatg ccaggtgaac agggacaatt    240
gcatcaatgt ttgcgctggc aaacagtcgt gcgaggacga gtgtcctgtg tgcccggacc    300
tgtacgtcaa gcccctgatg gttcagggca ttaacgatac gaatatagtg gcaccacccc    360
aggtacctat taatacgacc aacattattc ggctgaccaa cgatatcaac aatataatcg    420
```

```
aacatcaaat ccaaaatcgc aatgaggtca atgtccaggt gaatcagaat gtctcgaagg    480
tgggaggacg ttttggactg ggctacactg acaagggatc gtgctgttat gtggtgcgtt    540
tggatcgcga gtgtaagaat gaagatggac gcgactgcag agaaagaagc cgtcagcgga    600
tctgtggcga aaagtgtcag                                                620
```

<210> SEQ ID NO 216
<211> LENGTH: 409
<212> TYPE: DNA
<213> ORGANISM: Drosophila

<400> SEQUENCE: 216

```
attatcccta aatccgtaca gggcaacgat gagtcttaag ggtctcaatc tggccaaagg     60
gcaaatgatc aaactttaac agttgctggc acaagaaata gaggacgaaa gccagcagga   120
gcggaatgag ctatcaaacg atgatttcat agccaatgca ctggataaag tgcaagttta   180
tgtggaggct ggtaagccag aggcttttgt ccagctcaaa gaaccgctat tatacaaatt   240
taagattacc tcaaatggag tagctactgg atcttcggaa tcggataagt ttcaacgcgc   300
agacgccaag gaaattgctc gctggaaatc tgaccatgta ataaatttgg attgcatttc   360
agacgaggac tacgagcagt taagccaaat tcaaaccgat gaaaggact                409
```

<210> SEQ ID NO 217
<211> LENGTH: 626
<212> TYPE: DNA
<213> ORGANISM: Drosophila

<400> SEQUENCE: 217

```
atctagtact ccgttgtcat aagatccagt cacacacaag tttccaactc atatatatac     60
acattgtaaa ttaacttagg cctgttaact aaacaagatg gcagaaccag gagaacaacg   120
aaaattcgta ttgggacgct gttgtatttt ccactgcgcc gggaaggctt caataattat   180
acccttgatc acactgccaa ttcttattta tggctttcag accgacatgg ccgagttcaa   240
gtgcctgtgg cttattgtta ccatggccct gctgtggatc accgaaaccc taccgatata   300
tgtcacggca ttgtttcccc ttgtcttttg ccctctcctt ggtcttgtga atgcctctat   360
agtctgcaaa cagtacttta ccgacaccat tgtggtattc cttggtgggc ttattgtggc   420
cttgggaatt gagtacagta atctacacac cagaattgcc ctgagggtca ttcggattgt   480
cggtggaagt cctagacgtt tattcgtagg cttgatgagc gtgagcacgt ttatgggatt   540
gtggatatcc aactcagccg gaacgggcat gatgtgcccc attgtcaaag cgctggtcaa   600
tgaattgggt accaacaaaa tatttt                                         626
```

<210> SEQ ID NO 218
<211> LENGTH: 446
<212> TYPE: DNA
<213> ORGANISM: Drosophila

<400> SEQUENCE: 218

```
ctattatggc tatagaaccg atttctgcag ttccttcttt attatccgac taccttagga     60
ctccgtcttg cccaccgaac ttacagtggg accctactgt taagatttgc ctcccaaact   120
tggattataa tcaatatgtg cctaagggac ttctgaacaa cccgagctta cctgggtcgc   180
cgtaactcgc ctgtgcaac  acctggaaga aaacctggag gaagttctgg tggtggcact   240
aaggaaactc ttgaaagaaa gcctgtgcaa cgtcctgttg cgaaacctag tgttagttct   300
ggcggaggct ctgggggaag tactgaagaa aaaccaggag gaagtgctgg cggggctct    360
```

```
ggtggaagtc ctaaggataa gcctgtagaa agttctggag caagtcctgg agaaaaacca      420
gcaggtagtc cggagagcat accaga                                           446
```

<210> SEQ ID NO 219
<211> LENGTH: 636
<212> TYPE: DNA
<213> ORGANISM: Drosophila

<400> SEQUENCE: 219

```
cagaaatctt acaaaattac agtcagctac atagtatttg tttaacaatt ttgatttcaa       60
attattgcaa gtaaacgatg cagccccgaa ataaattaag caagtgtttg atctatataa      120
cgccctgtgt gcagcaattg tgtttctatg cactaggcg acatttactg gccatgcagt      180
ccttgtccgc ccaaaggaat cggaagtctg atgtctccga aagaaggca gtagagacaa      240 cagtcgaatg ggggcgtggc ccccaagcgg gcgaccgcct tccaacagcc gttagtctgc      300
tccgtcgaaa ttcgacagat tccgcgagga acgaggtgaa accgcattc attcgatacg       360 aaaagtctat gaacgaattg gccaaaagtg cccgaaagct atataaaat gcccggctaa       420 ggagcttgcc tttgaggaag cccatgatgc gaggaaaaat cggtgactct gatgcaagac      480
ccctaagaac accggtgccc agtgcttggg ccataaccga gcgggaaaat aaatagctgg      540
cataagcaga agagatggtt ttaaggcaag gaaatgcgtg taaatgcgtg taattttact     600
taagtctgta gatatatatc caaatatatt tttcct                                636
```

<210> SEQ ID NO 220
<211> LENGTH: 620
<212> TYPE: DNA
<213> ORGANISM: Drosophila

<400> SEQUENCE: 220

```
cagctttatt cgaaaagcca tttgcaccaa gatttgcaat catcgaactc cctttacaga       60
atgcaaaatt gattgcagcg tatcagcggc aaatttagca aacagaaaac agcatgcgaa      120
ggaaaaagaa aagtgtaatg atagcgccaa ggaaccaaat ccgactttag tgccaattgt      180
gccgtgcgaa atgctgttag tgccgcgttg ttgttcgtgt ccatgttgtg attacataat      240
gagacgctgc tgaaagtcaa agtccaagga gaagtcccaa gtgtgtatgt aagccaggcg     300
gcagccatat ctcaacttgc cgccactaac tcagccgaag tagaaggcga agcaaaagcc      360
taaggaccag ccctccatct gcaggataac gaggagcgtg aggagccgca ggaggatgcc      420
cttcggccgc aagtccccgc tggaggcact ggcccttccc ggcgtcatgc tcgcctacaa      480
gtacagccag ttccgccagc gccgccggga ggccgccagc cgacgggtca ccgagcgcga      540
actctcggcg ctgcaccata aaatcgacaa actactgagt aaactggagg aggaaagcga      600
gccggatcct ccaacctccc                                                   620
```

<210> SEQ ID NO 221
<211> LENGTH: 620
<212> TYPE: DNA
<213> ORGANISM: Drosophila

<400> SEQUENCE: 221

```
aaaattcgac gttgctgttt ttttttggttt aacattctct atatacattt ttttaaaaat       60
atggatataa cggtaccgcc gccggactcg cactggtcgt tgaggtttgt ggacatcgtg      120 aagcctttc caaaacatac tttggccaat gccacttata agatcattcg cttcttttac      180
```

```
ccacccttg ccctggaaac cgtcgatgtc acccacgtgg tcagcgatcc cgagctgaat    240
agtttaaacg tggggctgtt tgtggtagtt cccttaattc tggcctgcat cggctatggg    300
gtgtacaaat atgtgcggag tatgcataca gtggctaaac ggacaccatt aaaattgtac    360
gagcttgaac agcgtatgaa agacaagtac ggtccggaat acaagcaggg aatctggaag    420
cgaaaggaca tttctgaccc cctcctatta accactgatc catccgaacc aaaagcaaag    480
agatgtgaaa gcagcaatgc ccactggctg cgcaaaaccg atagatccga tgattaatta    540
aatcaacact cagttggatc cccactcgga tatgactggg gatcttaaaa tcgagaatcg    600
aggaaagtac cttctcgaat                                                620

<210> SEQ ID NO 222
<211> LENGTH: 607
<212> TYPE: DNA
<213> ORGANISM: Drosophila
<220> FEATURE:
<221> NAME/KEY: misc_feature
<222> LOCATION: (1)...(607)
<223> OTHER INFORMATION: n = A,T,C or G

<400> SEQUENCE: 222
tcagcgttgt ggtggcaagt ttgcgccctt cttttgcgcc aatgtcacct gtctgcagta     60
ctattgcgaa cactgttggg ccgtcatcca ttcgcgacct ggacgcgaat atcacaagcc    120
gctggtcaag gagggagccg accggccgcg tgcggtcccc tttcgctggt gttaacggcg    180
gcgctggtag gccgcgctgc acgacgagag acgccaacag agggagcaac gacaccggtt    240
gttaaacgca gcgctggcag tgcccagaat cataacagaa tcatcaggat cgggaggagt    300
cgcagaagga gcgggagtgg cagcactaga tgccgctggc ggagatgcgg atcgaaggcg    360
aagaatctag tagataacca ttagagacaa cacacgcacc accaacaccc actcacacac    420
aacagtcgga tactattctc ataagcaaaa gacaattgcc cggtggaatc acccattccg    480
aagggcaagg tgcaaataca acgggagctg gacaaaggtg tcccttttgaa tagccaccag    540 agtctacagt tttagaggcg agaaacgaaa gcaacatnag ttttagttct tatttattcg    600
gcaatca                                                              607

<210> SEQ ID NO 223
<211> LENGTH: 500
<212> TYPE: DNA
<213> ORGANISM: Drosophila

<400> SEQUENCE: 223
gccgagggcg ccgttctggc cgtttggcga tattgtgaca tgaactccaa gaggaagcca     60
ccacacatcc ccaaactgga gctgtacgaa tctccggact atgaaggttg gacccggggt    120
gtcttcaagg cggaggctca gaatttagct cgcaggatgt gtgatacacc tgcctgttgc    180
atgacaccaa cgcttttgc ccaggccacg gtagatgcgc tgtgcccctg tggcattacc    240
gtcgaaatcc gcaccatgga gtggattgaa cagcagcgtc ttcattcgtt cctcatgatt    300
gccaagggca gctgtgagcc accggttctg atggagatca cctattgcgg caccaatccc    360
gaggacaaac ccatttttgtt cctgggcaag ggcattacct tcaactcggg cgccatgaat    420
ctgaggaaat gcagggggaat ggaggagtac agggcttgca tgtcgggagc tgcatcctgt    480
gtggccatga tgcgttgcgt                                                500

<210> SEQ ID NO 224
<211> LENGTH: 562
```

```
<212> TYPE: DNA
<213> ORGANISM: Drosophila

<400> SEQUENCE: 224
caacaacgat cacttcaggc tgtacgagaa aattatatgt gcgaggattt cgaaactgga      60
tcaagcaaaa aggacgaaaa ccaaacaaga gcaaaatatt ctaggctaat caaaagcaca     120 gtgagggca aggagcattc tatcgaaaat gccttcggaa cagcatacga atataaaagt      180
ggcggttcgc gtacggccgt ataatgtccg tgaattggag caaaaacagc ggagtattat     240
caaggtcatg gatcgttcgg cactgctgtt cgatcccgac gaggaggacg atgagttctt     300
ctttcagggc gccaagcaac cgtaccgcga catcaccaag cggatgaaca aaaagttgac     360
catggaattc gacagggtat tcgatataga caattccaac caggatctgt tcgaggagtg     420
cacggcgccg ctggtcgacg cggtgttaaa tggatacaac tgctcggtat ttgtatatgg     480
agccactggc gccggaaaaa cattcacaat gctgggcagc gaggctcatc cgggtctgac     540
ctatcttacc atgcaagatc tc                                              562

<210> SEQ ID NO 225
<211> LENGTH: 900
<212> TYPE: DNA
<213> ORGANISM: Drosophila

<400> SEQUENCE: 225
gctgccggcg ctttacagta ctggattatt tgcaaccggc ttattattgc acaaaaatct      60
agtgaaatgt cctcgccagc ccccaaatcg ccagagcttt cggataaaag caagaaatac     120
gacagacaaa tcaggctgtg gggagagcat ggacagacgc tattggaggc agccacagta     180
tgtttggtga atgttacggc cgtcggctgt gaaactgcca agggactggt gctacccggt     240
atcggaggct tcactgtggc cgatggcagc accgtcaagg aggaggatct gggcaacaat     300
ttcttcctcg attccagcta tctgggcaaa tctaaagcat tggcttgcat gcaacttctc     360
caggaactca atcccgacgt aaatggcgat tatgtcgacg agagtgccga ctttttatta     420
gccaacagac cgaacttctt cgacagcttc gatttagtga ttgcctccaa tctcaatgag     480
cagactttgc ttctcctggc cgaacggtta tgggagctta cgttccatt aatctactgc      540 cgatcgcttg gcatgcttgg cacaatgctt gcaaatacgg aacactgca tcgtggaggc      600 gcatccggat aatcgacagt ttgatctgcg tctggagcat ccattcgatg ctttgcggga     660
gcatctcgac ggcaccgagg tgaccagtaa ggtgccctgg ttgctggttc ttcacaaata     720
ccttaatgtg tggcaaaaac aacaagcgga tgggactcaa acgcctcgaa attacaaaga     780
gaagaatcag ttgaaggaga ccattagaga ggagatgaag gcggatgagg aaaactatga     840
agaggccatc aaggcggtca atacagcctt tggagcggga caggttccca aaagcctgaa     900

<210> SEQ ID NO 226
<211> LENGTH: 550
<212> TYPE: DNA
<213> ORGANISM: Drosophila

<400> SEQUENCE: 226
catagacttc aattccaaat atcacatcga tgtggacttc gaggtgccca agaagctgca      60
gtggtattac gccctgctt tctttggctt ttggcttgtg ctctatctct cgctggtcaa      120
cacccaaatg aaccacatgc cgcgcccact gaccgcagc gatgaagcca gtcatcccaa      180
ttcctttatt gcccagcgag ccgaggacac cctgattgag ctgaccagga ttggaccgcg     240
```

```
ggtggtgggc agcatggcca acgaggagag cgccgtggag ttcctgcgcg ccgaggtagc    300
caaagtggag tccgaaatga cgaccttct ggagatcgaa gtggatgtgc agcaggccag    360
tggagcctac atgcactggg agatggtcaa catgtatcag gcattcaga atgtggtggt    420
gaaactctcc gaaaagaact cgaccaacga gaattacctg ctgatcaata gtcactacga    480
ttcggtgccc ggaagtccag gagctggcga tgatggttcc atggtcgtta ccatgttgga    540
ggtgatgcgt                                                          550

<210> SEQ ID NO 227
<211> LENGTH: 977
<212> TYPE: DNA
<213> ORGANISM: Drosophila

<400> SEQUENCE: 227
agacatatac catttcaagg agttttttt agtaaaataa aacgagaaaa ctaacaaaaa     60
aaggttcgtt tatcgcattg aatcaataaa aaacaatggt gtacaccggt tacgtaagca   120
acggattgca gaatgctgag gaaactgcat gggtgccgta tggagatccc aatgactggt   180
cacatggtct ggcagtttat gatggtttgg aactgatgag cggcaatgag gaggagttgc   240
agccctcatt gaaccgggtg atgaaaaaca tcgactacga cctggccatg aagcatccat   300
tggagcatac ctggactttg tggcacttgg agaacgatcg taccaagcgc tgggccgaaa   360
tgctcgtcga tgtgaccagc ttcaacaccg ttgaggactt cttcagtgtg tactactttg   420
tgaagccgcc atcggatctg aagatattca atgactacat ggtcttcaag aaaaatattc   480
gtcccatgtg ggaggatgac accaataaga acgtggtcg ttggatactg ctcctggaca   540
aggcctccag gacctatata gataagatgt ggcacgattt gcttttgtgc atgattggcg   600
agtgcttcca gcactcggac gagatatgtg gagtggtcat caatgtgcgc aacaaggcta   660
ataagctatc cctttggacg aaggactctc gcaatgtaga ggctatcctg tccattggca   720
ggcagataaa ggagctgctg catctgggca ttatggaaat ccagtaccag gtgcacaagg   780
atgccatggt gaaccatgga cccaatgtca atgccattta cacattgtag gccaatttcc   840
aagggcgcca tagtacattt ccaacgatag tacataagcc ttatacattt gtcaaactca   900
cattttatcc cacgcgcacc aatgcttttc gagatagata tcggttgtac catgaataaa   960
gtattgcgta gagcagt                                                  977

<210> SEQ ID NO 228
<211> LENGTH: 497
<212> TYPE: DNA
<213> ORGANISM: Drosophila

<400> SEQUENCE: 228
tacagattgt attttcgaat tcttttaagc aaaatttcag tgttcagaaa aagtaaaaaa     60
aaagtaaaac catcggcact ctcattcttc agaatcgttt ggttgttagg tcttaggatt   120
aatagcttgc gcattgattg ttggctgaag cacagatgtc tgttcgcaac tcacgccccc   180
agttatcgtg gccggagcgg gtaagtccgc aaaggactat tgacactcca acggcatccg   240
gagaaatgtt gactcgtcgt caatcggcac cagcgttggt cgtgccgccg gaggagacca   300
cgcacgttgt ggtggtcaag cggcaatccc cggacgcagc cgctgccgga gaactggtgc   360
cgtctaggcg gaaggactcg gtggctgtgc agtcgggaat tgtggccact gggccattgg   420
acacaacacg cagtggtgca agagacgatt ttctaatggc tttgctcgag tgcccggtgt   480
gctttggcta cataatg                                                  497
```

<210> SEQ ID NO 229
<211> LENGTH: 700
<212> TYPE: DNA
<213> ORGANISM: Drosophila

<400> SEQUENCE: 229

```
aagtgccatc tctagccgac gggtgggata gaatctccaa ttgggatttc catccagtga      60
tttcctaatt aaattaattt tttccaattg cccaaaggca taggcatatt tcgcaaaacg     120
aacaaatatg tttgcttgaa gcgcatagaa tcacaaacaa aagtgcaaat ctcagagctt     180
aaaaaccaga gcaaaggaga ataacggaag aggaggcaag caaaaagaca aagaggagtg     240
caaaaaatac agcaaacatc atgcacagga catatgtaag ccatgcgata tacgccattt     300
ggctggttat attcgccact gccggcataa tgcccagct  agacctggat cagatccaga     360
cccagctgcc cgaccagctg aggaagtcaa actttagcgt gaacgacgcc aaggagctat     420
ttcgcaacaa atgcatcgag gtggccggcg aggaggcggg cgtcgaggca tacggcgaga     480
tcgagtccgg attcatggtg ctaaccgagt gcctcaatgg cattgtcaac tacacggcaa     540
tgcagcagga gatacaggaa gcgtcgccca agggcgaact ggatgtggtc ttcaacaagt     600
actgcagccg gcgttcgaat gccgtcgagt gtgtggatgc gttcacggcc aaactggtgc     660
cctgtctggt gcaggaggag cgcgagggcc aggatgtcat                           700
```

<210> SEQ ID NO 230
<211> LENGTH: 594
<212> TYPE: DNA
<213> ORGANISM: Drosophila

<400> SEQUENCE: 230

```
atctattggt agaaagtaag aaaaaaaaaa ttctcaaaat ttaagttata tacaaatttg      60
gagtgaaata ttttataaac actttcggag tatctcgagc tttccacaca tcgaaaatga     120
atttttgttc agtgccttac gaagctgact acggcatgta cgccgattcc aagatgaaga     180
gcgttcctca gtacccccta agcatgggag taggtcaggg tcaaggacag tccatggcca     240
tgcagcccct gaatccaccg cagatgaatc tgcagatgca gatgcccgtg tgccagtcgg     300
gcgctttgtc gtacccaatg cagggtatgc cgctgggcat gatgcaaggg ggcaatcaga     360
tgacccccat gtccacgatg tccacccagc tgccgattgg agcggtgact cccctgagca     420
gcatgaccat gatgcccatg atgggcaatc ccatgggcgc catcgatgcc cccgggatca     480
atgcagtgct gcctgacctg cagccgatga cctcgatggg tcagatgcag ccgctgcaac     540
agtacaatcc cagtggatct accacccaaa tgcatcaagg acgtctgacg ggcg           594
```

<210> SEQ ID NO 231
<211> LENGTH: 550
<212> TYPE: DNA
<213> ORGANISM: Drosophila

<400> SEQUENCE: 231

```
ttcagataat cgtagatgtt ttttatcata agcgaataaa aaagttagca ttaattggtt      60
taaagtagtg cgtcaaaatt cggaaatcca cagaatgacc atccaaggac tgaagtgtga     120
cctcagcccg acggtgacca cttgtctgca gctgaaggac tgcgtccgtc cggactgctg     180
tcccatccgg gacccattcc ctacgatgc  cgagtgcttc gttagggaca ttggccagga     240
gctggacaaa ctgacgcgcc gacacgagcg catgttcgtc aagcggcggc gtctgatgga     300
```

```
aatggccata cccaggcgac gcacctgccg ctttgtgccg aaatgcgcct gctcatttcc      360
caagtccatc gagatggtgc gaccatgtga cgcccagaat cacacacgca ccgagcaact      420
agctctgccc acgtccgtc gattgcttca caggcggcga acggccattc tggcgggcga      480
ctcaattggg gagtccatac tgaacagatg gcttcgctac agctatctat cgctgtacag     540
tcgtctcacg                                                             550

<210> SEQ ID NO 232
<211> LENGTH: 492
<212> TYPE: DNA
<213> ORGANISM: Drosophila

<400> SEQUENCE: 232
atccagatga aggtttttgc tgtcttggtc ttggcaattg ccacagtttc tgctgatatc       60
ctgcgccagg acactccagt acatccccgt gatagctcag ctgttccgtc catagatggt     120
cgcattacca atggaaacaa ggcagctgct aaccagtttc cctaccaggt gggactcagt     180
tttaaaagct cggctggcag ttggtggtgc ggtggttcaa taatagcgaa acatgggta      240 ctaactgctg ctcattgcac caaggagcc tcttccgtga ccatctacta tgggtccacc      300
gttcgcacta gtgccaaact gaagaaaaag gtctccagct ccaagtttgt gcagcatgcc     360
ggctacaatg cggctacttt gcgcaacgac atctccctga tcaagactcc atccgtcact    420
tttacggttt ccataaataa gattgccctg cccgccatcg ccagcagcta ctccacctac    480
gccggacaga ct                                                          492

<210> SEQ ID NO 233
<211> LENGTH: 461
<212> TYPE: DNA
<213> ORGANISM: Drosophila

<400> SEQUENCE: 233
ctacttggag ttctcggatc cgccagagta cctaacttac cccctggtct ttccgatcaa       60
ggactggccc gccaaacgcg atccctcctt catgggcatc ttcttcagca agtgccgtgt     120
aggacgaatt tatccatcgg atattgacca gcggacgccc ggtgtttact tccgagtgga     180
acgtgatctg atgggacgta cggaccgatt cggcgtggag gtgcgggaac gcaccatgtg     240
ggacatccgt cagggagtcg tgggcgccga taccttcatc cccaagcacg tggtgatcgc     300
cacctggaag aacgtctcct tcgccggtgg catcgacaac tccctctaca cgacaaacac     360
cttccaaatg gtcctggcca ctgacgaggt ctacacctat attattttca actatgccgg    420
tctgaactgg ctttctcata ctgaggccgg aggtgatacg a                          461

<210> SEQ ID NO 234
<211> LENGTH: 583
<212> TYPE: DNA
<213> ORGANISM: Drosophila

<400> SEQUENCE: 234
ttcgaagtga acggtcaatg ggaaaaatgt tcgccagcag aggaatgctg gtgcttggag       60
tgcttctggt atcagcaatt ggtggccaat cggaatcgat cccctgcaaa ctcatcgatg     120
cagaacatgg caaagtgtgc gtctgcacgg cggactattg ggattatctg gagaatcccg     180
tcctgacgga cgaaaatgag tggttcctta tctccagttc caaacaggga cttcggttct     240
ccacaactag tgacaaattc ggtaaggagg agaagtttac cgcgcaggat tatgtggaac    300
ccacgcagga gactgcgaat gcgacaatcc tgtctcgttt gctcgataag gtggtggaca    360
```

```
gtgcttttac cttggagtcc cgggagagtt ccataactcg cactgtaacc ctgcgactgg      420
acagaagtaa gacccaccac aagatggttg gtttcggtgg cagctacacc ggagcagtgg      480
aatacctggt tgagaacttc aagcattcgg aactggctga ccatctgtac aagtgctttt      540
acgccgagga tggactgtgc ttcaatctca tgcgagtttc cat                        583
```

<210> SEQ ID NO 235
<211> LENGTH: 569
<212> TYPE: DNA
<213> ORGANISM: Drosophila

<400> SEQUENCE: 235

```
caccaaacga aagtcattcg tatactttac aatccatttg atattttgat attttcacaa       60
gttagtcggg agttgtgcaa taatgaattg tttggagaag aaatcgccgg aggcaaatcc      120
agagtgtaag ggcaggacga ttgagttaaa tccgggatct gcttgcccgg ctccgctaat      180
ctgtcccctg ccgacggaac caccctccca ccgactgaaa aagccaccgc agcccgccct      240
ggtagccttg acacctcatc ccgatgaggc cgcccaacag cacctggtcc aaaatattat      300
gggttctgcc caagagcatc agaagctaca ggcggatctc aagcgggag ttgaccaaca      360 gcagatgcaa ttggccgata tgcgagctga acagtacaag caatcgaaca agccactcag      420
aatggaggaa gtgcagtttg cgcgttccat ggaccccgaa gcagatgact tgcggaatcc      480
accgtgctac ttgccccaac agggcgatga gttgcctcac aaggaccagc tgatgcccat      540
gggtccgatt ggtccatggg catcgggca                                        569
```

<210> SEQ ID NO 236
<211> LENGTH: 612
<212> TYPE: DNA
<213> ORGANISM: Drosophila

<400> SEQUENCE: 236

```
attttctaga agtaagcctt acataatgga tgtatcccag tcagatggcc caacagaaaa       60
tgaggctggc ggaatgaaga acattacaca tcagttcgag ttcatgtcta ataggttgaa      120
ggagcatatg aaatacaaca tcctccgtaa cgctgtgttt tacaagaaga ttcccctgca      180
gaagaaacta aaacttgccc ttgaaagaaa tatcggtccc catgcctata taatagttaa      240
cgatacaatc tacaagtgcc aagtgttcgt actccgcatc tactgcaagc tgtttaccaa      300
caacctcaag cggggtgaca tagtcaagtt tcccagggac gcgatgagca atgagtgctt      360
tgaattggcc tatacctgga tgactaataa tgcgatacat ttgccacgtg acaagataat      420
aaatttgctc gcggccgcaa aatgtttgca gtgcattccc ttgatcaagc gcatctttga      480
gtttcttaac gactaccgaa cccattgcga actttttttca tttagctgct atttgaaggc      540
caaagatatg ggtatgaccc aggtagccga catgatggtg tccagagtga ccaagtcctt      600
cctggtacta gt                                                          612
```

<210> SEQ ID NO 237
<211> LENGTH: 505
<212> TYPE: DNA
<213> ORGANISM: Drosophila

<400> SEQUENCE: 237

```
ctcctctttt gaacccctca cctcatctaa caaacattgc caaagtgctc gtagctaata       60
gaaacccctg tcgaaattcg attcccaact aacctatcca cttttggac gcatccacag      120
```

```
caacaagcag caccacggat cccgagacag aagactccag gcggggcgcg gaggatgatt    180
tgcctgcccc gccgccactg acctccggat cttctattcc ggtgccggag tacgtgcccg    240
agcagtccac acagctgaca ccctgtccct gctgcagtcg caccttcgcc gtggacacgc    300
tgcgcaagca cgtcgtcatc tgcgagaagg cctccaagaa gcgcaagatc ttcgactcgt    360
cgcgccaacg ccgcgatgga accgctctct ccacgtacgt gctgcccaag aactttggcc    420
ttcccaatgc ggaacgcacg gcgggattac catctcctcc gatcaacagt cgcgagacca    480
cgtcagtaaa tgctgctccc gagac                                           505
```

<210> SEQ ID NO 238
<211> LENGTH: 649
<212> TYPE: DNA
<213> ORGANISM: Drosophila

<400> SEQUENCE: 238

```
tagcctgaaa tatagttgcc aagcttgggt tgtcgatttt cttcattcgg tcgagcttag     60
cctagcagtg ctcaacctgt ctaaaagcta aagctacaaa tatatttata acttgtgaaa    120
aagtgtgaga tccagtgata gtccgtccat aaagtgcctt caagccacat agtgaaaatg    180
tcgatctttg accatcccga acagctgaaa atgctgcagg gccttctgaa tcccaatcag    240
agaagaggcg gcattgacta cagcagtagc gaggatgagg aggagtcaat ggttgtcaat    300
aagatgaacc ctggaacaat tggacgtcct aatggggagg atggaaccgc taagggtaag    360
aagaaaaaga agcccaaccc tttgtgcact cccttggtgg aggaagagaa aaaacagccc    420
gagagtctgg aagaatggca agatcagcag gagaaggaag acatggatat acttgaatcg    480
cggaagactc ccgagtatac gatgacctat cgccaagcag tgggcactga ggatgtcttc    540
ttgcagatgg gcaatcgcac tggatcctcg gccagctgtg aggacctcat tttggaggtt    600
tccctgccgg acgaggaaat gactgctgac aaaatgtcgc tcagcttgc                 649
```

<210> SEQ ID NO 239
<211> LENGTH: 599
<212> TYPE: DNA
<213> ORGANISM: Drosophila

<400> SEQUENCE: 239

```
aaacatttaa cgataataag cataagaatg agctctcttg ttgataccag tcactcggat     60
atcgatgaca atgactcctt ccactcgttc gaccaaagcg aagatatcat ggacaacctt    120
agcctctcgc tctcggagag cgactgcgac agcgccgcgg actttgattc cggctcggcg    180
gatgagattt ccatggaaaa aaaaatgggt ggtgcacccg cccagctggg ccagggcgca    240
ggaaatactt tgaagcccac gccttccgac gtcttcgtaa agccaaagtc gcccgttttg    300
gaggtccatt ccagcgactc atacacctgc gatggcgtct ccgctggcaa gcccacacag    360
gttgcgggct gtttcaagtc tcccaagaag tttaccgttt cgccgatcag tgagcaaaag    420
cagagaccac tgcccttgtg tcccagagat gttccgggac tttcctcgag ccagatacca    480
tgcataaaac actttgacct tgaccactca gtaacagtcc gaaaagagca cctgatctcc    540
aatcccgaaa cggaggcctt acaataacac cgccttcacc gaaatttgga tcgattcgc     599
```

<210> SEQ ID NO 240
<211> LENGTH: 525
<212> TYPE: DNA
<213> ORGANISM: Drosophila

<400> SEQUENCE: 240

```
agtagtcggt attttgttgg tgatctcctt agttggacac gagacaaacg caaaaagtgt    60
ggccaacacc ttggccaacc aaatcggtca ggatgcttcc gatttcggta atgaattagg   120
ccaagaggtc atccaatatg ccaagaagc tgccaacagc ggcttgaagt acggagaagc   180
agcggaaaat gcctcctccg gttgggaact tggaatggat ggcagcattt ttggtcacga   240
attgggagat gagggcaatt tgttgggaca ggaggtttcc aatagcgcta ttaactttgg   300
acatcaagtg tcccaggaag cggaagaggc agccagtgca gaactcaaag ccatggcaag   360
ccaatctgcc aatcaatcca gtaagaaatc tgtcagtaag cgtgatttaa caagtagcaa   420
cgagaatcct tcggttacct gtgcttgcac ctgttccacc gatggcgctg cttccaaagt   480
gggaaataag gtagcagagt cggccggaaa ggcagctcat gatgt               525

<210> SEQ ID NO 241
<211> LENGTH: 372
<212> TYPE: DNA
<213> ORGANISM: Drosophila

<400> SEQUENCE: 241
acatccggag cggactcctc tgggaacaaa ccgccaatag aagggtactc gaagcgattg    60
tgaaagagct tgtgaccaat tcgtgaggtg tgcgtttcga cggactcgga ggtcactgca   120
tacacgacat agtcgttgat atggacctgg ataacaggtg ccgtgaagct gtagctggcc   180
actggctttt cgttctcact gtaccacttt ccttgcgcag agaactggta cagaaagccg   240
tccacactgc tggccacgag gagggcgtgt cctatgcacc tctggtgctg agaagactta   300
agcgtccggc ggtttacgtg cttaaacgtg gtcacagcac tgggcacctg gtggttgccc   360
atgtcatact ca                                                      372

<210> SEQ ID NO 242
<211> LENGTH: 550
<212> TYPE: DNA
<213> ORGANISM: Drosophila

<400> SEQUENCE: 242
gtatagcgga acgcaacaaa gcccggacaa cccgaccact gtcttttac cgcattcgcc     60 aaataatcag tcagccagcg gagagaaacc tggcggtgcc acatcaaaat caccaaacgc   120
agccaaaact tcgccaacaa tgacggacta cctgtcgctg cactcgcgac tcgcccaggt   180
gggccaggag cacctgctca gttctggcc ggaactaacg aatgacgaac gcatcgacct   240
ggtgcgggac atcgaggagc tgaatctgga cgagatcaag ctgtatttcg accgcgccac   300
ggtctcaatg aacgagaatg gcatcaagct ggacgatcgc ctgcagccgc tgcccgaggg   360
caagctaatc tccattgcca gggcgccgct ggagaaattg gacgcctacc gagacgaggg   420
tctcctccag atcagcaacg gacatgtcgc tgtgctgctt atggcaggcg gacaaggcac   480
acgacttggc ttcgatcatc ccaagggaat gtacgatgtg ggactgcagt ctcgaaagac   540
cctgttccgc                                                         550

<210> SEQ ID NO 243
<211> LENGTH: 720
<212> TYPE: DNA
<213> ORGANISM: Drosophila

<400> SEQUENCE: 243
agaaaaaata aattatttat ttgaaattta aagtcaactt gtcatttaat gtcttgtaga    60
```

-continued

| | |
|---|---|
| cttttgaaag tcttacgata cattagtatc tatatacatg gttcattcta cattctatat | 120 |
| tagtgatgat ttctttagct agtaatacat tttaattata ttcggctttg atgattttct | 180 |
| gattttttcc gaacggattt tcgtagaccc tttcgatctc ataatggctc attttattgc | 240 |
| gatggacggt caggagagct cattttgaat ttctgttcgc agacaccgca tttgtagcac | 300 |
| atagccggga catccggttt ggggagattt tcagtctctg ttgcaattgg ttttcgggaa | 360 |
| tgcgttgcag gcgcatacgc tctatatcct ccgaacggcg ctggttgacc ctagcattta | 420 |
| cataaggatc agcagcaaaa tttgcctcta cttcattgcc cggaatcaca gcaatcagat | 480 |
| gtccctttcg gttacgatgg atattcaggt gcgaaccgca caacaaagct ctcgccgcac | 540 |
| actccacact gatatggtcg ctcgcccgtg tggcgccgca tatggatctt aaggtcgttg | 600 |
| gactgcacaa agctcttgct gcacattttg caggagtacg gcctttgacc cgtgtgcaat | 660 |
| cgcacttgtg tccacttgtg tcgcgccagc ttgttctgcg aaataaactt cttggagcag | 720 |

<210> SEQ ID NO 244
<211> LENGTH: 478
<212> TYPE: DNA
<213> ORGANISM: Drosophila

<400> SEQUENCE: 244

| | |
|---|---|
| gatttatgag ttggccaccc tgaagaagcg acgtcacttg gagctgccga gcaaccatcg | 60 |
| caatgcggag atacagcaga tgatctttac caatgactcc agatcggtgg ccctgatcac | 120 |
| ccgcccgccg gaggaaaccc ttattatgtt ggtgctggac aagaccagta cagtgatcga | 180 |
| gggcagggcc acaatcccgg gatctcatgg aggcgccgag tgcatcgctg gcaatccaaa | 240 |
| cgattgcaat tttatggcgg tcggaggcga gcgcacgttg ttgctgatga gtaaatcgga | 300 |
| gcgaggattt agtatcagca ataatctgaa ggtgaaatat agggtcacct cgatggcttt | 360 |
| tctatcgctg gacctgctga tgattggtac gtcggatgat cagttgatcc tggtggagaa | 420 |
| cggcgagcag aagttggctc aaaaggcgag cgatgcggac actgtggact tgatgatc | 478 |

<210> SEQ ID NO 245
<211> LENGTH: 600
<212> TYPE: DNA
<213> ORGANISM: Drosophila

<400> SEQUENCE: 245

| | |
|---|---|
| tcggcagaaa aatatttctg gaataacaaa aacagacaaa attacccgta tccgaaccga | 60 |
| gtcgttattc caacaccaaa catgaactgg cacaagggca acattgcgga ggccgtggcg | 120 |
| gcatcaaagg ccaagggcgc cgtgtttgtc gtcttcatcg agggccagga cgaaatgacc | 180 |
| cgaaaactag agcggttcgt ggatgacagt caggtgcgct cccgcctgga aacctccgat | 240 |
| tttgtcgcca tcaaagtcca gggaaatagc tccgcctacg acagttcat gtcgttatac | 300 |
| aaaatcgtgc caattccctc gctcttcttt attggcaaaa cgggtacacc tctggagata | 360 |
| gccactgggg ttacgccag cgtagatgaa ctgacgaaa agatcgataa ggttctgatc | 420 |
| ctggcgggaa aacgaaccga gcctgtggca gccagcagct cttcatgtgc gaagacactt | 480 |
| gaccccaatg aagtcaggag cttcgccgga gcagatggct caagcagcac tggggaatct | 540 |
| caagtagttc aaacagcatc agaaaacttt agagatcctg aaaccacctc agtttcaaac | 600 |

<210> SEQ ID NO 246
<211> LENGTH: 546
<212> TYPE: DNA
<213> ORGANISM: Drosophila

<400> SEQUENCE: 246

```
tcaaggcggt agagctgcag tccaccagtc ccacgccacc taaaggatac aggccagcgg    60
aagctcaaca caaagaagcg aaatggaggc gtcagcaagt ataaatttgc agccggtggt   120
gaacgttcct acgatttata aggatccctg gtacatgatc acagtgctgg tcctctatct   180
gtacttcgtc accaaagcgg gtccgcattt catggaatgg cgcaaacctt acgagctcaa   240
gcgacttatc ttgctacata atttcatcca ggtggtttcc tgcatatatg ctatcaaaga   300
ggtcctgtac attacggaca acaccatata catcttttgg aagtgccgcg catcgggag    360
cagcccagag ctcgtgaggc ggtactacaa cttggcctac tttctcttct ggctgaagat   420
ctctgagctg attgaaaccg tgatctttgt gcttcgcaag aaacaaaacc aggtgtccaa   480
gctgcacatc tttcatcact tctccacggt aacgctggtc tacgcactga tcaacttcaa   540
cgaaaa                                                              546
```

<210> SEQ ID NO 247
<211> LENGTH: 608
<212> TYPE: DNA
<213> ORGANISM: Drosophila

<400> SEQUENCE: 247

```
gcaccacata gtgtttaaga tctattggca aatttcaaac gtatttcct taccttttcgc    60
gagttttttc ggtctagatt tgtagttttg taaatacgat aaccgtttac tttaatcgaa   120
gttgttcgtt tttggcgaga taaactgaat tcaattggat tgatcgccac ccacgcccaa   180
ccacatccac tgacgcctcc tggcgacatt tactggcctg cctctgctgc tgttgctgct   240
gccgacgacg atttgtttgt tttgtgccaa ctttgatgac tcaccggaga gactcagact   300
ggaactgaat ctgagactga gtctgagccg gtctgcggc agctaaacaa gctcagtcgc    360
gtcatcacct tgaccaaagc ccacacacga gctctgcagc aatcgcatcg aattcaaacg   420
actgccatcg catcgaacag actccatttg gcaatggcgt cacaaggttc cggagatatg   480
aagacctcaa ggctggcgca aatgcagatg cgtttccagc agcgcacgca acaggagcag   540
gaggtgcgta tgcgggagct gatgagcacg aagtcaagtg ccgagaacct ggccactgga   600
gcacccag                                                            608
```

<210> SEQ ID NO 248
<211> LENGTH: 641
<212> TYPE: DNA
<213> ORGANISM: Drosophila

<400> SEQUENCE: 248

```
cataaatata caggtactgg tctgaaacat ttattacaaa aaattcaaaa acaaaaata    60
tagcgaagaa ggataaagac catgtacaac aatattaagg gcctacacat aaatgaatac   120
cagagggaga atggagataa taccagaaag ctggcgtgtg aaggtacagt gaagctaaac   180
gccaatgccc aagaatttgt gccacgttac aagagggaac aaccagcaaa agatgatgct   240
atagttggta acagtaacat gagcaacacc aataacgacg accaaaaacc aaaatctaac   300
cttatgttgc cgtggaaagg atttccgaat aaatctcaaa aaccttctcg caatgtggac   360
tacatagttc taccgagcac caaaagattt aaaaagccca ttggccaaca actcgtggaa   420
aatgttccca ctacgccctc aaaagtccat ttaaatgatc ctgttccagc tggaaatcgc   480
attgatcacg aggaaaggcg ccgcgaacac gatagaaaaa tcgctgtgga agccttaaag   540
```

```
ttggccgaac agcgtagaat gagggatcct gtcattgccc ccacggaggg caatgaaaac    600
tcaaagaacg tgccgccaat tataaatatc tcacgatctc c                       641
```

<210> SEQ ID NO 249
<211> LENGTH: 590
<212> TYPE: DNA
<213> ORGANISM: Drosophila

<400> SEQUENCE: 249

```
attgacaagc aaaatcactc acaacgcttt tgttagcagt tgaaatcaac tgtgtgaaat     60
atttttttg aaaataaatt ttttttaga aattttaaga ccaaagacaa aattgaaaaa      120
tgtgttcacg cgatacggcg tcaaatcaat tgattgacta taagaacaat gactccgagg    180
tgcaaaggga gatcacgaca tccagtggaa ctccagttgg cgtcaaggat gccatacaga    240
cggtgggacc aagggtcct gccctgctgc aggatttcca gttcctcgac gaggtgatgc     300
acttcgactc ggagcggatt cccgaacggg tggcctacgc caagggagcc ggcgcctttg    360
gttacttcga gtgcacccat gacatttcaa aattctgtgc agcctccata ttcgataagg    420
ttagaaaacg aactgccgtc gcgatgagat tctcggtggc ctgcgtgaa cagggatctg     480
cggatacggt acgtgaacag cgcggatttg ccgtcaaatt ctacaccgac gacggcatct    540
gggacattgt gggttgcaac atgcccgtgc attatgtccg ggatcccatg               590
```

<210> SEQ ID NO 250
<211> LENGTH: 644
<212> TYPE: DNA
<213> ORGANISM: Drosophila

<400> SEQUENCE: 250

```
ctcacaagac tgccgagcac caaattgggg atcctcccca aaaagaggcg gcagctgatt     60
tcgaggcagc catcgatgcc gctggctttg aatgttcaa catcctcctg ctggtggccg     120
ccgtgccagc ggccatgggc accgtctacg agacctccac gatgtcctac atcctgccca    180
gcgccgagtg tgatcttaag ctgagcctcc tggacaaggg catcctgaat gccattacct    240
atgcgggcat gatcagttcg gcggtgcttt ggggctactt ggccgacatc aagggcagaa    300
gaaacctcct gattgtgggc tatgccgccg atacgatatg cgttttgggc ggagcactca    360
gtcaaagtag gatccaactg atggttttta ataccttgg aggcttttgt atgagtggcc     420
cctttgccgt tcttatgacc tatttgacgg aactccatgg acggaagcat cgacagcgta    480
tcatgatgat ggtgggcatc atgttctcaa ttgcaacgct aacgctaccg ggactggcca    540
tgctgatatt gcccgagacg tggaacattc agatctggac tttgtcgttg acatcctggc    600
agttttcgt cgccgtcacc gcacttccca gtcttctgag cttt                      644
```

<210> SEQ ID NO 251
<211> LENGTH: 375
<212> TYPE: DNA
<213> ORGANISM: Drosophila

<400> SEQUENCE: 251

```
ctcacacaga attataatca caaaaaaaaa aaaaccgaca ttttcttaaa aattcctaaa     60
tggagaacaa caattgcgag ggcgagcaac catcgacatc cggtgcattc tgtaggtgct    120
ccgagtctgg cattggtata tctgccgtcc tggatctcgc tcagtcggag tactccctgg    180
acaccacgcc ggaagctgtg atggcgagtg catgtcgtct ggagaacgag aacgatggta    240
atgataccga tgaggatgtg gagatctgct tcaccagctt gatgcccgat caccgtaagc    300
```

| | |
|---|---|
| gcttgtatat ggactgcaag ctgtctcttc cggcgggcgg aagagtgccc atgcgcggcg | 360 |
| gcgcagaagc cattt | 375 |

<210> SEQ ID NO 252
<211> LENGTH: 524
<212> TYPE: DNA
<213> ORGANISM: Drosophila

<400> SEQUENCE: 252

| | |
|---|---|
| cagccactat agtgaaagct tcgatctgtg ttgaatgggt ctgcgatctg gtgtctgggg | 60 |
| tttgggggat ctgcccactt tgctgctcac ttcggtcgct ccggctgctt tcactcgacc | 120 |
| caattccagg ggcaatcttc taaccagttt agaagtgtcc actttggagc gagtcacgat | 180 |
| ttcctggact ggaaaaacac gcgcccctcg agaaaacgg ggcagtgatc tcagcgatgt | 240 |
| gtccatcatc aagcgaatgc gtggagtgga agttctggct cttagtgtca acaagatcag | 300 |
| cacgctgtcg accttcgagg attgcaccaa actgcaggag ctatatttgc gcaagaacag | 360 |
| catctctgac atcaacgaga tcgcctacct acaaaatctt ccgagtctca ggaatctctg | 420 |
| gctggaggaa aatccctgct gcgaacgagc gggtcccaac tatcgttcga tcgtattacg | 480 |
| cgccctgccg aacctcaaga aactcgacaa tgttgaggtc acac | 524 |

<210> SEQ ID NO 253
<211> LENGTH: 598
<212> TYPE: DNA
<213> ORGANISM: Drosophila

<400> SEQUENCE: 253

| | |
|---|---|
| ttcgacccat cccctccaaa tccaatcagt caaacatttc ttaccacaca cgtacaaccc | 60 |
| gaacccccgct tagtcatttc aaattcaagt atatagacta cattgatttt ggaagagtta | 120 |
| gccacaatgt tcatccgcgg agatgcgcca caagcttccc ggggcaaaat tccccagatc | 180 |
| cccagctcca tgacgcccta tgtggcggca gtgaagcgcg gaccctacac aatgaccaat | 240 |
| ccggtgtaca acacccacaa tcccaacctg gtgggcttgg atggccaggt ggaggattcc | 300 |
| cggcccaagc acacctttaa tgtgaagagg caagagctgg agaataacta ccggcaccac | 360 |
| cagcggctga tccccgtgcc cacttcccgg aggacgatgc ccaagatccg atcccacata | 420 |
| gtgatgaacg agcagcggga gctgtatcgc cagcaccgcg atcgaatgtc caacatcaag | 480 |
| ggcaaggtca acacctatct gccgcccccg aaggtgcaga tcgagggaaa tggcatggag | 540 |
| ctctcctaca tggagatgct gaccgcactc tacaagaaga gcaacaacac gctgcgga | 598 |

<210> SEQ ID NO 254
<211> LENGTH: 600
<212> TYPE: DNA
<213> ORGANISM: Drosophila

<400> SEQUENCE: 254

| | |
|---|---|
| cttttcgagt atgataggtg tatttcgttt tgtgcctcca aaatttcaga tattattcag | 60 |
| ctacacacag acaggcctcc caaatttgta agctctgtaa attcaaaacc agaactgctg | 120 |
| caggccagtg gcgaagttaa tttgtcagag gaaaactcaa gccatctcca tggataaaaa | 180 |
| ccacaagtcg gaagagggt ttggacgttc aatgtctagt agcagtcgcc gcgtcatgtg | 240 |
| gaagctcaac gaggaggagg agacattcga ctccttggtc aattatcggc ggcttccttc | 300 |
| gcgcagccta aaccgaagtc aggtgaccga tgtgcccacc aagggacaca ctacctccga | 360 |

```
aaattgccag ctgccagcgc aagagttgga aacaaagagc gccaccaacg aacaaggtgc      420
attgggcata atgtcggtta gcctaccgca acaaccagg aattcccatc aatcgtcggc       480
cacgtcactg ccggaggcca agggatgcac tgccaccgaa aactgccagt tgctagcgca      540
agaggcggaa acaaagaacg ccagcaacga acaaggtgga ttgggcaaaa tgtcggttag      600
```

<210> SEQ ID NO 255
<211> LENGTH: 613
<212> TYPE: DNA
<213> ORGANISM: Drosophila

<400> SEQUENCE: 255

```
cataaacaaa taaaacgatt tgaagatgaa tccgctaaca aatatgaaaa atgtgctcaa       60
actgagcgaa cacgaactgc aacatggcgg aaagaagagc tggcacgaca tgtacaagga     120
ctcagcctgg attttcgtcg caggatttcc gtatacccta actgagggcg acttggtttg     180
cgtattctcg cagtacggcg aagtggtcaa catcaatcta attcgagatt caaaaacggg     240
aaagtccaag ggcttctgct tcctgtgcta cgaggaccag agatccacag tgctggccgt     300
ggacaacctg aatggcatca agatcctcga taggacacta agggtcgatc acgtggccga     360
ctacaagcct cccaaggaaa acgagaagat ggacgaggaa acccttcgcc tttacatgga     420
gggctgtgcg ccgaaacctc aacttcagca catcaagact gagaagaaag acagcaaaaa     480
ttatagatga taagataagg ttagcttaaa catagcaaag catgcaaaca gaattttat      540 attaacttaa atttttagt tattaaacgc taaattatac tactaaaaaa aaaaaatcaa       600
aactgaaatt cta                                                         613
```

<210> SEQ ID NO 256
<211> LENGTH: 664
<212> TYPE: DNA
<213> ORGANISM: Drosophila

<400> SEQUENCE: 256

```
cggaacgtcg agcgcacgaa ttcggaatta tcgttgaaac aaacgtcgcc gcgtgtgatc       60
gaaaatccaa gttaggctca ttcgttggga agctgcgagt tcactctctc tcacacacac     120
acgcacgaat attaccccg gcgcgttta cttccatctc gctcccacaa aggcggaaga       180
gttaaacaca aaaaaaaaag aaaaatagaa agaaattat aaacgaaaaa ctgccaccgc      240
cgctgctcaa taatttgtgc atttttaag tttcatcaca atgtcctcaa atctaattta      300
aataagtaag aagtgtaaca agcgacacgc agcgaaacaa atagcgctga atagaggagc     360
acgccaaggc aaacagcaac aaatggccaa caattgaatg gcggccatca gttggcccca     420
gcggcatcca ttgagcaatc aacaccattt ctcccacatc aaatcaagca ccacttccag     480
caacaccatc acctcaacca cctcagtcac caccgccgtc acagctttgg gaatcagaac     540
cacagtccaa gacccagtcg aaaccaccac caccaccagt aaaagccaca gcctagcagg     600
accacaacca ctgagctcca tcgccaacaa ataccagaac cgggtgcagc tgctcgaatt     660
attt                                                                   664
```

<210> SEQ ID NO 257
<211> LENGTH: 628
<212> TYPE: DNA
<213> ORGANISM: Drosophila

<400> SEQUENCE: 257

```
aagtataaag ccttgcggat ccaaagttaa ctgctgattt tccaagaaca acagttaaga       60
```

```
tcaaaaattt cttaaaatgc ccgaacaagt cacagatcag gagaaccagg ctccacagca      120
gcagactact gctgtgcatg cctacaatcc cgaagtcctg caggatatgt tgcccgtgta      180
ttacaggcgc ctctttcccc acctgccctt ctaccgttgg ctatcgtatg gatcatccga      240
ggatgctatc ttttccaatc gtgaaatttc ctttacactg caggacgata tctacatacg      300
ttacctctgc tttgataccc aagctgaatt ggaaaaggag atctgctcga ggaatcctat      360
taagattgac ataggaccag taatgcattc caaacccaaa aaccatcgtt caattcctgg      420
cggcttaacg cccgtacaac gtgaactcgt ttttgatata gatatgacgg attacgacga      480
ggtgcgtacc tgttgctctg gagcaggggt atgcctgaaa tgctggaagt ttatggtgct      540
ggctgccagg gttttggatg tcgctttgcg cgaggatttc ggtttcgagc acataatctg      600
gattttctca ggtagacgag gtatccat                                        628
```

<210> SEQ ID NO 258
<211> LENGTH: 600
<212> TYPE: DNA
<213> ORGANISM: Drosophila

<400> SEQUENCE: 258

```
ctggcacaga tcaacagact gacgttgtaa ttgcatctgg aggtttacca aggctgggac       60
tccttctaca gcacaacaaa agcaacattg tgaaggaggc tgcctggacg gtcagcaaca      120
tcacagcagg taaccagaag cagatccagg ctgtgattca ggccggcatc ttccagcagc      180
tgcgcaccgt gctggagaag ggtgatttca aggctcaaaa agaggctgcc tgggcggtga      240
caaacaccac gacatctggc actcccgaac agatcgtcga tctaattgag aagtacaaaa      300
tattgaagcc ttttatcgat ttgctggaca caaaggatcc gcgtaccatc aaggtggtgc      360
agacgggcct atccaatctg tttgccctgg cggagaaact tggtggcacc gagaacctat      420
gcttgatggt cgaggagatg ggcggtctag acaagctgga aactctgcag cagcacgaga      480
acgaggaggt ctacaagaag gcctacgcca tcattgacac atacttcagc aacggcgacg      540
acgaggccga gcaagagctc gcacctcagg aggtcaacgg agccctcgag ttcaatgcca      600
```

<210> SEQ ID NO 259
<211> LENGTH: 3312
<212> TYPE: DNA
<213> ORGANISM: Drosophila

<400> SEQUENCE: 259

```
tttttttttt actatttccc ccagcggtc agacggttga cgttcccaat tcggcatttc        60
aatttggcat acgtccccga aaatggagc tagcctagcc agagtccaac aggattaggc       120
caaactcatt gcgaaacgaa acgcctgaag atacatctac aagccgtgat tgcgtgcgac      180
aattgcacag tatttacgtc agcatcggtt aagtgaggca attgcaccat ggacttcaag      240
gaataccgcc aaaggggcaa ggagatggtc gactatattg cagactatct ggagaacatc      300
cgggaacgcg gagttttttcc ggatgtcagt ccgggctata tgcgccagtt actgccggag      360
tccgctccga tcgaaggtga accgtggccg aaaatattct cggatgtgga gcgtatcgtg      420
atgccgggca taacccactg gcaatcgccc cacatgcacg cctactttcc ggccctcaac      480
tccatgcctt ccctactggg cgacatgctg gcggatgcga ttaactgcct gggattcacc      540
tgggcgagct cgccagcctg caccgaactg gagatcatag tgatgaactg gctgggcaag      600
atgatcggtc tgccggatgc ctttctccac ctgagctccc aaagtcaggg cggtggagtg      660
```

-continued

| | |
|---|---|
| ctgcagacca ctgccagtga agctactcta gtttgtctgc tggcgggacg gactcgggct | 720 |
| attcagcgat tccatgagcg acatcctggc tatcaggatg cggagatcaa cgcccggctg | 780 |
| gtggcctact gctccgatca ggcgcactcc agtgtggaga aggcggcgct cattggactc | 840 |
| gtgaggatgc gttacatcga ggcggatgag gacctggcga tgcgcggcaa actgttgcgc | 900 |
| gaggccatcg aggatgacat taagcagggc ctggtcccct tctgggtctg cgccacactc | 960 |
| gggaccaccg gcagctgcag cttcgataac ctggaggaga ttggcatcgt tgtgcggag | 1020 |
| caccacctgt ggctccacgt tgacgccgcg tacgccggca cgccttcat ctgcccggag | 1080 |
| tttcgcacct ggctgcgtgg cattgagcgg gcggattcga tagccttcaa tccgtccaag | 1140 |
| tggctgatgt tgcacttcga tgcgaccgca ttgtgggttc gggatagcac cgctgtccac | 1200 |
| aggaccttca atgtggagcc gctgtatctg cagcacgaga attccggagt ggcagtggac | 1260 |
| tttatgcact ggcagatacc gctgagtcgc cgattccgtg ccctgaaggt gtggttcgtc | 1320 |
| ctgcgatcct acgggatcaa aggcctacag cgccacattc gcgaaggcgt tcgattggct | 1380 |
| cagaaattcg aggccctcgt cctggccgat catcgtttcg agctgcccgc taaaaggcat | 1440 |
| cttggcctgg tggtattccg gatacgcggc gataatgaga taaccgagaa gttgctgaag | 1500 |
| aggctgaatc accgaggcaa ccttcattgc atcccatcgt cgctgaaggg acagtatgtc | 1560 |
| atccgcttta ccatcacatc gacgcacacg accttggacg atattgtcaa ggattggatg | 1620 |
| gagatccgtc aggtggcctc cactgtgctg gaggagatga acatcacaat ttcgaatcgc | 1680 |
| gtctatctca aggaaaccaa ggagaaaaac gaagccttcg gctcgagtct tctgctctct | 1740 |
| aattctccgc tctcgcctaa ggtggtaaat ggctcctttg cggctatatt cgatgcggat | 1800 |
| gagttcctgg ccaaaaccta tgccggcgtt cggatagcgc caggaatc gccatcgatg | 1860 |
| agacgacgtg tgcgtggcat cctcatgtcg ggcaagcagt tctcgctgga ctcccacatg | 1920 |
| gacgtggtgg ttcagacgac cctggacgcc ggcaatggag ccactcgtac cagcaccacc | 1980 |
| aactcctatg ccacaccac ttctgcggcc caggcaaact cggagaggca ggccagcatc | 2040 |
| caagaggaca cgaggagtc gccggaagaa actgaattgc tgtcactgtg caggaccagc | 2100 |
| aatgtaccca gccccgagca cgcccactcc ctatccactc ctagtcgcag ctgtagctcc | 2160 |
| agctcccact cactgaccca ctctctcact caatcctcag cgcgatcctc accagtcaac | 2220 |
| caatttcgac acattacttt gtgcgcagtg cccagtcaaa gccatctttc aatgcccctt | 2280 |
| gccatgcccc tgcccaatcg caatgtcacc gtgtccgtgg atagcctcct gaacccggtc | 2340 |
| accacctgca acgtctacca tggcaagcgg tttctggagc ccctcgagaa tctcgcccag | 2400 |
| accagtgcct ccttcagcag cagcatcttt cgcctgccga cacccatggc cacgcccacc | 2460 |
| cgggaatcgc cggaggatcc ggactggccg gcaaagacct tcagccagct gctgttggag | 2520 |
| cgctactcct cgcagtccca gtccctgggc aataactcct cgacggagag cagcagtctc | 2580 |
| agcggcgggg ccactcccac gcccactccc atgagcagcc tggatgaatt ggtgacacca | 2640 |
| ctgctgctct cattcgcatc cccctcgcag ccgatgctct ccgcccatgg cattggcgag | 2700 |
| ggtcagcggg agcggggcag cgactcggat gccaccgttt gttcgacaac ctcatcgatg | 2760 |
| gagtcgcttt agtgatagcc ttaaaaattc catattaagt tttactatac tatgaatcta | 2820 |
| aggacagaag aagtacctaa ttatatgatc tttttctctt tgtttaaacc aagaagtagt | 2880 |
| tggtaatgat ccaactatac atcttatttg tttagcttac tcaatctgaa gttacacatt | 2940 |
| ttatttggat cccatgactt acgttattat tcaatataat ttgacatctc agttcattgt | 3000 |
| atataagtgt gattgggaaa gagggtaaa tcatcgaacg ctgctgtgca atcaatcaat | 3060 |

-continued

```
aatgcaatca atcgtaattc caatcaatgt tgtgccgtac cgttaatcta caaaatatgc      3120
atgcccatac cataatacta taaatttcct attttaagct aacaatcggt caagactcaa      3180
aactcaaaaa cttaccggct tacatatgta tctccatgtc taatcaattt cagtgtgatt      3240
aaagtttcaa agttctagtt acaacacaaa aaaaaaaaaa aaaaaaaaaa aaaaaaaaaa      3300
aaaaaaaaaa aa                                                         3312
```

<210> SEQ ID NO 260
<211> LENGTH: 2873
<212> TYPE: DNA
<213> ORGANISM: Drosophila

<400> SEQUENCE: 260

```
atgcagagtc tgcggatctc gggatgcacg cccagcggta cgggtggctc ggccacgccc        60
tcgccggtgg gcctggtgga tccgaatttc atagtcagca actatgtggc cgcctcgccg       120
caggaggagc gcttcattca gatcattcag gccaaggagc tcaagataca ggaaatgcaa       180
agggccctcc agttcaagga caacgaaata gccgagctaa agtcgcactt ggacaaattc       240
cagagtgtct ttcccttcag ccgtggcagt gcggctggtt gtgcgggcac gggcggagcg       300
tcgggatctg gagccggcgg aagtggcggc agtggtcccg gcaccgccac aggtgccaca       360
cgcaagtcgg gtcagaattt ccagaggcag agggcattgg gtatctccgc cgagccacag       420
agcgagtcct cgctgctcct cgagcacgtc agctttccca aatacgacaa ggatgagcgc       480
tcccgtgaac ttatcaaggc tgccatattg gataatgatt tcatgaagaa tctggatctg       540
acgcagatcc gcgagatcgt tgactgcatg tatccggtta agtatccagc caagaatctg       600
atcatcaagg agggagatgt cggaagcatc gtttatgtca tggaagatgg acgcgtcgag       660
gtttcccgcg agggcaagta cctctccaca ttgtcgggag cgaaggtcct tggcgaattg       720
gcgatcctgt acaactgcca gcggacggcg accatcaccg cgatcaccga gtgcaacctg       780
tgggccatcg agcgccagtg cttccagacc atcatgatgc gaacgggcct gatccggcag       840
gcggagtaca gcgatttcct caagagtgtg cccatcttca aagacctggc ggaagacacg       900
ctcatcaaaa tctccgatgt cttggaggag acgcactacc agcgtggcga ccacatagtg       960
cgccagggcg cccgaggcga taccttcttc atcatctcca agggaaaagt gcgagtgacg      1020
atcaagcagc aggacaggca ggaggagaag ttcattcgca tgctgggcaa aggggatttc      1080
tttggagaga aggctctcca gggcgatgat ctgcgcacgg cgaatattat ttgcgagtcc      1140
gccgatggcg tcagttgtct ggtcatcgat cgcgagacct tcaatcagct aatttccaat      1200
ctagacgaga tcaagcatcg ctacgacgac gagggcgcca tggaacgcag aaagatcaac      1260
gaggaattcc gggacattaa cctcacagat ctgcgcgtca tcgcaaccct tggagttgga      1320
ggcttcggtc gcgtagagct ggtccaaact aatgaagata gctccaggtc cttcgcgctc      1380
aagcagatga aaagtcaca gattgtggag acgcgtcagc agcaacacat catgtccgag      1440
aaggagatca tgggcgaggc caattgccag ttcatcgtga agctgttcaa gaccttcaag      1500
gacaagaagt acctgtacat gctgatggag agttgcctgg gcggagagct ctggacgatt      1560
ctacgggaca agggcaactt cgacgacagc accacccgct tctacacggc atgtgtggtg      1620
gaggcctttg attacttgca ctcgcgtaac atcatctacc gcgatcttaa gccggagaac      1680
ctgctgctca tgaacgagg atatgggaag ctggtggact ttggctttgc caagaagctg      1740
cagacgggca ggaagacctg gactttctgc ggcactccag agtacgtggc tcccgaggtg      1800
```

```
attctcaacc ggggccacga catcagtgcg gattactggt cgctgggagt gctcatgttc      1860
gagttactta ctggtacccc tccattcacg ggctcggatc ccatgcgcac ctacaacatt      1920
atacttaagg gcatcgacgc catcgaattc caaggaata  tcacccgcaa tgccagcaac      1980
ctgatcaaga agctctgtcg cgacaatcca gccgagcgtt tgggctacca gcgtggggga      2040
atcagcgaga tccaaaagca caaatggttc gatggcttct attggtgggg cctgcagaac      2100
tgcacactgg aaccgcccat taagcccgcc gtgaaaagcg ttgtggatac aacaaacttt      2160
gatgactatc ctcccgatcc tgaggtccg  ccgccagatg atgtcactgg atgggacaag      2220
gacttctgag gagaatcaga acccgtttcc tagacgatgc tctctaaacg cttctgctgc      2280
agaaaaccag gaggatatga agccaggga  agaaaaattg atcttaagtg cgccatatgt      2340
acgccaaagc caacagcaac agtcagcagc tcgcatcgaa aagctgccat aaaaaaaaac      2400
aaagaaacgt agcagtcgca aggtcaaggg ccgacacaaa agcacaatca tccatcgtcg      2460
tagctccatt tgagatttat agatacgtct ccgtgatgtt ataaccatga tgtgcaacgc      2520
aatgaatcta ttaacgagtt tataactatt  atttttataat gaggatatat gtgtctagtt      2580
cgcttggaat tgatgtaaat tgtaagtagg tctgtgactc tgtttcagag ctctgttagc      2640
catgtgcatt gtataaattc agctatttgt atctattaaa tattttaac  ataattatta      2700 cacatcattg ttaaagcata caaatcgggt tgccttatag tctgtaagag aacatttgaa      2760
agcaacattt gaccaagatc ttccgtcaca catttcttaa aattctatgt ggcctctcta      2820
ctgtctttca ttagtcttag cgatcatgtc tattatatgt acgataacat gcc             2873

<210> SEQ ID NO 261
<211> LENGTH: 1080
<212> TYPE: DNA
<213> ORGANISM: Drosophila

<400> SEQUENCE: 261
actgcataac caaatatttg cgtggctcca actcgactcc gtatttgcct gggctgaagg       60
accgccgctg cctgcggatg acatgtattg gtcctgcgga tgacaccgat actgacgctc      120
ttgggttgcg tggtcgggcg gtctcccgca gtgggttatc cagtccaggt tgctatataa      180
gtcgaggatg cgccaaccga cgttcattcg caagtctcct gctgcaggtg ttccgtgctc      240
agttcctgct cctggccacc ctttcagctc ctcggactaa tggctcgctt cacgtacctt      300
gtcgcccttg tgcttctggc catttgctgc cagtggggat aatgcggcgc catggccatg      360
ccggatgagg agcgctatgt gcgcaaggag tacaatcggg atctcctcga ctggttcaac      420
aacgtgggcg tgggacagtt cagtcccggc caagtggcca ctctctgtcg ctatccgctg      480
atcctcgaga actccttggg cccatccgtg cccatcagga agcgcaactc ggagctaatc      540
aactccttgt tgagtctgcc caagaacatg aacgatgcgg gcaagtaaga acggaaaatg      600
ctgaaggatt aggacgaccc accactgaaa gttggaacct ggacaagaac ttattatttg      660
atgttatcgt atgatttttt ggtgcgtcga aggaaaatga aaatccgcag ataaaagccg      720
gtgtagtcat ctaatagaga gaaagaccg  tataacttt  gttgctttaa acctaaatag      780
aaaaatatac aagtagccta ttgtagaaat gttgtatatt attaggctta ctgctgaaat      840
aaacgttttc tggattgttt cgacttgaaa tctggtacaa caactagtca ggattttat       900 tcttaatcac agatactaaa gctagttaaa gatattggtt atccccgtaa agggcgaacc      960
```

```
aatgaaagcc aaaggtgttc tcaaagtaga ttttgttcaa tgctacgatt ggaataaata    1020
gatgtttcta gcttagaata gcagccccat ttcgtttatt gacttcattt attatgctat    1080
```